US007659276B2

(12) United States Patent
Hulme et al.

(10) Patent No.: US 7,659,276 B2
(45) Date of Patent: Feb. 9, 2010

(54) MELANIN CONCENTRATING HORMONE RECEPTOR ANTAGONIST

(75) Inventors: Christopher Hulme, Indianapolis, IN (US); Paul Tempest, Brookline, MA (US); Vu Ma, Simi Valley, CA (US); Thomas Nixey, Newbury Park, CA (US); Guity Balow, Fallbrook, CA (US)

(73) Assignee: Amgen, Inc., Thousand Oaks, CA (US)

( * ) Notice: Subject to any disclaimer, the term of this patent is extended or adjusted under 35 U.S.C. 154(b) by 0 days.

(21) Appl. No.: 12/367,083

(22) Filed: Feb. 6, 2009

(65) Prior Publication Data

US 2009/0143405 A1 Jun. 4, 2009

Related U.S. Application Data

(62) Division of application No. 10/916,011, filed on Aug. 11, 2004, now Pat. No. 7,514,438.

(60) Provisional application No. 60/494,735, filed on Aug. 13, 2003.

(51) Int. Cl.
*A61K 31/41* (2006.01)
*A61K 31/4439* (2006.01)
*A61K 31/454* (2006.01)
*A61K 31/496* (2006.01)

(52) U.S. Cl. ............... 514/253.09; 514/254.05; 544/364; 544/366

(58) Field of Classification Search .............. None
See application file for complete search history.

(56) References Cited

U.S. PATENT DOCUMENTS

| 6,472,394 B1 | 10/2002 | McKittrick et al. |
| 6,552,188 B2 | 4/2003 | Kodama et al. |
| 7,078,414 B2 | 7/2006 | Kleemann et al. |
| 7,078,430 B2 | 7/2006 | Kumar et al. |
| 7,087,638 B2 | 8/2006 | Walter et al. |
| 7,091,235 B2 | 8/2006 | Friedman et al. |
| 2002/0182655 A1 | 12/2002 | Kostenis et al. |
| 2003/0229119 A1 | 12/2003 | Kym et al. |

FOREIGN PATENT DOCUMENTS

| CA | 2 356 412 A1 | 7/2000 |
| CA | 2 383 147 A1 | 3/2001 |
| EP | 0 127 124 A2 | 12/1984 |
| WO | 96/14307 A1 | 5/1996 |
| WO | 98/03492 A1 | 1/1998 |
| WO | 98/03493 A1 | 1/1998 |
| WO | 98/03494 A1 | 1/1998 |
| WO | 98/10068 A2 | 3/1998 |
| WO | 00/39279 A3 | 7/2000 |
| WO | 01/05947 A1 | 1/2001 |
| WO | 01/21577 A2 | 3/2001 |
| WO | 02/04433 A2 | 1/2002 |
| WO | 02/094799 A2 | 11/2002 |
| WO | 03/015769 A1 | 2/2003 |
| WO | 03/045313 A2 | 6/2003 |
| WO | 03/073999 A2 | 9/2003 |
| WO | 03/087044 A2 | 10/2003 |
| WO | 03/087046 A1 | 10/2003 |

OTHER PUBLICATIONS

Carpenter et al. Expert Opinion in Therapeutic Patents, vol. 12(11) p. 1639-1646 (2002).*
Bednarek et al. Journal of Biological Chemistry, vol. 277, p. 13821-13826 (2002).*
Dyke et al. Expert Opin.Ther.Patents, vol. 15, p. 1303-1313 (2005).*
Banker, G. S., et al., Modern Pharmaceuticals, 1996, p. 596, Third Edition, Revised and Expanded.
Edwards, P. D., et al., "Discovery and Biological Activity of Orally Active Peptidyl Trifluoromethyl Ketone Inhibitors of Human Neutrophil Elastase," Journal of Medicinal Chemistry, 1997, pp. 1876-1885, vol. 40, No. 12.
International Search Report, PCT/US04/25970, dated Mar. 3, 2005, 3 pages.
Lythgoe, D. J., Abstract of WO 1992/469592.
Marsh, D.J. et al., "Melanin-Concentratiing Hormone 1 Receptor-Deficient Mice Are Lean, Hyperactive, and Hyperphagic and Have Altered Metabolism", PNAS, (2002), pp. 3240-3245, vol. 99:5.
Nabeya, A., et al., "Diaziridines. 2. Isomerization of N-Carbamoyldiaziridines," Journal of Organic Chemistry, 1979, pp. 3935-3938, vol. 44, No. 22.
Stamos, I. K., "Aldehyde-Enamines from α-Oxocarboxylic Acids. A Facile and General Route to Aldehydes Via Decarboxylation of α-Oxocarboxylic Acids Carrying β-Hydrogens," Tetrahedron Letters, 1982, pp. 459-462, vol. 23, No. 4.

(Continued)

*Primary Examiner*—Emily Bernhardt
(74) *Attorney, Agent, or Firm*—Senniger Powers LLP

(57) ABSTRACT

Novel compounds, or pharmaceutically-acceptable salts, tautomers or prodrugs thereof, of Formula I

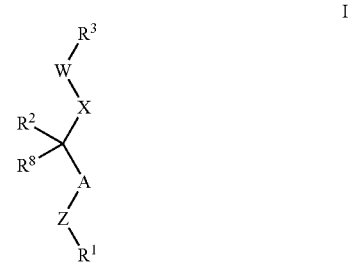

wherein A, W, X, Z, $R^1$-$R^3$, and $R^8$ are as defined in the specification, are provided. Also provided are methods of treating or preventing a melanin concentrating hormone-mediated disorder in a subject, comprising administering to a subject in need of such treatment or prevention a compound of Formula I.

8 Claims, No Drawings

OTHER PUBLICATIONS

Supplementary Partial European Search Report, PCT/US2004/025970, dated Oct. 31, 2007, 6 pages.

Walker, G. N., et al., "Synthesis of Varied Heterocyclic and Substituted Aryl Alkyl Secondary Amines, Related Schiff Bases, and Amides," Journal of Medicinal Chemistry, Jul. 1966, pp. 624-630, vol. 9.

Weikert, R. J., et al., "Synthesis and Anthelmintic Activity of 3'-Benzoylurea Derivatives of 6-Phenyl-2,3,5,6-Tetrahydroimidazo[2,1-b]thiazole," Journal of Medicinal Chemistry, 1991, pp. 1630-1633, vol. 34, No. 5.

Wissner, A., et al., "Analogues of Platelet Activating Factor. 7. Bis-Aryl Amide and Bis-Aryl Urea Receptor Antagonists of PAF," Journal of Medicinal Chemistry, 1992, pp. 4779-4789, vol. 35, No. 26.

Wolff, M. E., Burger's Medicinal Chemistry and Drug Discovery, 1995, pp. 975-977, Fifth Edition, vol. 1: Principles and Practice.

* cited by examiner

MELANIN CONCENTRATING HORMONE RECEPTOR ANTAGONIST

CROSS-REFERENCE TO RELATED APPLICATIONS

This application is a divisional of U.S. patent application Ser. No. 10/916,011 filed Aug. 11, 2004, which is a non-provisional of U.S. Provisional Patent Application No. 60/494,735 filed Aug. 13, 2003.

BACKGROUND OF THE INVENTION

In 1999, 61% of adults, 13% of children aged 6 to 11 years and 14% of adolescents aged 12 to 19 years in the United States were overweight. Increases in occurrence of overweight and obesity has been seen in all age, racial and ethnic groups, and in both men and women.

Epidemiological studies show an increase in mortality associated with overweight and obesity. Individuals who are obese (body mass index ("BMI")>30) have a 50-100% increased risk of premature death from all causes compared to individuals with a BMI in the range of 20 to 25. BMI is calculated according to the formula:

$$BMI = \frac{\text{Weight in pounds}}{(\text{Height in inches})^2} \times 703$$

An estimated 300,000 deaths a year in the United States may be attributable to obesity. Overweight and obesity are associated with an increased risk for coronary heart disease; type 2 diabetes; endometrial, colon, postmenopausal breast, and other cancers; and certain musculoskeletal disorders, such as knee osteoarthritis.

Both modest and large weight gains are associated with significantly increased risk of disease. For example, a weight gain of 11 to 18 pounds increases a person's risk of developing type 2 diabetes to twice that of individuals who have not gained weight, while those who gain 44 pounds or more have four times the risk of type 2 diabetes. A gain of approximately 10 to 20 pounds results in an increased risk of coronary heart disease (nonfatal myocardial infarction and death) of 1.25 times in women and 1.6 times in men. Higher levels of body weight gain of 22 pounds in men and 44 pounds in women result in an increased coronary heart disease risk of 1.75 and 2.65, respectively. In women with a BMI of 34 or greater, the risk of developing endometrial cancer is increased by more than six times. Overweight and obesity are also known to exacerbate many chronic conditions such as hypertension and elevated cholesterol. Overweight and obese individuals also may suffer from social stigmatization, discrimination, and poor body image. Although obesity-associated morbidities occur most frequently in adults, important consequences of excess weight as well as antecedents of adult disease occur in overweight children and adolescents. Overweight children and adolescents are more likely to become overweight or obese adults; this concern is greatest among adolescents. Type 2 diabetes, high blood lipids, and hypertension as well as early maturation and orthopedic problems also occur with increased frequency in overweight youth. A common consequence of childhood overweight is psychosocial-specifically discrimination. See The Surgeon General's Call To Action To Prevent and Decrease Overweight and Obesity, U.S. Dept. of Health and Human Services, 2001. Thus, the need exists for methods of controlling weight and treating obesity.

Melanin-concentrating hormone (MCH) is a cyclic, 19-amino acid hypothalamic neuropeptide derived from a larger pro-hormone precursor of MCH, Pmch. Pmch-deficient mice are lean, hypophagic, and have an increased metabolic rate. Transgenic mice over-expressing Pmch are hyperphagic and develop mild obesity. Consequently, MCH has been implicated in the regulation of energy homeostasis, through actions on motor activity, metabolism, food intake and neuroendocrine function.

Two receptors have been identified in MCH, and are designated MCH 1 receptor and MCH 2 receptor. The MCH 1 and MCH 2 receptors are G protein-coupled receptors (GPCRs) believed to be responsible for the actions of MCH. G proteins are heterotrimeric proteins that control cellular responses to stimuli by cycling between a GTP-bound active state, which regulates the activity of a number of effector proteins, and a GDP-bound inactive state. GPCRs accelerate activation of the G protein by increasing the GDP/GTP exchange rate.

MCH 1 receptor-deficient mice have normal body weights, yet are lean and have reduced fat mass. Surprisingly, MCH 1 receptor-deficient mice are hyperphagic when maintained on regular chow, and their leanness is a consequence of hyperactivity and altered metabolism. Consistent with the hyperactivity, MCH 1 receptor-deficient mice are less susceptible to diet-induced obesity. Importantly, chronic central infusions of MCH induce hyperphagia and mild obesity in wild-type mice, but not in MCH 1 receptor-deficient mice. Marsh et al., *Proc. Nat. Acad. Sci.*, 99(5), 3241 (2002).

Because MCH has been shown to be an important regulator of food intake and energy balance, compounds capable of modulating the activity of MCH receptors, particularly MCH 1 receptors, are highly desirable for the treatment of eating disorders and metabolic disorders.

PCT Publication No. WO 02/04433 describes phenylcycloalkylmethylamino and phenylalkenylamino derivatives as modulators of MCH 1 receptors useful in the treatment of certain metabolic, feeding and sexual disorders.

U.S. Pat. No. 6,472,394 describes the use of amide derivatives of 1,4-disubstituted piperidine as MCH antagonists for the treatment of obesity and diabetes.

SUMMARY OF THE INVENTION

Among the several objects of certain embodiments of the present invention, therefore, may be noted the provision of melanin concentrating hormone receptor antagonists; the provision of pharmaceutical compositions comprising melanin concentrating hormone receptor antagonists; the provision of methods of treating, preventing, or otherwise ameliorating melanin concentrating hormone-mediated disorders in a subject; the provision of methods for treating, preventing or otherwise ameliorating obesity in a subject; and the provision of methods of achieving sustained body weight loss in a subject.

Briefly therefore, the present invention is directed to a melanin concentrating hormone receptor antagonist of Formula I as defined herein.

The present invention is also directed to pharmaceutical compositions comprising a compound of Formula I, as defined herein, and a pharmaceutically acceptable carrier, adjuvant, or diluent.

The present invention is also directed to a method of inhibiting a GPCR, comprising contacting a compound of Formula I, as defined herein, with a GPCR, wherein the compound of Formula I is present at a concentration sufficient to inhibit the binding of a GPCR ligand in vitro. This method includes inhibiting a GPCR in vivo, e.g., in a subject given an amount of a compound of Formula I that would be sufficient to inhibit the binding of a ligand to the GCPR in vitro. Examples of GPCRs which may be inhibited according to the present invention include, but are not limited to the following GPCR families: Acetylcholine muscarinic, Adenosine, adrenergic, adrenergic, alpha-adrenergic, angiotensin, AR, Cannabinoid, DA, dopamine, His, imidazoline, Leukotriene, mAch, MCH, Opioid, serotonergic, serotonin, and Somatostatin.

Inhibition of the binding of a GPCR ligand to GPCRs is useful in the treatment of numerous disorders, including digestive tract disorders; mucolytic asthma; arrhythmia; ischemia; reperfusion injury; bronchospasm associated with asthma, emphysema and chronic bronchitis; acute and chronic respiratory diseases, including cystic fibrosis; cardio-stimulant; chronic bronchitis; neurological depression; heart failure; benign prostate hypertrophy; diabetes; muscle spasm; myocardial infarction; stroke; Alzheimer's disease; anorexia; cachexia; multiple sclerosis; hyperprolactinemia; psychotropism; mydriasis in ocular examination and surgery; deficitary and productive schizophrenia, psychasthenia and non-endogenous depression; kidney disease; vasodilation; chronic gastritis; glaucoma; depression; rhinitis, including allergic rhinitis; pain, including cancer pain, musculoskeletal pain, post-operative pain; eye disease; dyspepsia; cough; ulcer, including gastrointestinal, gastric and esophageal ulcers; *helicobacter pylori* prophylaxis infection; oesophagitis; allergies, including non-asthma allergies; cold; asthma; conjuctivitis; urticaria; diarrhea; Creutzfeldt-Jakob disease; dysmenorrhoea; drug addiction and drug overdose; septic shock treatment; cerebral ischaemia; drug posoning; head trauma; inflammation; pruritus; tardive dyskinesia; emesis; anxiety; motility dysfunction; cluster headaches; hypertension; cancer; irritable bowel syndrome; hemotherapy-induced nausea and vomiting; thrombosis; dementia; opiate-induced nausea and vomiting; bipolar depression; migraine; sleep disorders; traumatic shock; gastritis; gastro-oesophageal reflux; psychosis; Parkinson disease; Dependence treatment; Pre-eclampsia; Raynaud's disease; Vasospasm; haemostasis; nausea and vomiting; spasms; post-operative nausea and vomiting; alcoholism, alcohol addiction; bulimia; nicotine addiction; obsessive-compulsive disorder; panic disorder; post-traumatic stress disorder; premenstrual syndrome; and dermatitis, including allergic dermatitis.

The present invention is also directed to methods of inhibiting the binding of MCH to MCH receptors comprising contacting a compound of Formula I with cells expressing MCH receptors, wherein the compound is present at a concentration sufficient to inhibit MCH binding to MCH receptors in vitro. This method includes inhibiting the binding of MCH to MCH receptors in vivo, e.g., in a subject given an amount of a compound of Formula I that would be sufficient to inhibit the binding of MCH to the MCH receptors in vitro. The amount of a compound of Formula I that would be sufficient to inhibit the binding of MCH to the MCH receptor in vitro may be readily determined via a MCH receptor binding assay, such as the assay described hereinbelow in Example 7.

The present invention is also directed to methods for altering the signal-transducing activity of MCH receptors, particularly the MCH receptor-mediated release of intracellular calcium, said method comprising exposing cells expressing such receptors to an effective amount of a compound of the invention. This method includes altering the signal-transducing activity of MCH receptors in vivo, e.g., in a subject given an amount of a compound of Formula I that would be sufficient to alter the signal-transducing activity of MCH receptors in vitro. The amount of a compound that would be sufficient to alter the signal-transducing activity of MCH receptors may be determined via a MCH receptor signal transduction assay, such as the calcium mobilization assay described hereinbelow in Example 6.

The present invention is also directed to methods of using compounds of Formula I and appropriately labeled derivatives thereof as standards and reagents in determining the ability of a potential pharmaceutical to bind to MCH receptor.

The present invention is also directed to methods of treating, preventing, or otherwise ameliorating melanin concentrating hormone-mediated disorders in a subject, the method comprising administering a compound of Formula I or a pharmaceutical composition comprising a compound of Formula I and a pharmaceutically-acceptable carrier, adjuvant, or diluent to said subject.

The present invention is also directed to methods of treating or preventing obesity in a subject, the method comprising administering a compound of Formula I or a pharmaceutical composition comprising a compound of Formula I and a pharmaceutically-acceptable carrier, adjuvant, or diluent to said subject.

The present invention is also directed to methods of treating or preventing conditions such as feeding disorders, including obesity, bulimia and bulimia nervosa; sexual or reproductive disorders; depression and anxiety; epileptic seizure; hypertension; cerebral hemorrhage; congestive heart failure; sleep disturbances; or any condition in which antagonism of an MCH receptor is beneficial.

The present invention is also directed to methods of treating eating disorders, particularly obesity and bulimia nervosa, comprising administering to a subject in need of such treatment a compound of Formula I in combination with leptin, a leptin receptor agonist, or a melanocortin receptor 4 (MC4) agonist.

The present invention is also directed to methods of using compounds of Formula I as positive controls in assays for activity of GPCRs, particularly MCH.

The present invention is also directed to methods of using appropriately labeled compounds of Formula I as probes for the localization of GPCRs, particularly MCH, in tissue sections.

Other objects and features will be in part apparent and in part pointed out hereinafter.

ABBREVIATIONS AND DEFINITIONS

The term "alkyl", where used alone or within other terms such as "haloalkyl", "alkylsulfonyl", "alkoxyalkyl" and "hydroxyalkyl", is a linear or branched radical having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. Examples of such radicals include methyl, ethyl, propyl (e.g., n-propyl and isopropyl), butyl (e.g., n-butyl, isobutyl, sec-butyl, and tert-butyl), pentyl (e.g., n-pentyl and iso-amyl), hexyl, and the like.

The term "cycloalkyl" is a saturated carbocyclic radical having three to twelve carbon atoms. The cycloalkyl radical may be mono-, bi-, or tricyclic. More preferred cycloalkyl radicals are "lower cycloalkyl" radicals having three to about eight carbon atoms. Examples of such radicals include cyclopropyl, cyclobutyl, cyclopentyl, and cyclohexyl.

The term "alkenyl" is a linear or branched radical having at least one carbon-carbon double bond and having two to about twenty carbon atoms or, preferably, two to about twelve carbon atoms. More preferred alkyl radicals are "lower alkenyl" radicals having two to about six carbon atoms. Examples of alkenyl radicals include ethenyl, propenyl, allyl, butenyl and 4-methylbutenyl. The terms "alkenyl" and "lower alkenyl" also are radicals having "cis" and "trans" orientations, or alternatively, "E" and "Z" orientations.

The term "cycloalkenyl" is a partially unsaturated carbocyclic radical having three to twelve carbon atoms. The cycloalkenyl radicals may be mono-, bi-, or tricyclic. More preferred cycloalkenyl radicals are "lower cycloalkenyl" radicals having four to about eight carbon atoms. Examples of such radicals include cyclobutenyl, cyclopentenyl, cyclopentadienyl, and cyclohexenyl.

The term "alkynyl" is a linear or branched radical having at least one carbon-carbon triple bond and having two to about twenty carbon atoms or, preferably, two to about twelve carbon atoms. More preferred alkynyl radicals are "lower alkynyl" radicals having two to about ten carbon atoms. Most preferred are lower alkynyl radicals having two to about six carbon atoms. Examples of such radicals include propargyl, butynyl, and the like.

The terms "carboxy" or "carboxyl", whether used alone or with other terms, such as "carboxyalkyl", is —$CO_2$H.

The term "carboxyalkyl" is an alkyl radical as defined above substituted with a carboxy radical. More preferred are "lower carboxyalkyl" radicals, which are lower alkyl radicals as defined above substituted with a carboxy radical, and may be additionally substituted on the alkyl radical with halo. Examples of such lower carboxyalkyl radicals include carboxymethyl, carboxyethyl and carboxypropyl.

The term "halo" is a halogen such as fluorine, chlorine, bromine or iodine.

The term "haloalkyl" is an alkyl radical as defined above wherein any one or more of the carbon atoms is substituted with halo as defined above. Specifically included are mono-haloalkyl, dihaloalkyl and polyhaloalkyl radicals. A monohaloalkyl radical, for one example, may have either an iodo, bromo, chloro or fluoro atom within the radical. Dihalo and polyhaloalkyl radicals may have two or more of the same halo atoms or a combination of different halo radicals. More preferred haloalkyl radicals are "lower haloalkyl" having one to six carbon atoms. Examples of lower haloalkyl radicals include fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl and dichloropropyl.

The terms "alkoxy" and "alkyloxy" are linear or branched oxy-containing radicals each having alkyl portions of one to about ten carbon atoms. More preferred alkoxy radicals are "lower alkoxy" radicals having one to six carbon atoms. Examples of such radicals include methoxy, ethoxy, propoxy, butoxy and tert-butoxy. The "alkoxy" radicals may be further substituted with one or more halo atoms, such as fluoro, chloro or bromo, to provide haloalkoxy radicals. More preferred haloalkoxy radicals are "lower haloalkoxy" radicals having one to six carbon atoms and one or more halo radicals. Examples of such radicals include fluoromethoxy, chloromethoxy, trifluoromethoxy, trifluoroethoxy, fluoroethoxy and fluoropropoxy.

The term "alkoxyalkyl" is an alkyl radical having one or more alkoxy radicals attached to the alkyl radical, that is, to form monoalkoxyalkyl and polyalkoxyalkyl radicals. More preferred alkoxyalkyl radicals are "lower alkoxyalkyl" radicals having two to twelve carbon atoms. Examples of such radicals include methoxymethyl, methoxyethyl, methoxypropyl, ethoxymethyl, ethoxyethyl, ethoxypropyl, dimethoxymethyl, dimethoxyethyl, methoxy(ethoxy)ethyl, dimethoxypropyl, and methoxy(ethoxy)propyl.

The term "alkoxycarbonyl" is a radical containing an alkoxy radical, as defined above, attached via an oxygen atom to a carbonyl radical, i.e., an ester radical. More preferred are "lower alkoxycarbonyl" radicals with alkyl portions having one to six carbons. Examples of such lower alkoxycarbonyl radicals include substituted or unsubstituted methoxycarbonyl, ethoxycarbonyl, propoxycarbonyl, butoxycarbonyl and hexyloxycarbonyl.

The term "hydroxyalkyl" is a linear or branched alkyl radical having one to about ten carbon atoms, any one of which may be substituted with one or more hydroxyl radicals. More preferred hydroxyalkyl radicals are "lower hydroxyalkyl" radicals having one to six carbon atoms and one or more hydroxyl radicals. Examples of such radicals include hydroxymethyl, hydroxyethyl, hydroxypropyl, hydroxybutyl and hydroxyhexyl.

The term "alkylamino" is an amino group that has been substituted with one or two alkyl radicals. Preferred are "lower N-alkylamino" radicals having alkyl portions having one to six carbon atoms. Suitable lower alkylamino may be mono- or dialkylamino, such as N-methylamino, N-ethylamino, N,N-dimethylamino, N,N-diethylamino or the like.

The term "alkylaminoalkyl" is a radical having one or more alkyl radicals attached to the nitrogen atom of an aminoalkyl radical.

The term "alkylaminocarbonyl" is an aminocarbonyl group that has been substituted with one or two alkyl radicals on the amino nitrogen atom. Preferred are "N-alkylaminocarbonyl" "N,N-dialkylaminocarbonyl" radicals. More preferred are "lower N-alkylaminocarbonyl" and "lower N,N-dialkylaminocarbonyl" radicals with lower alkyl portions as defined above.

The term "alkylthio" is a radical containing an alkyl radical of one to about ten carbon atoms attached to a divalent sulfur atom. More preferred alkylthio radicals are "lower alkylthio" radicals having alkyl radicals of one to six carbon atoms. Examples of such lower alkylthio radicals are methylthio, ethylthio, propylthio, butylthio and hexylthio.

The term "alkylthioalkyl" is a radical containing an alkylthio radical attached through the divalent sulfur atom to an alkyl radical of one to about ten carbon atoms. More preferred alkylthioalkyl radicals are "lower alkylthioalkyl" radicals having alkyl radicals of one to six carbon atoms. Examples of such lower alkylthioalkyl radicals include methylthiomethyl, methylthioethyl, ethylthioethyl, and ethylthiopropyl.

The term "alkylsulfinyl" is a radical containing a linear or branched alkyl radical, of one to ten carbon atoms, attached to a divalent —S(=O)— radical. More preferred alkylsulfinyl radicals are "lower alkylsulfinyl" radicals having alkyl radicals of one to six carbon atoms. Examples of such lower alkylsulfinyl radicals include methylsulfinyl, ethylsulfinyl, butylsulfinyl and hexylsulfinyl.

The term "aminoalkyl" is an alkyl radical substituted with one or more amino radicals. More preferred are "lower aminoalkyl" radicals of one to six carbon atoms. Examples of such radicals include aminomethyl, aminoethyl, and the like.

The term "aminocarbonyl" is an amide group of the formula —C(=O)$NH_2$.

The term "carbonyl", whether used alone or with other terms, such as "alkoxycarbonyl", is —(C=O)—.

The term "aryl", alone or in combination, is a carbocyclic aromatic system containing one, two or three rings wherein such rings may be attached together in a pendent manner or may be fused, and wherein at least one of the rings is aromatic. The term "aryl" includes aromatic radicals such as phenyl, naphthyl, tetrahydronaphthyl, indane and biphenyl. Aryl moieties may also be substituted at a substitutable position with one or more substituents selected independently from alkyl, alkoxyalkyl, alkylaminoalkyl, carboxyalkyl, alkoxycarbonylalkyl, aminocarbonylalkyl, alkoxy, aralkoxy, hydroxyl, amino, halo, nitro, alkylamino, acyl, cyano, carboxy, aminocarbonyl, alkoxycarbonyl and aralkoxycarbonyl.

The terms "heterocyclyl" and "heterocyclo" are saturated or partially unsaturated heteroatom-containing ring-shaped radicals having one, two, or three rings wherein such rings may be attached together in a pendent manner or may be fused, where the heteroatoms may be selected from nitrogen, sulfur and oxygen. Examples of saturated heterocyclyl and heterocyclo radicals include saturated 3- to 6-membered heteromonocylic radicals containing one to four nitrogen atoms (e.g., pyrrolidinyl, imidazolidinyl, piperidino, piperazinyl, etc.); saturated 3- to 6-membered heteromonocyclic group containing one to two oxygen atoms and one to three nitrogen atoms (e.g., morpholinyl, etc.); saturated 3- to 6-membered heteromonocyclic group containing one to two sulfur atoms and one to three nitrogen atoms (e.g., thiazolidinyl, etc.). Examples of partially unsaturated heterocyclyl and heterocyclo radicals include dihydrothiophene, dihydropyran, dihydrofuran and dihydrothiazole.

The term "heteroaryl" is an aromatic heteroatom-containing ring-shaped radical having one, two, or three rings wherein at least one ring is aromatic. Examples of heteroaryl radicals include unsaturated 3- to 6-membered heteromonocyclic group containing one to four nitrogen atoms, e.g., pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g. 1H-tetrazolyl, 2H-tetrazolyl, etc.), etc.; unsaturated condensed heterocyclyl group containing one to five nitrogen atoms, e.g., indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3- to 6-membered heteromonocyclic group containing an oxygen atom, e.g., pyranyl, furyl, etc.; unsaturated 3- to 6-membered heteromonocyclic group containing a sulfur atom, e.g., thienyl, etc.; unsaturated 3- to 6-membered heteromonocyclic group containing one to two oxygen atoms and one to three nitrogen atoms, e.g., oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing one to two oxygen atoms and one to three nitrogen atoms (e.g., benzoxazolyl, benzoxadiazolyl, etc.); unsaturated 3- to 6-membered heteromonocyclic group containing one to two sulfur atoms and one to three nitrogen atoms, e.g., thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing one to two sulfur atoms and one to three nitrogen atoms (e.g., benzothiazolyl, benzothiadiazolyl, etc.) and the like. The term "heteroaryl" also includes radicals where heteroaryl radicals are fused with aryl radicals. Examples of such fused bicyclic radicals include benzofuran, benzothiophene, and the like. Said heterocyclyl group may be substituted at a substitutable position with one or more substituents selected independently from alkyl, hydroxyl, halo, alkoxy, oxo, amino and alkylamino.

The terms "heterocyclylalkyl" and "heterocycloalkyl" are saturated and partially unsaturated heterocyclyl-substituted alkyl radicals, such as pyrrolidinylmethyl, and heteroaryl-substituted alkyl radicals, such as pyridylmethyl, quinolylmethyl, thienylmethyl, furylethyl, and quinolylethyl. The heteroaryl in said heteroaralkyl may be additionally substituted with halo, alkyl, alkoxy, halkoalkyl and haloalkoxy.

The term "acyl" is a radical provided by the residue after removal of hydroxyl from an organic acid. Examples of such acyl radicals include alkanoyl and aroyl radicals.

The term "alkanoyl" or "alkylcarbonyl" are alkyl radicals as defined herein attached to a carbonyl radical. Examples of such alkanoyl radicals include formyl, acetyl, propionyl, butyryl, isobutyryl, valeryl, isovaleryl, pivaloyl, hexanoyl, and trifluoroacetyl.

The terms "arylcarbonyl" (also called "aroyl") and "aralkylcarbonyl" include radicals having aryl or aralkyl radicals, as defined herein, attached to a carbonyl radical. Examples of such radicals include substituted or unsubstituted phenylcarbonyl, naththoyl, and benzylcarbonyl. The aryl in said aroyl and aralkylcarbonyl radicals may be additionally substituted.

The term "aralkoxy" is an aralkyl radical as defined herein attached through an oxygen atom to other radicals.

The term "aralkoxyalkyl" is an aralkoxy radical as defined herein attached through an oxygen atom to an alkyl radical.

The terms "aralkyl" and "arylalkyl" are aryl-substituted alkyl radicals such as benzyl, diphenylmethyl, triphenylmethyl, phenylethyl, and diphenylethyl. The aryl in said aralkyl may be additionally substituted with halo, alkyl, alkoxy, halkoalkyl and haloalkoxy. The terms benzyl and phenylmethyl are interchangeable.

The term "aralkylamino" is an aralkyl radical as defined herein attached through an amino nitrogen atom to other radicals. The terms "N-arylaminoalkyl" and "N-aryl-N-alkyl-aminoalkyl" are amino groups which have been substituted with one aryl radical or one aryl and one alkyl radical, respectively, and having the amino group attached to an alkyl radical. Examples of such radicals include N-phenylaminomethyl and N-phenyl-N-methylaminomethyl.

The term "aralkylthio" is an aralkyl radical attached to a sulfur atom.

The term "aralkylthioalkyl" is an aralkylthio radical attached through a sulfur atom to an alkyl radical.

The term "arylamino" is an amino group that has been substituted with one or two aryl radicals. An example of such arylamino radicals is N-phenylamino. The "arylamino" radicals may be further substituted on the aryl ring portion of the radical.

The term "aryloxyalkyl" is a radical having an aryl radical attached to an alkyl radical through a divalent oxygen atom.

The term "arylthioalkyl" is a radical having an aryl radical attached to an alkyl radical through a divalent sulfur atom.

The term "sulfonyl", whether used alone or linked to other terms such as alkylsulfonyl, is a divalent $-SO_2-$ radical.

The term "alkylsulfonyl" is an alkyl radical attached to a sulfonyl radical, where alkyl is defined as above. More preferred alkylsulfonyl radicals are "lower alkylsulfonyl" radicals having one to six carbon atoms. Examples of such lower alkylsulfonyl radicals include methylsulfonyl, ethylsulfonyl and propylsulfonyl. The "alkylsulfonyl" radicals may be further substituted with one or more halo atoms, such as fluoro, chloro or bromo, to provide haloalkylsulfonyl radicals.

The terms "sulfamyl", "aminosulfonyl" and "sulfonamidyl" are $-SO_2NH_2$.

The term "pharmaceutically acceptable" is used adjectivally herein to mean that the modified noun is appropriate for use in a pharmaceutical product; that is the "pharmaceutically-acceptable" material is relatively safe and/or non-toxic, though not necessarily providing a separable therapeutic benefit by itself. Pharmaceutically-acceptable cations include metallic ions and organic ions. More preferred metallic ions include, but are not limited to, appropriate alkali metal salts, alkaline earth metal salts and other physiologically-acceptable metal ions. Exemplary ions include aluminum, calcium, lithium, magnesium, potassium, sodium and zinc, in their usual valences. Preferred organic ions include protonated tertiary amines and quaternary ammonium cations, including in part, trimethylamine, diethylamine, N,N'-dibenzylethylenediamine, chloroprocaine, choline, diethanolamine, ethylenediamine, meglumine (N-methylglucamine) and procaine. Exemplary pharmaceutically acceptable acids include without limitation hydrochloric acid, hydrobromic acid, phosphoric acid, sulfuric acid, methanesulfonic acid, acetic acid, formic acid, tartaric acid, maleic acid, malic acid, citric acid, isocitric acid, succinic acid, lactic acid, gluconic acid, glucuronic acid, pyruvic acid, oxalacetic acid, fumaric acid, propionic acid, aspartic acid, glutamic acid, benzoic acid, and the like.

The term "prodrug" refers to a chemical compound that can be converted into a therapeutic compound by metabolic or simple chemical processes within the body of the subject.

The term "subject" for purposes of treatment or prevention includes any human or animal subject who is in need of treatment. The subject can be a domestic livestock species, a laboratory animal species, a zoo animal or a companion animal. In one embodiment, the subject is a mammal. In another embodiment, the mammal is a human being.

The term "PBS" stands for phosphate buffered saline.

The term "HEPES" stands for N-2-hydroxyethylpiperazine-N'-2-ethanesulfonic acid.

The term "BSA" stands for bovine serum albumin.

The term "STI" stands for soybean trypsin inhibitor.

The term "Pefabloc" stands for (4-(2-aminoethyl)benzenesulfonylfluoride, HCl salt.

The term "Phosphoramidon" stands for N-α-L-rhamnopyranosyloxy(hydroxyphosphinyl)-L-leucyl-L-tryptophan.

The term "FCC" stands for flash column chromatography.

The term "$K_i$" stands for inhibitory rate constant.

The term "FLIPR" stands for fluorometric imaging plate reader.

The term "HEK 293" stands for the human embryonic kidney 293 cell line.

The term "Boc" stands for tert-butoxycarbonyl.

The term "DIC" stands for diisopropylcarbodiimide.

The term "DCM" stands for dichloromethane.

The term "DBU" stands for 1,8-diazabicyclo[5.4.0]undec-7-ene.

The term "phosgene" stands for $COCl_2$.

The term "DCE" stands for dichloroethane.

The term "DMF" stands for dimethylformamide.

The term "EtOAc" stands for ethyl acetate.

The term "HOBt" stands for 1-Hydroxybenzotriazole hydrate.

The term "MeOH" stands for methanol.

The term "TFA" stands for trifluoroacetic acid.

The MCH receptor antagonists employed in the present invention can exist in tautomeric, geometric or stereoisomeric forms. The present invention contemplates all such compounds, including cis- and trans-geometric isomers, E- and Z-geometric isomers, R- and S-enantiomers, diastereomers, d- and l-isomers, the racemic mixtures thereof and other mixtures thereof. Pharmaceutically acceptable salts of such tautomeric, geometric or stereoisomeric forms are also included within the invention. The terms "cis" and "trans", as used herein, denote a form of geometric isomerism in which two carbon atoms connected by a double bond and each substituted by a hydrogen and another group, will each have a hydrogen atom on the same side of the double bond ("cis") or on opposite sides of the double bond ("trans"). Some of the compounds described herein contain alkenyl groups, and are meant to include both cis and trans or "E" and "Z" geometric forms. Furthermore, some of the compounds described herein contain one or more stereocenters and are meant to include R, S, and mixtures or R and S forms for each stereocenter present.

The MCH receptor antagonists utilized in the present invention may be in the form of free bases or pharmaceutically-acceptable acid addition salts thereof. The term "pharmaceutically-acceptable salts" are salts commonly used to form alkali metal salts and to form addition salts of free acids or free bases. The nature of the salt may vary, provided that it is pharmaceutically acceptable. Suitable pharmaceutically-acceptable acid addition salts of compounds for use in the present methods may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, examples of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, mesylic, 4-hydroxybenzoic, phenylacetic, mandelic, embonic (pamoic), methanesulfonic, ethanesulfonic, benzenesulfonic, pantothenic, 2-hydroxyethanesulfonic, toluenesulfonic, sulfanilic, cyclohexylaminosulfonic, stearic, algenic, hydroxybutyric, salicylic, galactaric and galacturonic acid. Suitable pharmaceutically-acceptable base addition salts of compounds of use in the present methods include metallic salts made from aluminum, calcium, lithium, magnesium, potassium, sodium and zinc or organic salts made from N,N'-dibenzylethylenediamine, chloroprocaine, choline, diethanolamine, ethylenediamine, meglumine (N-methylglucamine), and procaine. All of these salts may be prepared by conventional means from the corresponding compound by reacting, for example, the appropriate acid or base with the compound of any Formula set forth herein.

The MCH receptor antagonists useful in the practice of the present invention can be formulated into pharmaceutical compositions and administered by any means that will deliver a therapeutically effective dose. Such compositions can be administered orally, parenterally, by inhalation spray, rectally, intradermally, transdermally, or topically, in dosage unit formulations containing conventional nontoxic pharmaceutically-acceptable carriers, adjuvants, and vehicles as desired. Topical administration may also involve the use of transdermal administration such as transdermal patches or iontophoresis devices. The term parenteral as used herein includes subcutaneous, intravenous, intramuscular, or intrasternal injection, or infusion techniques. Formulation of drugs is discussed in, e.g., Hoover, Remington's Pharmaceutical Sciences, (1975), and Liberman & Lachman, Eds., Pharmaceutical Dosage Forms, (1980).

Injectable preparations, for example, sterile injectable aqueous or oleaginous suspensions, can be formulated according to the known art using suitable dispersing or wetting agents and suspending agents. The sterile injectable preparation may also be a sterile injectable solution or suspension in a nontoxic parenterally-acceptable diluent or solvent. Among the acceptable vehicles and solvents that may be employed are water, Ringer's solution, and isotonic sodium chloride solution. In addition, sterile, fixed oils are conventionally employed as a solvent or suspending medium. For this purpose, any bland fixed oil may be employed, including synthetic mono- or diglycerides. In addition, fatty acids such as oleic acid are useful in the preparation of injectables. Dimethyl acetamide, surfactants including ionic and nonionic detergents, and polyethylene glycols can be used. Mixtures of solvents and wetting agents such as those discussed above are also useful.

Suppositories for rectal administration of the compounds discussed herein can be prepared by mixing the active agent with a suitable non-irritating excipient such as cocoa butter, synthetic mono-, di-, or triglycerides, fatty acids, or polyethylene glycols, which are solid at ordinary temperatures but liquid at the rectal temperature, and which will therefore melt in the rectum and release the drug.

Solid dosage forms for oral administration may include capsules, tablets, pills, powders, and granules. In such solid dosage forms, the compounds are ordinarily combined with one or more adjuvants appropriate to the indicated route of administration. If administered per os, the compounds can be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets can contain a controlled-release formulation as can be provided in a dispersion of active compound in hydroxypropylmethyl cellulose. In the case of capsules, tablets, and pills, the dosage forms can also comprise buffering agents such as sodium citrate, or magnesium or calcium carbonate or bicarbonate. Tablets and pills can additionally be prepared with enteric coatings.

For therapeutic purposes, formulations for parenteral administration can be in the form of aqueous or non-aqueous isotonic sterile injection solutions or suspensions. These solutions and suspensions can be prepared from sterile powders or granules having one or more of the carriers or diluents mentioned for use in the formulations for oral administration. The compounds can be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Liquid dosage forms for oral administration can include pharmaceutically acceptable emulsions, solutions, suspensions, syrups, and elixirs containing inert diluents commonly used in the art, such as water. Such compositions can also comprise adjuvants, such as wetting agents, emulsifying and suspending agents, and sweetening, flavoring, and perfuming agents.

The amount of active ingredient that can be combined with the carrier materials to produce a single dosage of the MCH receptor antagonist will vary depending upon the patient and the particular mode of administration. In general, the pharmaceutical compositions may contain an MCH receptor antagonist in the range of about 1 to about 250 mg, more typically, in the range of about 10 to about 200 mg and still more typically, between about 25 to about 150 mg. A daily dose of about 0.01 to about 80 mg/kg body weight, or more typically, between about 0.5 to about 50 mg/kg body weight and even more typically, from about 1 to about 25 mg/kg body weight, may be appropriate. The daily dose can be administered in one to about four doses per day.

The MCH receptor antagonists are administered in such an amount as will be therapeutically effective in the treatment, control, or prevention of the disorder or condition being treated. It will be appreciated that the amount of active ingredients contained in an individual dose of each dosage form need not in itself constitute an effective amount, as the necessary effective amount could be reached by administration of a number of individual doses. Those skilled in the art will appreciate that the quantity of active MCH receptor antagonist to be administered will vary depending upon the age, sex, and body weight of the subject to be treated, the type of disease, or syndrome to be treated, the particular method and scheduling of administration, and what other MCH receptor antagonist, if any, is co-administered. Dosage amounts for an individual patient may thus be above or below the typical dosage ranges. Generally speaking, the MCH receptor antagonist can be employed in any amount known to be effective at treating, preventing or controlling the disorder or condition being treated. The doses may be single doses or multiple doses per day, with the number of doses taken per day and the time allowed between doses varying depending on the individual needs of the patient. Optimization of treatment, including dosage amount, method and time of administration, is thus best determined by a skilled practitioner through close monitoring of patients on an individual basis. Those skilled in the art will appreciate that dosages may also be determined with guidance from Goodman & Goldman, *The Pharmacological Basis of Therapeutics*, 9th Ed. (1996), App. II, pp. 1707-1711 and from Goodman & Goldman, *The Pharmacological Basis of Therapeutics*, 10th Ed. (2001), App. II, pp. 475-493.

DESCRIPTION OF THE PREFERRED EMBODIMENTS

In one embodiment of the present invention, the MCH receptor antagonist is a compound of Formula I, or a pharmaceutically-acceptable salt, tautomer or prodrug thereof, having the following structure:

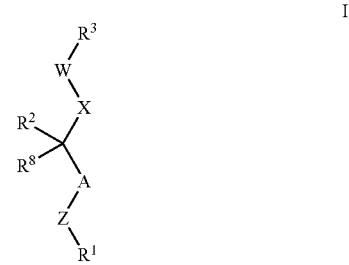

I wherein

A is selected from the group consisting of heteroaryl, —C(=O)—, and —C(=O)NH—;

W is selected from the group consisting of a bond, —C(=O)—, alkyl, alkenyl, aryl, aralkenyl and heterocyclo;

X is selected from the group consisting of XA:

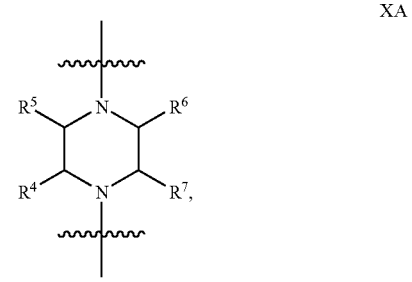

XA

XB:

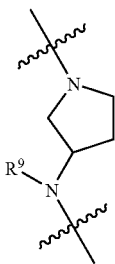

and XC:

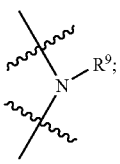

Z is selected from the group consisting of a bond, alkyl, cycloalkyl, aryl, aralkyl, heteroaryl, and heterocyclo;

$R^1$ is selected from the group consisting of alkyl, aryl, aralkyl, alkoxycarbonyl, heterocyclo, aryloxy, heteroaryl, and alkylphosphonate, wherein $R^1$ is optionally substituted by one or more substituents selected from the group consisting of alkyl, hydroxy, carboxyl, halo, cyano and keto;

$R^2$ is selected from the group consisting of hydrogen, alkyl, cycloalkyl, aryl, aralkyl, aroyl, heterocyclo, heteroaryl, and aralkoxy, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of alkoxy, aryloxy, haloalkyl, halo, aryl, aralkenyl, aralkyl, alkyl, haloalkylaryl, haloaryloxy, alkylaryloxy, heteroaryl, cyano, hydroxy, hydroxyalkoxy, alkoxycarbonyl, alkylthio, N-(alkylcarbonyl)amino, and nitro;

$R^3$ is selected from the group consisting of hydrogen, aryl, alkoxy, aralkoxy, heteroaryl and heterocyclocarbonyl, wherein $R^3$ is optionally substituted by one or more substituents selected from the group consisting of halo, aryl, haloaryl, alkoxy, alkyl, carboxyl, aryloxy, keto, and hydroxy;

$R^4$, $R^5$, $R^6$, $R^7$, and $R^9$ are independently selected from the group consisting of hydrogen, alkyl, and halo; and $R^8$ is hydrogen or alkyl, or $R^2$ and $R^8$ together with the atom to which they are both attached form a 5- or 6-membered cycloalkyl or heterocyclo group;

provided that Z is not methyl when X is XB or XC, further provided that W is not pyrrolidyl when X is XC, and further provided that $R^3$ is not aryl- or haloaryl-substituted indolyl.

In another embodiment, the MCH receptor antagonist consists of compounds of Formula I, or a pharmaceutically-acceptable salt, tautomer or prodrug thereof, wherein A is selected from the group consisting of 5- or 6-membered heteroaryl, —C(=O)—, and —C(=O)NH—;

W is selected from the group consisting of a bond, —C(=O)—, lower alkyl, lower alkenyl, aryl, aralkenyl and 3- to 10-membered heterocyclo;

Z is selected from the group consisting of a bond, lower alkyl, lower cycloalkyl, aryl, aralkyl and 3- to 10-membered heterocyclo;

$R^1$ is selected from the group consisting of lower alkyl, aryl, aralkyl, lower alkoxycarbonyl, 3- to 10-membered heterocyclo, aryloxy, 3- to 10-membered heteroaryl, and lower alkylphosphonate, wherein $R^1$ is optionally substituted by one or more substituents selected from the group consisting of lower alkyl, hydroxy, carboxyl, halo, cyano and keto;

$R^2$ is selected from the group consisting of hydrogen, lower alkyl, lower cycloalkyl, aryl, aralkyl, aroyl, 3- to 10-membered heterocyclo, 3- to 10-membered heteroaryl, and aralkoxy, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of lower alkoxy, aryloxy, lower haloalkyl, halo, aryl, aralkenyl, aralkyl, lower alkyl, haloalkylaryl, haloaryloxy, alkylaryloxy, 5- or 6-membered heteroaryl, cyano, hydroxy, lower hydroxyalkoxy, lower alkoxycarbonyl, lower alkylthio, N-(lower alkylcarbonyl)amino, and nitro;

$R^3$ is selected from the group consisting of hydrogen, aryl, lower alkoxy, aralkoxy, furyl, thienyl, pyrrolyl, pyrazolyl, imidazolyl, triazolyl, isoxazolyl, oxazolyl, indolyl, benzofuryl, thiazolyl, isothiazolyl, oxadiazolyl, oxatriazolyl, dioxazole, tetrazolyl, benzodioxolyl, and (3- to 10-membered heterocyclo)carbonyl, wherein $R^3$ is optionally substituted by one or more substituents selected from the group consisting of halo, aryl, haloaryl, lower alkoxy, lower alkyl, carboxyl, aryloxy, keto, and hydroxy;

$R^4$, $R^5$, $R^6$, $R^7$, and $R^9$ are independently selected from the group consisting of hydrogen, lower alkyl, and halo; and $R^8$ is hydrogen or lower alkyl, or $R^2$ and $R^8$ together with the atom to which they are both attached form a 5- or 6-membered cycloalkyl or heterocyclo group.

In another embodiment, the MCH receptor antagonist consists of compounds of Formula I, or a pharmaceutically-acceptable salt, tautomer or prodrug thereof, wherein A is selected from the group consisting of furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, —C(=O)—, and —C(=O)NH—;

W is selected from the group consisting of a bond, —C(=O)—, methyl, ethyl, propyl, butyl, pentyl, hexyl, ethenyl, propenyl, allyl, butenyl, pentenyl, phenyl, naphthyl, tetrahydronaphthyl, biphenyl, phenylethenyl, phenylpropenyl, phenylallyl, phenylbutenyl, phenylpentenyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl;

Z is selected from the group consisting of a bond, methyl, ethyl, propyl, butyl, pentyl, hexyl, cyclopropyl, cyclobutyl, cyclopentyl, cyclohexyl, phenyl, naphthyl, tetrahydronaphthyl, biphenyl, benzyl, diphenylmethyl, triphenylmethyl, phenylethyl, diphenylethyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl;

$R^1$ is selected from the group consisting of methyl, ethyl, propyl, butyl, pentyl, hexyl, phenyl, naphthyl, tetrahydronaphthyl, biphenyl, benzyl, diphenylmethyl, triphenylmethyl, phenylethyl, diphenylethyl, methoxycarbonyl, ethoxycarbonyl, propoxycarbonyl, butoxycarbonyl, pentyloxycarbonyl, hexyloxycarbonyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, tetrahydrofuryl, phenoxy, naphthyloxy, tetrahydronaphthyloxy, biphenylyloxy, furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, monomethylphosphonate, dimethylphosphonate, monoethylphosphonate, diethylphosphonate, monopropylphosphonate, and dipropylphosphonate, wherein $R^1$ is optionally substituted by one or more substituents selected from the group consisting of methyl, ethyl, propyl, butyl, pentyl, hexyl, hydroxy, carboxyl, fluoro, chloro, bromo, iodo, cyano and keto;

$R^2$ is selected from the group consisting of hydrogen, methyl, ethyl, propyl, butyl, pentyl, hexyl, cyclopropyl, cyclobutyl, cyclopentyl, cyclohexyl, phenyl, naphthyl, tetrahydronaphthyl, biphenyl, benzyl, diphenylmethyl, triphenylmethyl, phenylethyl, diphenylethyl, phenylcarbonyl, naphthylcarbonyl, tetrahydronaphthylcarbonyl, biphenylcarbonyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, tetrahydrofuryl, furyl, thienyl, pyrrolyl, pyrazolyl, imidazolyl, triazolyl, isoxazolyl, oxazolyl, indolyl, benzofuryl, thiazolyl, isothiazolyl, oxadiazolyl, oxatriazolyl, dioxazole, tetrazolyl, benzodioxolyl, phenylmethoxy, phenylethoxy, phenylpropoxy, phenylbutoxy, phenylpentyloxy, and phenylhexyloxy, or $R^2$ and $R^8$ together with the atom to which they are both attached form a 5- or 6-membered cycloalkyl or heterocyclo group selected from the group consisting of cyclopentyl, cyclohexyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl, wherein $R^2$ or the cycloalkyl or heterocyclo group formed with $R^8$ is optionally substituted by one or more substituents selected from the group consisting of methoxy, ethoxy, propoxy, butoxy, pentyloxy, hexyloxy, phenoxy, naphthyloxy, tetrahydronaphthyloxy, biphenylyloxy, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl, dichloropropyl, fluoro, chloro, bromo, iodo, phenyl, naphthyl, tetrahydronaphthyl, biphenyl, phenylethenyl, phenylpropenyl, phenylallyl, phenylbutenyl, phenylpentenyl, benzyl, diphenylmethyl, triphenylmethyl, phenylethyl, diphenylethyl, methyl, ethyl, propyl, butyl, pentyl, hexyl, fluoromethylphenyl, difluoromethylphenyl, trifluoromethylphenyl, chloromethylphenyl, dichloromethylphenyl, trichloromethylphenyl, trichloromethylphenyl, bis(fluoromethyl)phenyl, bis(difluoromethyl)phenyl, bis(trifluoromethyl)phenyl, bis(chloromethyl)phenyl, bis(dichloromethyl)phenyl, bis(trichloromethyl)phenyl, bis(trichloromethyl)phenyl, chlorophenoxy, bromophenoxy, fluorophenoxy, dichlorophenoxy, dibromophenoxy, difluorophenoxy, chlorobromophenoxy, chlorofluorophenoxy, bromofluorophenoxy, methylphenoxy, ethylphenoxy, propylphenoxy, dimethylphenoxy, diethylphenoxy, dipropylphenoxy, methylnaphthyloxy, ethylnaphthyloxy, propylnaphthyloxy, dimethylnaphthyloxy, diethylnaphthyloxy, dipropylnaphthyloxy, methylbiphenylyloxy, ethylbiphenylyloxy, propylbiphenylyloxy, dimethylbiphenylyloxy, diethylbiphenylyloxy, dipropylbiphenylyloxy, furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, cyano, hydroxy, hydroxymethoxy, hydroxyethoxy, hydroxypropoxy, hydroxybutoxy, hydroxypentyloxy, hydroxyhexyloxy, methoxycarbonyl, ethoxycarbonyl, propoxycarbonyl, butoxycarbonyl, pentyloxycarbonyl, hexyloxycarbonyl, methylthio, ethylthio, propylthio, butylthio, pentylthio, hexylthio, N-(methylcarbonyl)amino, N-(ethylcarbonyl)amino, N-(propylcarbonyl)amino, N-(butylcarbonyl)amino, N-(pentylcarbonyl)amino, N-(hexylcarbonyl)amino, and nitro;

$R^3$ is selected from the group consisting of hydrogen, phenyl, naphthyl, tetrahydronaphthyl, biphenyl, methoxy, ethoxy, propoxy, butoxy, pentyloxy, hexyloxy, phenylmethoxy, phenylethoxy, phenylpropoxy, phenylbutoxy, phenylpentyloxy, phenylhexyloxy, furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, pyrrolidinylcarbonyl, imidazolidinylcarbonyl, piperidinylcarbonyl, piperazinylcarbonyl, morpholinylcarbonyl, thiazolidinylcarbonyl, dihydrothienylcarbonyl, dihydropyranylcarbonyl, dihydrofurylcarbonyl, dihydrothiazolylcarbonyl, and tetrahydrofurylcarbonyl, wherein $R^3$ is optionally substituted by one or more substituents selected from the group consisting of fluoro, chloro, bromo, iodo, phenyl, naphthyl, tetrahydronaphthyl, biphenyl, chlorophenyl, bromophenyl, fluorophenyl, dichlorophenyl, dibromophenyl, difluorophenyl, chlorobromophenyl, chlorofluorophenyl, bromofluorophenyl, methoxy, ethoxy, propoxy, butoxy, pentyloxy, hexyloxy, methyl, ethyl, propyl, butyl, pentyl, hexyl, carboxyl, phenoxy, naphthyloxy, tetrahydronaphthyloxy, biphenylyloxy, keto, and hydroxy;

$R^4$, $R^5$, $R^6$, $R^7$, and $R^9$ are independently selected from the group consisting of hydrogen, methyl, ethyl, propyl, butyl, pentyl, hexyl, fluoro, chloro, bromo, and iodo; and $R^8$ is selected from the group consisting of hydrogen, methyl, ethyl, propyl, butyl, pentyl, and hexyl, or $R^2$ and $R^8$ together with the atom to which they are both attached form a 5- or 6-membered cycloalkyl or heterocyclo group selected from the group consisting of cyclopropyl, cyclobutyl, cyclopentyl, cyclohexyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl.

In another embodiment, the MCH receptor antagonist consists of compounds of Formula I, or a pharmaceutically-acceptable salt, tautomer or prodrug thereof, wherein A is selected from the group consisting of furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, —C(=O)—, and —C(=O)NH—;

W is selected from the group consisting of a bond, —C(=O)—, alkyl, alkenyl, aryl, aralkenyl and heterocyclo;

X is selected from the group consisting of XA:

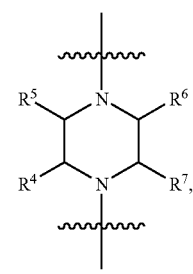

XA

XB:

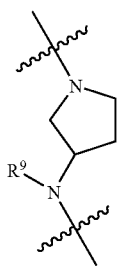

and XC:

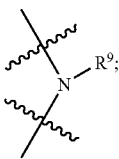

Z is selected from the group consisting of a bond, alkyl, cycloalkyl, aryl, aralkyl, heteroaryl, and heterocyclo;

$R^1$ is selected from the group consisting of alkyl, aryl, aralkyl, alkoxycarbonyl, heterocyclo, aryloxy, heteroaryl, and alkylphosphonate, wherein $R^1$ is optionally substituted by one or more substituents selected from the group consisting of alkyl, hydroxy, carboxyl, halo, cyano and keto;

$R^2$ is selected from the group consisting of hydrogen, alkyl, cycloalkyl, aryl, aralkyl, aroyl, heterocyclo, heteroaryl, and aralkoxy, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of alkoxy, aryloxy, haloalkyl, halo, aryl, aralkenyl, aralkyl, alkyl, haloalkylaryl, haloaryloxy, alkylaryloxy, heteroaryl, cyano, hydroxy, hydroxyalkoxy, alkoxycarbonyl, alkylthio, N-(alkylcarbonyl)amino, and nitro;

$R^3$ is selected from the group consisting of hydrogen, aryl, alkoxy, aralkoxy, heteroaryl and heterocyclocarbonyl, wherein $R^3$ is optionally substituted by one or more substituents selected from the group consisting of halo, aryl, haloaryl, alkoxy, alkyl, carboxyl, aryloxy, keto, and hydroxy;

$R^4$, $R^5$, $R^6$, $R^7$, and $R^9$ are independently selected from the group consisting of hydrogen, alkyl, and halo; and $R^8$ is hydrogen or alkyl, or $R^2$ and $R^8$ together with the atom to which they are both attached form a 5- or 6-membered cycloalkyl or heterocyclo group;

provided that Z is not methyl when X is XB or XC, further provided that W is not pyrrolidyl when X is XC, and further provided that $R^3$ is not aryl- or haloaryl-substituted indolyl;

or a pharmaceutically-acceptable salt, tautomer or prodrug thereof.

In another embodiment, the MCH receptor antagonist consists of compounds of Formula I, or a pharmaceutically-acceptable salt, tautomer or prodrug thereof, wherein A is selected from the group consisting of furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, —C(=O)—, and —C(=O)NH—;

W is selected from the group consisting of a bond, —C(=O)—, lower alkyl, lower alkenyl, aryl, aralkenyl and 3- to 10-membered heterocyclo;

Z is selected from the group consisting of a bond, lower alkyl, lower cycloalkyl, aryl, aralkyl and 3- to 10-membered heterocyclo;

$R^1$ is selected from the group consisting of lower alkyl, aryl, aralkyl, lower alkoxycarbonyl, 3- to 10-membered heterocyclo, aryloxy, 3- to 10-membered heteroaryl, and lower alkylphosphonate, wherein $R^1$ is optionally substituted by one or more substituents selected from the group consisting of lower alkyl, hydroxy, carboxyl, halo, cyano and keto;

$R^2$ is selected from the group consisting of hydrogen, lower alkyl, lower cycloalkyl, aryl, aralkyl, aroyl, 3- to 10-membered heterocyclo, 3- to 10-membered heteroaryl, and aralkoxy, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of lower alkoxy, aryloxy, lower haloalkyl, halo, aryl, aralkenyl, aralkyl, lower alkyl, haloalkylaryl, haloaryloxy, alkylaryloxy, 5- or 6-membered heteroaryl, cyano, hydroxy, lower hydroxyalkoxy, lower alkoxycarbonyl, lower alkylthio, N-(lower alkylcarbonyl)amino, and nitro;

$R^3$ is selected from the group consisting of hydrogen, aryl, lower alkoxy, aralkoxy, furyl, thienyl, pyrrolyl, pyrazolyl, imidazolyl, triazolyl, isoxazolyl, oxazolyl, indolyl, benzofuryl, thiazolyl, isothiazolyl, oxadiazolyl, oxatriazolyl, dioxazole, tetrazolyl, benzodioxolyl, and (3- to 10-membered heterocyclo)carbonyl, wherein $R^3$ is optionally substituted by one or more substituents selected from the group consisting of halo, aryl, haloaryl, lower alkoxy, lower alkyl, carboxyl, aryloxy, keto, and hydroxy;

$R^4$, $R^5$, $R^6$, $R^7$, and $R^9$ are independently selected from the group consisting of hydrogen, lower alkyl, and halo; and $R^8$ is hydrogen or lower alkyl, or $R^2$ and $R^8$ together with the atom to which they are both attached form a 5- or 6-membered cycloalkyl or heterocyclo group.

In another embodiment, the MCH receptor antagonist is selected from a subclass of compounds of Formula I represented by Formula II:

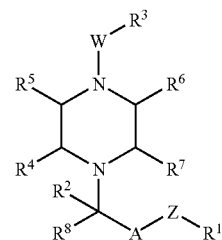

II wherein

A is selected from the group consisting of furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, —C(=O)—, and —C(=O)NH—;

W is selected from the group consisting of a bond, —C(=O)—, alkyl, alkenyl, aryl, aralkenyl and heterocyclo;

Z is selected from the group consisting of a bond, alkyl, cycloalkyl, aryl, aralkyl, heteroaryl, and heterocyclo;

$R^1$ is selected from the group consisting of alkyl, aryl, aralkyl, alkoxycarbonyl, heterocyclo, aryloxy, heteroaryl, and alkylphosphonate, wherein $R^1$ is optionally substituted by one or more substituents selected from the group consisting of alkyl, hydroxy, carboxyl, halo, cyano and keto;

$R^2$ is selected from the group consisting of hydrogen, alkyl, cycloalkyl, aryl, aralkyl, aroyl, heterocyclo, heteroaryl, and aralkoxy, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of alkoxy, aryloxy, haloalkyl, halo, aryl, aralkenyl, aralkyl, alkyl, haloalkylaryl, haloaryloxy, alkylaryloxy, heteroaryl, cyano, hydroxy, hydroxyalkoxy, alkoxycarbonyl, alkylthio, N-(alkylcarbonyl)amino, and nitro;

$R^3$ is selected from the group consisting of hydrogen, aryl, alkoxy, aralkoxy, heteroaryl and heterocyclocarbonyl, wherein $R^3$ is optionally substituted by one or more substituents selected from the group consisting of halo, aryl, haloaryl, alkoxy, alkyl, carboxyl, aryloxy, keto, and hydroxy;

$R^4$, $R^5$, $R^6$, and $R^7$ are independently selected from the group consisting of hydrogen, alkyl, and halo; and $R^8$ is hydrogen or alkyl, or $R^2$ and $R^8$ together with the atom to which they are both attached form a 5- or 6-membered cycloalkyl or heterocyclo group;

provided that $R^3$ is not aryl- or haloaryl-substituted indolyl;

or a pharmaceutically-acceptable salt, tautomer or prodrug thereof.

In another embodiment, the MCH receptor antagonist consists of compounds of Formula II, or a pharmaceutically-acceptable salt, tautomer or prodrug thereof, wherein A is selected from the group consisting of 5- or 6-membered heteroaryl, —C(=O)—, and —C(=O)NH—;

W is selected from the group consisting of a bond, —C(=O)—, lower alkyl, lower alkenyl, aryl, aralkenyl and 3- to 10-membered heterocyclo;

Z is selected from the group consisting of a bond, lower alkyl, lower cycloalkyl, aryl, aralkyl and 3- to 10-membered heterocyclo;

$R^1$ is selected from the group consisting of lower alkyl, aryl, aralkyl, lower alkoxycarbonyl, 3- to 10-membered heterocyclo, aryloxy, 3- to 10-membered heteroaryl, and lower alkylphosphonate, wherein $R^1$ is optionally substituted by one or more substituents selected from the group consisting of lower alkyl, hydroxy, carboxyl, halo, cyano and keto;

$R^2$ is selected from the group consisting of hydrogen, lower alkyl, lower cycloalkyl, aryl, aralkyl, aroyl, 3- to 10-membered heterocyclo, 3- to 10-membered heteroaryl, and aralkoxy, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of lower alkoxy, aryloxy, lower haloalkyl, halo, aryl, aralkenyl, aralkyl, lower alkyl, haloalkylaryl, haloaryloxy, alkylaryloxy, 5- or 6-membered heteroaryl, cyano, hydroxy, lower hydroxyalkoxy, lower alkoxycarbonyl, lower alkylthio, N-(lower alkylcarbonyl)amino, and nitro;

$R^3$ is selected from the group consisting of hydrogen, aryl, lower alkoxy, aralkoxy, furyl, thienyl, pyrrolyl, pyrazolyl, imidazolyl, triazolyl, isoxazolyl, oxazolyl, indolyl, benzofuryl, thiazolyl, isothiazolyl, oxadiazolyl, oxatriazolyl, dioxazole, tetrazolyl, benzodioxolyl, and (3- to 10-membered heterocyclo)carbonyl, wherein $R^3$ is optionally substituted by one or more substituents selected from the group consisting of halo, aryl, haloaryl, lower alkoxy, lower alkyl, carboxyl, aryloxy, keto, and hydroxy;

$R^4$, $R^5$, $R^6$, and $R^7$ are independently selected from the group consisting of hydrogen, lower alkyl, and halo; and $R^8$ is hydrogen or lower alkyl, or $R^2$ and $R^8$ together with the atom to which they are both attached form a 5- or 6-membered cycloalkyl or heterocyclo group.

In another embodiment, the MCH receptor antagonist consists of compounds of Formula II, or a pharmaceutically-acceptable salt, tautomer or prodrug thereof, wherein A is selected from the group consisting of furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, —C(=O)—, and —C(=O)NH—;

W is selected from the group consisting of a bond, —C(=O)—, methyl, ethyl, propyl, butyl, pentyl, hexyl, ethenyl, propenyl, allyl, butenyl, pentenyl, phenyl, naphthyl, tetrahydronaphthyl, biphenyl, phenylethenyl, phenylpropenyl, phenylallyl, phenylbutenyl, phenylpentenyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl;

Z is selected from the group consisting of a bond, methyl, ethyl, propyl, butyl, pentyl, hexyl, cyclopropyl, cyclobutyl, cyclopentyl, cyclohexyl, phenyl, naphthyl, tetrahydronaphthyl, biphenyl, benzyl, diphenylmethyl, triphenylmethyl, phenylethyl, diphenylethyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl;

$R^1$ is selected from the group consisting of methyl, ethyl, propyl, butyl, pentyl, hexyl, phenyl, naphthyl, tetrahydronaphthyl, biphenyl, benzyl, diphenylmethyl, triphenylmethyl, phenylethyl, diphenylethyl, methoxycarbonyl, ethoxycarbonyl, propoxycarbonyl, butoxycarbonyl, pentyloxycarbonyl, hexyloxycarbonyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, tetrahydrofuryl, phenoxy, naphthyloxy, tetrahydronaphthyloxy, biphenylyloxy, furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, monomethylphosphonate, dimethylphosphonate, monoethylphosphonate, diethylphosphonate, monopropylphosphonate, and dipropylphosphonate, wherein $R^1$ is optionally substituted by one or more substituents selected from the group consisting of methyl, ethyl, propyl, butyl, pentyl, hexyl, hydroxy, carboxyl, fluoro, chloro, bromo, iodo, cyano and keto;

$R^2$ is selected from the group consisting of hydrogen, methyl, ethyl, propyl, butyl, pentyl, hexyl, cyclopropyl, cyclobutyl, cyclopentyl, cyclohexyl, phenyl, naphthyl, tetrahydronaphthyl, biphenyl, benzyl, diphenylmethyl, triphenylmethyl, phenylethyl, diphenylethyl, phenylcarbonyl, naphthylcarbonyl, tetrahydronaphthylcarbonyl, biphenylcarbonyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, tetrahydrofuryl, furyl, thienyl, pyrrolyl, pyrazolyl, imidazolyl, triazolyl, isoxazolyl, oxazolyl, indolyl, benzofuryl, thiazolyl, isothiazolyl, oxadiazolyl, oxatriazolyl, dioxazole, tetrazolyl, benzodioxolyl, phenylmethoxy, phenylethoxy, phenylpropoxy, phenylbutoxy, phenylpentyloxy, and phenylhexyloxy, or $R^2$ and $R^8$ together with the atom to which they are both attached form a 5- or 6-membered cycloalkyl or heterocyclo group selected from the group consisting of cyclopentyl, cyclohexyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl, wherein $R^2$ or the cycloalkyl or heterocyclo group formed with $R^8$ is optionally substituted by one or more substituents selected from the group consisting of methoxy, ethoxy, propoxy, butoxy, pentyloxy, hexyloxy, phenoxy, naphthyloxy, tetrahydronaphthyloxy, biphenylyloxy, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl, dichloropropyl, fluoro, chloro, bromo, iodo, phenyl, naphthyl, tetrahydronaphthyl, biphenyl, phenylethenyl, phenylpropenyl, phenylallyl, phenylbutenyl, phenylpentenyl, benzyl, diphenylmethyl, triphenylmethyl, phenylethyl, diphenylethyl, methyl, ethyl, propyl, butyl, pentyl, hexyl, fluoromethylphenyl, difluoromethylphenyl, trifluoromethylphenyl, chloromethylphenyl, dichloromethylphenyl, trichloromethylphenyl, trichloromethylphenyl, bis(fluoromethyl)phenyl, bis(difluoromethyl)phenyl, bis(trifluoromethyl)phenyl, bis(chloromethyl)phenyl, bis(dichloromethyl)phenyl, bis(trichloromethyl)phenyl, bis(trichloromethyl)phenyl, chlorophenoxy, bromophenoxy, fluorophenoxy, dichlorophenoxy, dibromophenoxy, difluorophenoxy, chlorobromophenoxy, chlorofluorophenoxy, bromofluorophenoxy, methylphenoxy, ethylphenoxy, propylphenoxy, dimethylphenoxy, diethylphenoxy, dipropylphenoxy, methylnaphthyloxy, ethylnaphthyloxy, propylnaphthyloxy, dimethylnaphthyloxy, diethylnaphthyloxy, dipropylnaphthyloxy, methylbiphenylyloxy, ethylbiphenylyloxy, propylbiphenylyloxy, dimethylbiphenylyloxy, diethylbiphenylyloxy, dipropylbiphenylyloxy, furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, cyano, hydroxy, hydroxymethoxy, hydroxyethoxy, hydroxypropoxy, hydroxybutoxy, hydroxypentyloxy, hydroxyhexyloxy, methoxycarbonyl, ethoxycarbonyl, propoxycarbonyl, butoxycarbonyl, pentyloxycarbonyl, hexyloxycarbonyl, methylthio, ethylthio, propylthio, butylthio, pentylthio, hexylthio, N-(methylcarbonyl)amino, N-(ethylcarbonyl)amino, N-(propylcarbonyl)amino, N-(butylcarbonyl)amino, N-(pentylcarbonyl)amino, N-(hexylcarbonyl)amino, and nitro;

$R^3$ is selected from the group consisting of hydrogen, phenyl, naphthyl, tetrahydronaphthyl, biphenyl, methoxy, ethoxy, propoxy, butoxy, pentyloxy, hexyloxy, phenylmethoxy, phenylethoxy, phenylpropoxy, phenylbutoxy, phenylpentyloxy, phenylhexyloxy, furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, pyrrolidinylcarbonyl, imidazolidinylcarbonyl, piperidinylcarbonyl, piperazinylcarbonyl, morpholinylcarbonyl, thiazolidinylcarbonyl, dihydrothienylcarbonyl, dihydropyranylcarbonyl, dihydrofurylcarbonyl, dihydrothiazolylcarbonyl, and tetrahydrofurylcarbonyl, wherein $R^3$ is optionally substituted by one or more substituents selected from the group consisting of fluoro, chloro, bromo, iodo, phenyl, naphthyl, tetrahydronaphthyl, biphenyl, chlorophenyl, bromophenyl, fluorophenyl, dichlorophenyl, dibromophenyl, difluorophenyl, chlorobromophenyl, chlorofluorophenyl, bromofluorophenyl, methoxy, ethoxy, propoxy, butoxy, pentyloxy, hexyloxy, methyl, ethyl, propyl, butyl, pentyl, hexyl, carboxyl, phenoxy, naphthyloxy, tetrahydronaphthyloxy, biphenylyloxy, keto, and hydroxy;

$R^4$, $R^5$, $R^6$, and $R^7$ are independently selected from the group consisting of hydrogen, methyl, ethyl, propyl, butyl, pentyl, hexyl, fluoro, chloro, bromo, and iodo; and $R^8$ is selected from the group consisting of hydrogen, methyl, ethyl, propyl, butyl, pentyl, and hexyl, or $R^2$ and $R^8$ together with the atom to which they are both attached form a 5- or 6-membered cycloalkyl or heterocyclo group selected from the group consisting of cyclopropyl, cyclobutyl, cyclopentyl, cyclohexyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl.

In another embodiment, the MCH receptor antagonist is selected from a subclass of compounds of Formula I represented by Formula III:

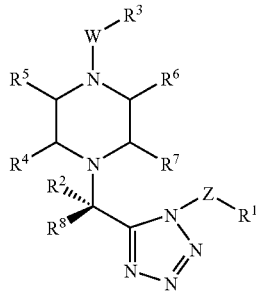

III wherein

W is selected from the group consisting of a bond, —C(=O)—, alkyl, alkenyl, aryl, aralkenyl and heterocyclo;

Z is selected from the group consisting of a bond, alkyl, cycloalkyl, aryl, aralkyl, heteroaryl, and heterocyclo;

$R^1$ is selected from the group consisting of alkyl, aryl, aralkyl, alkoxycarbonyl, heterocyclo, aryloxy, heteroaryl, and alkylphosphonate, wherein $R^1$ is optionally substituted by one or more substituents selected from the group consisting of alkyl, hydroxy, carboxyl, halo, cyano and keto;

$R^2$ is selected from the group consisting of hydrogen, alkyl, cycloalkyl, aryl, aralkyl, aroyl, heterocyclo, heteroaryl, and aralkoxy, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of alkoxy, aryloxy, haloalkyl, halo, aryl, aralkenyl, aralkyl, alkyl, haloalkylaryl, haloaryloxy, alkylaryloxy, heteroaryl, cyano, hydroxy, hydroxyalkoxy, alkoxycarbonyl, alkylthio, N-(alkylcarbonyl)amino, and nitro;

$R^3$ is selected from the group consisting of hydrogen, aryl, alkoxy, aralkoxy, heteroaryl and heterocyclocarbonyl, wherein $R^3$ is optionally substituted by one or more substituents selected from the group consisting of halo, aryl, haloaryl, alkoxy, alkyl, carboxyl, aryloxy, keto, and hydroxy;

$R^4$, $R^5$, $R^6$, and $R^7$ are independently selected from the group consisting of hydrogen, alkyl, and halo; and $R^8$ is hydrogen or alkyl, or $R^2$ and $R^8$ together with the atom to which they are both attached form a 5- or 6-membered cycloalkyl or heterocyclo group;

provided that $R^3$ is not aryl- or haloaryl-substituted indolyl;

or a pharmaceutically-acceptable salt, tautomer or prodrug thereof.

In another embodiment, the MCH receptor antagonist consists of compounds of Formula III, or a pharmaceutically-acceptable salt, tautomer or prodrug thereof, wherein each of $R^4$, $R^5$, $R^6$ and $R^7$ are hydrogen.

In another embodiment, the MCH receptor antagonist consists of compounds of Formula III, or a pharmaceutically-acceptable salt, tautomer or prodrug thereof, wherein each of $R^4$, $R^5$, $R^6$ and $R^7$ are hydrogen, and wherein W is selected from the group consisting of a bond, —C(=O)—, lower alkyl, lower alkenyl, aryl, aralkenyl and 3- to 10-membered heterocyclo;

Z is selected from the group consisting of a bond, lower alkyl, lower cycloalkyl, aryl, aralkyl and 3- to 10-membered heterocyclo;

$R^1$ is selected from the group consisting of lower alkyl, aryl, aralkyl, lower alkoxycarbonyl, 3- to 10-membered heterocyclo, aryloxy, 3- to 10-membered heteroaryl, and lower alkylphosphonate, wherein $R^1$ is optionally substituted by one or more substituents selected from the group consisting of lower alkyl, hydroxy, carboxyl, halo, cyano and keto;

$R^2$ is selected from the group consisting of hydrogen, lower alkyl, lower cycloalkyl, aryl, aralkyl, aroyl, 3- to 10-membered heterocyclo, 3- to 10-membered heteroaryl, and aralkoxy, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of lower alkoxy, aryloxy, lower haloalkyl, halo, aryl, aralkenyl, aralkyl, lower alkyl, haloalkylaryl, haloaryloxy, alkylaryloxy, 5- or 6-membered heteroaryl, cyano, hydroxy, lower hydroxyalkoxy, lower alkoxycarbonyl, lower alkylthio, N-(lower alkylcarbonyl)amino, and nitro;

$R^3$ is selected from the group consisting of hydrogen, aryl, lower alkoxy, aralkoxy, furyl, thienyl, pyrrolyl, pyrazolyl, imidazolyl, triazolyl, isoxazolyl, oxazolyl, indolyl, benzofuryl, thiazolyl, isothiazolyl, oxadiazolyl, oxatriazolyl, dioxazole, tetrazolyl, benzodioxolyl, and (3- to 10-membered heterocyclo)carbonyl, wherein $R^3$ is optionally substituted by one or more substituents selected from the group consisting of halo, aryl, haloaryl, lower alkoxy, lower alkyl, carboxyl, aryloxy, keto, and hydroxy;

$R^8$ is hydrogen or lower alkyl, or $R^2$ and $R^8$ together with the atom to which they are both attached form a 5- or 6-membered cycloalkyl or heterocyclo group.

In another embodiment, the MCH receptor antagonist consists of compounds of Formula III, or a pharmaceutically-acceptable salt, tautomer or prodrug thereof, wherein each of $R^4$, $R^5$, $R^6$ and $R^7$ are hydrogen, and wherein W is selected from the group consisting of a bond, —C(=O)—, methyl, ethyl, propyl, butyl, pentyl, hexyl, ethenyl, propenyl, allyl, butenyl, pentenyl, phenyl, naphthyl, tetrahydronaphthyl, biphenyl, phenylethenyl, phenylpropenyl, phenylallyl, phenylbutenyl, phenylpentenyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl;

Z is selected from the group consisting of a bond, methyl, ethyl, propyl, butyl, pentyl, hexyl, cyclopropyl, cyclobutyl, cyclopentyl, cyclohexyl, phenyl, naphthyl, tetrahydronaphthyl, biphenyl, benzyl, diphenylmethyl, triphenylmethyl, phenylethyl, diphenylethyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl;

$R^1$ is selected from the group consisting of methyl, ethyl, propyl, butyl, pentyl, hexyl, phenyl, naphthyl, tetrahydronaphthyl, biphenyl, benzyl, diphenylmethyl, triphenylmethyl, phenylethyl, diphenylethyl, methoxycarbonyl, ethoxycarbonyl, propoxycarbonyl, butoxycarbonyl, pentyloxycarbonyl, hexyloxycarbonyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, tetrahydrofuryl, phenoxy, naphthyloxy, tetrahydronaphthyloxy, biphenylyloxy, furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, monomethylphosphonate, dimethylphosphonate, monoethylphosphonate, diethylphosphonate, monopropylphosphonate, and dipropylphosphonate, wherein $R^1$ is optionally substituted by one or more substituents selected from the group consisting of methyl, ethyl, propyl, butyl, pentyl, hexyl, hydroxy, carboxyl, fluoro, chloro, bromo, iodo, cyano and keto;

$R^2$ is selected from the group consisting of hydrogen, methyl, ethyl, propyl, butyl, pentyl, hexyl, cyclopropyl, cyclobutyl, cyclopentyl, cyclohexyl, phenyl, naphthyl, tetrahydronaphthyl, biphenyl, benzyl, diphenylmethyl, triphenylmethyl, phenylethyl, diphenylethyl, phenylcarbonyl, naphthylcarbonyl, tetrahydronaphthylcarbonyl, biphenylcarbonyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, tetrahydrofuryl, furyl, thienyl, pyrrolyl, pyrazolyl, imidazolyl, triazolyl, isoxazolyl, oxazolyl, indolyl, benzofuryl, thiazolyl, isothiazolyl, oxadiazolyl, oxatriazolyl, dioxazole, tetrazolyl, benzodioxolyl, phenylmethoxy, phenylethoxy, phenylpropoxy, phenylbutoxy, phenylpentyloxy, and phenylhexyloxy, or $R^2$ and $R^8$ together with the atom to which they are both attached form a 5- or 6-membered cycloalkyl or heterocyclo group selected from the group consisting of cyclopentyl, cyclohexyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl, wherein $R^2$ or the cycloalkyl or heterocyclo group formed with $R^8$ is optionally substituted by one or more substituents selected from the group consisting of methoxy, ethoxy, propoxy, butoxy, pentyloxy, hexyloxy, phenoxy, naphthyloxy, tetrahydronaphthyloxy, biphenylyloxy, fluoromethyl, difluoromethyl, trifluoromethyl, chloromethyl, dichloromethyl, trichloromethyl, trichloromethyl, pentafluoroethyl, heptafluoropropyl, difluorochloromethyl, dichlorofluoromethyl, difluoroethyl, difluoropropyl, dichloroethyl, dichloropropyl, fluoro, chloro, bromo, iodo, phenyl, naphthyl, tetrahydronaphthyl, biphenyl, phenylethenyl, phenylpropenyl, phenylallyl, phenylbutenyl, phenylpentenyl, benzyl, diphenylmethyl, triphenylmethyl, phenylethyl, diphenylethyl, methyl, ethyl, propyl, butyl, pentyl, hexyl, fluoromethylphenyl, difluoromethylphenyl, trifluoromethylphenyl, chloromethylphenyl, dichloromethylphenyl, trichloromethylphenyl, trichloromethylphenyl, bis(fluoromethyl)phenyl, bis(difluoromethyl)phenyl, bis(trifluoromethyl)phenyl, bis(chloromethyl)phenyl, bis(dichloromethyl)phenyl, bis(trichloromethyl)phenyl, bis(trichloromethyl)phenyl, chlorophenoxy, bromophenoxy, fluorophenoxy, dichlorophenoxy, dibromophenoxy, difluorophenoxy, chlorobromophenoxy, chlorofluorophenoxy, bromofluorophenoxy, methylphenoxy, ethylphenoxy, propylphenoxy, dimethylphenoxy, diethylphenoxy, dipropylphenoxy, methylnaphthyloxy, ethylnaphthyloxy, propylnaphthyloxy, dimethylnaphthyloxy, diethylnaphthyloxy, dipropylnaphthyloxy, methylbiphenylyloxy, ethylbiphenylyloxy, propylbiphenylyloxy, dimethylbiphenylyloxy, diethylbiphenylyloxy, dipropylbiphenylyloxy, furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, cyano, hydroxy, hydroxymethoxy, hydroxyethoxy, hydroxypropoxy, hydroxybutoxy, hydroxypentyloxy, hydroxyhexyloxy, methoxycarbonyl, ethoxycarbonyl, propoxycarbonyl, butoxycarbonyl, pentyloxycarbonyl, hexyloxycarbonyl, methylthio, ethylthio, propylthio, butylthio, pentylthio, hexylthio, N-(methylcarbonyl)amino, N-(ethylcarbonyl)amino, N-(propylcarbonyl)amino, N-(butylcarbonyl)amino, N-(pentylcarbonyl)amino, N-(hexylcarbonyl)amino, and nitro;

$R^3$ is selected from the group consisting of hydrogen, phenyl, naphthyl, tetrahydronaphthyl, biphenyl, methoxy, ethoxy, propoxy, butoxy, pentyloxy, hexyloxy, phenylmethoxy, phenylethoxy, phenylpropoxy, phenylbutoxy, phenylpentyloxy, phenylhexyloxy, furyl, thienyl, pyrrolyl, pyrazolyl, imidazolyl, triazolyl, isoxazolyl, oxazolyl, indolyl, thiazolyl, isothiazolyl, oxadiazolyl, oxatriazolyl, dioxazole, tetrazolyl, benzodioxolyl, pyrrolidinylcarbonyl, imidazolidinylcarbonyl, piperidinylcarbonyl, piperazinylcarbonyl, morpholinylcarbonyl, thiazolidinylcarbonyl, dihydrothienylcarbonyl, dihydropyranylcarbonyl, dihydrofurylcarbonyl, dihydrothiazolylcarbonyl, and tetrahydrofurylcarbonyl, wherein $R^3$ is optionally substituted by one or more substituents selected from the group consisting of fluoro, chloro, bromo, iodo, phenyl, naphthyl, tetrahydronaphthyl, biphenyl, chlorophenyl, bromophenyl, fluorophenyl, dichlorophenyl, dibromophenyl, difluorophenyl, chlorobromophenyl, chlorofluorophenyl, bromofluorophenyl, methoxy, ethoxy, propoxy, butoxy, pentyloxy, hexyloxy, carboxyl, phenoxy, naphthyloxy, tetrahydronaphthyloxy, biphenylyloxy, keto, and hydroxy;

$R^8$ is selected from the group consisting of hydrogen, methyl, ethyl, propyl, butyl, pentyl, and hexyl, or $R^2$ and $R^8$ together with the atom to which they are both attached form a 5- or 6-membered cycloalkyl or heterocyclo group selected from the group consisting of cyclopropyl, cyclobutyl, cyclopentyl, cyclohexyl, pyrrolidinyl, imidazolidinyl, piperidinyl, piperazinyl, morpholinyl, thiazolidinyl, dihydrothienyl, dihydropyranyl, dihydrofuryl, dihydrothiazolyl, and tetrahydrofuryl.

In another embodiment, the MCH receptor antagonist is selected from a subclass of compounds of Formula I represented by Formula IV:

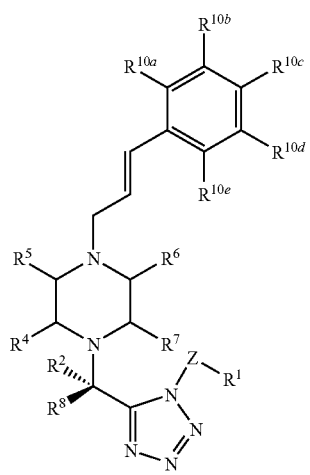

wherein
Z is selected from the group consisting of a bond, alkyl, aryl, aralkyl, heteroaralkyl, and heterocyclo;

$R^1$ is selected from the group consisting of alkoxycarbonyl, alkyl, cycloalkyl, aralkyl, aryl, heteroaryl, and heterocyclo, wherein $R^1$ is optionally substituted by one or more substituents selected from the group consisting of alkyl, halo, and keto;

$R^2$ is selected from the group consisting of alkyl, aryl, heterocyclo, and heteroaryl, or $R^2$ and $R^8$ together with the atom to which they are both attached form a 5- or 6-membered cycloalkyl or heterocyclo group, wherein $R^2$ or the cycloalkyl or heterocyclo group formed with $R^1$ is optionally substituted by one or more substituents selected from the group consisting of alkoxy, alkyl, alkylaryloxy, alkylthio, aralkenyl, aralkoxy, aralkyl, aryloxy, cyano, halo, haloalkyl, haloalkylaryl, haloaryloxy, heteroaryl, hydroxy, hydroxyalkoxy, N-(alkylcarbonyl)amino, and nitro;

$R^4$, $R^5$, $R^6$, and $R^7$ are independently selected from the group consisting of hydrogen, alkyl and halo; and $R^{10a}$, $R^{10b}$, $R^{10c}$, $R^{10d}$, and $R^{10e}$ are independently selected from the group consisting of hydrogen, alkyl, hydroxy, and alkoxy;

or a pharmaceutically-acceptable salt, tautomer or prodrug thereof.

In another embodiment, the MCH receptor antagonist consists of compounds of Formula IV, or a pharmaceutically-acceptable salt, tautomer or prodrug thereof, wherein Z is selected from the group consisting of a bond, lower alkyl, aryl, lower aralkyl, lower heteroaralkyl, and 3- to 10-membered heterocyclo;

$R^1$ is selected from the group consisting of lower alkoxycarbonyl, lower alkyl, lower cycloalkyl, lower aralkyl, aryl, 3- to 10-membered heteroaryl, and 3- to 10-membered heterocyclo, wherein $R^1$ is optionally substituted by one or more substituents selected from the group consisting of lower alkyl, halo, and keto;

$R^2$ is selected from the group consisting of lower alkyl, aryl, 3- to 10-membered heterocyclo, and 3- to 10-membered heteroaryl, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of lower alkoxy, lower alkyl, lower alkylaryloxy, lower alkylthio, lower aralkenyl, lower aralkoxy, lower aralkyl, aryloxy, cyano, halo, lower haloalkyl, lower haloalkylaryl, haloaryloxy, 3- to 10-membered heteroaryl, hydroxy, lower hydroxyalkoxy, N-(lower alkylcarbonyl)amino, and nitro;

$R^4$, $R^5$, $R^6$, $R^7$, and $R^9$ are independently selected from the group consisting of hydrogen, lower alkyl, and halo; and $R^{10a}$, $R^{10b}$, $R^{10c}$, $R^{10d}$, and $R^{10e}$ are independently selected from the group consisting of hydrogen, lower alkyl, hydroxy, and lower alkoxy.

In another embodiment, the MCH receptor antagonist consists of compounds of Formula IV, or a pharmaceutically-acceptable salt, tautomer or prodrug thereof, wherein Z is selected from the group consisting of a bond, methyl, ethyl, propyl, t-butyl, phenyl, tetrahydronaphthyl, biphenyl, naphthyl, phenylpropyl, indolylethyl, and piperidyl;

$R^1$ is selected from the group consisting of methoxycarbonyl, ethoxycarbonyl, t-butoxycarbonyl, isopropyl, n-butyl, t-butyl, cyclopropyl, cyclobutyl, cyclopentyl, cyclohexyl, benzyl, phenyl, tetrahydronaphthyl, indolyl, tetrahydrofuryl, pyrrolidinyl, and morpholinyl, wherein $R^1$ is optionally substituted by one or more substituents selected from the group consisting of methyl, ethyl, propyl, bromo, fluoro, chloro, and keto;

$R^2$ is selected from the group consisting of methyl, phenyl, biphenyl, naphthyl, tetrahydrofuryl, pyrrolidinyl, morpholinyl, piperidyl, thienyl, pyrrolyl, and pyridyl, or $R^2$ and $R^8$ together with the atom to which they are both attached form a piperidyl or cyclohexyl group, wherein $R^2$ or the piperidyl or cyclohexyl group formed with $R^8$ is optionally substituted by one or more substituents selected from the group consisting of methoxy, ethoxy, methyl, ethyl, isopropyl, isobutyl, methylphenoxy, methylthio, phenylethenyl, benzyloxy, phenylethoxy, benzyl, phenoxy, cyano, fluoro, chloro, bromo, trifluoromethyl, trifluoromethylphenyl, dichlorophenoxy, imidazole, benzodioxole, hydroxy, hydroxyethoxy, N-(methylcarbonyl)amino, and nitro;

$R^4$, $R^5$, $R^6$, $R^7$, and $R^9$ are independently selected from the group consisting of hydrogen, methyl, ethyl, n-propyl, isopropyl, fluoro, chloro, and bromo; and $R^{10a}$, $R^{10b}$, $R^{10c}$, $R^{10d}$, and $R^{10e}$ are independently selected from the group consisting of hydrogen, methyl, hydroxy, and methoxy.

In another embodiment, the MCH receptor antagonist is selected from a subclass of compounds of Formula I represented by Formula V:

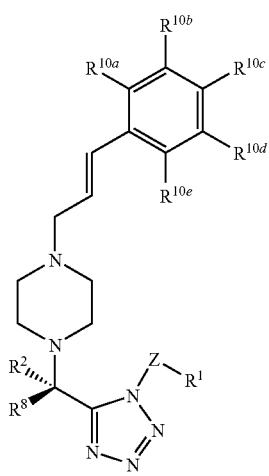

V wherein

Z is selected from the group consisting of a bond, alkyl, aralkyl, heteroaralkyl, and heterocyclo;

$R^1$ is selected from the group consisting of alkoxycarbonyl, alkyl, aralkyl, aryl, heteroaryl, and heterocyclo, wherein $R^1$ is optionally substituted by one or more substituents selected from the group consisting of alkyl, halo, and keto;

$R^2$ is selected from the group consisting of alkyl, aryl, and heteroaryl, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of alkoxy, alkyl, alkylaryloxy, alkylthio, aralkenyl, aralkoxy, aralkyl, aryloxy, cyano, halo, haloalkyl, haloalkylaryl, haloaryloxy, heteroaryl, hydroxy, hydroxyalkoxy, N-(alkylcarbonyl)amino, and nitro;

$R^{10a}$, $R^{10b}$, $R^{10c}$, $R^{10d}$, and $R^{10e}$ are independently selected from the group consisting of hydrogen, alkyl, hydroxy, and alkoxy;

or a pharmaceutically-acceptable salt, tautomer or prodrug thereof.

In another embodiment, the MCH receptor antagonist consists of compounds of Formula V, or a pharmaceutically-acceptable salt, tautomer or prodrug thereof, wherein Z is selected from the group consisting of a bond, lower alkyl, lower aralkyl, lower heteroaralkyl, and 3- to 10-membered heterocyclo;

$R^1$ is selected from the group consisting of lower alkoxycarbonyl, lower alkyl, lower aralkyl, aryl, 3- to 10-membered heteroaryl, and 3- to 10-membered heterocyclo, wherein $R^1$ is optionally substituted by one or more substituents selected from the group consisting of lower alkyl, halo, and keto;

$R^2$ is selected from the group consisting of lower alkyl, aryl, and 3- to 10-membered heteroaryl, or $R^2$ and $R^8$ together with the atom to which they are both attached form a 5- or 6-membered cycloalkyl or heterocyclo group, wherein $R^2$ or the cycloalkyl or heterocyclo group formed with $R^8$ is optionally substituted by one or more substituents selected from the group consisting of lower alkoxy, lower alkyl, lower alkylaryloxy, lower alkylthio, lower aralkenyl, lower aralkoxy, lower aralkyl, aryloxy, cyano, halo, lower haloalkyl, lower haloalkylaryl, haloaryloxy, 3- to 10-membered heteroaryl, hydroxy, lower hydroxyalkoxy, N-(lower alkylcarbonyl) amino, and nitro;

$R^{10a}$, $R^{10b}$, $R^{10c}$, $R^{10d}$, and $R^{10e}$ are independently selected from the group consisting of hydrogen, lower alkyl, hydroxy, and lower alkoxy.

In another embodiment, the MCH receptor antagonist consists of compounds of Formula V, or a pharmaceutically-acceptable salt, tautomer or prodrug thereof, wherein Z is selected from the group consisting of a bond, methyl, ethyl, propyl, t-butyl, phenylpropyl, indolylethyl, and piperidyl;

$R^1$ is selected from the group consisting of methoxycarbonyl, ethoxycarbonyl, t-butoxycarbonyl, isopropyl, n-butyl, t-butyl, benzyl, phenyl, tetrahydronaphthyl, indolyl, tetrahydrofuryl, pyrrolidinyl, and morpholinyl, wherein $R^1$ is optionally substituted by one or more substituents selected from the group consisting of methyl, chloro, and keto;

$R^2$ is selected from the group consisting of methyl, phenyl, biphenyl, naphthyl, thienyl, pyrrolyl, and pyridyl, or $R^2$ and $R^8$ together with the atom to which they are both attached form a piperidyl or cyclohexyl group, wherein $R^2$ or the piperidyl or cyclohexyl group formed with $R^8$ is optionally substituted by one or more substituents selected from the group consisting of methoxy, ethoxy, methyl, ethyl, isopropyl, isobutyl, methylphenoxy, methylthio, phenylethenyl, benzyloxy, phenylethoxy, benzyl, phenoxy, cyano, fluoro, chloro, bromo, trifluoromethyl, trifluoromethylphenyl, dichlorophenoxy, imidazole, benzodioxole, hydroxy, hydroxyethoxy, N-(methylcarbonyl)amino, and nitro;

$R^{10a}$, $R^{10b}$, $R^{10c}$, $R^{10d}$, and $R^{10e}$ are independently selected from the group consisting of hydrogen, methyl, hydroxy, and methoxy.

In another embodiment, the compound of Formula I is selected from the group of compounds listed in Table 1.

TABLE 1

| Compound No. | Structure |
|---|---|
| 1 | 1-{[1-(2,6-dimethylphenyl)-1H-tetrazol-5-yl]phenylmethyl}-4-(3-phenylallyl)piperazine<br>MS m/z repeat (M + H); MW 464.62 |
| 4 | 1-{[1-(2,6-dimethylphenyl)-1H-tetrazol-5-yl]phenylmethyl}-4-(3-phenylallyl)piperazine<br>MS m/z repeat (M + H); MW 464.62 |
| 11 | 1-{biphenyl-4-yl-[1-(2,6-dimethylphenyl)-1H-tetrazol-5-yl]methyl}-4-(3-phenylallyl)piperazine<br>MS m/z repeat (M + H); MW 540.2 |

TABLE 1-continued
| Compound No. | Structure |
|---|---|
| 12 | 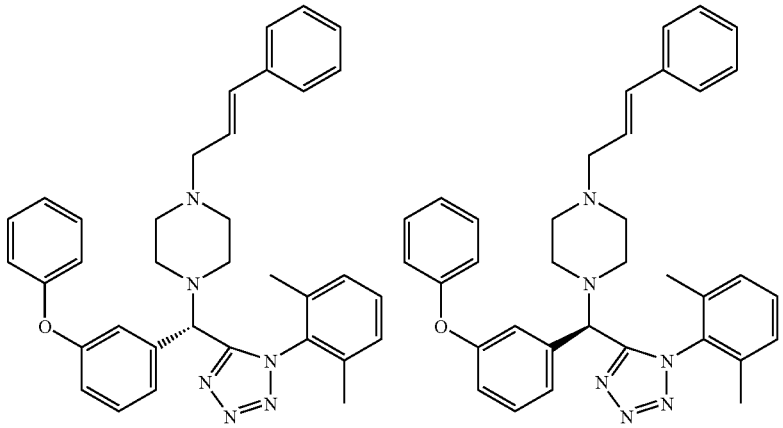<br>1-[[1-(2,6-dimethylphenyl)-1H-tetrazol-5-yl]-(3-phenoxyphenyl)methyl]-4-(3-phenylallyl)piperazine<br>MS m/z 557.32 (M + H); MW 556.7 |
| 14 | 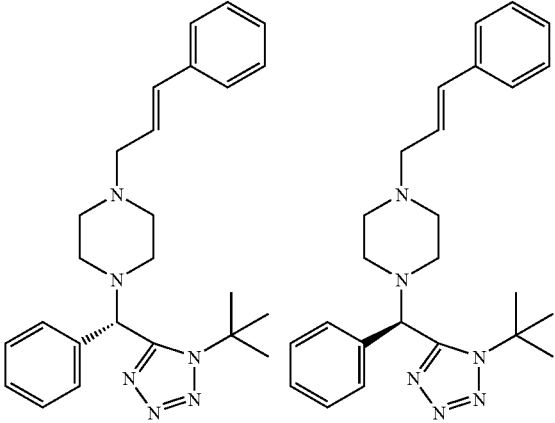<br>1-[(1-tert-butyl-1H-tetrazol-5-yl)phenylmethyl]-4-(3-phenylallyl)piperazine<br>MS m/z 417.3 (M + H); MW 416.6 |
| 15 | 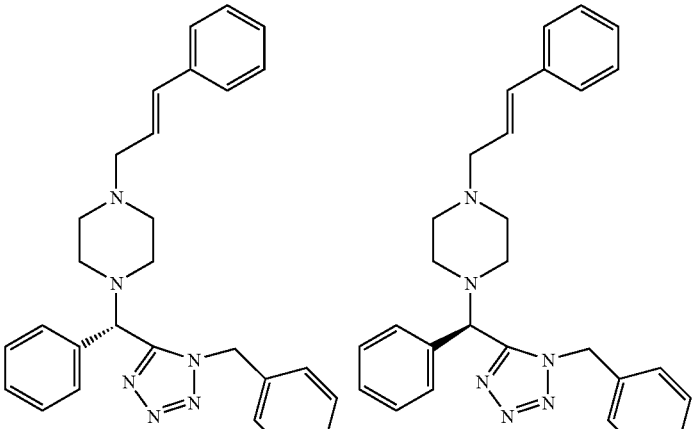<br>1-[(1-benzyl-1H-tetrazol-5-yl)phenylmethyl]-4-(3-phenylallyl)piperazine<br>MS m/z 451.28 (M + H); MW 450.6 |

TABLE 1-continued
| Compound No. | Structure |
|---|---|
| 16 | 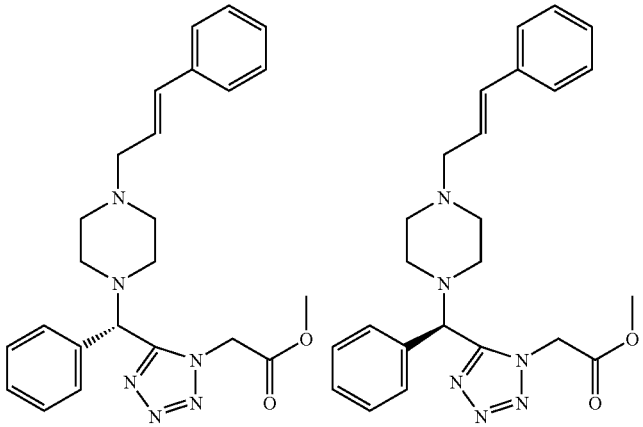<br>(5-{phenyl-[4-(3-phenylallyl)piperazin-1-yl]methyl}tetrazol-1-yl) acetic acid methyl ester<br>MS m/z 433.26 (M + H); MW 432.5 |
| 17 | 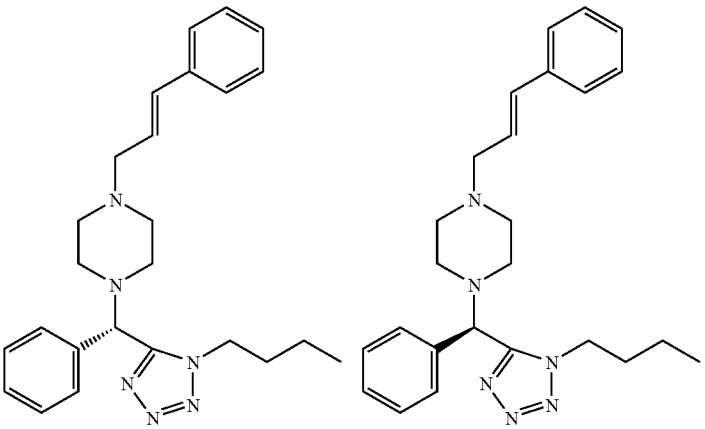<br>1-[(1-butyl-1H-tetrazol-5-yl)phenylmethyl]-4-(3-phenylallyl)piperazine<br>MS m/z 417.31 (M + H); MW 416.6 |
| 19 | 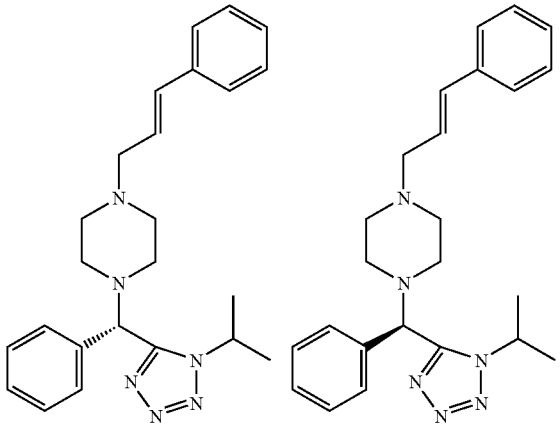<br>1-[(1-isopropyl-1H-tetrazol-5-yl)phenylmethyl]-4-(3-phenylallyl)piperazine<br>MS m/z 403.28 (M + H); MW 402.5 |

TABLE 1-continued
| Compound No. | Structure |
|---|---|
| 20 | 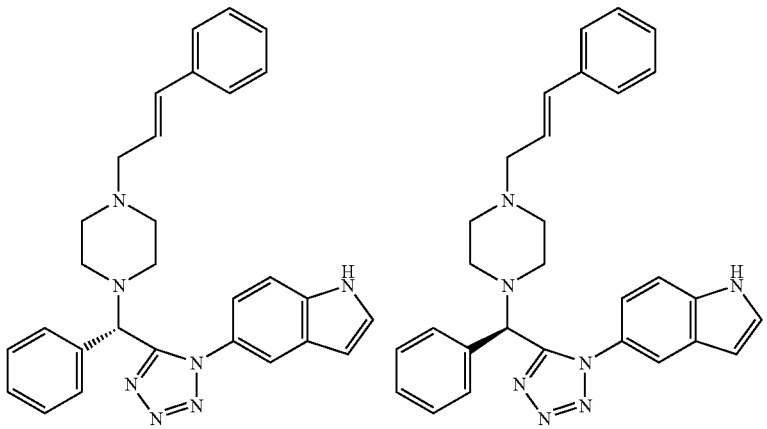<br>5-(5-{phenyl-[4-(3-phenylallyl)piperazin-1-yl]methyl}tetrazol-1-yl)-1H-indole<br>MS m/z 276.28 (M + H); MW 475.6 |
| 21 | 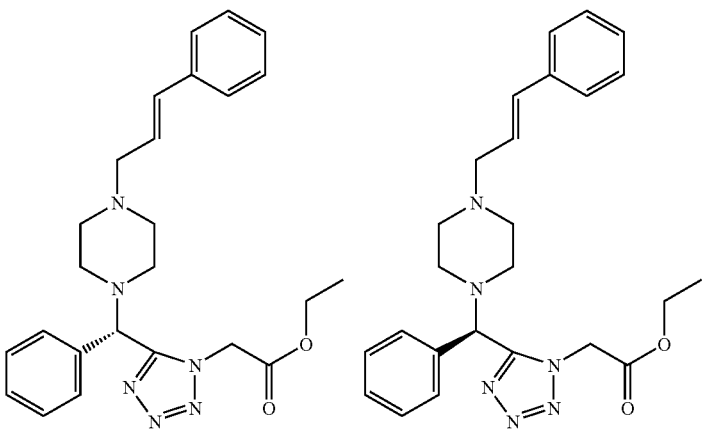<br>(5-{phenyl-[4-(3-phenylallyl)piperazin-1-yl]methyl}tetrazol-1-yl) acetic acid ethyl ester<br>MS m/z 447.29 (M + H); MW 446.6 |
| 22 | 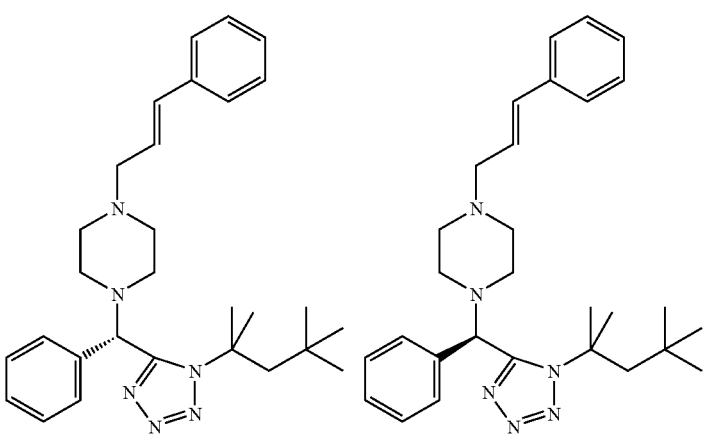<br>1-(3-phenylallyl)-4-{phenyl-[1-(1,1,3,3-tetramethylbutyl)-1H-tetrazol-5-yl]methyl}piperazine<br>MS m/z 473.37 (M + H); MW 472.7 |

TABLE 1-continued
| Compound No. | Structure |
|---|---|
| 24 | 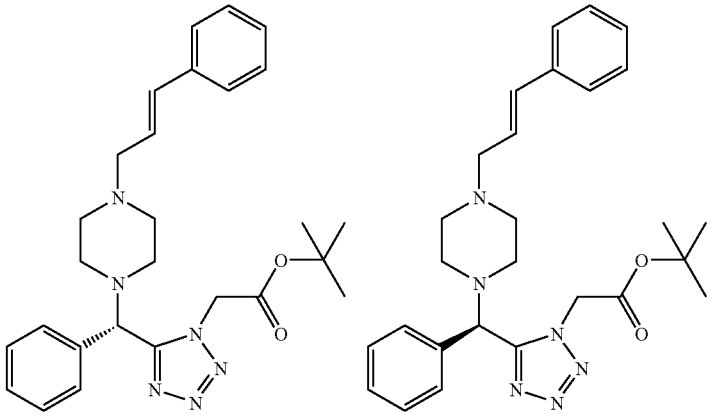<br>(5-{phenyl-[4-(3-phenylallyl)piperazin-1-yl]methyl}tetrazol-1-yl) acetic acid tert-butyl ester<br>MS m/z 475.3 (M + H); MW 474.6 |
| 26 | 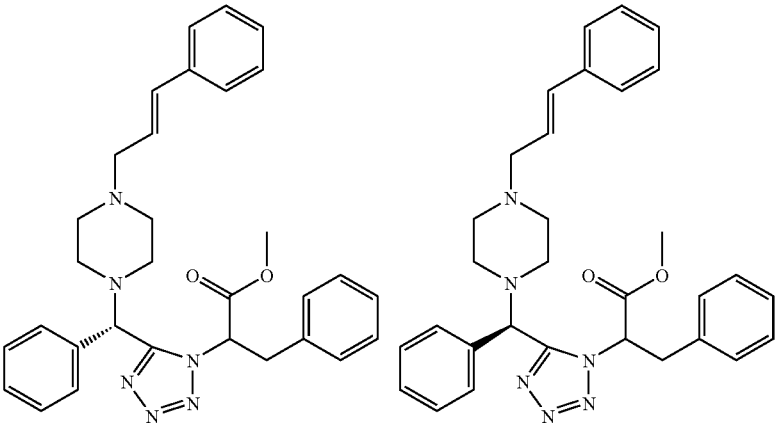<br>3-phenyl-2-(5-{phenyl-[4-(3-phenylallyl)piperazin-1-yl]methyl}tetrazol-1-yl) propionic acid methyl ester<br>MS m/z 523.32 (M + H); MW 522.7 |
| 27 | 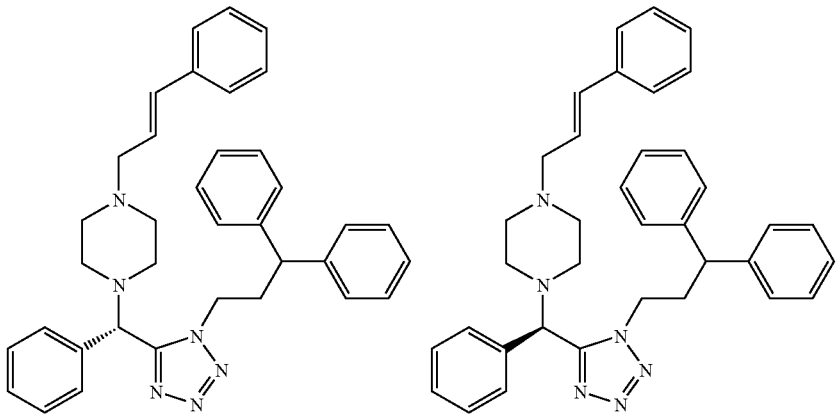<br>1-{[1-(3,3-diphenylpropyl)-1H-tetrazol-5-yl]phenylmethyl}-4-(3-phenylallyl)piperazine<br>MS m/z 555.4 (M + H); MW 554.7 |

TABLE 1-continued
| Compound No. | Structure |
|---|---|
| 28 | 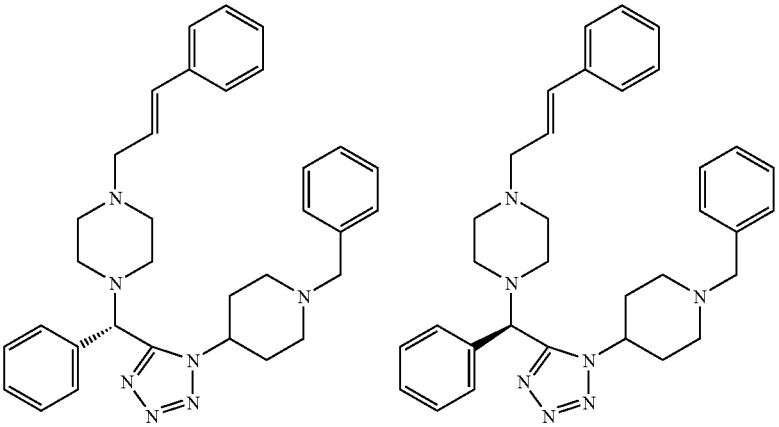<br>1-{[1-(1-benzylpiperidin-4-yl)-1H-tetrazol-5-yl]phenylmethyl}-4-(3-phenylallyl)piperazine<br>MS m/z 534.37 (M + H); MW 533.7 |
| 29 | 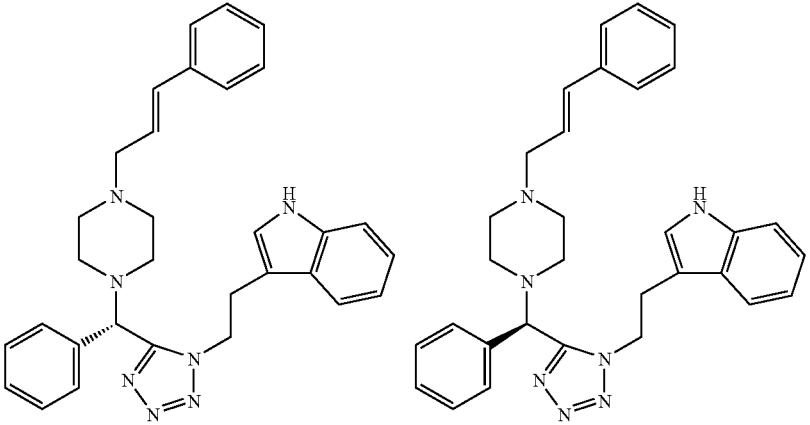<br>3-[2-(5-{phenyl-[4-(3-phenylallyl)piperazin-1-yl]methyl}tetrazol-1-yl)ethyl]-1H-indole<br>MS m/z 504.33 (M + H); MW 503.7 |
| 30 | 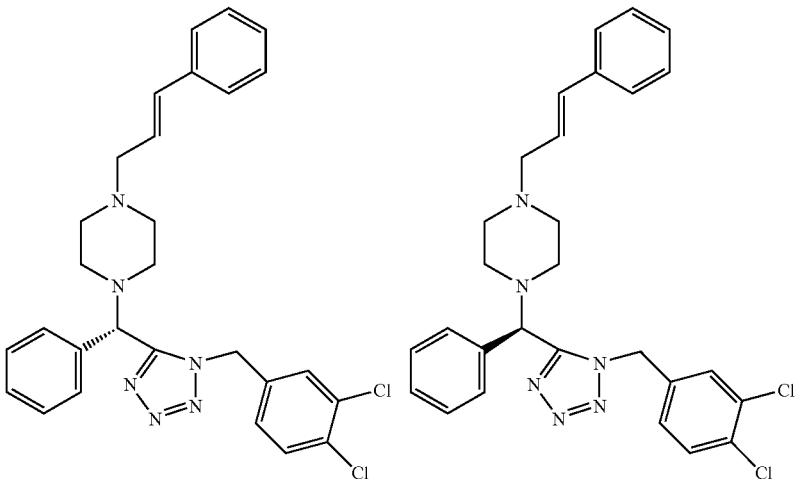<br>1-{[1-(3,4-dichlorobenzyl)-1H-tetrazol-5-yl]phenylmethyl}-4-(3-phenylallyl)piperazine<br>MS m/z 519.22 (M + H); MW 519.5 |

TABLE 1-continued
| Compound No. | Structure |
|---|---|
| 31 | 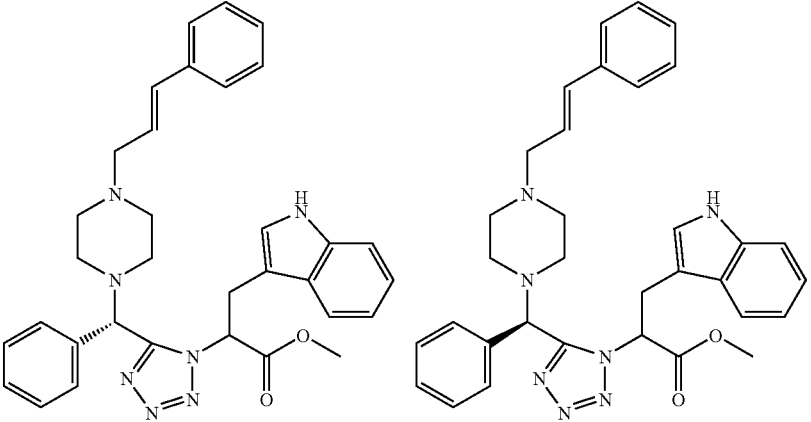<br>3-(1H-indol-3-yl)-2-(5-{phenyl-[4-(3-phenylallyl)piperazin-1-yl]methyl}tetrazol-1-yl) propionic acid methyl ester<br>MS m/z 562.34 (M + H); MW 561.7 |
| 33 | 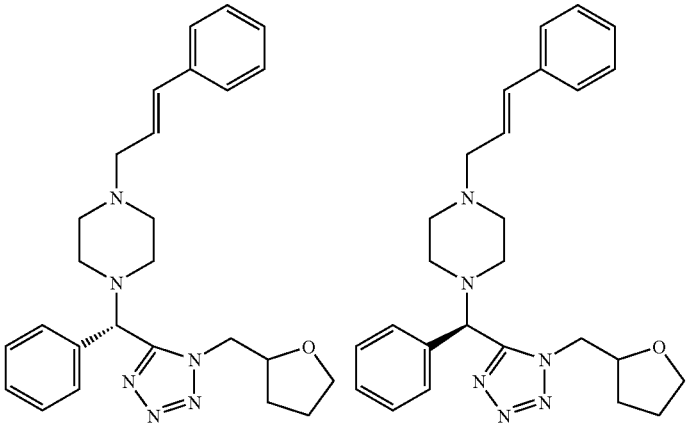<br>1-(3-phenylallyl)-4-{phenyl-[1-(tetrahydrofuran-2-ylmethyl)-1H-tetrazol-5-yl]methyl}piperazine<br>MS m/z 445.31 (M + H); MW 444.6 |
| 35 | 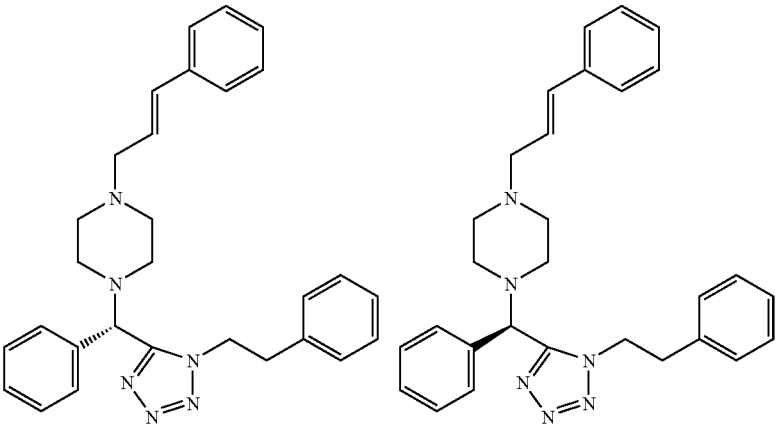<br>1-[(1-phenethyl-1H-tetrazol-5-yl)phenylmethyl]-4-(3-phenylallyl)piperazine<br>MS m/z 465.29 (M + H); MW 464.6 |

TABLE 1-continued
| Compound No. | Structure |
|---|---|
| 36 | 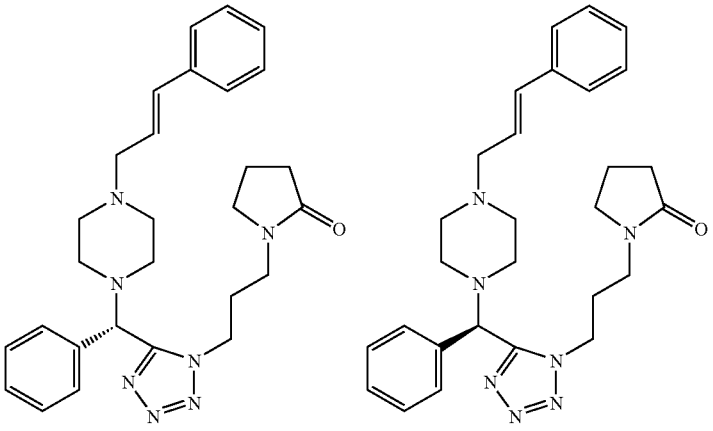
1-[3-(5-{phenyl-[4-(3-phenylallyl)piperazin-1-yl]methyl}tetrazol-1-yl)propyl]pyrrolidin-2-one
MS m/z 486.34 (M + H); MW 485.6 |
| 37 | 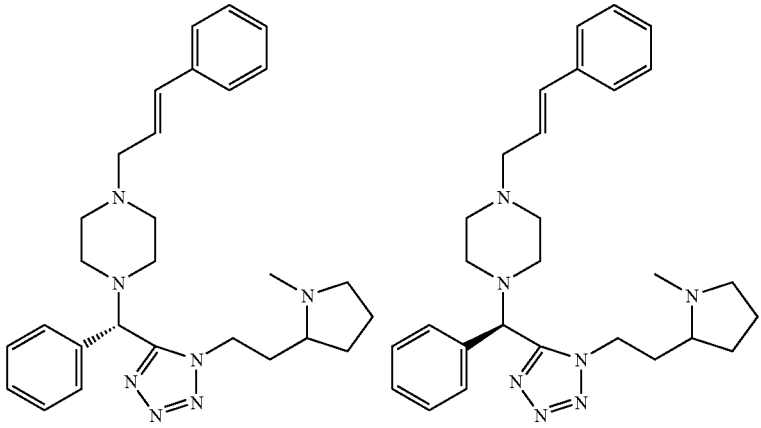
1-({1-[2-(1-methyl-pyrrolidin-2-yl)ethyl]-1H-tetrazol-5-yl}phenylmethyl)-4-(3-phenylallyl)piperazine
MS m/z 472.35 (M + H); MW 471.6 |
| 38 | 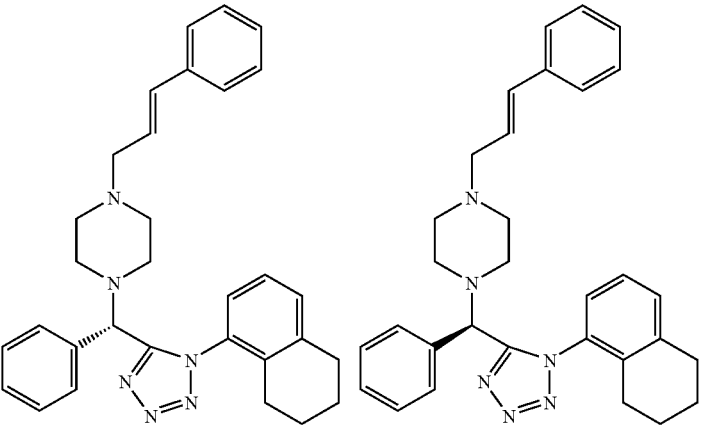
1-(3-phenylallyl)-4-{phenyl-[1-(5,6,7,8-tetrahydronaphthalen-1-yl)-1H-tetrazol-5-yl]methyl}piperazine
MS m/z 491.33 (M + H); MW 490.7 |

TABLE 1-continued
| Compound No. | Structure |
|---|---|
| 39 | 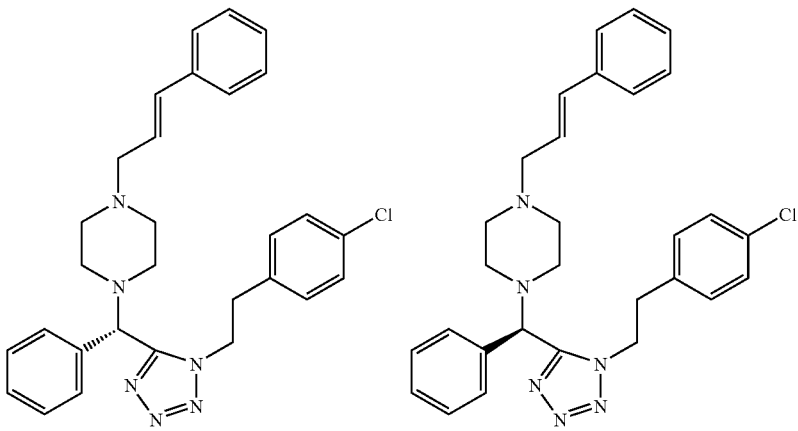<br>1-({1-[2-(4-chlorophenyl)ethyl]-1H-tetrazol-5-yl}phenylmethyl)-4-(3-phenylallyl)piperazine<br>MS m/z 499.27 (M + H); MW 499.1 |
| 42 | 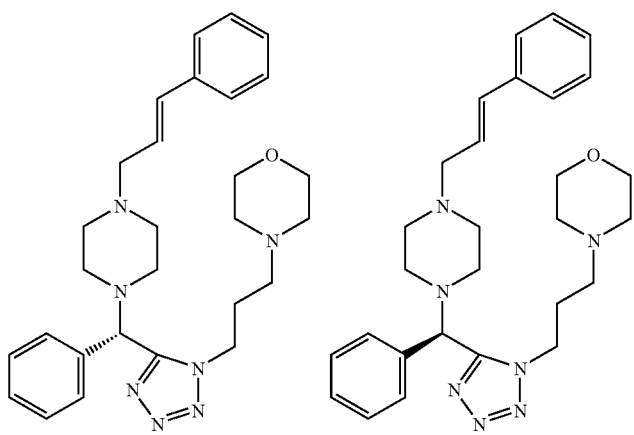<br>4-[3-(5-{phenyl-[4-(3-phenylallyl)piperazin-1-yl]methyl}tetrazol-1-yl)propyl]morpholine<br>MS m/z 488.35 (M + H); MW 487.6 |
| 46 | 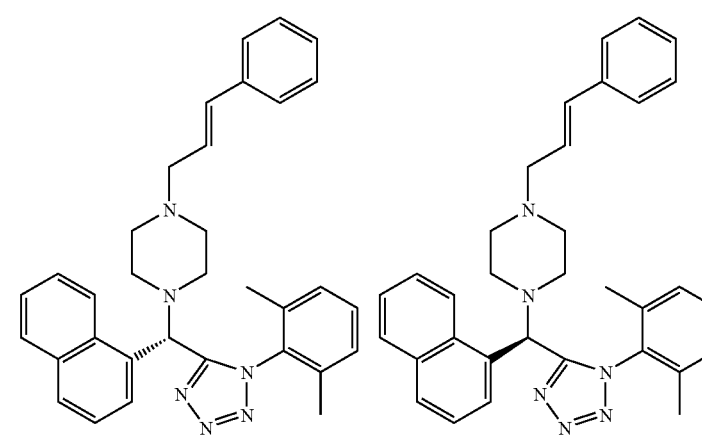<br>1-{[1-(2,6-dimethylphenyl)-1H-tetrazol-5-yl]naphthalen-1-ylmethyl}-4-(3-phenylallyl)piperazine<br>MS m/z 567.35 (M + H); MW 566.7 |

TABLE 1-continued
| Compound No. | Structure |
|---|---|
| 48 | 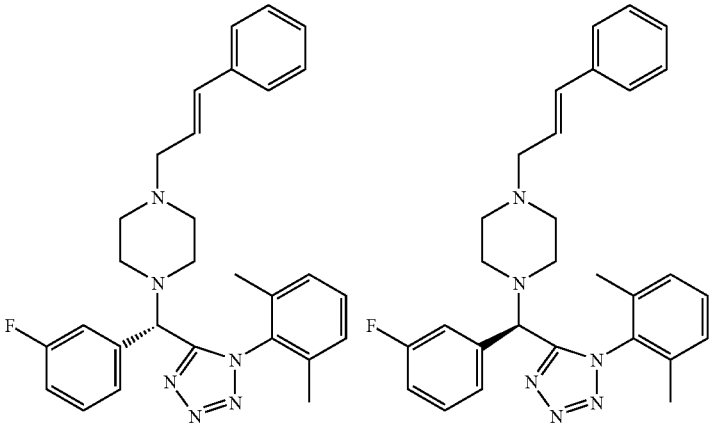<br>1-[[1-(2,6-dimethylphenyl)-1H-tetrazol-5-yl]-(3-fluorophenyl)methyl]-4-(3-phenylallyl)piperazine<br>MS m/z 483.3 (M + H); MW 482.6 |
| 52 | 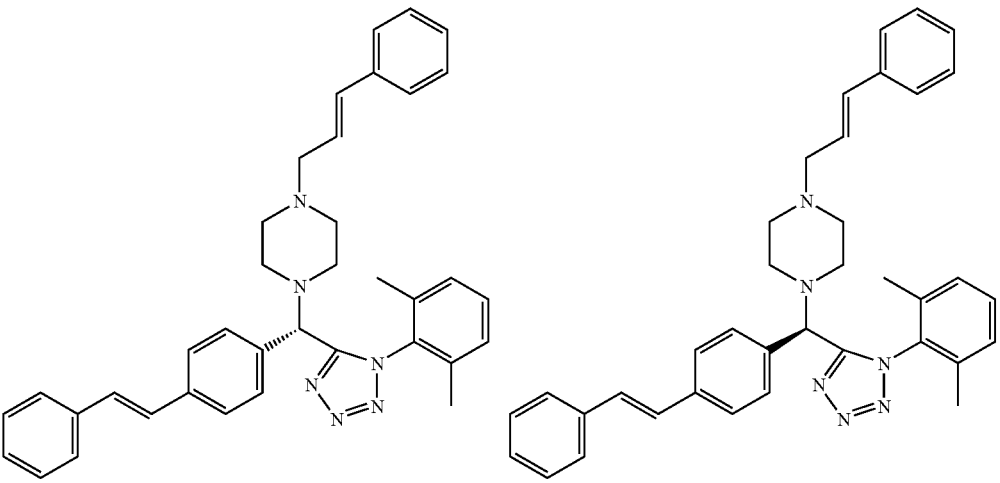<br>1-[[1-(2,6-dimethylphenyl)-1H-tetrazol-5-yl]-(4-styrylphenyl)methyl]-4-(3-phenylallyl)piperazine<br>MS m/z 567.35 (M + H); MW 566.7 |
| 53 | 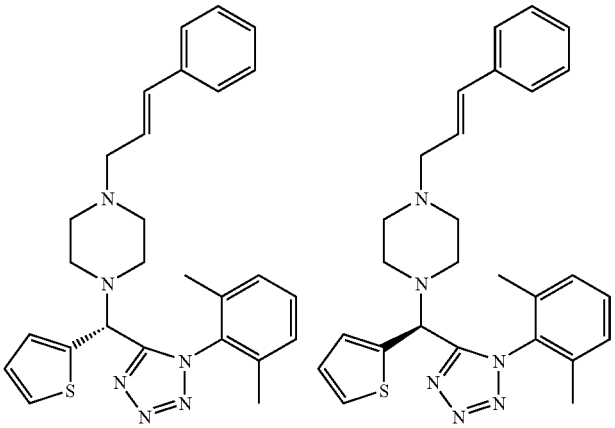<br>1-{[1-(2,6-dimethylphenyl)-1H-tetrazol-5-yl]thiophen-2-ylmethyl}-4-(3-phenylallyl)piperazine<br>MS m/z 471.25 (M + H); MW 470.6 |

TABLE 1-continued
| Compound No. | Structure |
|---|---|
| 55 | 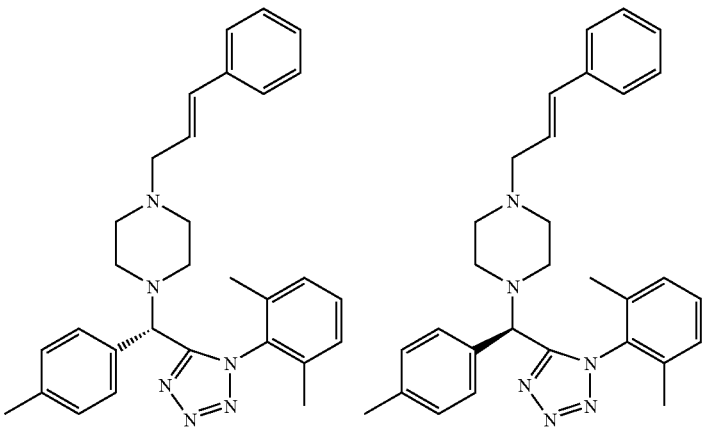<br>1-{[1-(2,6-dimethylphenyl)-1H-tetrazol-5-yl]-p-tolylmethyl}-4-(3-phenylallyl)piperazine<br>MS m/z 479.32 (M + H); MW 478.6 |
| 56 | 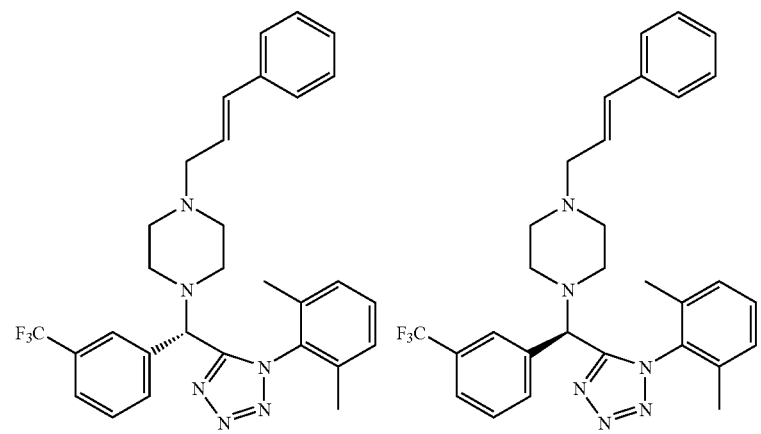<br>1-[[1-(2,6-dimethylphenyl)-1H-tetrazol-5-yl]-(3-trifluoromethylphenyl)methyl]-4-(3-phenylallyl)piperazine<br>MS m/z 533.31 (M + H); MW 532.6 |
| 57 | 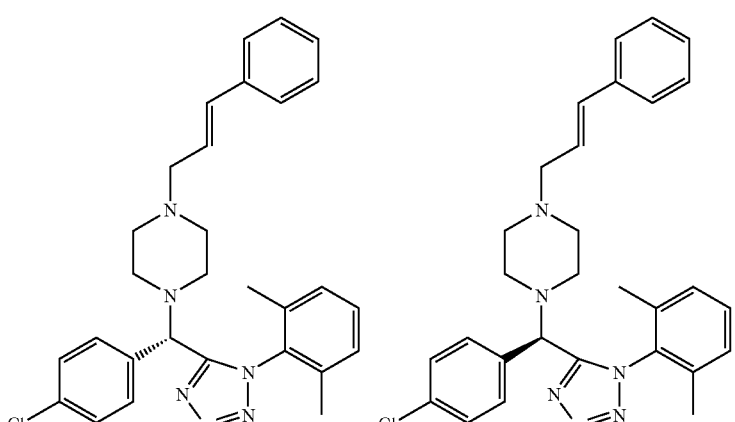<br>1-{(4-chlorophenyl)-[1-(2,6-dimethylphenyl)-1H-tetrazol-5-yl]methyl}-4-(3-phenylallyl)piperazine<br>MS m/z 499.25 (M + H); MW 499.1 |

TABLE 1-continued
| Compound No. | Structure |
|---|---|
| 58 | 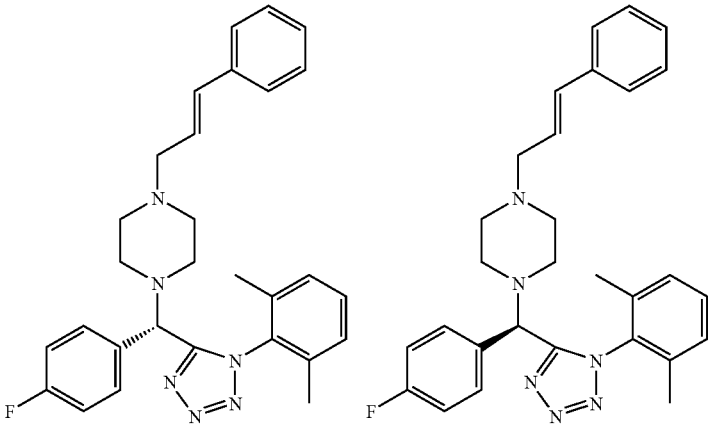<br>1-[[1-(2,6-dimethylphenyl)-1H-tetrazol-5-yl]-(4-fluorophenyl)methyl]-4-(3-phenylallyl)piperazine<br>MS m/z 483.3 (M + H); MW 482.6 |
| 60 | 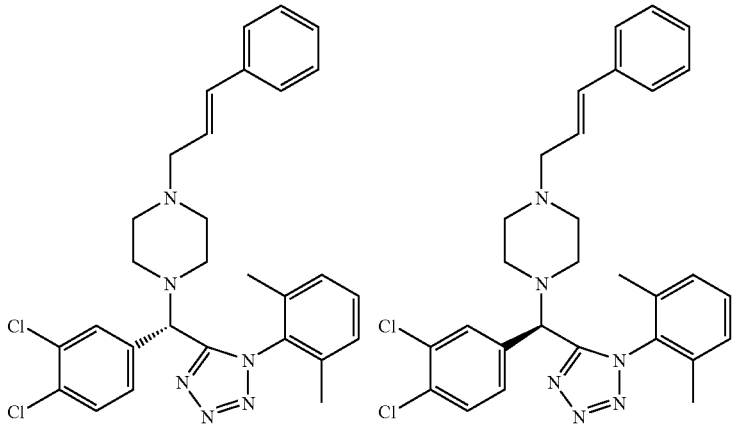<br>1-{(3,4-dichlorophenyl)-[1-(2,6-dimethylphenyl)-1H-tetrazol-5-yl]methyl}-4-(3-phenylallyl)piperazine<br>MS m/z 533.23 (M + H); MW 533.5 |
| 61 | 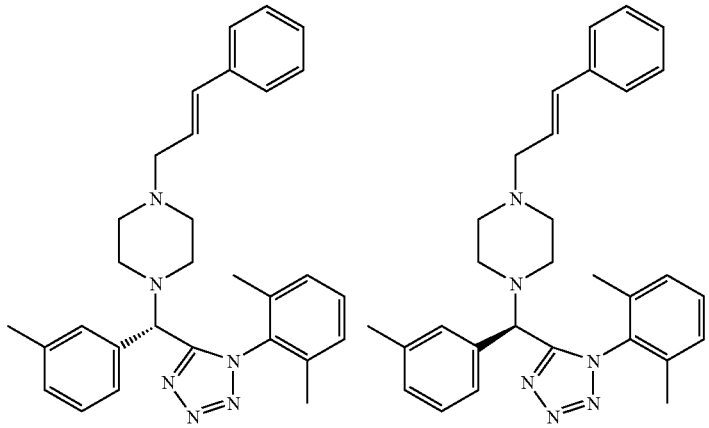<br>1-{[1-(2,6-dimethylphenyl)-1H-tetrazol-5-yl]-m-tolylmethyl}-4-(3-phenylallyl)piperazine<br>MS m/z 479.33 (M + H); MW 478.6 |

TABLE 1-continued
| Compound No. | Structure |
|---|---|
| 62 | 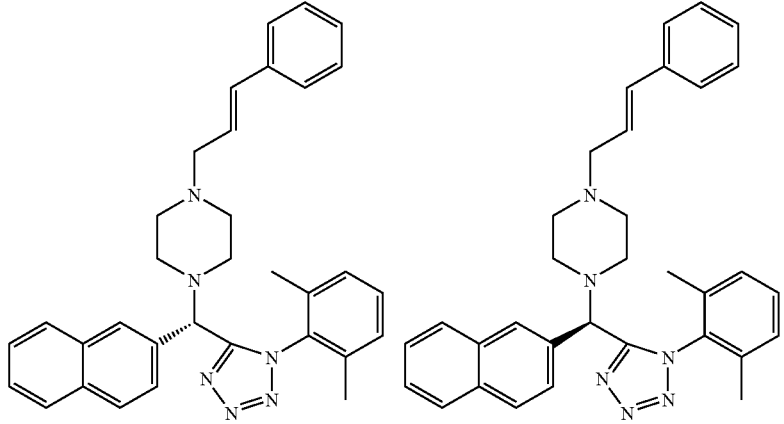
1-{[1-(2,6-dimethylphenyl)-1H-tetrazol-5-yl]naphthalen-2-ylmethyl}-4-(3-phenylallyl)piperazine
MS m/z 515.32 (M + H); MW 514.7 |
| 63 | 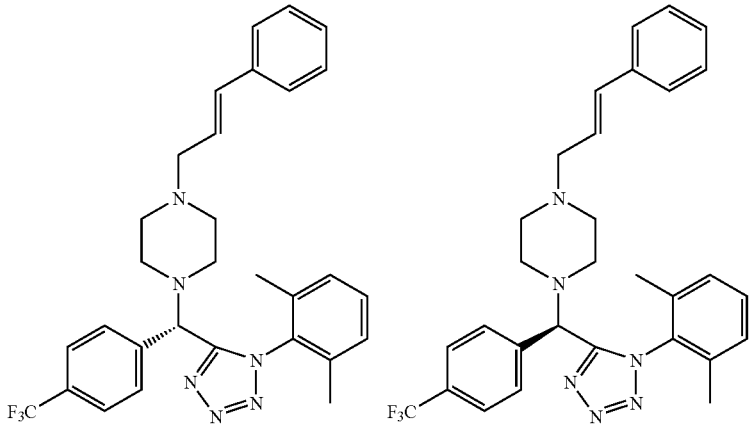
1-[[1-(2,6-dimethylphenyl)-1H-tetrazol-5-yl]-(4-trifluoromethylphenyl)methyl]-4-(3-phenylallyl)piperazine
MS m/z 533.31 (M + H); MW 532.6 |
| 64 | 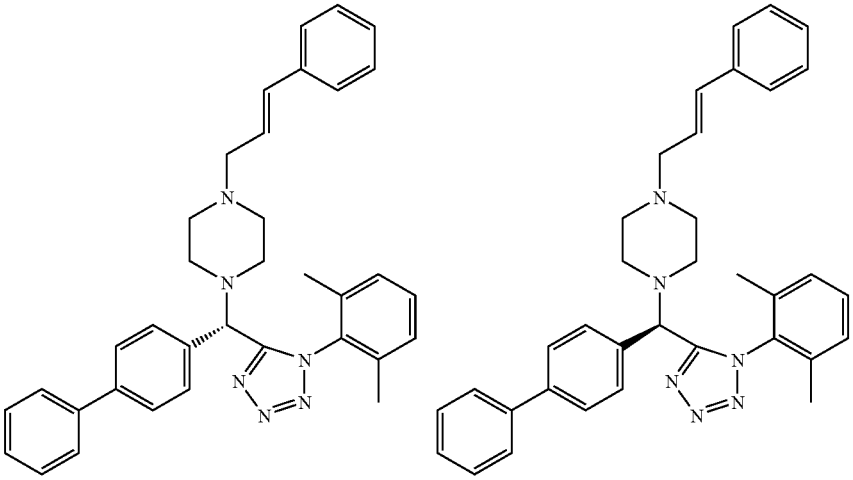
1-{biphenyl-4-yl-[1-(2,6-dimethylphenyl)-1H-tetrazol-5-yl]methyl}-4-(3-phenylallyl)piperazine
MS m/z 541.33 (M + H); MW 540.7 |

TABLE 1-continued
| Compound No. | Structure |
| --- | --- |
| 65 | 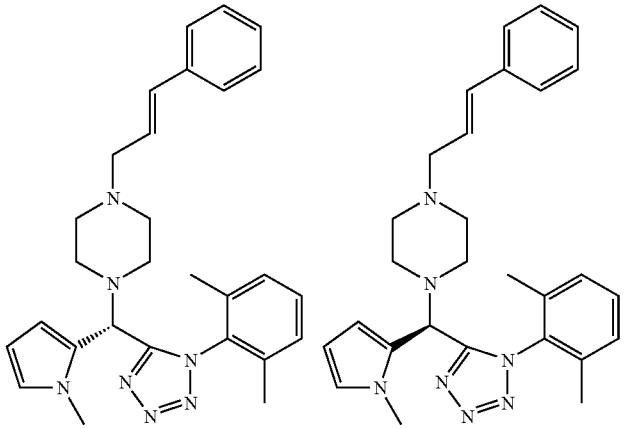
1-[[1-(2,6-dimethylphenyl)-1H-tetrazol-5-yl]-(1-methyl-1H-pyrrol-2-yl)methyl]-4-(3-phenylallyl)piperazine
MS m/z repeat (M + H); MW 467.6 |
| 66 | 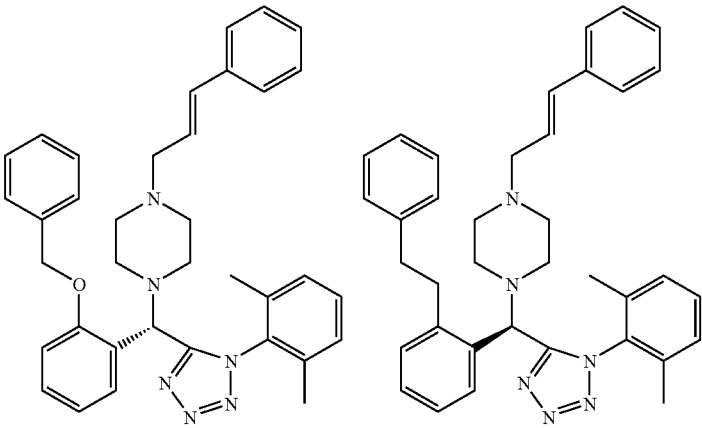
1-{(2-benzyloxyphenyl)-[1-(2,6-dimethylphenyl)-1H-tetrazol-5-yl]methyl}-4-(3-phenylallyl)piperazine
MS m/z 571.34 (M + H); MW 570.7 |
| 67 | 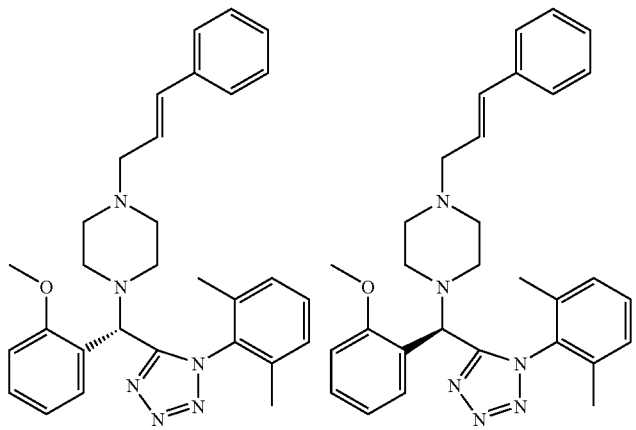
1-[[1-(2,6-dimethylphenyl)-1H-tetrazol-5-yl]-(2-methoxyphenyl)methyl]-4-(3-phenylallyl)piperazine
MS m/z 495.31 (M + H); MW 494.6 |

TABLE 1-continued
| Compound No. | Structure |
|---|---|
| 68 | 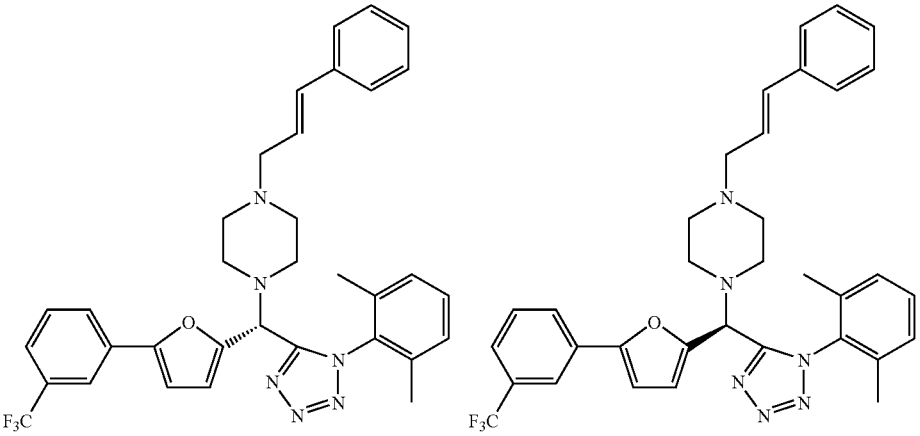<br>1-{[1-(2,6-dimethylphenyl)-1H-tetrazol-5-yl]-[5-(3-trifluoromethylphenyl)furan-2-yl]methyl}-4-(3-phenylallyl)piperazine<br>MS m/z 599.32 (M + H); MW 598.7 |
| 69 | 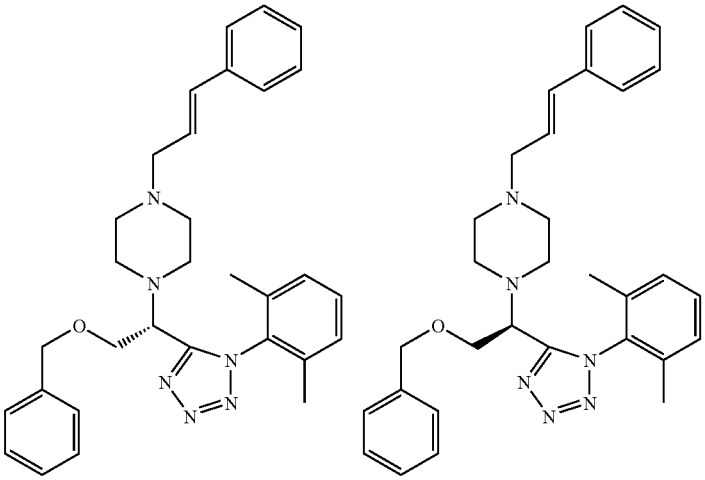<br>1-{2-benzyloxy-1-[1-(2,6-dimethylphenyl)-1H-tetrazol-5-yl]ethyl}-4-(3-phenylallyl)piperazine<br>MS m/z 509.3 (M + H); MW 508.7 |
| 70 | 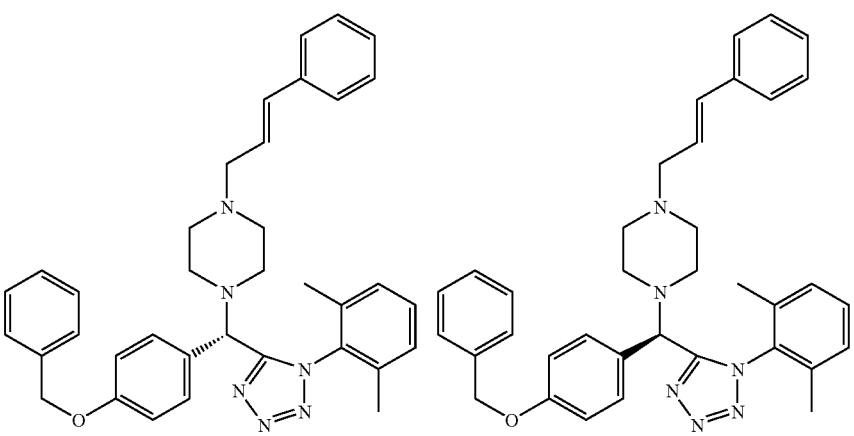<br>1-{(4-benzyloxyphenyl)-[1-(2,6-dimethylphenyl)-1H-tetrazol-5-yl]methyl}-4-(3-phenylallyl)piperazine<br>MS m/z 571.35 (M + H); MW 570.7 |

TABLE 1-continued
| Compound No. | Structure |
|---|---|
| 71 | 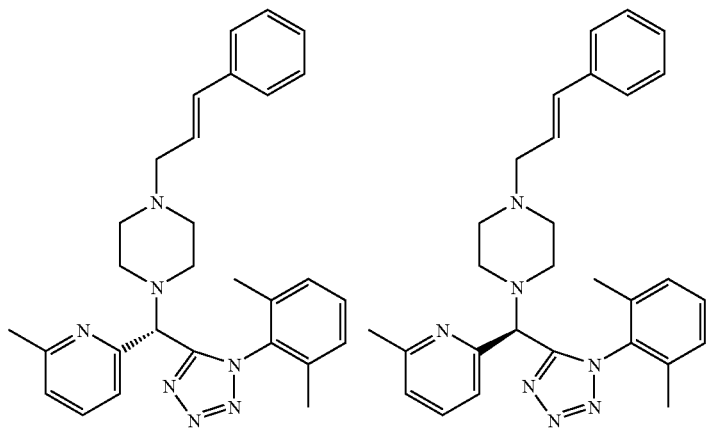<br>1-[[1-(2,6-dimethylphenyl)-1H-tetrazol-5-yl]-(6-methylpyridin-2-yl)methyl]-4-(3-phenylallyl)piperazine<br>MS m/z 480.31 (M + H); MW 479.6 |
| 72 | 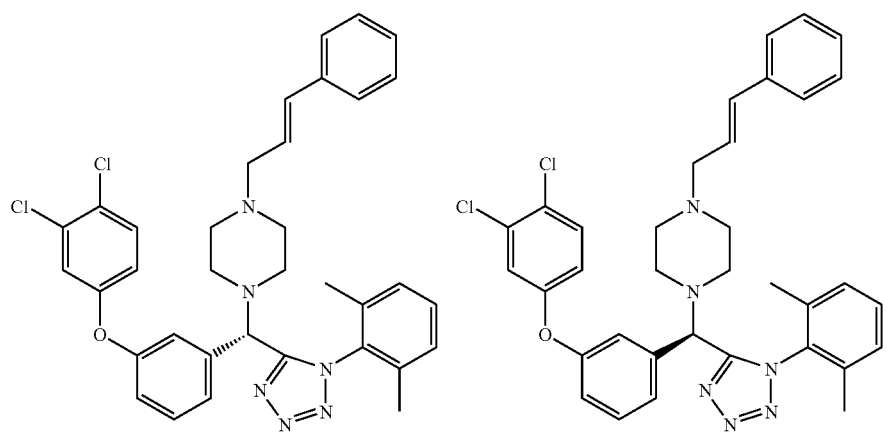<br>1-{[3-(3,4-dichlorophenoxy)phenyl]-[1-(2,6-dimethylphenyl)-1H-tetrazol-5-yl]methyl}-4-(3-phenylallyl)piperazine<br>MS m/z 625.26 (M + H); MW 625.6 |
| 73 | 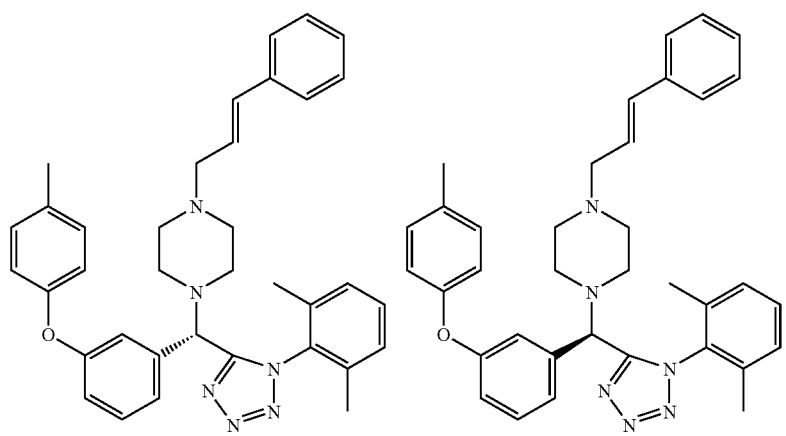<br>1-[[1-(2,6-dimethylphenyl)-1H-tetrazol-5-yl]-(3-p-tolyloxyphenyl)methyl]-4-(3-phenylallyl)piperazine<br>MS m/z 571.3 (M + H); MW 570.7 |

TABLE 1-continued
| Compound No. | Structure |
|---|---|
| 74 | 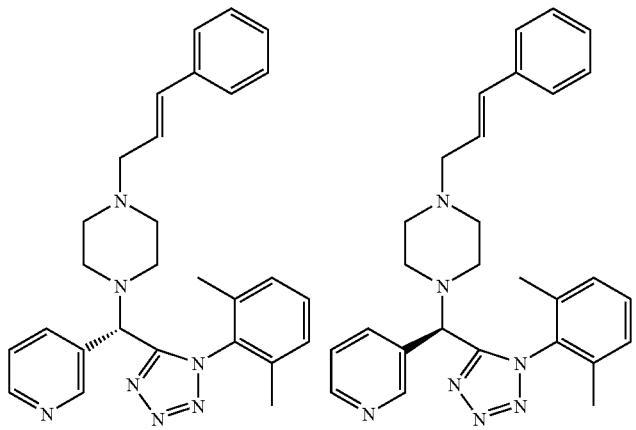<br>1-{[1-(2,6-dimethylphenyl)-1H-tetrazol-5-yl]pyridin-3-ylmethyl}-4-(3-phenylallyl)piperazine<br>MS m/z 466.3 (M + H); MW 465.6 |
| 75 | 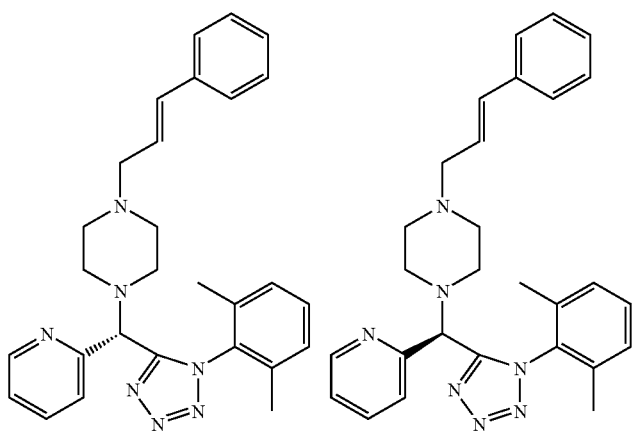<br>1-{[1-(2,6-dimethylphenyl)-1H-tetrazol-5-yl]pyridin-2-ylmethyl}-4-(3-phenylallyl)piperazine<br>MS m/z 466.3 (M + H); MW 465.6 |
| 76 | 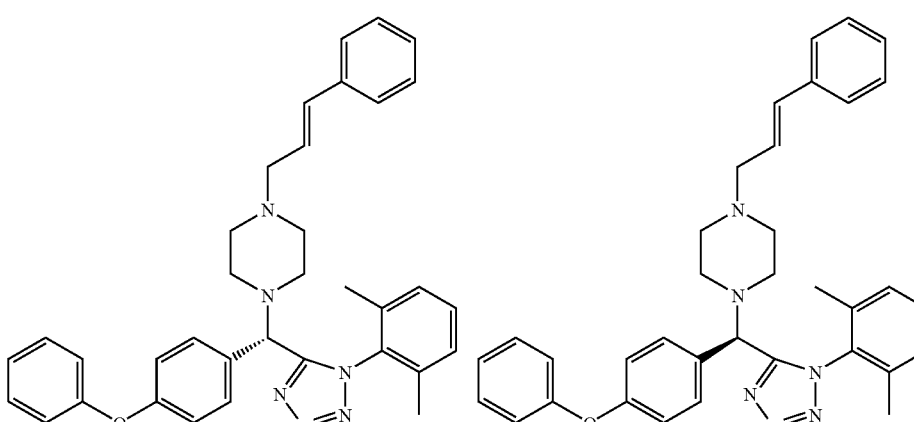<br>1-[[1-(2,6-dimethylphenyl)-1H-tetrazol-5-yl]-(4-phenoxyphenyl)methyl]-4-(3-phenylallyl)piperazine<br>MS m/z 557.3 (M + H); MW 556.7 |

TABLE 1-continued

| Compound No. | Structure |
|---|---|
| 77 | 1-[[1-(2,6-dimethylphenyl)-1H-tetrazol-5-yl]-(3-methoxyphenyl)methyl]-4-(3-phenylallyl)piperazine<br>MS m/z 495.31 (M + H); MW 494.6 |
| 78 | 1-[[1-(2,6-dimethylphenyl)-1H-tetrazol-5-yl]-(4-imidazol-1-ylphenyl)methyl]-4-(3-phenylallyl)piperazine<br>MS m/z 531.3 (M + H); MW 530.7 |
| 79 | 3-{[1-(2,6-dimethylphenyl)-1H-tetrazol-5-yl]-[4-(3-phenylallyl)piperazin-1-yl]methyl}benzonitrile<br>MS m/z 490.28 (M + H); MW 489.6 |

TABLE 1-continued
| Compound No. | Structure |
| --- | --- |
| 80 | 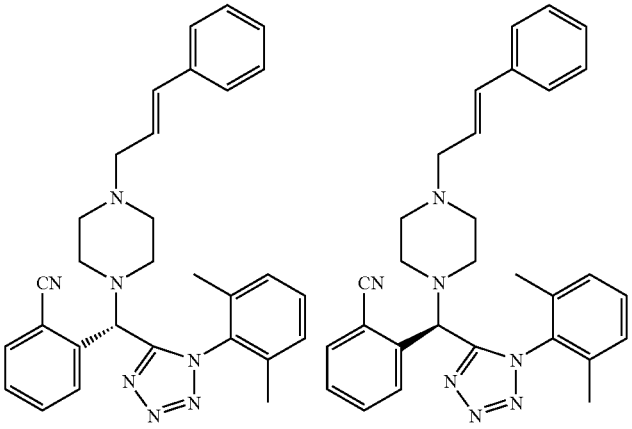
2-{[1-(2,6-dimethylphenyl)-1H-tetrazol-5-yl]-[4-(3-phenylallyl)piperazin-1-yl]methyl}benzonitrile
MS m/z 490.31 (M + H); MW 489.6 |
| 81 | 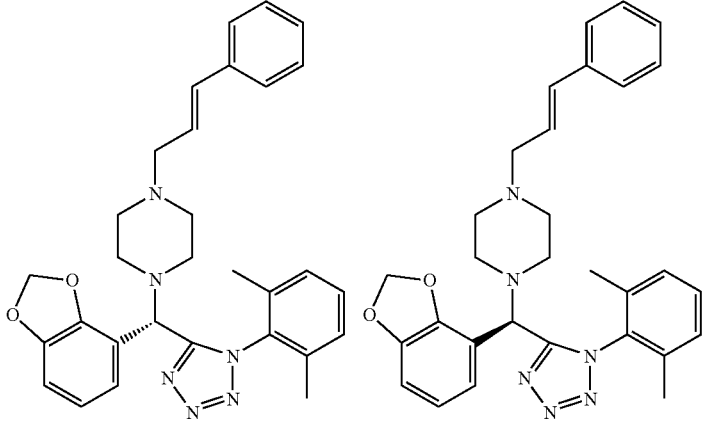
1-{benzo[1,3]dioxol-4-yl-[1-(2,6-dimethylphenyl)-1H-tetrazol-5-yl]methyl}-4-(3-phenylallyl)piperazine
MS m/z repeat (M + H); MW 508 |
| 82 | 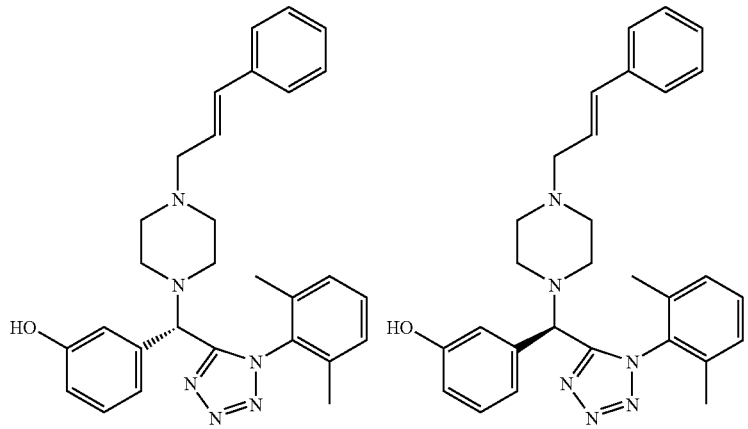
3-{[1-(2,6-dimethylphenyl)-1H-tetrazol-5-yl]-[4-(3-phenylallyl)piperazin-1-yl]methyl}phenol
MS m/z 481.3 (M + H); MW 480.6 |

TABLE 1-continued
| Compound No. | Structure |
|---|---|
| 83 | 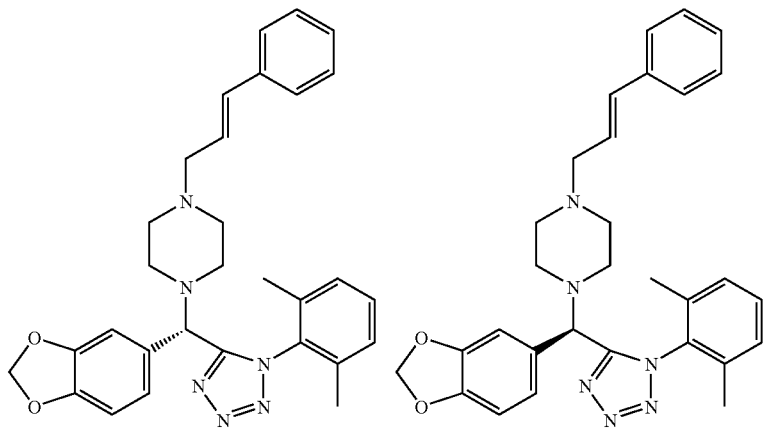<br>1-{benzo[1,3]dioxol-5-yl-[1-(2,6-dimethylphenyl)-1H-tetrazol-5-yl]methyl}-4-(3-phenylallyl)piperazine<br>MS m/z 509.3 (M + H); MW 508.6 |
| 84 | 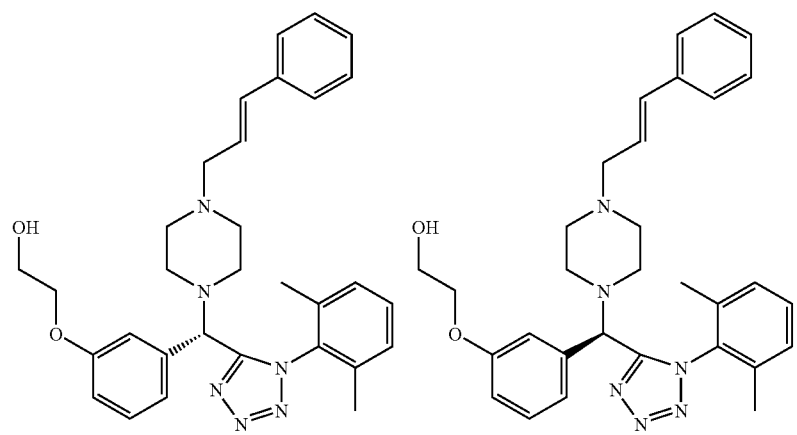<br>2-(3-{[1-(2,6-dimethylphenyl)-1H-tetrazol-5-yl]-[4-(3-phenylallyl)piperazin-1-yl]methyl}phenoxy)ethanol<br>MS m/z repeat (M + H); MW 524.67 |
| 85 | 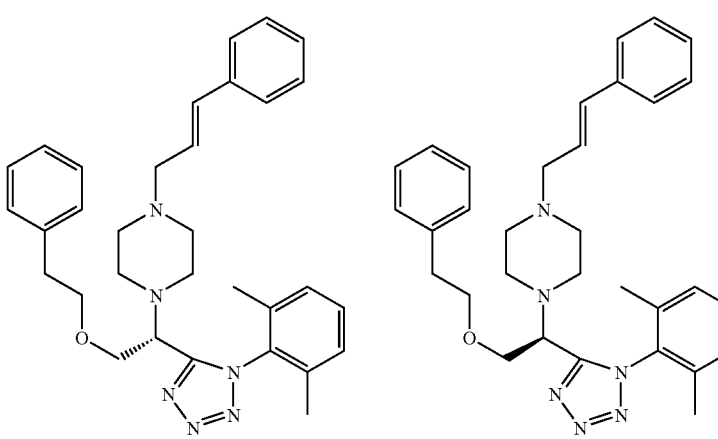<br>1-{1-[1-(2,6-dimethylphenyl)-1H-tetrazol-5-yl]-2-phenethyloxyethyl}-4-(3-phenylallyl)piperazine<br>MS m/z 523.35 (M + H); MW 522.7 |

TABLE 1-continued
| Compound No. | Structure |
|---|---|
| 86 | 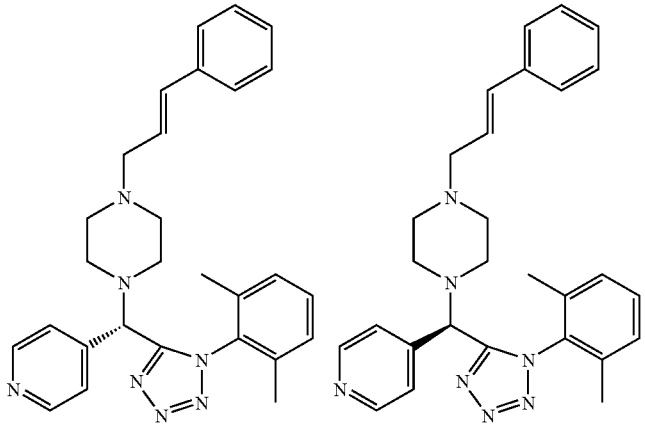
1-{[1-(2,6-dimethylphenyl)-1H-tetrazol-5-yl]pyridin-4-ylmethyl}-4-(3-phenylallyl)piperazine
MS m/z 466.31 (M + H); MW 465.6 |
| 87 | 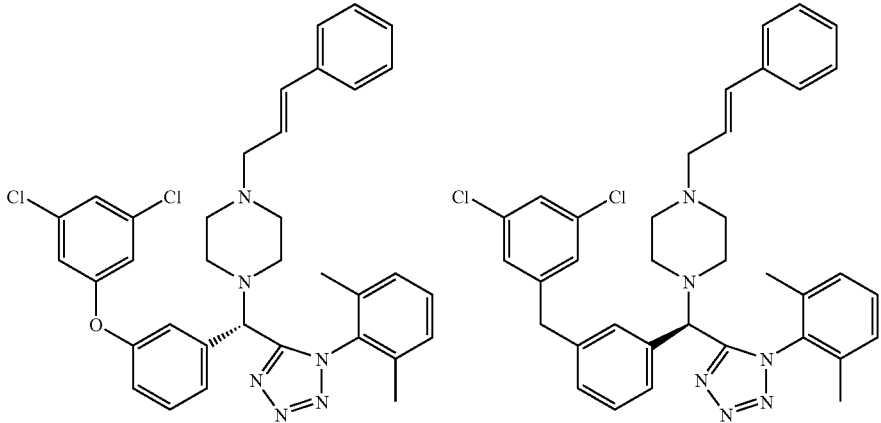
1-{[3-(3,5-dichloro-phenoxy)-phenyl]-[1-(2,6-dimethylphenyl)-1H-tetrazol-5-yl]methyl}-4-(3-phenylallyl)piperazine
MS m/z 625.25 (M + H); MW 625.6 |
| 91 | 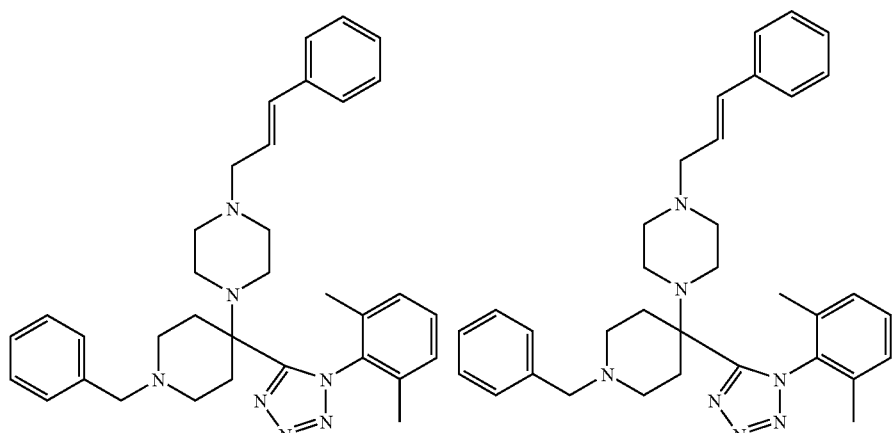
1-{1-benzyl-4-[1-(2,6-dimethylphenyl)-1H-tetrazol-5-yl]piperidin-4-yl}-4-(3-phenylallyl)piperazine
MS m/z xxxx (M + H); MW 547.7 |

TABLE 1-continued
| Compound No. | Structure |
|---|---|
| 92 | 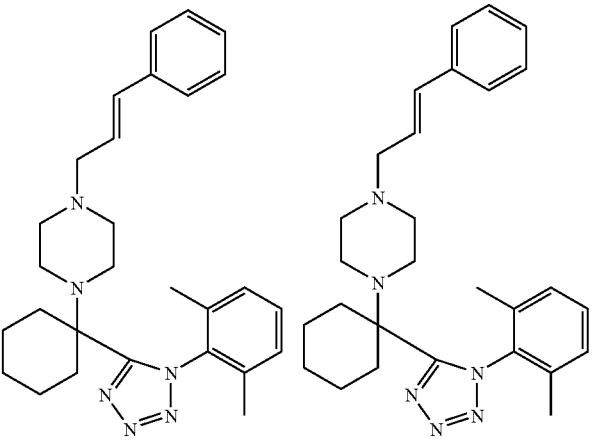<br>1-{1-[1-(2,6-dimethylphenyl)-1H-tetrazol-5-yl]cyclohexyl}-4-(3-phenylallyl)piperazine<br>MS m/z repeat (M + H); MW 456.64 |
| 99 | 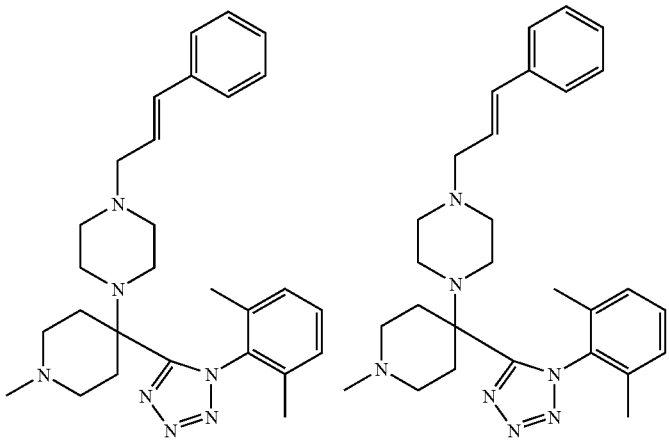<br>1-{4-[1-(2,6-dimethylphenyl)-1H-tetrazol-5-yl]-1-methylpiperidin-4-yl}-4-(3-phenylallyl)piperazine<br>MS m/z xxxx (M + H); MW 471.6 |
| 103 | 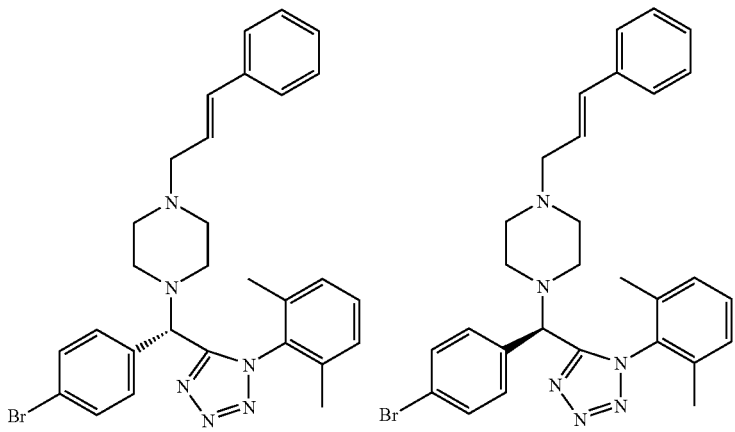<br>1-{(4-bromophenyl)-[1-(2,6-dimethylphenyl)-1H-tetrazol-5-yl]methyl}-4-(3-phenylallyl)piperazine<br>MS m/z 543.2 (M + H); MW 543.5 |

TABLE 1-continued
| Compound No. | Structure |
|---|---|
| 116 | 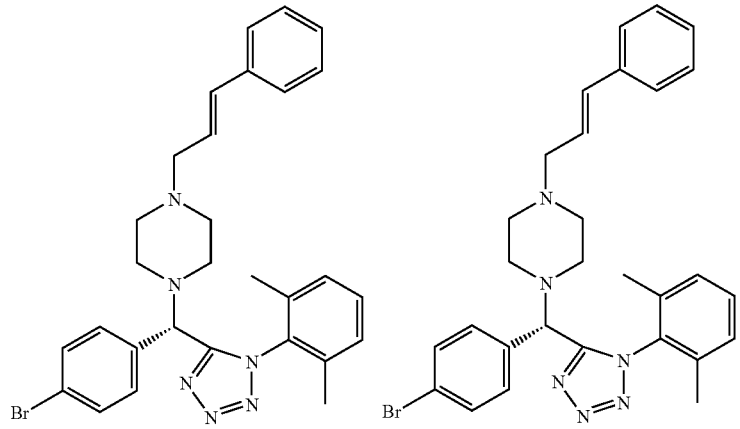<br>1-{(4-bromophenyl)-[1-(2,6-dimethylphenyl)-1H-tetrazol-5-yl]methyl}-4-(3-phenylallyl)piperazine<br>MS m/z 543.2 (M + H); MW 543.5 |
| 118 | 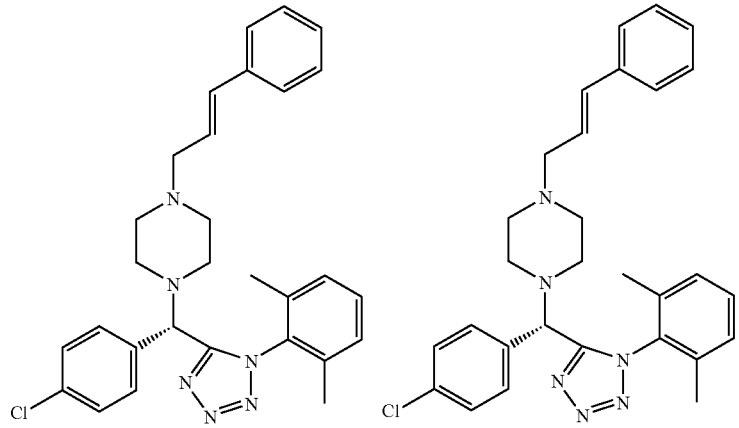<br>1-{(4-chlorophenyl)-[1-(2,6-dimethylphenyl)-1H-tetrazol-5-yl]methyl}-4-(3-phenylallyl)piperazine<br>MS m/z 499.27 (M + H); MW 499.1 |
| 119 | 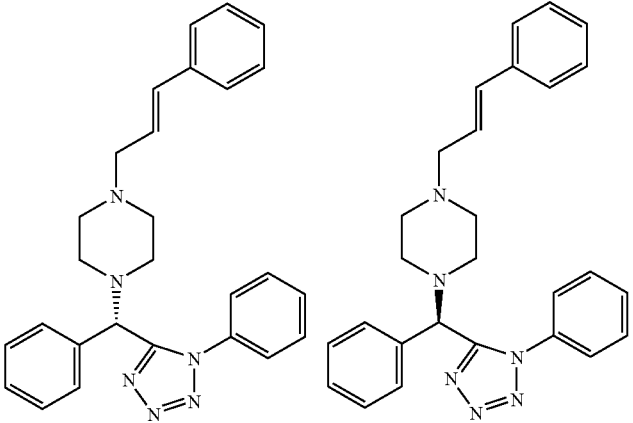<br>1-(3-phenylallyl)-4-[phenyl-(1-phenyl-1H-tetrazol-5-yl)methyl]piperazine<br>MS m/z 503.3 (M + H); MW 436.5 |

TABLE 1-continued
| Compound No. | Structure |
|---|---|
| 121 | 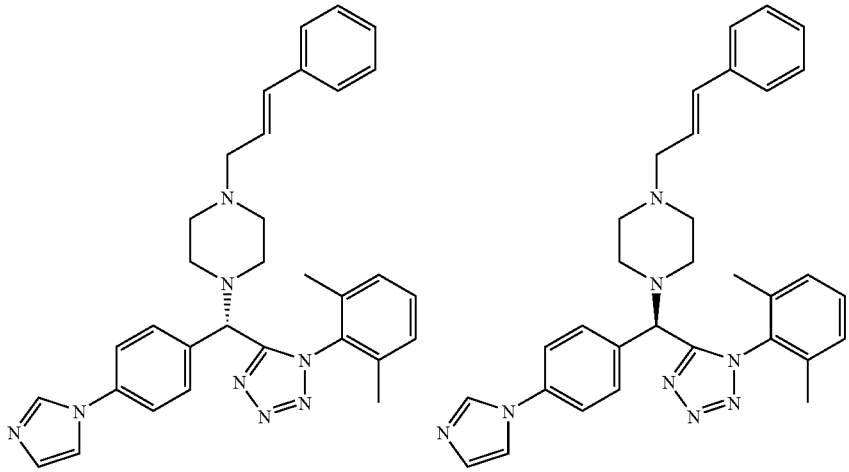<br>1-[(4-imidazol-1-ylphenyl)-(1-phenyl-1H-tetrazol-5-yl)methyl]-4-(3-phenylallyl)piperazine<br>MS m/z 503.3 (M + H); MW 502.6 |
| 122 | 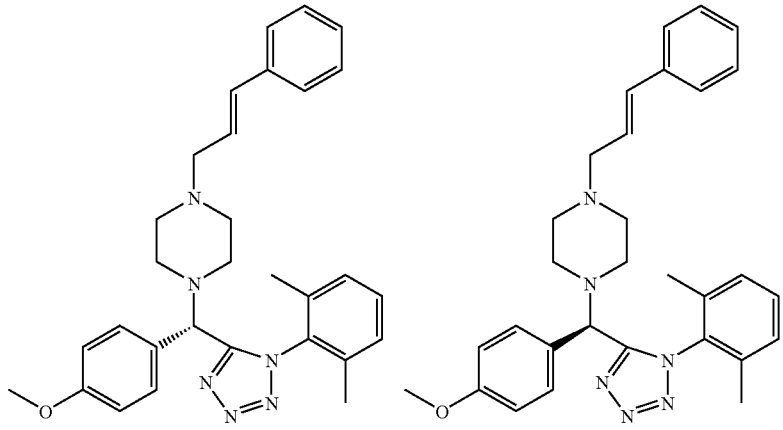<br>1-[[1-(2,6-dimethylphenyl)-1H-tetrazol-5-yl]-(4-methoxyphenyl)methyl]-4-(3-phenylallyl)piperazine<br>MS m/z 495.31 (M + H); MW 494.6 |
| 123 | 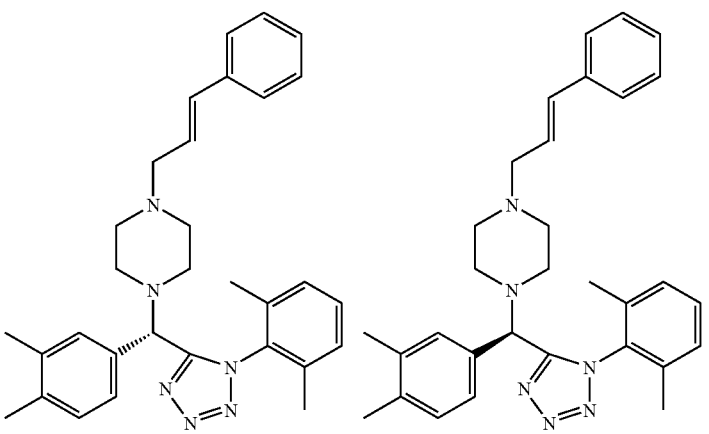<br>1-{(3,4-dimethylphenyl)-[1-(2,6-dimethylphenyl)-1H-tetrazol-5-yl]methyl}-4-(3-phenylallyl)piperazine<br>MS m/z 493.31 (M + H); MW 492.7 |

TABLE 1-continued
| Compound No. | Structure |
|---|---|
| 124 | 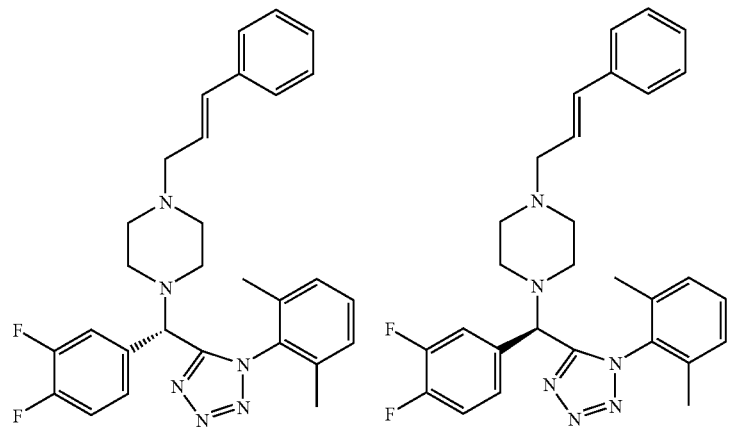 1-{(3,4-difluorophenyl)-[1-(2,6-dimethylphenyl)-1H-tetrazol-5-yl]methyl}-4-(3-phenylallyl)piperazine<br>MS m/z 501.27 (M + H); MW 500.6 |
| 125 | 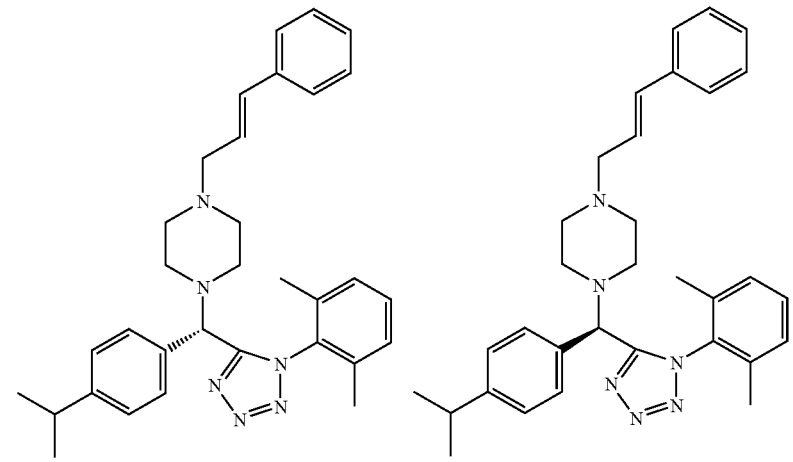 1-[[1-(2,6-dimethylphenyl)-1H-tetrazol-5-yl]-(4-isopropylphenyl)methyl]-4-(3-phenylallyl)piperazine<br>MS m/z 507.34 (M + H); MW 506.7 |
| 126 | 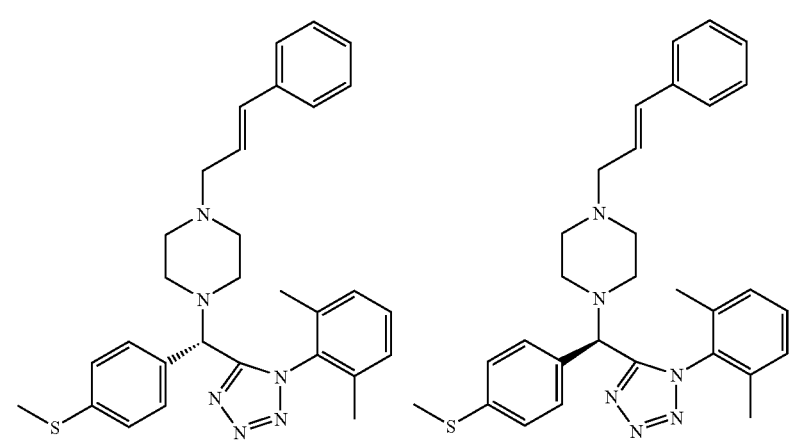 1-[[1-(2,6-dimethylphenyl)-1H-tetrazol-5-yl]-(4-methylsulfanylphenyl)methyl]-4-(3-phenylallyl)piperazine<br>MS m/z 511.28 (M + H); MW 510.7 |

TABLE 1-continued
| Compound No. | Structure |
|---|---|
| 127 | 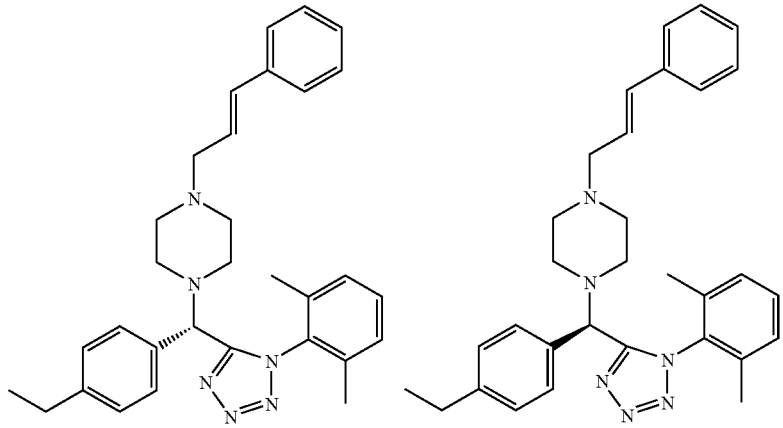<br>1-[[1-(2,6-dimethylphenyl)-1H-tetrazol-5-yl]-(4-ethylphenyl)methyl]-4-(3-phenylallyl)piperazine<br>MS m/z 493.32 (M + H); MW 492.7 |
| 128 | 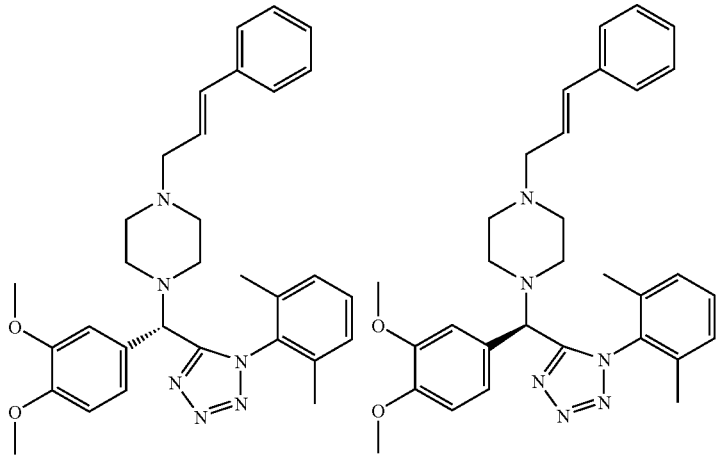<br>1-{(3,4-dimethoxyphenyl)-[1-(2,6-dimethylphenyl)-1H-tetrazol-5-yl]methyl}-4-(3-phenylallyl)piperazine<br>MS m/z 525.33 (M + H); MW 524.7 |

TABLE 1-continued
| Compound No. | Structure |
|---|---|
| 129 | 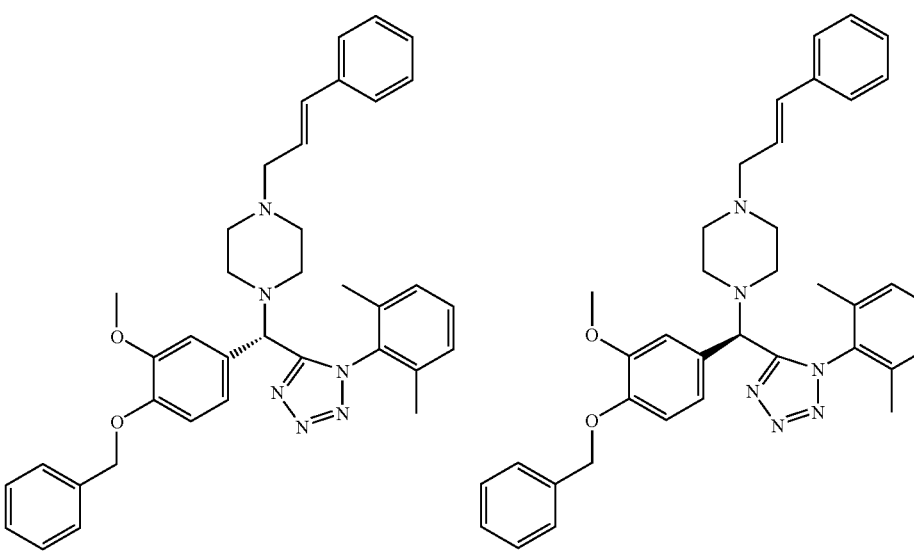<br>1-{(4-benzyloxy-3-methoxyphenyl)-[1-(2,6-dimethylphenyl)-1H-tetrazol-5-yl]methyl}-4-(3-phenylallyl)piperazine<br>MS m/z 601.35 (M + H); MW 600.8 |
| 130 | 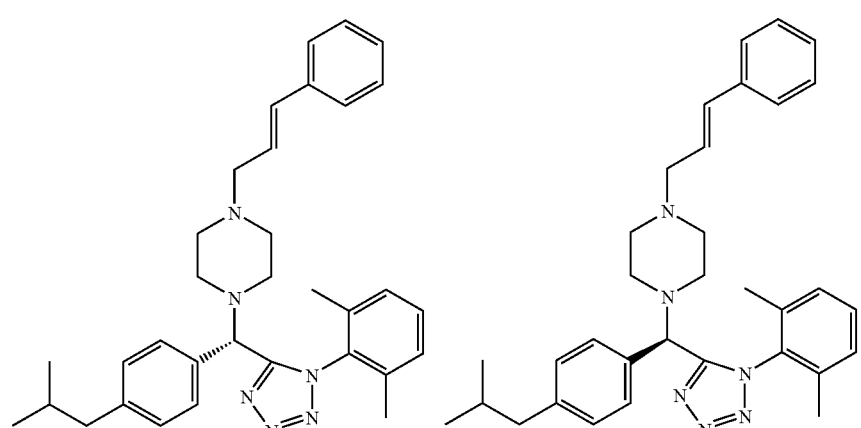<br>1-[[1-(2,6-dimethylphenyl)-1H-tetrazol-5-yl]-(4-isobutylphenyl)methyl]-4-(3-phenylallyl)piperazine<br>MS m/z 521.35 (M + H); MW 520.7 |

TABLE 1-continued
| Compound No. | Structure |
|---|---|
| 131 | 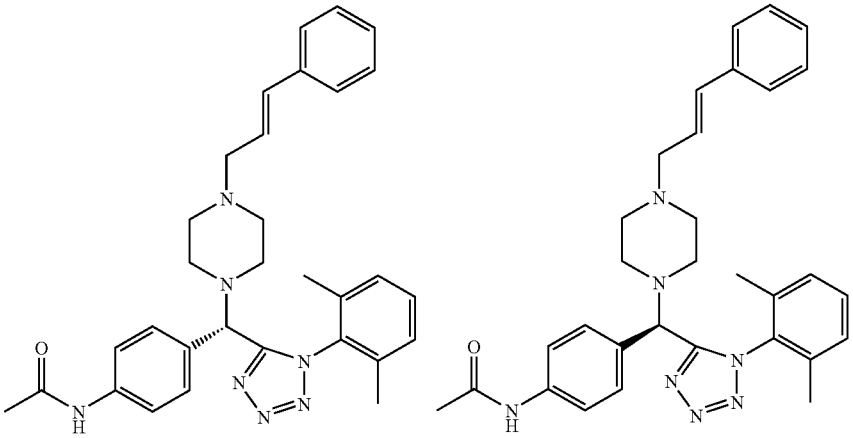<br>n-(4-{[1-(2,6-dimethylphenyl)-1H-tetrazol-5-yl]-[4-(3-phenylallyl)piperazin-1-yl]methyl}phenyl)acetamide<br>MS m/z 522.31 (M + H); MW 521.7 |
| 133 | 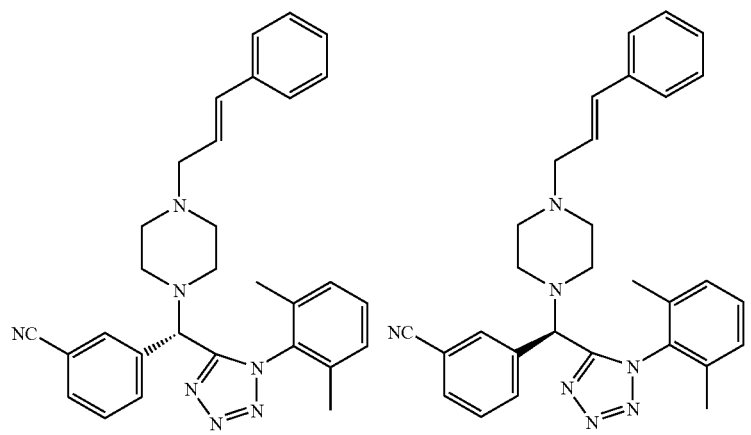<br>3-{[1-(2,6-dimethylphenyl)-1H-tetrazol-5-yl]-[4-(3-phenylallyl)piperazin-1-yl]methyl}benzonitrile<br>MS m/z 490.300 (M + H); MW 489.6 |
| 134 | 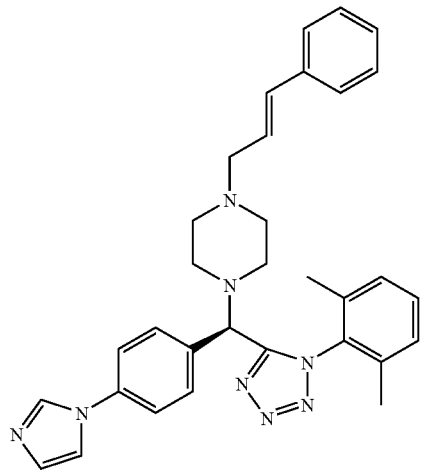<br>1-[[1-(2,6-dimethylphenyl)-1H-tetrazol-5-yl]-(4-imidazol-1-ylphenyl)methyl]-4-(3-phenylallyl)piperazine<br>MS m/z 531.33 (M + H); MW 530.7 |

TABLE 1-continued
| Compound No. | Structure |
|---|---|
| 135 | 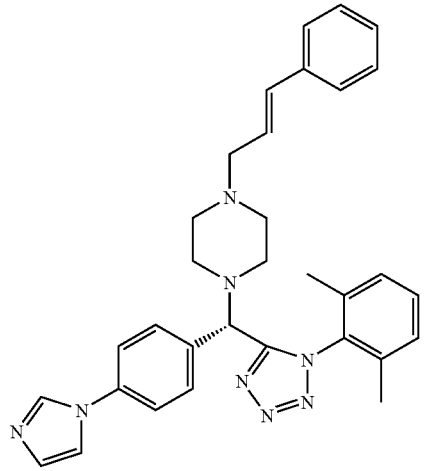<br>1-[[1-(2,6-dimethylphenyl)-1H-tetrazol-5-yl]-(4-imidazol-1-ylphenyl)methyl]-4-(3-phenylallyl)piperazine<br>MS m/z 531.33 (M + H); MW 530.7 |
| 136 | 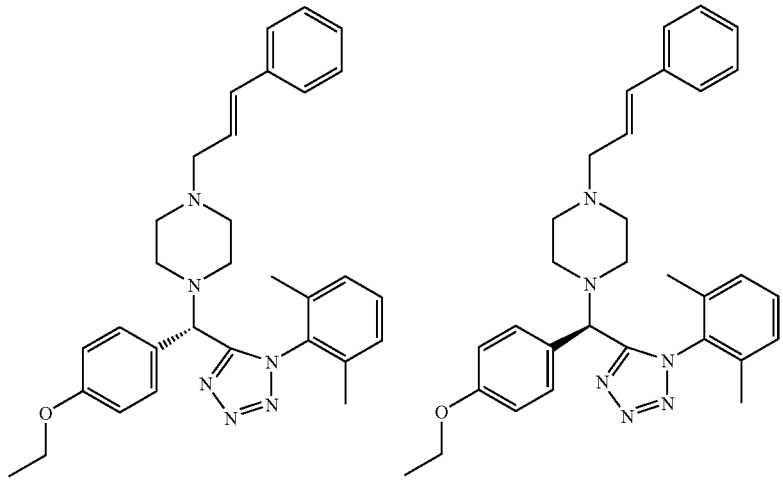<br>1-[[1-(2,6-dimethylphenyl)-1H-tetrazol-5-yl]-(4-ethoxyphenyl)methyl]-4-(3-phenylallyl)piperazine<br>MS m/z 509.32 (M + H); MW 508.7 |

TABLE 1-continued
| Compound No. | Structure |
|---|---|
| 137 | 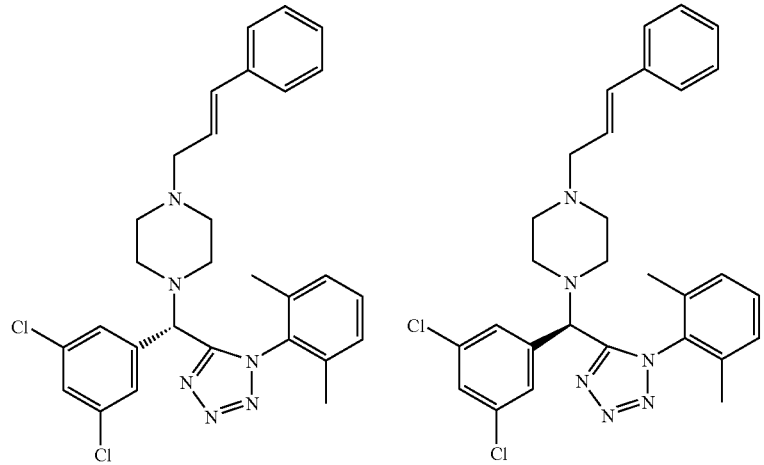<br>1-{(3,5-dichlorophenyl)-[1-(2,6-dimethylphenyl)-1H-tetrazol-5-yl]methyl}-4-(3-phenylallyl)piperazine<br>MS m/z 533.23 (M + H); MW 533.5 |
| 138 | 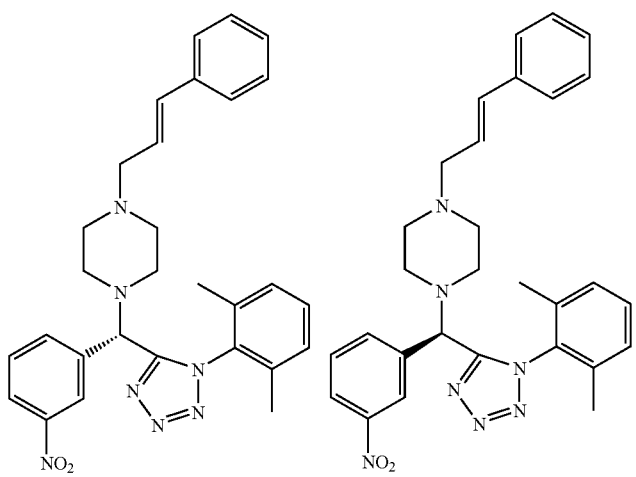<br>1-[[1-(2,6-dimethylphenyl)-1H-tetrazol-5-yl]-(3-nitrophenyl)methyl]-4-(3-phenylallyl)piperazine<br>MS m/z 510.29 (M + H); MW 509.6 |

TABLE 1-continued
| Compound No. | Structure |
|---|---|
| 139 | 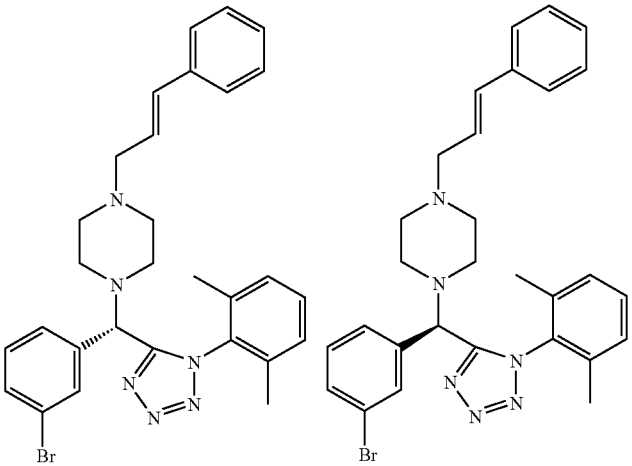<br>1-{(3-bromophenyl)-[1-(2,6-dimethylphenyl)-1H-tetrazol-5-yl]methyl}-4-(3-phenylallyl)piperazine<br>MS m/z 543.22 (M + H); MW 543.5 |
| 140 | 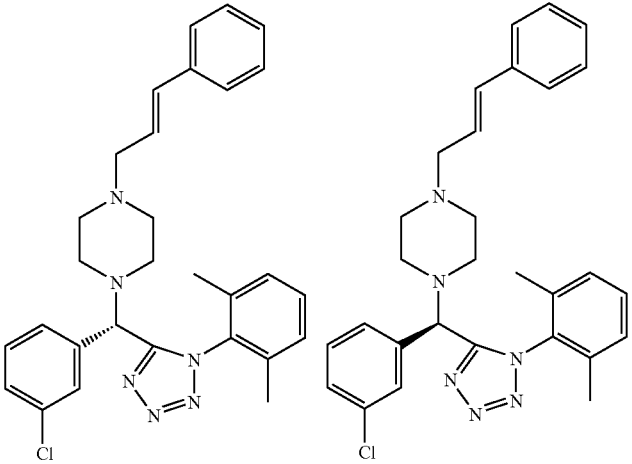<br>1-{(3-chlorophenyl)-[1-(2,6-dimethylphenyl)-1H-tetrazol-5-yl]methyl}-4-(3-phenylallyl)piperazine<br>MS m/z 500.26 (M + H); MW 499.1 |
| 142 | 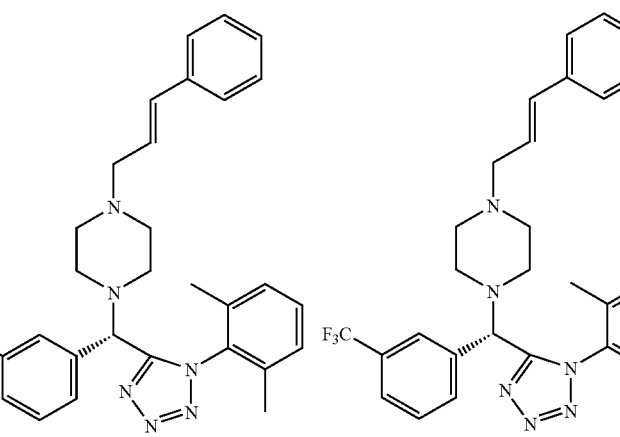<br>1-[[1-(2,6-dimethylphenyl)-1H-tetrazol-5-yl]-(3-trifluoromethylphenyl)methyl]-4-(3-phenylallyl)piperazine<br>MS m/z 533.27 (M + H); MW 532.6 |

TABLE 1-continued
| Compound No. | Structure |
| --- | --- |
| 143 | 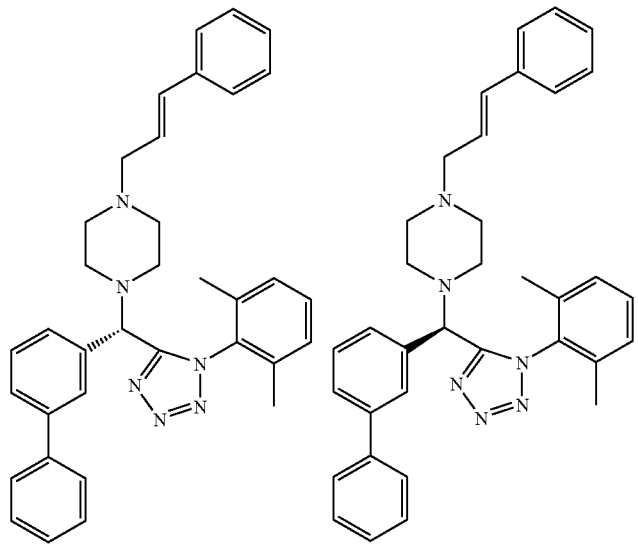
1-{biphenyl-3-yl-[1-(2,6-dimethylphenyl)-1H-tetrazol-5-yl]methyl}-4-(3-phenylallyl)piperazine
MS m/z 541.34 (M + H); MW 540.7 |
| 144 | 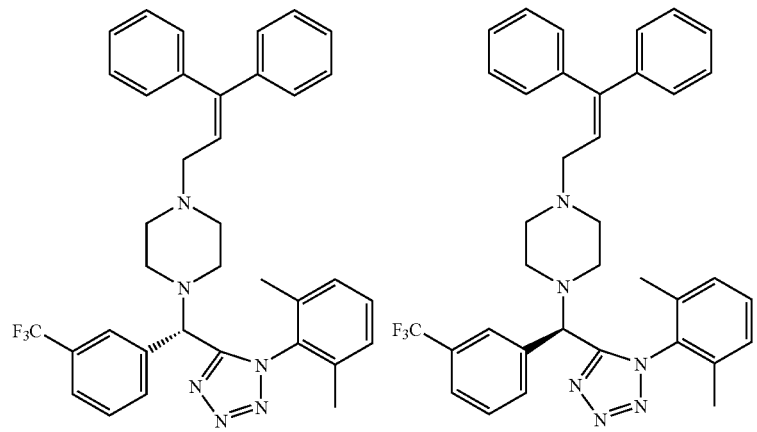
1-[[1-(2,6-dimethylphenyl)-1H-tetrazol-5-yl]-(3-trifluoromethylphenyl)methyl]-4-(3,3-diphenylallyl)piperazine
MS m/z 609.32 (M + H); MW 608.7 |

TABLE 1-continued

| Compound No. | Structure |
|---|---|
| 147 | 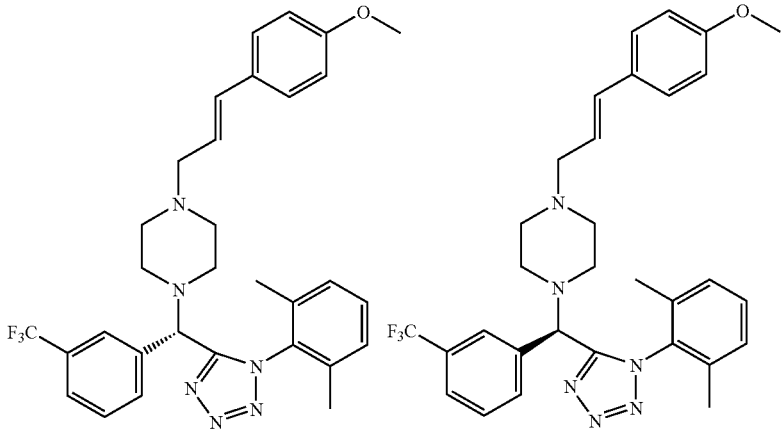<br>1-[[1-(2,6-dimethylphenyl)-1H-tetrazol-5-yl]-(3-trifluoromethylphenyl)methyl]-4-[3-(4-methoxyphenyl)allyl]piperazine<br>MS m/z 563.29 (M + H); MW 562.6 |
| 148 | 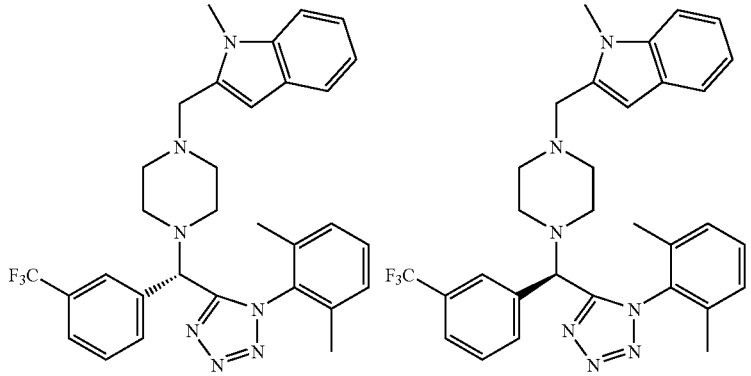<br>2-{4-[[1-(2,6-dimethylphenyl)-1H-tetrazol-5-yl]-(3-trifluoromethylphenyl)methyl]piperazin-1-ylmethyl}-1-methyl-1H-indole<br>MS m/z 560.32 (M + H); MW 559.6 |
| 150 | 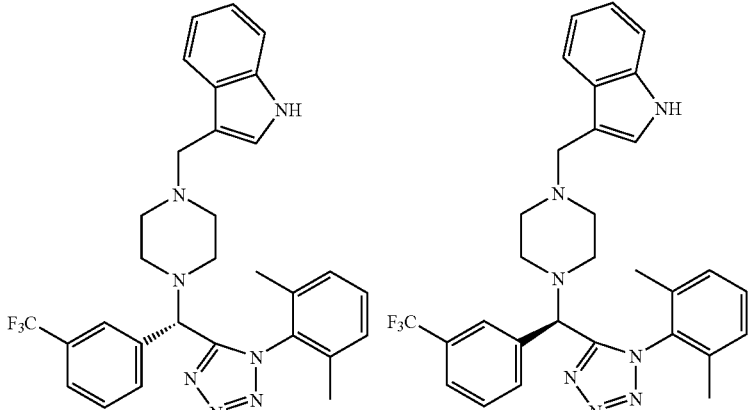<br>3-{4-[[1-(2,6-dimethylphenyl)-1H-tetrazol-5-yl]-(3-trifluoromethylphenyl)methyl]piperazin-1-ylmethyl}-1H-indole<br>MS m/z 417.23 (M + H); MW 545.6 |

TABLE 1-continued
| Compound No. | Structure |
|---|---|
| 151 | 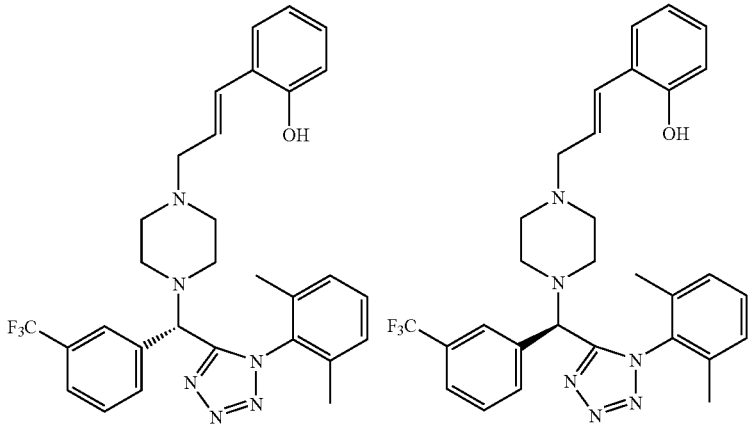
2-(3-{4-[[1-(2,6-dimethylphenyl)-1H-tetrazol-5-yl]-(3-trifluoromethylphenyl)methyl]piperazin-1-yl}propenyl)phenol
MS m/z 549.30 (M + H); MW 548.6 |
| 154 | 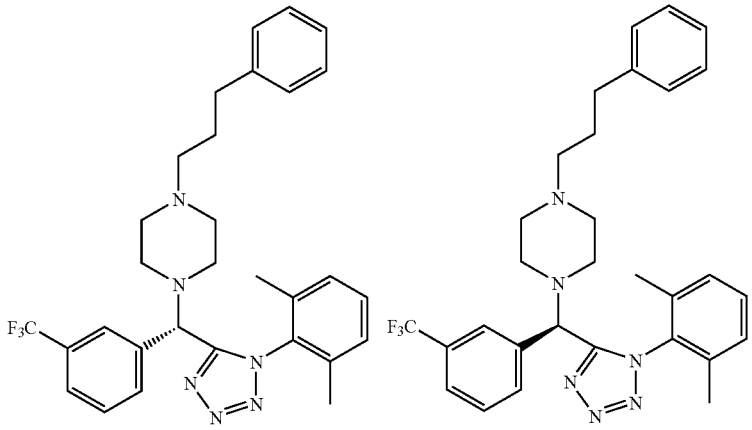
1-[[1-(2,6-dimethylphenyl)-1H-tetrazol-5-yl]-(3-trifluoromethylphenyl)methyl]-4-(3-phenylpropyl)piperazine
MS m/z 535.3 (M + H); MW 534.6 |
| 156 | 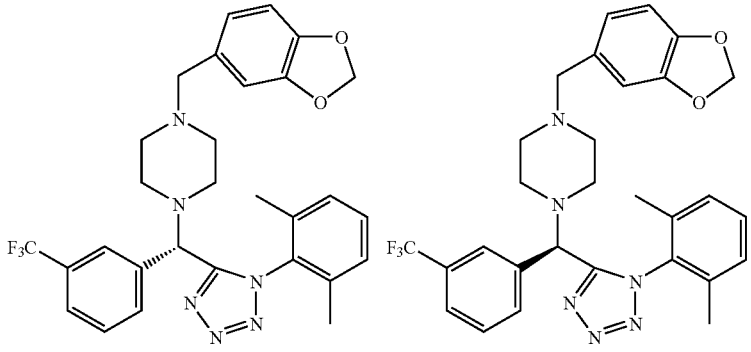
1-benzo[1,3]dioxol-5-ylmethyl-4-[[1-(2,6-dimethylphenyl)-1H-tetrazol-5-yl]-(3-trifluoromethylphenyl)methyl]piperazine
MS m/z 551.25 (M + H); MW 550.6 |

TABLE 1-continued

| Compound No. | Structure |
|---|---|
| 162 | 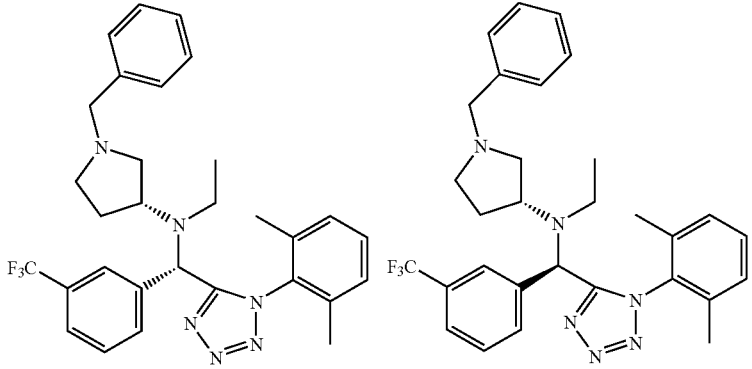<br>(1-benzylpyrrolidin-3-yl)-[[1-(2,6-dimethylphenyl)-1H-tetrazol-5-yl]-(3-trifluoromethylphenyl)methyl]ethylamine<br>MS m/z 535.29 (M + H); MW 534.6 |
| 163 | 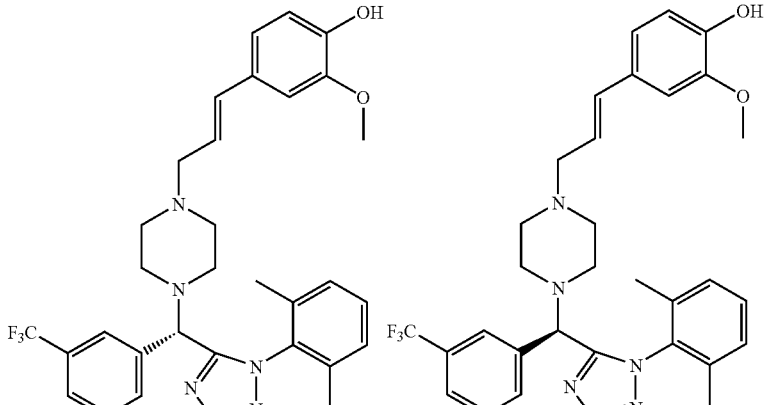<br>4-(3-{4-[[1-(2,6-dimethylphenyl)-1H-tetrazol-5-yl]-(3-trifluoromethylphenyl)methyl]piperazin-1-yl}propenyl)-2-methoxyphenol<br>MS m/z 579.31 (M + H); MW 578.6 |
| 164 | 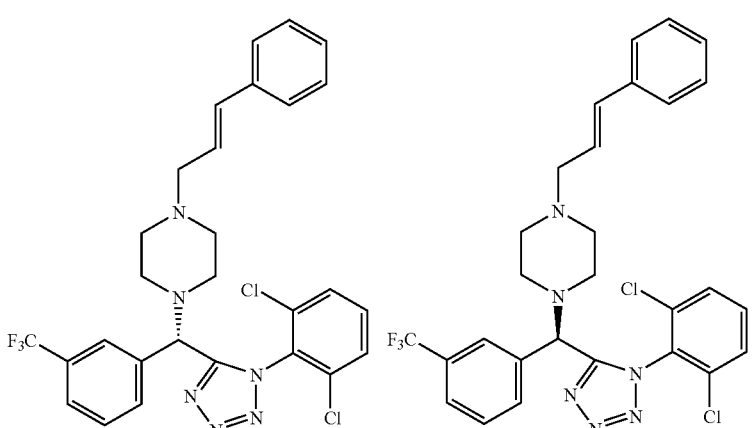<br>1-[[1-(2,6-dichlorophenyl)-1H-tetrazol-5-yl]-(3-trifluoromethylphenyl)methyl]-4-(3-phenylallyl)piperazine<br>MS m/z xxxx (M + H); MW 573.4 |

In another embodiment, the compound of Formula I is selected from the group of compounds of Formula V having the formula

TABLE 2

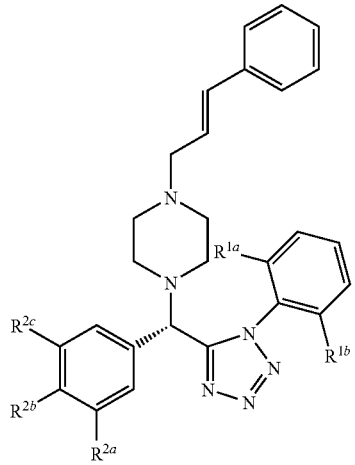

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 200 | H | CH$_3$ | CH$_3$ | H | H |
| 201 | H | CH$_3$ | CH$_3$ | CH$_3$ | H |
| 202 | H | CH$_3$ | CH$_3$ | OCH$_3$ | H |
| 203 | H | CH$_3$ | CH$_3$ | Cl | H |
| 204 | H | CH$_3$ | CH$_3$ | Br | H |
| 205 | H | CH$_3$ | CH$_3$ | F | H |
| 206 | H | CH$_3$ | CH$_3$ | H | CH$_3$ |
| 207 | H | CH$_3$ | CH$_3$ | CH$_3$ | CH$_3$ |
| 208 | H | CH$_3$ | CH$_3$ | H | OCH$_3$ |
| 209 | H | CH$_3$ | CH$_3$ | CH$_3$ | OCH$_3$ |
| 210 | H | CH$_3$ | CH$_3$ | OCH$_3$ | OCH$_3$ |
| 211 | H | CH$_3$ | CH$_3$ | Cl | OCH$_3$ |
| 212 | H | CH$_3$ | CH$_3$ | Br | OCH$_3$ |
| 213 | H | CH$_3$ | CH$_3$ | F | OCH$_3$ |
| 214 | H | CH$_3$ | CH$_3$ | H | Cl |
| 215 | H | CH$_3$ | CH$_3$ | CH$_3$ | Cl |
| 216 | H | CH$_3$ | CH$_3$ | OCH$_3$ | Cl |
| 217 | H | CH$_3$ | CH$_3$ | Cl | Cl |
| 218 | H | CH$_3$ | CH$_3$ | Br | Cl |
| 219 | H | CH$_3$ | CH$_3$ | F | Cl |
| 220 | H | CH$_3$ | CH$_3$ | H | Br |
| 221 | H | CH$_3$ | CH$_3$ | CH$_3$ | Br |
| 222 | H | CH$_3$ | CH$_3$ | OCH$_3$ | Br |
| 223 | H | CH$_3$ | CH$_3$ | Cl | Br |
| 224 | H | CH$_3$ | CH$_3$ | Br | Br |
| 225 | H | CH$_3$ | CH$_3$ | F | Br |
| 226 | H | CH$_3$ | CH$_3$ | H | F |
| 227 | H | CH$_3$ | CH$_3$ | CH$_3$ | F |
| 228 | H | CH$_3$ | CH$_3$ | OCH$_3$ | F |
| 229 | H | CH$_3$ | CH$_3$ | Cl | F |
| 230 | H | CH$_3$ | CH$_3$ | Br | F |
| 231 | H | CH$_3$ | CH$_3$ | F | F |
| 232 | H | CH$_3$ | OCH$_3$ | H | H |
| 233 | H | CH$_3$ | OCH$_3$ | CH$_3$ | H |
| 234 | H | CH$_3$ | OCH$_3$ | OCH$_3$ | H |
| 235 | H | CH$_3$ | OCH$_3$ | Cl | H |
| 236 | H | CH$_3$ | OCH$_3$ | Br | H |
| 237 | H | CH$_3$ | OCH$_3$ | F | H |
| 238 | H | CH$_3$ | OCH$_3$ | H | CH$_3$ |
| 239 | H | CH$_3$ | OCH$_3$ | CH$_3$ | CH$_3$ |
| 240 | H | CH$_3$ | OCH$_3$ | OCH$_3$ | CH$_3$ |
| 241 | H | CH$_3$ | OCH$_3$ | Cl | CH$_3$ |
| 242 | H | CH$_3$ | OCH$_3$ | Br | CH$_3$ |
| 243 | H | CH$_3$ | OCH$_3$ | F | CH$_3$ |
| 244 | H | CH$_3$ | OCH$_3$ | H | OCH$_3$ |
| 245 | H | CH$_3$ | OCH$_3$ | OCH$_3$ | OCH$_3$ |

TABLE 2-continued

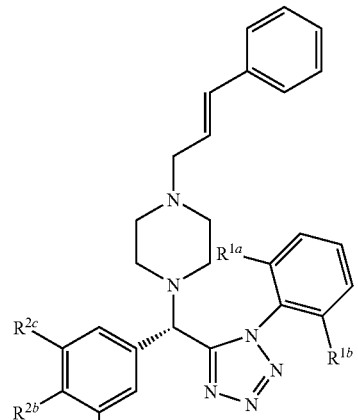

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 246 | H | CH$_3$ | OCH$_3$ | H | Cl |
| 247 | H | CH$_3$ | OCH$_3$ | CH$_3$ | Cl |
| 248 | H | CH$_3$ | OCH$_3$ | OCH$_3$ | Cl |
| 249 | H | CH$_3$ | OCH$_3$ | Cl | Cl |
| 250 | H | CH$_3$ | OCH$_3$ | Br | Cl |
| 251 | H | CH$_3$ | OCH$_3$ | F | Cl |
| 252 | H | CH$_3$ | OCH$_3$ | H | Br |
| 253 | H | CH$_3$ | OCH$_3$ | CH$_3$ | Br |
| 254 | H | CH$_3$ | OCH$_3$ | OCH$_3$ | Br |
| 255 | H | CH$_3$ | OCH$_3$ | Cl | Br |
| 256 | H | CH$_3$ | OCH$_3$ | Br | Br |
| 257 | H | CH$_3$ | OCH$_3$ | F | Br |
| 258 | H | CH$_3$ | OCH$_3$ | H | F |
| 259 | H | CH$_3$ | OCH$_3$ | CH$_3$ | F |
| 260 | H | CH$_3$ | OCH$_3$ | OCH$_3$ | F |
| 261 | H | CH$_3$ | OCH$_3$ | Cl | F |
| 262 | H | CH$_3$ | OCH$_3$ | Br | F |
| 263 | H | CH$_3$ | OCH$_3$ | F | F |
| 264 | H | CH$_3$ | Cl | H | H |
| 265 | H | CH$_3$ | Cl | CH$_3$ | H |
| 266 | H | CH$_3$ | Cl | OCH$_3$ | H |
| 267 | H | CH$_3$ | Cl | Cl | H |
| 268 | H | CH$_3$ | Cl | Br | H |
| 269 | H | CH$_3$ | Cl | F | H |
| 270 | H | CH$_3$ | Cl | H | CH$_3$ |
| 271 | H | CH$_3$ | Cl | CH$_3$ | CH$_3$ |
| 272 | H | CH$_3$ | Cl | OCH$_3$ | CH$_3$ |
| 273 | H | CH$_3$ | Cl | Cl | CH$_3$ |
| 274 | H | CH$_3$ | Cl | Br | CH$_3$ |
| 275 | H | CH$_3$ | Cl | F | CH$_3$ |
| 276 | H | CH$_3$ | Cl | H | OCH$_3$ |
| 277 | H | CH$_3$ | Cl | CH$_3$ | OCH$_3$ |
| 278 | H | CH$_3$ | Cl | OCH$_3$ | OCH$_3$ |
| 279 | H | CH$_3$ | Cl | Cl | OCH$_3$ |
| 280 | H | CH$_3$ | Cl | Br | OCH$_3$ |
| 281 | H | CH$_3$ | Cl | F | OCH$_3$ |
| 282 | H | CH$_3$ | Cl | H | Cl |
| 283 | H | CH$_3$ | Cl | Cl | Cl |
| 284 | H | CH$_3$ | Cl | H | Br |
| 285 | H | CH$_3$ | Cl | CH$_3$ | Br |
| 286 | H | CH$_3$ | Cl | OCH$_3$ | Br |
| 287 | H | CH$_3$ | Cl | Cl | Br |
| 288 | H | CH$_3$ | Cl | Br | Br |
| 289 | H | CH$_3$ | Cl | F | Br |
| 290 | H | CH$_3$ | Cl | H | F |
| 291 | H | CH$_3$ | Cl | CH$_3$ | F |
| 292 | H | CH$_3$ | Cl | OCH$_3$ | F |
| 293 | H | CH$_3$ | Cl | Cl | F |
| 294 | H | CH$_3$ | Cl | F | F |
| 295 | H | CH$_3$ | Br | H | H |

TABLE 2-continued

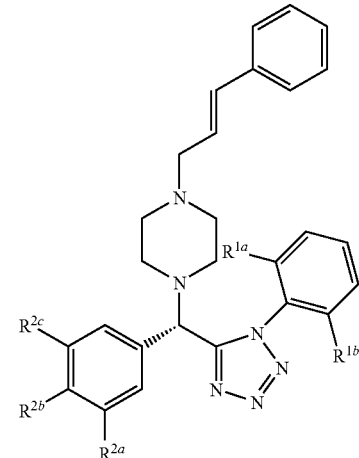

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 296 | H | CH₃ | Br | CH₃ | H |
| 297 | H | CH₃ | Br | OCH₃ | H |
| 298 | H | CH₃ | Br | Cl | H |
| 299 | H | CH₃ | Br | Br | H |
| 300 | H | CH₃ | Br | F | H |
| 301 | H | CH₃ | Br | H | CH₃ |
| 302 | H | CH₃ | Br | CH₃ | CH₃ |
| 303 | H | CH₃ | Br | OCH₃ | CH₃ |
| 304 | H | CH₃ | Br | Cl | CH₃ |
| 305 | H | CH₃ | Br | Br | CH₃ |
| 306 | H | CH₃ | Br | F | CH₃ |
| 307 | H | CH₃ | Br | H | OCH₃ |
| 308 | H | CH₃ | Br | CH₃ | OCH₃ |
| 309 | H | CH₃ | Br | OCH₃ | OCH₃ |
| 310 | H | CH₃ | Br | Cl | OCH₃ |
| 311 | H | CH₃ | Br | Br | OCH₃ |
| 312 | H | CH₃ | Br | F | OCH₃ |
| 313 | H | CH₃ | Br | H | Cl |
| 314 | H | CH₃ | Br | CH₃ | Cl |
| 315 | H | CH₃ | Br | OCH₃ | Cl |
| 316 | H | CH₃ | Br | Cl | Cl |
| 317 | H | CH₃ | Br | Br | Cl |
| 318 | H | CH₃ | Br | F | Cl |
| 319 | H | CH₃ | Br | H | Br |
| 320 | H | CH₃ | Br | Br | Br |
| 321 | H | CH₃ | Br | H | F |
| 322 | H | CH₃ | Br | CH₃ | F |
| 323 | H | CH₃ | Br | OCH₃ | F |
| 324 | H | CH₃ | Br | Cl | F |
| 325 | H | CH₃ | Br | Br | F |
| 326 | H | CH₃ | Br | F | F |
| 327 | H | CH₃ | F | H | H |
| 328 | H | CH₃ | F | CH₃ | H |
| 329 | H | CH₃ | F | OCH₃ | H |
| 330 | H | CH₃ | F | Cl | H |
| 331 | H | CH₃ | F | Br | H |
| 332 | H | CH₃ | F | F | H |
| 333 | H | CH₃ | F | H | CH₃ |
| 334 | H | CH₃ | F | CH₃ | CH₃ |
| 335 | H | CH₃ | F | OCH₃ | CH₃ |
| 336 | H | CH₃ | F | Cl | CH₃ |
| 337 | H | CH₃ | F | Br | CH₃ |
| 338 | H | CH₃ | F | F | CH₃ |
| 339 | H | CH₃ | F | H | OCH₃ |
| 340 | H | CH₃ | F | CH₃ | OCH₃ |
| 341 | H | CH₃ | F | OCH₃ | OCH₃ |
| 342 | H | CH₃ | F | Cl | OCH₃ |
| 343 | H | CH₃ | F | Br | OCH₃ |
| 344 | H | CH₃ | F | F | OCH₃ |
| 345 | H | CH₃ | F | H | Cl |

TABLE 2-continued

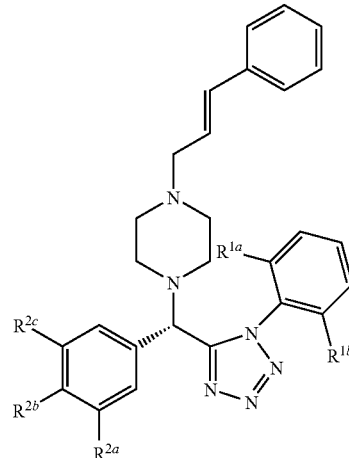

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 346 | H | CH₃ | F | CH₃ | Cl |
| 347 | H | CH₃ | F | OCH₃ | Cl |
| 348 | H | CH₃ | F | Cl | Cl |
| 349 | H | CH₃ | F | Br | Cl |
| 350 | H | CH₃ | F | F | Cl |
| 351 | H | CH₃ | F | H | Br |
| 352 | H | CH₃ | F | CH₃ | Br |
| 353 | H | CH₃ | F | OCH₃ | Br |
| 354 | H | CH₃ | F | Cl | Br |
| 355 | H | CH₃ | F | Br | Br |
| 356 | H | CH₃ | F | F | Br |
| 357 | H | CH₃ | F | H | F |
| 358 | H | CH₃ | F | F | F |
| 359 | H | OCH₃ | CH₃ | H | H |
| 360 | H | OCH₃ | CH₃ | H | CH₃ |
| 361 | H | OCH₃ | CH₃ | H | OCH₃ |
| 362 | H | OCH₃ | CH₃ | H | Cl |
| 363 | H | OCH₃ | CH₃ | H | Br |
| 364 | H | OCH₃ | CH₃ | H | F |
| 365 | H | OCH₃ | CH₃ | CH₃ | H |
| 366 | H | OCH₃ | CH₃ | CH₃ | CH₃ |
| 367 | H | OCH₃ | CH₃ | CH₃ | OCH₃ |
| 368 | H | OCH₃ | CH₃ | CH₃ | Cl |
| 369 | H | OCH₃ | CH₃ | CH₃ | Br |
| 370 | H | OCH₃ | CH₃ | CH₃ | F |
| 371 | H | OCH₃ | CH₃ | OCH₃ | H |
| 372 | H | OCH₃ | CH₃ | OCH₃ | OCH₃ |
| 373 | H | OCH₃ | CH₃ | OCH₃ | Cl |
| 374 | H | OCH₃ | CH₃ | OCH₃ | Br |
| 375 | H | OCH₃ | CH₃ | OCH₃ | F |
| 376 | H | OCH₃ | CH₃ | Cl | H |
| 377 | H | OCH₃ | CH₃ | Cl | OCH₃ |
| 378 | H | OCH₃ | CH₃ | Cl | Cl |
| 379 | H | OCH₃ | CH₃ | Cl | Br |
| 380 | H | OCH₃ | CH₃ | Cl | F |
| 381 | H | OCH₃ | CH₃ | Br | H |
| 382 | H | OCH₃ | CH₃ | Br | OCH₃ |
| 383 | H | OCH₃ | CH₃ | Br | Cl |
| 384 | H | OCH₃ | CH₃ | Br | Br |
| 385 | H | OCH₃ | CH₃ | Br | F |
| 386 | H | OCH₃ | CH₃ | F | H |
| 387 | H | OCH₃ | CH₃ | F | OCH₃ |
| 388 | H | OCH₃ | CH₃ | F | Cl |
| 389 | H | OCH₃ | CH₃ | F | Br |
| 390 | H | OCH₃ | CH₃ | F | F |
| 391 | H | OCH₃ | OCH₃ | H | H |
| 392 | H | OCH₃ | OCH₃ | H | CH₃ |
| 393 | H | OCH₃ | OCH₃ | H | OCH₃ |
| 394 | H | OCH₃ | OCH₃ | H | Cl |
| 395 | H | OCH₃ | OCH₃ | H | Br |

TABLE 2-continued

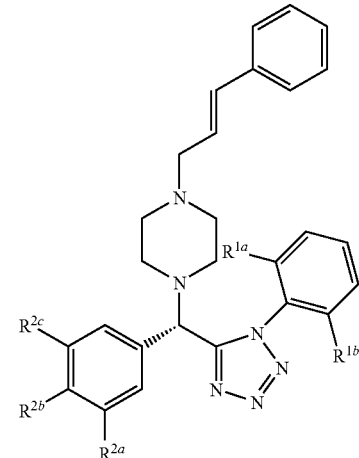

wherein $R^{1a}$, $R^{1b}$, $R^{2a}$, $R^{2b}$, and $R^{2c}$ are as defined in Table 2.

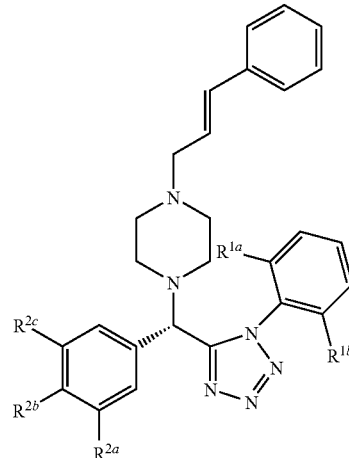

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ | Compound No. | $R^{1a}$ | $R^{1b}$ | $R^{2a}$ | $R^{2b}$ | $R^{2c}$ |
|---|---|---|---|---|---|---|---|---|---|---|---|
| 396 | H | OCH$_3$ | OCH$_3$ | H | F | 446 | H | OCH$_3$ | Cl | Br | CH$_3$ |
| 397 | H | OCH$_3$ | OCH$_3$ | CH$_3$ | H | 447 | H | OCH$_3$ | Cl | Br | OCH$_3$ |
| 398 | H | OCH$_3$ | OCH$_3$ | CH$_3$ | CH$_3$ | 448 | H | OCH$_3$ | Cl | Br | Br |
| 399 | H | OCH$_3$ | OCH$_3$ | CH$_3$ | Cl | 449 | H | OCH$_3$ | Cl | F | H |
| 400 | H | OCH$_3$ | OCH$_3$ | CH$_3$ | Br | 450 | H | OCH$_3$ | Cl | F | CH$_3$ |
| 401 | H | OCH$_3$ | OCH$_3$ | CH$_3$ | F | 451 | H | OCH$_3$ | Cl | F | OCH$_3$ |
| 402 | H | OCH$_3$ | OCH$_3$ | OCH$_3$ | H | 452 | H | OCH$_3$ | Cl | F | Br |
| 403 | H | OCH$_3$ | OCH$_3$ | OCH$_3$ | CH$_3$ | 453 | H | OCH$_3$ | Cl | F | F |
| 404 | H | OCH$_3$ | OCH$_3$ | OCH$_3$ | OCH$_3$ | 454 | H | OCH$_3$ | Br | H | H |
| 405 | H | OCH$_3$ | OCH$_3$ | OCH$_3$ | Cl | 455 | H | OCH$_3$ | Br | H | CH$_3$ |
| 406 | H | OCH$_3$ | OCH$_3$ | OCH$_3$ | Br | 456 | H | OCH$_3$ | Br | H | OCH$_3$ |
| 407 | H | OCH$_3$ | OCH$_3$ | OCH$_3$ | F | 457 | H | OCH$_3$ | Br | H | Cl |
| 408 | H | OCH$_3$ | OCH$_3$ | Cl | H | 458 | H | OCH$_3$ | Br | H | Br |
| 409 | H | OCH$_3$ | OCH$_3$ | Cl | CH$_3$ | 459 | H | OCH$_3$ | Br | H | F |
| 410 | H | OCH$_3$ | OCH$_3$ | Cl | Cl | 460 | H | OCH$_3$ | Br | CH$_3$ | H |
| 411 | H | OCH$_3$ | OCH$_3$ | Cl | Br | 461 | H | OCH$_3$ | Br | CH$_3$ | CH$_3$ |
| 412 | H | OCH$_3$ | OCH$_3$ | Cl | F | 462 | H | OCH$_3$ | Br | CH$_3$ | OCH$_3$ |
| 413 | H | OCH$_3$ | OCH$_3$ | Br | H | 463 | H | OCH$_3$ | Br | CH$_3$ | Cl |
| 414 | H | OCH$_3$ | OCH$_3$ | Br | CH$_3$ | 464 | H | OCH$_3$ | Br | CH$_3$ | F |
| 415 | H | OCH$_3$ | OCH$_3$ | Br | Cl | 465 | H | OCH$_3$ | Br | OCH$_3$ | H |
| 416 | H | OCH$_3$ | OCH$_3$ | Br | Br | 466 | H | OCH$_3$ | Br | OCH$_3$ | CH$_3$ |
| 417 | H | OCH$_3$ | OCH$_3$ | Br | F | 467 | H | OCH$_3$ | Br | OCH$_3$ | OCH$_3$ |
| 418 | H | OCH$_3$ | OCH$_3$ | F | H | 468 | H | OCH$_3$ | Br | OCH$_3$ | Cl |
| 419 | H | OCH$_3$ | OCH$_3$ | F | CH$_3$ | 469 | H | OCH$_3$ | Br | OCH$_3$ | F |
| 420 | H | OCH$_3$ | OCH$_3$ | F | Cl | 470 | H | OCH$_3$ | Br | Cl | H |
| 421 | H | OCH$_3$ | OCH$_3$ | F | Br | 471 | H | OCH$_3$ | Br | Cl | CH$_3$ |
| 422 | H | OCH$_3$ | OCH$_3$ | F | F | 472 | H | OCH$_3$ | Br | Cl | OCH$_3$ |
| 423 | H | OCH$_3$ | Cl | H | H | 473 | H | OCH$_3$ | Br | Cl | Cl |
| 424 | H | OCH$_3$ | Cl | H | CH$_3$ | 474 | H | OCH$_3$ | Br | Cl | F |
| 425 | H | OCH$_3$ | Cl | H | OCH$_3$ | 475 | H | OCH$_3$ | Br | Br | H |
| 426 | H | OCH$_3$ | Cl | H | Cl | 476 | H | OCH$_3$ | Br | Br | CH$_3$ |
| 427 | H | OCH$_3$ | Cl | H | Br | 477 | H | OCH$_3$ | Br | Br | OCH$_3$ |
| 428 | H | OCH$_3$ | Cl | H | F | 478 | H | OCH$_3$ | Br | Br | Cl |
| 429 | H | OCH$_3$ | Cl | CH$_3$ | H | 479 | H | OCH$_3$ | Br | Br | Br |
| 430 | H | OCH$_3$ | Cl | CH$_3$ | CH$_3$ | 480 | H | OCH$_3$ | Br | Br | F |
| 431 | H | OCH$_3$ | Cl | CH$_3$ | OCH$_3$ | 481 | H | OCH$_3$ | Br | F | H |
| 432 | H | OCH$_3$ | Cl | CH$_3$ | Br | 482 | H | OCH$_3$ | Br | F | CH$_3$ |
| 433 | H | OCH$_3$ | Cl | CH$_3$ | F | 483 | H | OCH$_3$ | Br | F | OCH$_3$ |
| 434 | H | OCH$_3$ | Cl | OCH$_3$ | H | 484 | H | OCH$_3$ | Br | F | Cl |
| 435 | H | OCH$_3$ | Cl | OCH$_3$ | CH$_3$ | 485 | H | OCH$_3$ | Br | F | F |
| 436 | H | OCH$_3$ | Cl | OCH$_3$ | OCH$_3$ | 486 | H | OCH$_3$ | F | H | H |
| 437 | H | OCH$_3$ | Cl | OCH$_3$ | Br | 487 | H | OCH$_3$ | F | H | CH$_3$ |
| 438 | H | OCH$_3$ | Cl | OCH$_3$ | F | 488 | H | OCH$_3$ | F | H | OCH$_3$ |
| 439 | H | OCH$_3$ | Cl | Cl | H | 489 | H | OCH$_3$ | F | H | Cl |
| 440 | H | OCH$_3$ | Cl | Cl | CH$_3$ | 490 | H | OCH$_3$ | F | H | Br |
| 441 | H | OCH$_3$ | Cl | Cl | OCH$_3$ | 491 | H | OCH$_3$ | F | H | F |
| 442 | H | OCH$_3$ | Cl | Cl | Cl | 492 | H | OCH$_3$ | F | CH$_3$ | H |
| 443 | H | OCH$_3$ | Cl | Cl | Br | 493 | H | OCH$_3$ | F | CH$_3$ | CH$_3$ |
| 444 | H | OCH$_3$ | Cl | Cl | F | 494 | H | OCH$_3$ | F | CH$_3$ | OCH$_3$ |
| 445 | H | OCH$_3$ | Cl | Br | H | 495 | H | OCH$_3$ | F | CH$_3$ | Cl |

TABLE 2-continued

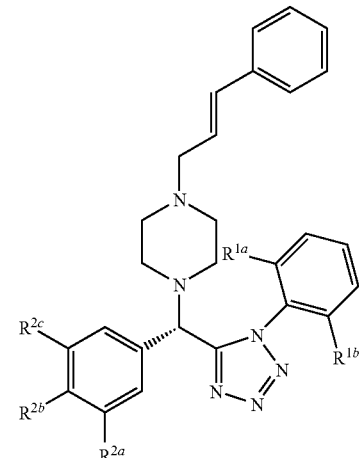

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 496 | H | OCH$_3$ | F | CH$_3$ | Br |
| 497 | H | OCH$_3$ | F | OCH$_3$ | H |
| 498 | H | OCH$_3$ | F | OCH$_3$ | CH$_3$ |
| 499 | H | OCH$_3$ | F | OCH$_3$ | OCH$_3$ |
| 500 | H | OCH$_3$ | F | OCH$_3$ | Cl |
| 501 | H | OCH$_3$ | F | OCH$_3$ | Br |
| 502 | H | OCH$_3$ | F | Cl | H |
| 503 | H | OCH$_3$ | F | Cl | CH$_3$ |
| 504 | H | OCH$_3$ | F | Cl | OCH$_3$ |
| 505 | H | OCH$_3$ | F | Cl | Cl |
| 506 | H | OCH$_3$ | F | Cl | Br |
| 507 | H | OCH$_3$ | F | Br | H |
| 508 | H | OCH$_3$ | F | Br | CH$_3$ |
| 509 | H | OCH$_3$ | F | Br | OCH$_3$ |
| 510 | H | OCH$_3$ | F | Br | Cl |
| 511 | H | OCH$_3$ | F | Br | Br |
| 512 | H | OCH$_3$ | F | F | H |
| 513 | H | OCH$_3$ | F | F | CH$_3$ |
| 514 | H | OCH$_3$ | F | F | OCH$_3$ |
| 515 | H | OCH$_3$ | F | F | Cl |
| 516 | H | OCH$_3$ | F | F | Br |
| 517 | H | OCH$_3$ | F | F | F |
| 518 | H | Cl | CH$_3$ | H | H |
| 519 | H | Cl | CH$_3$ | H | CH$_3$ |
| 520 | H | Cl | CH$_3$ | H | OCH$_3$ |
| 521 | H | Cl | CH$_3$ | H | Cl |
| 522 | H | Cl | CH$_3$ | H | Br |
| 523 | H | Cl | CH$_3$ | H | F |
| 524 | H | Cl | CH$_3$ | CH$_3$ | H |
| 525 | H | Cl | CH$_3$ | CH$_3$ | CH$_3$ |
| 526 | H | Cl | CH$_3$ | CH$_3$ | OCH$_3$ |
| 527 | H | Cl | CH$_3$ | CH$_3$ | Cl |
| 528 | H | Cl | CH$_3$ | CH$_3$ | Br |
| 529 | H | Cl | CH$_3$ | CH$_3$ | F |
| 530 | H | Cl | CH$_3$ | OCH$_3$ | H |
| 531 | H | Cl | CH$_3$ | OCH$_3$ | OCH$_3$ |
| 532 | H | Cl | CH$_3$ | OCH$_3$ | Cl |
| 533 | H | Cl | CH$_3$ | OCH$_3$ | Br |
| 534 | H | Cl | CH$_3$ | OCH$_3$ | F |
| 535 | H | Cl | CH$_3$ | Cl | H |
| 536 | H | Cl | CH$_3$ | Cl | OCH$_3$ |
| 537 | H | Cl | CH$_3$ | Cl | Cl |
| 538 | H | Cl | CH$_3$ | Cl | Br |
| 539 | H | Cl | CH$_3$ | Cl | F |
| 540 | H | Cl | CH$_3$ | Br | H |
| 541 | H | Cl | CH$_3$ | Br | OCH$_3$ |
| 542 | H | Cl | CH$_3$ | Br | Cl |
| 543 | H | Cl | CH$_3$ | Br | Br |
| 544 | H | Cl | CH$_3$ | Br | F |
| 545 | H | Cl | CH$_3$ | F | H |

TABLE 2-continued

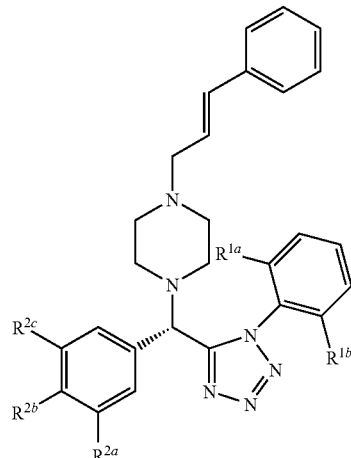

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 546 | H | Cl | CH$_3$ | F | OCH$_3$ |
| 547 | H | Cl | CH$_3$ | F | Cl |
| 548 | H | Cl | CH$_3$ | F | Br |
| 549 | H | Cl | CH$_3$ | F | F |
| 550 | H | Cl | OCH$_3$ | H | H |
| 551 | H | Cl | OCH$_3$ | H | CH$_3$ |
| 552 | H | Cl | OCH$_3$ | H | OCH$_3$ |
| 553 | H | Cl | OCH$_3$ | H | Cl |
| 554 | H | Cl | OCH$_3$ | H | Br |
| 555 | H | Cl | OCH$_3$ | H | F |
| 556 | H | Cl | OCH$_3$ | CH$_3$ | H |
| 557 | H | Cl | OCH$_3$ | CH$_3$ | CH$_3$ |
| 558 | H | Cl | OCH$_3$ | CH$_3$ | Cl |
| 559 | H | Cl | OCH$_3$ | CH$_3$ | Br |
| 560 | H | Cl | OCH$_3$ | CH$_3$ | F |
| 561 | H | Cl | OCH$_3$ | OCH$_3$ | H |
| 562 | H | Cl | OCH$_3$ | OCH$_3$ | CH$_3$ |
| 563 | H | Cl | OCH$_3$ | OCH$_3$ | OCH$_3$ |
| 564 | H | Cl | OCH$_3$ | OCH$_3$ | Cl |
| 565 | H | Cl | OCH$_3$ | OCH$_3$ | Br |
| 566 | H | Cl | OCH$_3$ | OCH$_3$ | F |
| 567 | H | Cl | OCH$_3$ | Cl | H |
| 568 | H | Cl | OCH$_3$ | Cl | CH$_3$ |
| 569 | H | Cl | OCH$_3$ | Cl | Cl |
| 570 | H | Cl | OCH$_3$ | Cl | Br |
| 571 | H | Cl | OCH$_3$ | Cl | F |
| 572 | H | Cl | OCH$_3$ | Br | H |
| 573 | H | Cl | OCH$_3$ | Br | CH$_3$ |
| 574 | H | Cl | OCH$_3$ | Br | Cl |
| 575 | H | Cl | OCH$_3$ | Br | Br |
| 576 | H | Cl | OCH$_3$ | Br | F |
| 577 | H | Cl | OCH$_3$ | F | H |
| 578 | H | Cl | OCH$_3$ | F | CH$_3$ |
| 579 | H | Cl | OCH$_3$ | F | Cl |
| 580 | H | Cl | OCH$_3$ | F | Br |
| 581 | H | Cl | OCH$_3$ | F | F |
| 582 | H | Cl | Cl | H | H |
| 583 | H | Cl | Cl | H | CH$_3$ |
| 584 | H | Cl | Cl | H | OCH$_3$ |
| 585 | H | Cl | Cl | H | Cl |
| 586 | H | Cl | Cl | H | Br |
| 587 | H | Cl | Cl | H | F |
| 588 | H | Cl | Cl | CH$_3$ | H |
| 589 | H | Cl | Cl | CH$_3$ | CH$_3$ |
| 590 | H | Cl | Cl | CH$_3$ | OCH$_3$ |
| 591 | H | Cl | Cl | CH$_3$ | Br |
| 592 | H | Cl | Cl | CH$_3$ | F |
| 593 | H | Cl | Cl | OCH$_3$ | H |
| 594 | H | Cl | Cl | OCH$_3$ | CH$_3$ |
| 595 | H | Cl | Cl | OCH$_3$ | OCH$_3$ |

TABLE 2-continued

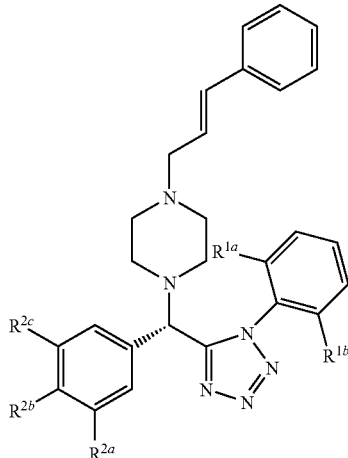

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 596 | H | Cl | Cl | OCH₃ | Br |
| 597 | H | Cl | Cl | OCH₃ | F |
| 598 | H | Cl | Cl | Cl | H |
| 599 | H | Cl | Cl | Cl | CH₃ |
| 600 | H | Cl | Cl | Cl | OCH₃ |
| 601 | H | Cl | Cl | Cl | Cl |
| 602 | H | Cl | Cl | Cl | Br |
| 603 | H | Cl | Cl | Cl | F |
| 604 | H | Cl | Cl | Br | H |
| 605 | H | Cl | Cl | Br | CH₃ |
| 606 | H | Cl | Cl | Br | OCH₃ |
| 607 | H | Cl | Cl | Br | Br |
| 608 | H | Cl | Cl | F | H |
| 609 | H | Cl | Cl | F | CH₃ |
| 610 | H | Cl | Cl | F | OCH₃ |
| 611 | H | Cl | Cl | F | Br |
| 612 | H | Cl | Cl | F | F |
| 613 | H | Cl | Br | H | H |
| 614 | H | Cl | Br | H | CH₃ |
| 615 | H | Cl | Br | H | OCH₃ |
| 616 | H | Cl | Br | H | Cl |
| 617 | H | Cl | Br | H | Br |
| 618 | H | Cl | Br | H | F |
| 619 | H | Cl | Br | CH₃ | H |
| 620 | H | Cl | Br | CH₃ | CH₃ |
| 621 | H | Cl | Br | CH₃ | OCH₃ |
| 622 | H | Cl | Br | CH₃ | Cl |
| 623 | H | Cl | Br | CH₃ | F |
| 624 | H | Cl | Br | OCH₃ | H |
| 625 | H | Cl | Br | OCH₃ | CH₃ |
| 626 | H | Cl | Br | OCH₃ | OCH₃ |
| 627 | H | Cl | Br | OCH₃ | Cl |
| 628 | H | Cl | Br | OCH₃ | F |
| 629 | H | Cl | Br | Cl | H |
| 630 | H | Cl | Br | Cl | CH₃ |
| 631 | H | Cl | Br | Cl | OCH₃ |
| 632 | H | Cl | Br | Cl | Cl |
| 633 | H | Cl | Br | Cl | F |
| 634 | H | Cl | Br | Br | H |
| 635 | H | Cl | Br | Br | CH₃ |
| 636 | H | Cl | Br | Br | OCH₃ |
| 637 | H | Cl | Br | Br | Cl |
| 638 | H | Cl | Br | Br | Br |
| 639 | H | Cl | Br | Br | F |
| 640 | H | Cl | Br | F | H |
| 641 | H | Cl | Br | F | CH₃ |
| 642 | H | Cl | Br | F | OCH₃ |
| 643 | H | Cl | Br | F | Cl |
| 644 | H | Cl | Br | F | F |
| 645 | H | Cl | F | H | H |

TABLE 2-continued

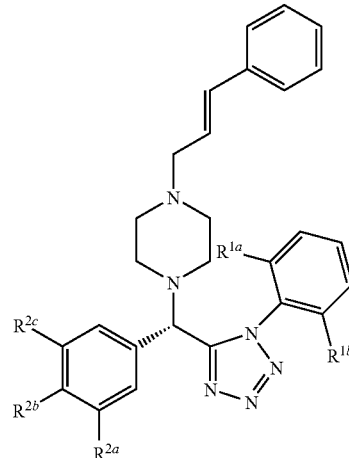

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 646 | H | Cl | F | H | CH₃ |
| 647 | H | Cl | F | H | OCH₃ |
| 648 | H | Cl | F | H | Cl |
| 649 | H | Cl | F | H | Br |
| 650 | H | Cl | F | H | F |
| 651 | H | Cl | F | CH₃ | H |
| 652 | H | Cl | F | CH₃ | CH₃ |
| 653 | H | Cl | F | CH₃ | OCH₃ |
| 654 | H | Cl | F | CH₃ | Cl |
| 655 | H | Cl | F | CH₃ | Br |
| 656 | H | Cl | F | OCH₃ | H |
| 657 | H | Cl | F | OCH₃ | CH₃ |
| 658 | H | Cl | F | OCH₃ | OCH₃ |
| 659 | H | Cl | F | OCH₃ | Cl |
| 660 | H | Cl | F | OCH₃ | Br |
| 661 | H | Cl | F | Cl | H |
| 662 | H | Cl | F | Cl | CH₃ |
| 663 | H | Cl | F | Cl | OCH₃ |
| 664 | H | Cl | F | Cl | Cl |
| 665 | H | Cl | F | Cl | Br |
| 666 | H | Cl | F | Br | H |
| 667 | H | Cl | F | Br | CH₃ |
| 668 | H | Cl | F | Br | OCH₃ |
| 669 | H | Cl | F | Br | Cl |
| 670 | H | Cl | F | Br | Br |
| 671 | H | Cl | F | F | H |
| 672 | H | Cl | F | F | CH₃ |
| 673 | H | Cl | F | F | OCH₃ |
| 674 | H | Cl | F | F | Cl |
| 675 | H | Cl | F | F | Br |
| 676 | H | Cl | F | F | F |
| 677 | H | Br | CH₃ | H | H |
| 678 | H | Br | CH₃ | H | CH₃ |
| 679 | H | Br | CH₃ | H | OCH₃ |
| 680 | H | Br | CH₃ | H | Cl |
| 681 | H | Br | CH₃ | H | Br |
| 682 | H | Br | CH₃ | H | F |
| 683 | H | Br | CH₃ | CH₃ | H |
| 684 | H | Br | CH₃ | CH₃ | CH₃ |
| 685 | H | Br | CH₃ | CH₃ | OCH₃ |
| 686 | H | Br | CH₃ | CH₃ | Cl |
| 687 | H | Br | CH₃ | CH₃ | Br |
| 688 | H | Br | CH₃ | CH₃ | F |
| 689 | H | Br | CH₃ | OCH₃ | H |
| 690 | H | Br | CH₃ | OCH₃ | OCH₃ |
| 691 | H | Br | CH₃ | OCH₃ | Cl |
| 692 | H | Br | CH₃ | OCH₃ | Br |
| 693 | H | Br | CH₃ | OCH₃ | F |
| 694 | H | Br | CH₃ | Cl | H |
| 695 | H | Br | CH₃ | Cl | OCH₃ |

TABLE 2-continued

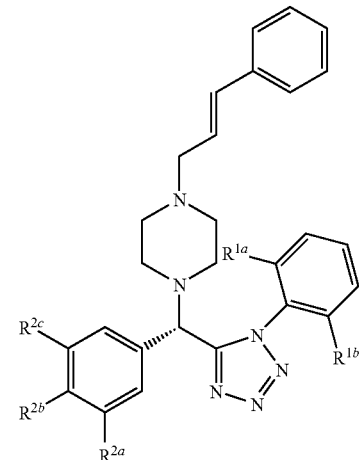

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 696 | H | Br | $CH_3$ | Cl | Cl |
| 697 | H | Br | $CH_3$ | Cl | Br |
| 698 | H | Br | $CH_3$ | Cl | F |
| 699 | H | Br | $CH_3$ | Br | H |
| 700 | H | Br | $CH_3$ | Br | $OCH_3$ |
| 701 | H | Br | $CH_3$ | Br | Cl |
| 702 | H | Br | $CH_3$ | Br | Br |
| 703 | H | Br | $CH_3$ | Br | F |
| 704 | H | Br | $CH_3$ | F | H |
| 705 | H | Br | $CH_3$ | F | $OCH_3$ |
| 706 | H | Br | $CH_3$ | F | Cl |
| 707 | H | Br | $CH_3$ | F | Br |
| 708 | H | Br | $CH_3$ | F | F |
| 709 | H | Br | $OCH_3$ | H | H |
| 710 | H | Br | $OCH_3$ | H | $CH_3$ |
| 711 | H | Br | $OCH_3$ | H | $OCH_3$ |
| 712 | H | Br | $OCH_3$ | H | Cl |
| 713 | H | Br | $OCH_3$ | H | Br |
| 714 | H | Br | $OCH_3$ | H | F |
| 715 | H | Br | $OCH_3$ | $CH_3$ | H |
| 716 | H | Br | $OCH_3$ | $CH_3$ | $CH_3$ |
| 717 | H | Br | $OCH_3$ | $CH_3$ | Cl |
| 718 | H | Br | $OCH_3$ | $CH_3$ | Br |
| 719 | H | Br | $OCH_3$ | $CH_3$ | F |
| 720 | H | Br | $OCH_3$ | $OCH_3$ | H |
| 721 | H | Br | $OCH_3$ | $OCH_3$ | $CH_3$ |
| 722 | H | Br | $OCH_3$ | $OCH_3$ | $OCH_3$ |
| 723 | H | Br | $OCH_3$ | $OCH_3$ | Cl |
| 724 | H | Br | $OCH_3$ | $OCH_3$ | Br |
| 725 | H | Br | $OCH_3$ | $OCH_3$ | F |
| 726 | H | Br | $OCH_3$ | Cl | H |
| 727 | H | Br | $OCH_3$ | Cl | $CH_3$ |
| 728 | H | Br | $OCH_3$ | Cl | Cl |
| 729 | H | Br | $OCH_3$ | Cl | Br |
| 730 | H | Br | $OCH_3$ | Cl | F |
| 731 | H | Br | $OCH_3$ | Br | H |
| 732 | H | Br | $OCH_3$ | Br | $CH_3$ |
| 733 | H | Br | $OCH_3$ | Br | Cl |
| 734 | H | Br | $OCH_3$ | Br | Br |
| 735 | H | Br | $OCH_3$ | Br | F |
| 736 | H | Br | $OCH_3$ | F | H |
| 737 | H | Br | $OCH_3$ | F | $CH_3$ |
| 738 | H | Br | $OCH_3$ | F | Cl |
| 739 | H | Br | $OCH_3$ | F | Br |
| 740 | H | Br | $OCH_3$ | F | F |
| 741 | H | Br | Cl | H | H |
| 742 | H | Br | Cl | H | $CH_3$ |
| 743 | H | Br | Cl | H | $OCH_3$ |
| 744 | H | Br | Cl | H | Cl |
| 745 | H | Br | Cl | H | Br |

TABLE 2-continued

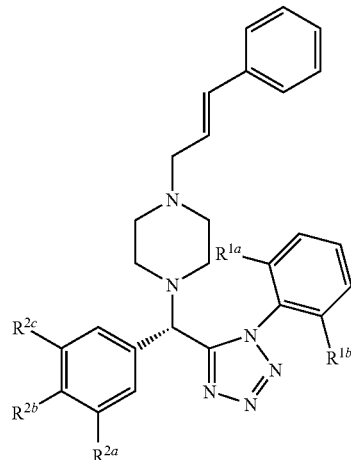

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 746 | H | Br | Cl | H | F |
| 747 | H | Br | Cl | $CH_3$ | H |
| 748 | H | Br | Cl | $CH_3$ | $CH_3$ |
| 749 | H | Br | Cl | $CH_3$ | $OCH_3$ |
| 750 | H | Br | Cl | $CH_3$ | Br |
| 751 | H | Br | Cl | $CH_3$ | F |
| 752 | H | Br | Cl | $OCH_3$ | H |
| 753 | H | Br | Cl | $OCH_3$ | $CH_3$ |
| 754 | H | Br | Cl | $OCH_3$ | $OCH_3$ |
| 755 | H | Br | Cl | $OCH_3$ | Br |
| 756 | H | Br | Cl | $OCH_3$ | F |
| 757 | H | Br | Cl | Cl | H |
| 758 | H | Br | Cl | Cl | $CH_3$ |
| 759 | H | Br | Cl | Cl | $OCH_3$ |
| 760 | H | Br | Cl | Cl | Cl |
| 761 | H | Br | Cl | Cl | Br |
| 762 | H | Br | Cl | Cl | F |
| 763 | H | Br | Cl | Br | H |
| 764 | H | Br | Cl | Br | $CH_3$ |
| 765 | H | Br | Cl | Br | $OCH_3$ |
| 766 | H | Br | Cl | Br | Br |
| 767 | H | Br | Cl | F | H |
| 768 | H | Br | Cl | F | $CH_3$ |
| 769 | H | Br | Cl | F | $OCH_3$ |
| 770 | H | Br | Cl | F | Br |
| 771 | H | Br | Cl | F | F |
| 772 | H | Br | Br | H | H |
| 773 | H | Br | Br | H | $CH_3$ |
| 774 | H | Br | Br | H | $OCH_3$ |
| 775 | H | Br | Br | H | Cl |
| 776 | H | Br | Br | H | Br |
| 777 | H | Br | Br | H | F |
| 778 | H | Br | Br | $CH_3$ | H |
| 779 | H | Br | Br | $CH_3$ | $CH_3$ |
| 780 | H | Br | Br | $CH_3$ | $OCH_3$ |
| 781 | H | Br | Br | $CH_3$ | Cl |
| 782 | H | Br | Br | $CH_3$ | F |
| 783 | H | Br | Br | $OCH_3$ | H |
| 784 | H | Br | Br | $OCH_3$ | $CH_3$ |
| 785 | H | Br | Br | $OCH_3$ | $OCH_3$ |
| 786 | H | Br | Br | $OCH_3$ | Cl |
| 787 | H | Br | Br | $OCH_3$ | F |
| 788 | H | Br | Br | Cl | H |
| 789 | H | Br | Br | Cl | $CH_3$ |
| 790 | H | Br | Br | Cl | $OCH_3$ |
| 791 | H | Br | Br | Cl | Cl |
| 792 | H | Br | Br | Cl | F |
| 793 | H | Br | Br | Br | H |
| 794 | H | Br | Br | Br | $CH_3$ |
| 795 | H | Br | Br | Br | $OCH_3$ |

TABLE 2-continued

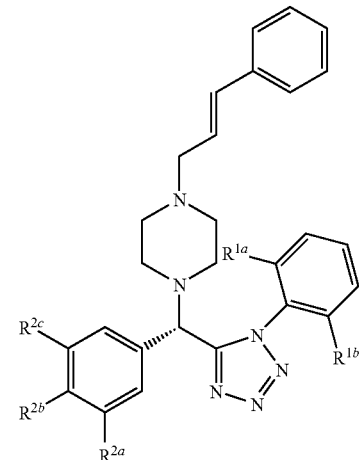

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 796 | H | Br | Br | Br | Cl |
| 797 | H | Br | Br | Br | Br |
| 798 | H | Br | Br | Br | F |
| 799 | H | Br | Br | F | H |
| 800 | H | Br | Br | F | $CH_3$ |
| 801 | H | Br | Br | F | $OCH_3$ |
| 802 | H | Br | Br | F | Cl |
| 803 | H | Br | Br | F | F |
| 804 | H | Br | F | H | H |
| 805 | H | Br | F | H | $CH_3$ |
| 806 | H | Br | F | H | $OCH_3$ |
| 807 | H | Br | F | H | Cl |
| 808 | H | Br | F | H | Br |
| 809 | H | Br | F | H | F |
| 810 | H | Br | F | $CH_3$ | H |
| 811 | H | Br | F | $CH_3$ | $CH_3$ |
| 812 | H | Br | F | $CH_3$ | $OCH_3$ |
| 813 | H | Br | F | $CH_3$ | Cl |
| 814 | H | Br | F | $CH_3$ | Br |
| 815 | H | Br | F | $OCH_3$ | H |
| 816 | H | Br | F | $OCH_3$ | $CH_3$ |
| 817 | H | Br | F | $OCH_3$ | $OCH_3$ |
| 818 | H | Br | F | $OCH_3$ | Cl |
| 819 | H | Br | F | $OCH_3$ | Br |
| 820 | H | Br | F | Cl | H |
| 821 | H | Br | F | Cl | $CH_3$ |
| 822 | H | Br | F | Cl | $OCH_3$ |
| 823 | H | Br | F | Cl | Cl |
| 824 | H | Br | F | Cl | Br |
| 825 | H | Br | F | Br | H |
| 826 | H | Br | F | Br | $CH_3$ |
| 827 | H | Br | F | Br | $OCH_3$ |
| 828 | H | Br | F | Br | Cl |
| 829 | H | Br | F | Br | Br |
| 830 | H | Br | F | F | H |
| 831 | H | Br | F | F | $CH_3$ |
| 832 | H | Br | F | F | $OCH_3$ |
| 833 | H | Br | F | F | Cl |
| 834 | H | Br | F | F | Br |
| 835 | H | Br | F | F | F |
| 836 | H | F | $CH_3$ | H | H |
| 837 | H | F | $CH_3$ | H | $CH_3$ |
| 838 | H | F | $CH_3$ | H | $OCH_3$ |
| 839 | H | F | $CH_3$ | H | Cl |
| 840 | H | F | $CH_3$ | H | Br |
| 841 | H | F | $CH_3$ | H | F |
| 842 | H | F | $CH_3$ | $CH_3$ | H |
| 843 | H | F | $CH_3$ | $CH_3$ | $CH_3$ |
| 844 | H | F | $CH_3$ | $CH_3$ | $OCH_3$ |
| 845 | H | F | $CH_3$ | $CH_3$ | Cl |

TABLE 2-continued

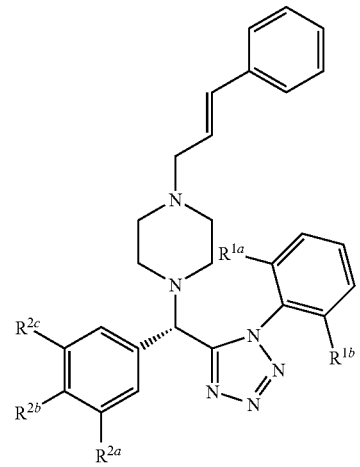

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 846 | H | F | $CH_3$ | $CH_3$ | Br |
| 847 | H | F | $CH_3$ | $CH_3$ | F |
| 848 | H | F | $CH_3$ | $OCH_3$ | H |
| 849 | H | F | $CH_3$ | $OCH_3$ | $OCH_3$ |
| 850 | H | F | $CH_3$ | $OCH_3$ | Cl |
| 851 | H | F | $CH_3$ | $OCH_3$ | Br |
| 852 | H | F | $CH_3$ | $OCH_3$ | F |
| 853 | H | F | $CH_3$ | Cl | H |
| 854 | H | F | $CH_3$ | Cl | $OCH_3$ |
| 855 | H | F | $CH_3$ | Cl | Cl |
| 856 | H | F | $CH_3$ | Cl | Br |
| 857 | H | F | $CH_3$ | Cl | F |
| 858 | H | F | $CH_3$ | Br | H |
| 859 | H | F | $CH_3$ | Br | $OCH_3$ |
| 860 | H | F | $CH_3$ | Br | Cl |
| 861 | H | F | $CH_3$ | Br | Br |
| 862 | H | F | $CH_3$ | Br | F |
| 863 | H | F | $CH_3$ | F | H |
| 864 | H | F | $CH_3$ | F | $OCH_3$ |
| 865 | H | F | $CH_3$ | F | Cl |
| 866 | H | F | $CH_3$ | F | Br |
| 867 | H | F | $CH_3$ | F | F |
| 868 | H | F | $OCH_3$ | H | H |
| 869 | H | F | $OCH_3$ | H | $CH_3$ |
| 870 | H | F | $OCH_3$ | H | $OCH_3$ |
| 871 | H | F | $OCH_3$ | H | Cl |
| 872 | H | F | $OCH_3$ | H | Br |
| 873 | H | F | $OCH_3$ | H | F |
| 874 | H | F | $OCH_3$ | $CH_3$ | H |
| 875 | H | F | $OCH_3$ | $CH_3$ | $CH_3$ |
| 876 | H | F | $OCH_3$ | $CH_3$ | Cl |
| 877 | H | F | $OCH_3$ | $CH_3$ | Br |
| 878 | H | F | $OCH_3$ | $CH_3$ | F |
| 879 | H | F | $OCH_3$ | $OCH_3$ | H |
| 880 | H | F | $OCH_3$ | $OCH_3$ | $CH_3$ |
| 881 | H | F | $OCH_3$ | $OCH_3$ | $OCH_3$ |
| 882 | H | F | $OCH_3$ | $OCH_3$ | Cl |
| 883 | H | F | $OCH_3$ | $OCH_3$ | Br |
| 884 | H | F | $OCH_3$ | $OCH_3$ | F |
| 885 | H | F | $OCH_3$ | Cl | H |
| 886 | H | F | $OCH_3$ | Cl | $CH_3$ |
| 887 | H | F | $OCH_3$ | Cl | Cl |
| 888 | H | F | $OCH_3$ | Cl | Br |
| 889 | H | F | $OCH_3$ | Cl | F |
| 890 | H | F | $OCH_3$ | Br | H |
| 891 | H | F | $OCH_3$ | Br | $CH_3$ |
| 892 | H | F | $OCH_3$ | Br | Cl |
| 893 | H | F | $OCH_3$ | Br | Br |
| 894 | H | F | $OCH_3$ | Br | F |
| 895 | H | F | $OCH_3$ | F | H |

TABLE 2-continued

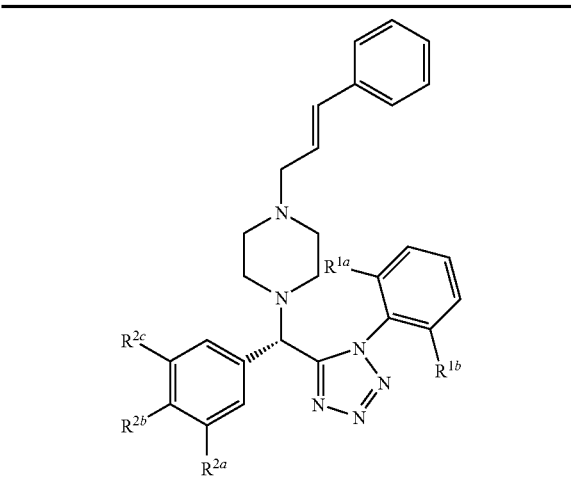

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 896 | H | F | OCH₃ | F | CH₃ |
| 897 | H | F | OCH₃ | F | Cl |
| 898 | H | F | OCH₃ | F | Br |
| 899 | H | F | OCH₃ | F | F |
| 900 | H | F | Cl | H | H |
| 901 | H | F | Cl | H | CH₃ |
| 902 | H | F | Cl | H | OCH₃ |
| 903 | H | F | Cl | H | Cl |
| 904 | H | F | Cl | H | Br |
| 905 | H | F | Cl | H | F |
| 906 | H | F | Cl | CH₃ | H |
| 907 | H | F | Cl | CH₃ | CH₃ |
| 908 | H | F | Cl | CH₃ | OCH₃ |
| 909 | H | F | Cl | CH₃ | Br |
| 910 | H | F | Cl | CH₃ | F |
| 911 | H | F | Cl | OCH₃ | H |
| 912 | H | F | Cl | OCH₃ | CH₃ |
| 913 | H | F | Cl | OCH₃ | OCH₃ |
| 914 | H | F | Cl | OCH₃ | Br |
| 915 | H | F | Cl | OCH₃ | F |
| 916 | H | F | Cl | Cl | H |
| 917 | H | F | Cl | Cl | CH₃ |
| 918 | H | F | Cl | Cl | OCH₃ |
| 919 | H | F | Cl | Cl | Cl |
| 920 | H | F | Cl | Cl | Br |
| 921 | H | F | Cl | Cl | F |
| 922 | H | F | Cl | Br | H |
| 923 | H | F | Cl | Br | CH₃ |
| 924 | H | F | Cl | Br | OCH₃ |
| 925 | H | F | Cl | Br | Br |
| 926 | H | F | Cl | F | H |
| 927 | H | F | Cl | F | CH₃ |
| 928 | H | F | Cl | F | OCH₃ |
| 929 | H | F | Cl | F | Br |
| 930 | H | F | Cl | F | F |
| 931 | H | F | Br | H | H |
| 932 | H | F | Br | H | CH₃ |
| 933 | H | F | Br | H | OCH₃ |
| 934 | H | F | Br | H | Cl |
| 935 | H | F | Br | H | Br |
| 936 | H | F | Br | H | F |
| 937 | H | F | Br | CH₃ | H |
| 938 | H | F | Br | CH₃ | CH₃ |
| 939 | H | F | Br | CH₃ | OCH₃ |
| 940 | H | F | Br | CH₃ | Cl |
| 941 | H | F | Br | CH₃ | F |
| 942 | H | F | Br | OCH₃ | H |
| 943 | H | F | Br | OCH₃ | CH₃ |
| 944 | H | F | Br | OCH₃ | OCH₃ |
| 945 | H | F | Br | OCH₃ | Cl |

TABLE 2-continued

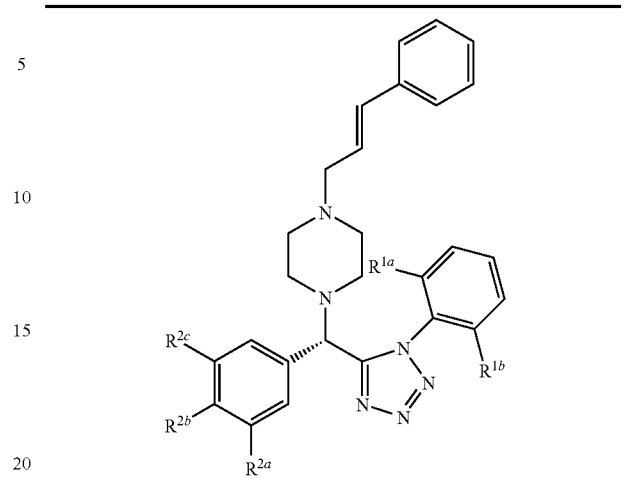

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 946 | H | F | Br | OCH₃ | F |
| 947 | H | F | Br | Cl | H |
| 948 | H | F | Br | Cl | CH₃ |
| 949 | H | F | Br | Cl | OCH₃ |
| 950 | H | F | Br | Cl | Cl |
| 951 | H | F | Br | Cl | F |
| 952 | H | F | Br | Br | H |
| 953 | H | F | Br | Br | CH₃ |
| 954 | H | F | Br | Br | OCH₃ |
| 955 | H | F | Br | Br | Cl |
| 956 | H | F | Br | Br | Br |
| 957 | H | F | Br | Br | F |
| 958 | H | F | Br | F | H |
| 959 | H | F | Br | F | CH₃ |
| 960 | H | F | Br | F | OCH₃ |
| 961 | H | F | Br | F | Cl |
| 962 | H | F | Br | F | F |
| 963 | H | F | F | H | H |
| 964 | H | F | F | H | CH₃ |
| 965 | H | F | F | H | OCH₃ |
| 966 | H | F | F | H | Cl |
| 967 | H | F | F | H | Br |
| 968 | H | F | F | H | F |
| 969 | H | F | F | CH₃ | H |
| 970 | H | F | F | CH₃ | CH₃ |
| 971 | H | F | F | CH₃ | OCH₃ |
| 972 | H | F | F | CH₃ | Cl |
| 973 | H | F | F | CH₃ | Br |
| 974 | H | F | F | OCH₃ | H |
| 975 | H | F | F | OCH₃ | CH₃ |
| 976 | H | F | F | OCH₃ | OCH₃ |
| 977 | H | F | F | OCH₃ | Cl |
| 978 | H | F | F | OCH₃ | Br |
| 979 | H | F | F | Cl | H |
| 980 | H | F | F | Cl | CH₃ |
| 981 | H | F | F | Cl | OCH₃ |
| 982 | H | F | F | Cl | Cl |
| 983 | H | F | F | Cl | Br |
| 984 | H | F | F | Br | H |
| 985 | H | F | F | Br | CH₃ |
| 986 | H | F | F | Br | OCH₃ |
| 987 | H | F | F | Br | Cl |
| 988 | H | F | F | Br | Br |
| 989 | H | F | F | F | H |
| 990 | H | F | F | F | CH₃ |
| 991 | H | F | F | F | OCH₃ |
| 992 | H | F | F | F | Cl |
| 993 | H | F | F | F | Br |
| 994 | H | F | F | F | F |
| 995 | CH₃ | CH₃ | CH₃ | H | H |

TABLE 2-continued

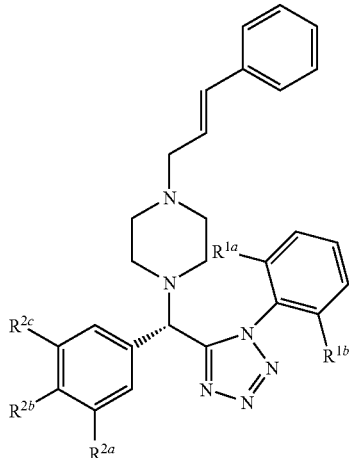

wherein $R^{1a}$, $R^{1b}$, $R^{2a}$, $R^{2b}$, and $R^{2c}$ are as defined in Table 2.

TABLE 2-continued

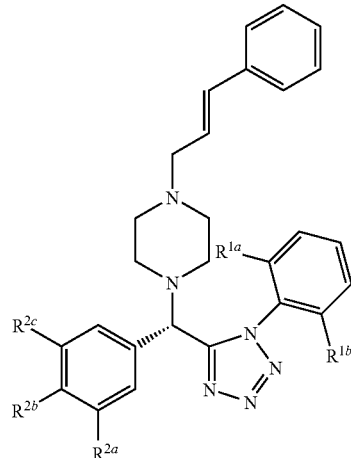

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ | Compound No. | $R^{1a}$ | $R^{1b}$ | $R^{2a}$ | $R^{2b}$ | $R^{2c}$ |
|---|---|---|---|---|---|---|---|---|---|---|---|
| 996 | CH₃ | CH₃ | CH₃ | CH₃ | H | 1046 | CH₃ | CH₃ | OCH₃ | F | Cl |
| 997 | CH₃ | CH₃ | CH₃ | OCH₃ | H | 1047 | CH₃ | CH₃ | OCH₃ | H | Br |
| 998 | CH₃ | CH₃ | CH₃ | Cl | H | 1048 | CH₃ | CH₃ | OCH₃ | CH₃ | Br |
| 999 | CH₃ | CH₃ | CH₃ | Br | H | 1049 | CH₃ | CH₃ | OCH₃ | OCH₃ | Br |
| 1000 | CH₃ | CH₃ | CH₃ | F | H | 1050 | CH₃ | CH₃ | OCH₃ | Cl | Br |
| 1001 | CH₃ | CH₃ | CH₃ | H | CH₃ | 1051 | CH₃ | CH₃ | OCH₃ | Br | Br |
| 1002 | CH₃ | CH₃ | CH₃ | CH₃ | CH₃ | 1052 | CH₃ | CH₃ | OCH₃ | F | Br |
| 1003 | CH₃ | CH₃ | CH₃ | H | OCH₃ | 1053 | CH₃ | CH₃ | OCH₃ | H | F |
| 1004 | CH₃ | CH₃ | CH₃ | CH₃ | OCH₃ | 1054 | CH₃ | CH₃ | OCH₃ | CH₃ | F |
| 1005 | CH₃ | CH₃ | CH₃ | OCH₃ | OCH₃ | 1055 | CH₃ | CH₃ | OCH₃ | OCH₃ | F |
| 1006 | CH₃ | CH₃ | CH₃ | Cl | OCH₃ | 1056 | CH₃ | CH₃ | OCH₃ | Cl | F |
| 1007 | CH₃ | CH₃ | CH₃ | Br | OCH₃ | 1057 | CH₃ | CH₃ | OCH₃ | Br | F |
| 1008 | CH₃ | CH₃ | CH₃ | F | OCH₃ | 1058 | CH₃ | CH₃ | OCH₃ | F | F |
| 1009 | CH₃ | CH₃ | CH₃ | H | Cl | 1059 | CH₃ | CH₃ | Cl | H | H |
| 1010 | CH₃ | CH₃ | CH₃ | CH₃ | Cl | 1060 | CH₃ | CH₃ | Cl | CH₃ | H |
| 1011 | CH₃ | CH₃ | CH₃ | OCH₃ | Cl | 1061 | CH₃ | CH₃ | Cl | OCH₃ | H |
| 1012 | CH₃ | CH₃ | CH₃ | Cl | Cl | 1062 | CH₃ | CH₃ | Cl | Cl | H |
| 1013 | CH₃ | CH₃ | CH₃ | Br | Cl | 1063 | CH₃ | CH₃ | Cl | Br | H |
| 1014 | CH₃ | CH₃ | CH₃ | F | Cl | 1064 | CH₃ | CH₃ | Cl | F | H |
| 1015 | CH₃ | CH₃ | CH₃ | H | Br | 1065 | CH₃ | CH₃ | Cl | H | CH₃ |
| 1016 | CH₃ | CH₃ | CH₃ | CH₃ | Br | 1066 | CH₃ | CH₃ | Cl | CH₃ | CH₃ |
| 1017 | CH₃ | CH₃ | CH₃ | OCH₃ | Br | 1067 | CH₃ | CH₃ | Cl | OCH₃ | CH₃ |
| 1018 | CH₃ | CH₃ | CH₃ | Cl | Br | 1068 | CH₃ | CH₃ | Cl | Cl | CH₃ |
| 1019 | CH₃ | CH₃ | CH₃ | Br | Br | 1069 | CH₃ | CH₃ | Cl | Br | CH₃ |
| 1020 | CH₃ | CH₃ | CH₃ | F | Br | 1070 | CH₃ | CH₃ | Cl | F | CH₃ |
| 1021 | CH₃ | CH₃ | CH₃ | H | F | 1071 | CH₃ | CH₃ | Cl | H | OCH₃ |
| 1022 | CH₃ | CH₃ | CH₃ | CH₃ | F | 1072 | CH₃ | CH₃ | Cl | CH₃ | OCH₃ |
| 1023 | CH₃ | CH₃ | CH₃ | OCH₃ | F | 1073 | CH₃ | CH₃ | Cl | OCH₃ | OCH₃ |
| 1024 | CH₃ | CH₃ | CH₃ | Cl | F | 1074 | CH₃ | CH₃ | Cl | Cl | OCH₃ |
| 1025 | CH₃ | CH₃ | CH₃ | Br | F | 1075 | CH₃ | CH₃ | Cl | Br | OCH₃ |
| 1026 | CH₃ | CH₃ | CH₃ | F | F | 1076 | CH₃ | CH₃ | Cl | F | OCH₃ |
| 1027 | CH₃ | CH₃ | OCH₃ | H | H | 1077 | CH₃ | CH₃ | Cl | H | Cl |
| 1028 | CH₃ | CH₃ | OCH₃ | CH₃ | H | 1078 | CH₃ | CH₃ | Cl | Cl | Cl |
| 1029 | CH₃ | CH₃ | OCH₃ | OCH₃ | H | 1079 | CH₃ | CH₃ | Cl | H | Br |
| 1030 | CH₃ | CH₃ | OCH₃ | Cl | H | 1080 | CH₃ | CH₃ | Cl | CH₃ | Br |
| 1031 | CH₃ | CH₃ | OCH₃ | Br | H | 1081 | CH₃ | CH₃ | Cl | OCH₃ | Br |
| 1032 | CH₃ | CH₃ | OCH₃ | F | H | 1082 | CH₃ | CH₃ | Cl | Cl | Br |
| 1033 | CH₃ | CH₃ | OCH₃ | H | CH₃ | 1083 | CH₃ | CH₃ | Cl | Br | Br |
| 1034 | CH₃ | CH₃ | OCH₃ | CH₃ | CH₃ | 1084 | CH₃ | CH₃ | Cl | F | Br |
| 1035 | CH₃ | CH₃ | OCH₃ | OCH₃ | CH₃ | 1085 | CH₃ | CH₃ | Cl | H | F |
| 1036 | CH₃ | CH₃ | OCH₃ | Cl | CH₃ | 1086 | CH₃ | CH₃ | Cl | CH₃ | F |
| 1037 | CH₃ | CH₃ | OCH₃ | Br | CH₃ | 1087 | CH₃ | CH₃ | Cl | OCH₃ | F |
| 1038 | CH₃ | CH₃ | OCH₃ | F | CH₃ | 1088 | CH₃ | CH₃ | Cl | Cl | F |
| 1039 | CH₃ | CH₃ | OCH₃ | H | OCH₃ | 1089 | CH₃ | CH₃ | Cl | F | F |
| 1040 | CH₃ | CH₃ | OCH₃ | OCH₃ | OCH₃ | 1090 | CH₃ | CH₃ | Br | H | H |
| 1041 | CH₃ | CH₃ | OCH₃ | H | Cl | 1091 | CH₃ | CH₃ | Br | CH₃ | H |
| 1042 | CH₃ | CH₃ | OCH₃ | CH₃ | Cl | 1092 | CH₃ | CH₃ | Br | OCH₃ | H |
| 1043 | CH₃ | CH₃ | OCH₃ | OCH₃ | Cl | 1093 | CH₃ | CH₃ | Br | Cl | H |
| 1044 | CH₃ | CH₃ | OCH₃ | Cl | Cl | 1094 | CH₃ | CH₃ | Br | Br | H |
| 1045 | CH₃ | CH₃ | OCH₃ | Br | Cl | 1095 | CH₃ | CH₃ | Br | F | H |

TABLE 2-continued

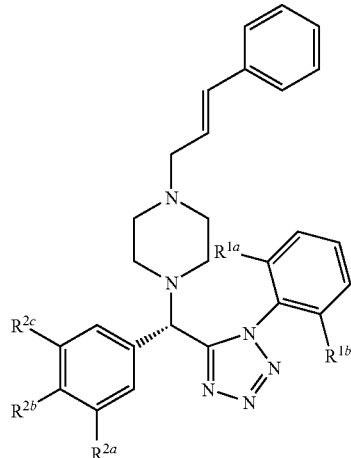

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1096 | CH₃ | CH₃ | Br | H | CH₃ |
| 1097 | CH₃ | CH₃ | Br | CH₃ | CH₃ |
| 1098 | CH₃ | CH₃ | Br | OCH₃ | CH₃ |
| 1099 | CH₃ | CH₃ | Br | Cl | CH₃ |
| 1100 | CH₃ | CH₃ | Br | Br | CH₃ |
| 1101 | CH₃ | CH₃ | Br | F | CH₃ |
| 1102 | CH₃ | CH₃ | Br | H | OCH₃ |
| 1103 | CH₃ | CH₃ | Br | CH₃ | OCH₃ |
| 1104 | CH₃ | CH₃ | Br | OCH₃ | OCH₃ |
| 1105 | CH₃ | CH₃ | Br | Cl | OCH₃ |
| 1106 | CH₃ | CH₃ | Br | Br | OCH₃ |
| 1107 | CH₃ | CH₃ | Br | F | OCH₃ |
| 1108 | CH₃ | CH₃ | Br | H | Cl |
| 1109 | CH₃ | CH₃ | Br | CH₃ | Cl |
| 1110 | CH₃ | CH₃ | Br | OCH₃ | Cl |
| 1111 | CH₃ | CH₃ | Br | Cl | Cl |
| 1112 | CH₃ | CH₃ | Br | Br | Cl |
| 1113 | CH₃ | CH₃ | Br | F | Cl |
| 1114 | CH₃ | CH₃ | Br | H | Br |
| 1115 | CH₃ | CH₃ | Br | Br | Br |
| 1116 | CH₃ | CH₃ | Br | H | F |
| 1117 | CH₃ | CH₃ | Br | CH₃ | F |
| 1118 | CH₃ | CH₃ | Br | OCH₃ | F |
| 1119 | CH₃ | CH₃ | Br | Cl | F |
| 1120 | CH₃ | CH₃ | Br | Br | F |
| 1121 | CH₃ | CH₃ | Br | F | F |
| 1122 | CH₃ | CH₃ | F | H | H |
| 1123 | CH₃ | CH₃ | F | CH₃ | H |
| 1124 | CH₃ | CH₃ | F | OCH₃ | H |
| 1125 | CH₃ | CH₃ | F | Cl | H |
| 1126 | CH₃ | CH₃ | F | Br | H |
| 1127 | CH₃ | CH₃ | F | F | H |
| 1128 | CH₃ | CH₃ | F | H | CH₃ |
| 1129 | CH₃ | CH₃ | F | CH₃ | CH₃ |
| 1130 | CH₃ | CH₃ | F | OCH₃ | CH₃ |
| 1131 | CH₃ | CH₃ | F | Cl | CH₃ |
| 1132 | CH₃ | CH₃ | F | Br | CH₃ |
| 1133 | CH₃ | CH₃ | F | F | CH₃ |
| 1134 | CH₃ | CH₃ | F | H | OCH₃ |
| 1135 | CH₃ | CH₃ | F | CH₃ | OCH₃ |
| 1136 | CH₃ | CH₃ | F | OCH₃ | OCH₃ |
| 1137 | CH₃ | CH₃ | F | Cl | OCH₃ |
| 1138 | CH₃ | CH₃ | F | Br | OCH₃ |
| 1139 | CH₃ | CH₃ | F | F | OCH₃ |
| 1140 | CH₃ | CH₃ | F | H | Cl |
| 1141 | CH₃ | CH₃ | F | CH₃ | Cl |
| 1142 | CH₃ | CH₃ | F | OCH₃ | Cl |
| 1143 | CH₃ | CH₃ | F | Cl | Cl |
| 1144 | CH₃ | CH₃ | F | Br | Cl |
| 1145 | CH₃ | CH₃ | F | F | Cl |

TABLE 2-continued

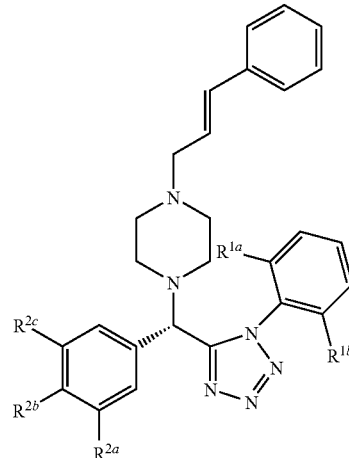

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1146 | CH₃ | CH₃ | F | H | Br |
| 1147 | CH₃ | CH₃ | F | CH₃ | Br |
| 1148 | CH₃ | CH₃ | F | OCH₃ | Br |
| 1149 | CH₃ | CH₃ | F | Cl | Br |
| 1150 | CH₃ | CH₃ | F | Br | Br |
| 1151 | CH₃ | CH₃ | F | F | Br |
| 1152 | CH₃ | CH₃ | F | H | F |
| 1153 | CH₃ | CH₃ | F | F | F |
| 1154 | CH₃ | OCH₃ | CH₃ | H | H |
| 1155 | CH₃ | OCH₃ | CH₃ | H | CH₃ |
| 1156 | CH₃ | OCH₃ | CH₃ | H | OCH₃ |
| 1157 | CH₃ | OCH₃ | CH₃ | H | Cl |
| 1158 | CH₃ | OCH₃ | CH₃ | H | Br |
| 1159 | CH₃ | OCH₃ | CH₃ | H | F |
| 1160 | CH₃ | OCH₃ | CH₃ | CH₃ | H |
| 1161 | CH₃ | OCH₃ | CH₃ | CH₃ | CH₃ |
| 1162 | CH₃ | OCH₃ | CH₃ | CH₃ | OCH₃ |
| 1163 | CH₃ | OCH₃ | CH₃ | CH₃ | Cl |
| 1164 | CH₃ | OCH₃ | CH₃ | CH₃ | Br |
| 1165 | CH₃ | OCH₃ | CH₃ | CH₃ | F |
| 1166 | CH₃ | OCH₃ | CH₃ | OCH₃ | H |
| 1167 | CH₃ | OCH₃ | CH₃ | OCH₃ | OCH₃ |
| 1168 | CH₃ | OCH₃ | CH₃ | OCH₃ | Cl |
| 1169 | CH₃ | OCH₃ | CH₃ | OCH₃ | Br |
| 1170 | CH₃ | OCH₃ | CH₃ | OCH₃ | F |
| 1171 | CH₃ | OCH₃ | CH₃ | Cl | H |
| 1172 | CH₃ | OCH₃ | CH₃ | Cl | OCH₃ |
| 1173 | CH₃ | OCH₃ | CH₃ | Cl | Cl |
| 1174 | CH₃ | OCH₃ | CH₃ | Cl | Br |
| 1175 | CH₃ | OCH₃ | CH₃ | Cl | F |
| 1176 | CH₃ | OCH₃ | CH₃ | Br | H |
| 1177 | CH₃ | OCH₃ | CH₃ | Br | OCH₃ |
| 1178 | CH₃ | OCH₃ | CH₃ | Br | Cl |
| 1179 | CH₃ | OCH₃ | CH₃ | Br | Br |
| 1180 | CH₃ | OCH₃ | CH₃ | Br | F |
| 1181 | CH₃ | OCH₃ | CH₃ | F | H |
| 1182 | CH₃ | OCH₃ | CH₃ | F | OCH₃ |
| 1183 | CH₃ | OCH₃ | CH₃ | F | Cl |
| 1184 | CH₃ | OCH₃ | CH₃ | F | Br |
| 1185 | CH₃ | OCH₃ | CH₃ | F | F |
| 1186 | CH₃ | OCH₃ | OCH₃ | H | H |
| 1187 | CH₃ | OCH₃ | OCH₃ | H | CH₃ |
| 1188 | CH₃ | OCH₃ | OCH₃ | H | OCH₃ |
| 1189 | CH₃ | OCH₃ | OCH₃ | H | Cl |
| 1190 | CH₃ | OCH₃ | OCH₃ | H | Br |
| 1191 | CH₃ | OCH₃ | OCH₃ | H | F |
| 1192 | CH₃ | OCH₃ | OCH₃ | CH₃ | H |
| 1193 | CH₃ | OCH₃ | OCH₃ | CH₃ | CH₃ |
| 1194 | CH₃ | OCH₃ | OCH₃ | CH₃ | Cl |
| 1195 | CH₃ | OCH₃ | OCH₃ | CH₃ | Br |

TABLE 2-continued

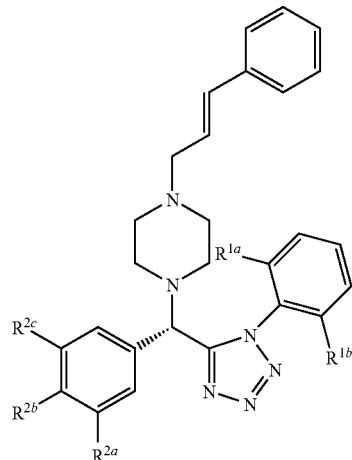

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1196 | CH₃ | OCH₃ | OCH₃ | CH₃ | F |
| 1197 | CH₃ | OCH₃ | OCH₃ | OCH₃ | H |
| 1198 | CH₃ | OCH₃ | OCH₃ | OCH₃ | CH₃ |
| 1199 | CH₃ | OCH₃ | OCH₃ | OCH₃ | OCH₃ |
| 1200 | CH₃ | OCH₃ | OCH₃ | OCH₃ | Cl |
| 1201 | CH₃ | OCH₃ | OCH₃ | OCH₃ | Br |
| 1202 | CH₃ | OCH₃ | OCH₃ | OCH₃ | F |
| 1203 | CH₃ | OCH₃ | OCH₃ | Cl | H |
| 1204 | CH₃ | OCH₃ | OCH₃ | Cl | CH₃ |
| 1205 | CH₃ | OCH₃ | OCH₃ | Cl | Cl |
| 1206 | CH₃ | OCH₃ | OCH₃ | Cl | Br |
| 1207 | CH₃ | OCH₃ | OCH₃ | Cl | F |
| 1208 | CH₃ | OCH₃ | OCH₃ | Br | H |
| 1209 | CH₃ | OCH₃ | OCH₃ | Br | CH₃ |
| 1210 | CH₃ | OCH₃ | OCH₃ | Br | Cl |
| 1211 | CH₃ | OCH₃ | OCH₃ | Br | Br |
| 1212 | CH₃ | OCH₃ | OCH₃ | Br | F |
| 1213 | CH₃ | OCH₃ | OCH₃ | F | H |
| 1214 | CH₃ | OCH₃ | OCH₃ | F | CH₃ |
| 1215 | CH₃ | OCH₃ | OCH₃ | F | Cl |
| 1216 | CH₃ | OCH₃ | OCH₃ | F | Br |
| 1217 | CH₃ | OCH₃ | OCH₃ | F | F |
| 1218 | CH₃ | OCH₃ | Cl | H | H |
| 1219 | CH₃ | OCH₃ | Cl | H | CH₃ |
| 1220 | CH₃ | OCH₃ | Cl | H | OCH₃ |
| 1221 | CH₃ | OCH₃ | Cl | H | Cl |
| 1222 | CH₃ | OCH₃ | Cl | H | Br |
| 1223 | CH₃ | OCH₃ | Cl | H | F |
| 1224 | CH₃ | OCH₃ | Cl | CH₃ | H |
| 1225 | CH₃ | OCH₃ | Cl | CH₃ | CH₃ |
| 1226 | CH₃ | OCH₃ | Cl | CH₃ | OCH₃ |
| 1227 | CH₃ | OCH₃ | Cl | CH₃ | Br |
| 1228 | CH₃ | OCH₃ | Cl | CH₃ | F |
| 1229 | CH₃ | OCH₃ | Cl | OCH₃ | H |
| 1230 | CH₃ | OCH₃ | Cl | OCH₃ | CH₃ |
| 1231 | CH₃ | OCH₃ | Cl | OCH₃ | OCH₃ |
| 1232 | CH₃ | OCH₃ | Cl | OCH₃ | Br |
| 1233 | CH₃ | OCH₃ | Cl | OCH₃ | F |
| 1234 | CH₃ | OCH₃ | Cl | Cl | H |
| 1235 | CH₃ | OCH₃ | Cl | Cl | CH₃ |
| 1236 | CH₃ | OCH₃ | Cl | Cl | OCH₃ |
| 1237 | CH₃ | OCH₃ | Cl | Cl | Cl |
| 1238 | CH₃ | OCH₃ | Cl | Cl | Br |
| 1239 | CH₃ | OCH₃ | Cl | Cl | F |
| 1240 | CH₃ | OCH₃ | Cl | Br | H |
| 1241 | CH₃ | OCH₃ | Cl | Br | CH₃ |
| 1242 | CH₃ | OCH₃ | Cl | Br | OCH₃ |
| 1243 | CH₃ | OCH₃ | Cl | Br | Br |
| 1244 | CH₃ | OCH₃ | Cl | F | H |
| 1245 | CH₃ | OCH₃ | Cl | F | CH₃ |

TABLE 2-continued

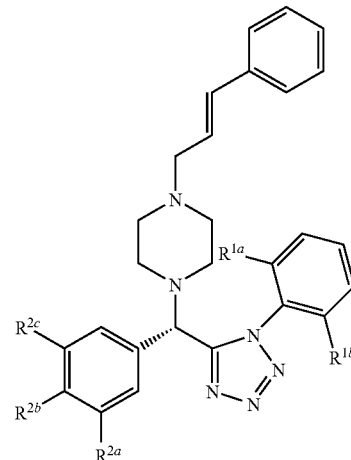

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1246 | CH₃ | OCH₃ | Cl | F | OCH₃ |
| 1247 | CH₃ | OCH₃ | Cl | F | Br |
| 1248 | CH₃ | OCH₃ | Cl | F | F |
| 1249 | CH₃ | OCH₃ | Br | H | H |
| 1250 | CH₃ | OCH₃ | Br | H | CH₃ |
| 1251 | CH₃ | OCH₃ | Br | H | OCH₃ |
| 1252 | CH₃ | OCH₃ | Br | H | Cl |
| 1253 | CH₃ | OCH₃ | Br | H | Br |
| 1254 | CH₃ | OCH₃ | Br | H | F |
| 1255 | CH₃ | OCH₃ | Br | CH₃ | H |
| 1256 | CH₃ | OCH₃ | Br | CH₃ | CH₃ |
| 1257 | CH₃ | OCH₃ | Br | CH₃ | OCH₃ |
| 1258 | CH₃ | OCH₃ | Br | CH₃ | Cl |
| 1259 | CH₃ | OCH₃ | Br | CH₃ | F |
| 1260 | CH₃ | OCH₃ | Br | OCH₃ | H |
| 1261 | CH₃ | OCH₃ | Br | OCH₃ | CH₃ |
| 1262 | CH₃ | OCH₃ | Br | OCH₃ | OCH₃ |
| 1263 | CH₃ | OCH₃ | Br | OCH₃ | Cl |
| 1264 | CH₃ | OCH₃ | Br | OCH₃ | F |
| 1265 | CH₃ | OCH₃ | Br | Cl | H |
| 1266 | CH₃ | OCH₃ | Br | Cl | CH₃ |
| 1267 | CH₃ | OCH₃ | Br | Cl | OCH₃ |
| 1268 | CH₃ | OCH₃ | Br | Cl | Cl |
| 1269 | CH₃ | OCH₃ | Br | Cl | F |
| 1270 | CH₃ | OCH₃ | Br | Br | H |
| 1271 | CH₃ | OCH₃ | Br | Br | CH₃ |
| 1272 | CH₃ | OCH₃ | Br | Br | OCH₃ |
| 1273 | CH₃ | OCH₃ | Br | Br | Cl |
| 1274 | CH₃ | OCH₃ | Br | Br | Br |
| 1275 | CH₃ | OCH₃ | Br | Br | F |
| 1276 | CH₃ | OCH₃ | Br | F | H |
| 1277 | CH₃ | OCH₃ | Br | F | CH₃ |
| 1278 | CH₃ | OCH₃ | Br | F | OCH₃ |
| 1279 | CH₃ | OCH₃ | Br | F | Cl |
| 1280 | CH₃ | OCH₃ | Br | F | F |
| 1281 | CH₃ | OCH₃ | F | H | H |
| 1282 | CH₃ | OCH₃ | F | H | CH₃ |
| 1283 | CH₃ | OCH₃ | F | H | OCH₃ |
| 1284 | CH₃ | OCH₃ | F | H | Cl |
| 1285 | CH₃ | OCH₃ | F | H | Br |
| 1286 | CH₃ | OCH₃ | F | H | F |
| 1287 | CH₃ | OCH₃ | F | CH₃ | H |
| 1288 | CH₃ | OCH₃ | F | CH₃ | CH₃ |
| 1289 | CH₃ | OCH₃ | F | CH₃ | OCH₃ |
| 1290 | CH₃ | OCH₃ | F | CH₃ | Cl |
| 1291 | CH₃ | OCH₃ | F | CH₃ | Br |
| 1292 | CH₃ | OCH₃ | F | OCH₃ | H |
| 1293 | CH₃ | OCH₃ | F | OCH₃ | CH₃ |
| 1294 | CH₃ | OCH₃ | F | OCH₃ | OCH₃ |
| 1295 | CH₃ | OCH₃ | F | OCH₃ | Cl |

TABLE 2-continued

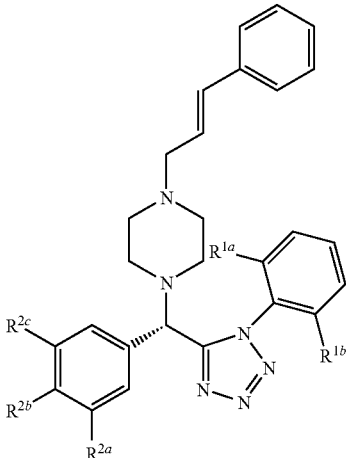

wherein $R^{1a}$, $R^{1b}$, $R^{2a}$, $R^{2b}$, and $R^{2c}$ are as defined in Table 2.

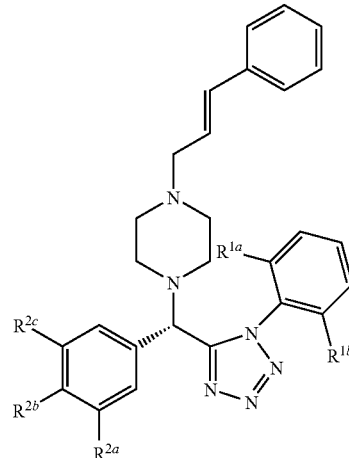

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1296 | CH₃ | OCH₃ | F | OCH₃ | Br |
| 1297 | CH₃ | OCH₃ | F | Cl | H |
| 1298 | CH₃ | OCH₃ | F | Cl | CH₃ |
| 1299 | CH₃ | OCH₃ | F | Cl | OCH₃ |
| 1300 | CH₃ | OCH₃ | F | Cl | Cl |
| 1301 | CH₃ | OCH₃ | F | Cl | Br |
| 1302 | CH₃ | OCH₃ | F | Br | H |
| 1303 | CH₃ | OCH₃ | F | Br | CH₃ |
| 1304 | CH₃ | OCH₃ | F | Br | OCH₃ |
| 1305 | CH₃ | OCH₃ | F | Br | Cl |
| 1306 | CH₃ | OCH₃ | F | Br | Br |
| 1307 | CH₃ | OCH₃ | F | F | H |
| 1308 | CH₃ | OCH₃ | F | F | CH₃ |
| 1309 | CH₃ | OCH₃ | F | F | OCH₃ |
| 1310 | CH₃ | OCH₃ | F | F | Cl |
| 1311 | CH₃ | OCH₃ | F | F | Br |
| 1312 | CH₃ | OCH₃ | F | F | F |
| 1313 | CH₃ | Cl | CH₃ | H | H |
| 1314 | CH₃ | Cl | CH₃ | H | CH₃ |
| 1315 | CH₃ | Cl | CH₃ | H | OCH₃ |
| 1316 | CH₃ | Cl | CH₃ | H | Cl |
| 1317 | CH₃ | Cl | CH₃ | H | Br |
| 1318 | CH₃ | Cl | CH₃ | H | F |
| 1319 | CH₃ | Cl | CH₃ | CH₃ | H |
| 1320 | CH₃ | Cl | CH₃ | CH₃ | CH₃ |
| 1321 | CH₃ | Cl | CH₃ | CH₃ | OCH₃ |
| 1322 | CH₃ | Cl | CH₃ | CH₃ | Cl |
| 1323 | CH₃ | Cl | CH₃ | CH₃ | Br |
| 1324 | CH₃ | Cl | CH₃ | CH₃ | F |
| 1325 | CH₃ | Cl | CH₃ | OCH₃ | H |
| 1326 | CH₃ | Cl | CH₃ | OCH₃ | OCH₃ |
| 1327 | CH₃ | Cl | CH₃ | OCH₃ | Cl |
| 1328 | CH₃ | Cl | CH₃ | OCH₃ | Br |
| 1329 | CH₃ | Cl | CH₃ | OCH₃ | F |
| 1330 | CH₃ | Cl | CH₃ | Cl | H |
| 1331 | CH₃ | Cl | CH₃ | Cl | OCH₃ |
| 1332 | CH₃ | Cl | CH₃ | Cl | Cl |
| 1333 | CH₃ | Cl | CH₃ | Cl | Br |
| 1334 | CH₃ | Cl | CH₃ | Cl | F |
| 1335 | CH₃ | Cl | CH₃ | Br | H |
| 1336 | CH₃ | Cl | CH₃ | Br | OCH₃ |
| 1337 | CH₃ | Cl | CH₃ | Br | Cl |
| 1338 | CH₃ | Cl | CH₃ | Br | Br |
| 1339 | CH₃ | Cl | CH₃ | Br | F |
| 1340 | CH₃ | Cl | CH₃ | F | H |
| 1341 | CH₃ | Cl | CH₃ | F | OCH₃ |
| 1342 | CH₃ | Cl | CH₃ | F | Cl |
| 1343 | CH₃ | Cl | CH₃ | F | Br |
| 1344 | CH₃ | Cl | CH₃ | F | F |
| 1345 | CH₃ | Cl | OCH₃ | H | H |
| 1346 | CH₃ | Cl | OCH₃ | H | CH₃ |
| 1347 | CH₃ | Cl | OCH₃ | H | OCH₃ |
| 1348 | CH₃ | Cl | OCH₃ | H | Cl |
| 1349 | CH₃ | Cl | OCH₃ | H | Br |
| 1350 | CH₃ | Cl | OCH₃ | H | F |
| 1351 | CH₃ | Cl | OCH₃ | CH₃ | H |
| 1352 | CH₃ | Cl | OCH₃ | CH₃ | CH₃ |
| 1353 | CH₃ | Cl | OCH₃ | CH₃ | Cl |
| 1354 | CH₃ | Cl | OCH₃ | CH₃ | Br |
| 1355 | CH₃ | Cl | OCH₃ | CH₃ | F |
| 1356 | CH₃ | Cl | OCH₃ | OCH₃ | H |
| 1357 | CH₃ | Cl | OCH₃ | OCH₃ | CH₃ |
| 1358 | CH₃ | Cl | OCH₃ | OCH₃ | OCH₃ |
| 1359 | CH₃ | Cl | OCH₃ | OCH₃ | Cl |
| 1360 | CH₃ | Cl | OCH₃ | OCH₃ | Br |
| 1361 | CH₃ | Cl | OCH₃ | OCH₃ | F |
| 1362 | CH₃ | Cl | OCH₃ | Cl | H |
| 1363 | CH₃ | Cl | OCH₃ | Cl | CH₃ |
| 1364 | CH₃ | Cl | OCH₃ | Cl | Cl |
| 1365 | CH₃ | Cl | OCH₃ | Cl | Br |
| 1366 | CH₃ | Cl | OCH₃ | Cl | F |
| 1367 | CH₃ | Cl | OCH₃ | Br | H |
| 1368 | CH₃ | Cl | OCH₃ | Br | CH₃ |
| 1369 | CH₃ | Cl | OCH₃ | Br | Cl |
| 1370 | CH₃ | Cl | OCH₃ | Br | Br |
| 1371 | CH₃ | Cl | OCH₃ | Br | F |
| 1372 | CH₃ | Cl | OCH₃ | F | H |
| 1373 | CH₃ | Cl | OCH₃ | F | CH₃ |
| 1374 | CH₃ | Cl | OCH₃ | F | Cl |
| 1375 | CH₃ | Cl | OCH₃ | F | Br |
| 1376 | CH₃ | Cl | OCH₃ | F | F |
| 1377 | CH₃ | Cl | Cl | H | H |
| 1378 | CH₃ | Cl | Cl | H | CH₃ |
| 1379 | CH₃ | Cl | Cl | H | OCH₃ |
| 1380 | CH₃ | Cl | Cl | H | Cl |
| 1381 | CH₃ | Cl | Cl | H | Br |
| 1382 | CH₃ | Cl | Cl | H | F |
| 1383 | CH₃ | Cl | Cl | CH₃ | H |
| 1384 | CH₃ | Cl | Cl | CH₃ | CH₃ |
| 1385 | CH₃ | Cl | Cl | CH₃ | OCH₃ |
| 1386 | CH₃ | Cl | Cl | CH₃ | Br |
| 1387 | CH₃ | Cl | Cl | CH₃ | F |
| 1388 | CH₃ | Cl | Cl | OCH₃ | H |
| 1389 | CH₃ | Cl | Cl | OCH₃ | CH₃ |
| 1390 | CH₃ | Cl | Cl | OCH₃ | OCH₃ |
| 1391 | CH₃ | Cl | Cl | OCH₃ | Br |
| 1392 | CH₃ | Cl | Cl | OCH₃ | F |
| 1393 | CH₃ | Cl | Cl | Cl | H |
| 1394 | CH₃ | Cl | Cl | Cl | CH₃ |
| 1395 | CH₃ | Cl | Cl | Cl | OCH₃ |

TABLE 2-continued

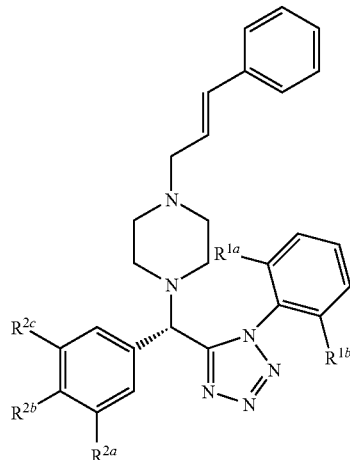

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1396 | CH₃ | Cl | Cl | Cl | Cl |
| 1397 | CH₃ | Cl | Cl | Cl | Br |
| 1398 | CH₃ | Cl | Cl | Cl | F |
| 1399 | CH₃ | Cl | Cl | Br | H |
| 1400 | CH₃ | Cl | Cl | Br | CH₃ |
| 1401 | CH₃ | Cl | Cl | Br | OCH₃ |
| 1402 | CH₃ | Cl | Cl | Br | Br |
| 1403 | CH₃ | Cl | Cl | F | H |
| 1404 | CH₃ | Cl | Cl | F | CH₃ |
| 1405 | CH₃ | Cl | Cl | F | OCH₃ |
| 1406 | CH₃ | Cl | Cl | F | Br |
| 1407 | CH₃ | Cl | Cl | F | F |
| 1408 | CH₃ | Cl | Br | H | H |
| 1409 | CH₃ | Cl | Br | H | CH₃ |
| 1410 | CH₃ | Cl | Br | H | OCH₃ |
| 1411 | CH₃ | Cl | Br | H | Cl |
| 1412 | CH₃ | Cl | Br | H | Br |
| 1413 | CH₃ | Cl | Br | H | F |
| 1414 | CH₃ | Cl | Br | CH₃ | H |
| 1415 | CH₃ | Cl | Br | CH₃ | CH₃ |
| 1416 | CH₃ | Cl | Br | CH₃ | OCH₃ |
| 1417 | CH₃ | Cl | Br | CH₃ | Cl |
| 1418 | CH₃ | Cl | Br | CH₃ | F |
| 1419 | CH₃ | Cl | Br | OCH₃ | H |
| 1420 | CH₃ | Cl | Br | OCH₃ | CH₃ |
| 1421 | CH₃ | Cl | Br | OCH₃ | OCH₃ |
| 1422 | CH₃ | Cl | Br | OCH₃ | Cl |
| 1423 | CH₃ | Cl | Br | OCH₃ | F |
| 1424 | CH₃ | Cl | Br | Cl | H |
| 1425 | CH₃ | Cl | Br | Cl | CH₃ |
| 1426 | CH₃ | Cl | Br | Cl | OCH₃ |
| 1427 | CH₃ | Cl | Br | Cl | Cl |
| 1428 | CH₃ | Cl | Br | Cl | F |
| 1429 | CH₃ | Cl | Br | Br | H |
| 1430 | CH₃ | Cl | Br | Br | CH₃ |
| 1431 | CH₃ | Cl | Br | Br | OCH₃ |
| 1432 | CH₃ | Cl | Br | Br | Cl |
| 1433 | CH₃ | Cl | Br | Br | Br |
| 1434 | CH₃ | Cl | Br | Br | F |
| 1435 | CH₃ | Cl | Br | F | H |
| 1436 | CH₃ | Cl | Br | F | CH₃ |
| 1437 | CH₃ | Cl | Br | F | OCH₃ |
| 1438 | CH₃ | Cl | Br | F | Cl |
| 1439 | CH₃ | Cl | Br | F | F |
| 1440 | CH₃ | Cl | F | H | H |
| 1441 | CH₃ | Cl | F | H | CH₃ |
| 1442 | CH₃ | Cl | F | H | OCH₃ |
| 1443 | CH₃ | Cl | F | H | Cl |
| 1444 | CH₃ | Cl | F | H | Br |
| 1445 | CH₃ | Cl | F | H | F |

TABLE 2-continued

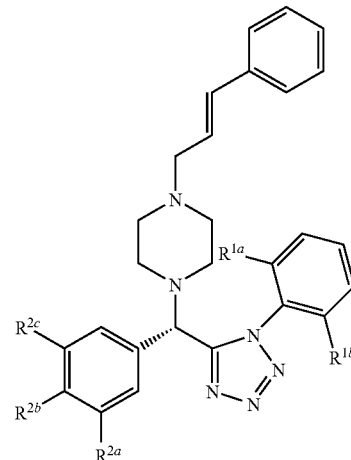

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1446 | CH₃ | Cl | F | CH₃ | H |
| 1447 | CH₃ | Cl | F | CH₃ | CH₃ |
| 1448 | CH₃ | Cl | F | CH₃ | OCH₃ |
| 1449 | CH₃ | Cl | F | CH₃ | Cl |
| 1450 | CH₃ | Cl | F | CH₃ | Br |
| 1451 | CH₃ | Cl | F | OCH₃ | H |
| 1452 | CH₃ | Cl | F | OCH₃ | CH₃ |
| 1453 | CH₃ | Cl | F | OCH₃ | OCH₃ |
| 1454 | CH₃ | Cl | F | OCH₃ | Cl |
| 1455 | CH₃ | Cl | F | OCH₃ | Br |
| 1456 | CH₃ | Cl | F | Cl | H |
| 1457 | CH₃ | Cl | F | Cl | CH₃ |
| 1458 | CH₃ | Cl | F | Cl | OCH₃ |
| 1459 | CH₃ | Cl | F | Cl | Cl |
| 1460 | CH₃ | Cl | F | Cl | Br |
| 1461 | CH₃ | Cl | F | Br | H |
| 1462 | CH₃ | Cl | F | Br | CH₃ |
| 1463 | CH₃ | Cl | F | Br | OCH₃ |
| 1464 | CH₃ | Cl | F | Br | Cl |
| 1465 | CH₃ | Cl | F | Br | Br |
| 1466 | CH₃ | Cl | F | F | H |
| 1467 | CH₃ | Cl | F | F | CH₃ |
| 1468 | CH₃ | Cl | F | F | OCH₃ |
| 1469 | CH₃ | Cl | F | F | Cl |
| 1470 | CH₃ | Cl | F | F | Br |
| 1471 | CH₃ | Cl | F | F | F |
| 1472 | CH₃ | Br | CH₃ | H | H |
| 1473 | CH₃ | Br | CH₃ | H | CH₃ |
| 1474 | CH₃ | Br | CH₃ | H | OCH₃ |
| 1475 | CH₃ | Br | CH₃ | H | Cl |
| 1476 | CH₃ | Br | CH₃ | H | Br |
| 1477 | CH₃ | Br | CH₃ | H | F |
| 1478 | CH₃ | Br | CH₃ | CH₃ | H |
| 1479 | CH₃ | Br | CH₃ | CH₃ | CH₃ |
| 1480 | CH₃ | Br | CH₃ | CH₃ | OCH₃ |
| 1481 | CH₃ | Br | CH₃ | CH₃ | Cl |
| 1482 | CH₃ | Br | CH₃ | CH₃ | Br |
| 1483 | CH₃ | Br | CH₃ | CH₃ | F |
| 1484 | CH₃ | Br | CH₃ | OCH₃ | H |
| 1485 | CH₃ | Br | CH₃ | OCH₃ | OCH₃ |
| 1486 | CH₃ | Br | CH₃ | OCH₃ | Cl |
| 1487 | CH₃ | Br | CH₃ | OCH₃ | Br |
| 1488 | CH₃ | Br | CH₃ | OCH₃ | F |
| 1489 | CH₃ | Br | CH₃ | Cl | H |
| 1490 | CH₃ | Br | CH₃ | Cl | OCH₃ |
| 1491 | CH₃ | Br | CH₃ | Cl | Cl |
| 1492 | CH₃ | Br | CH₃ | Cl | Br |
| 1493 | CH₃ | Br | CH₃ | Cl | F |
| 1494 | CH₃ | Br | CH₃ | Br | H |
| 1495 | CH₃ | Br | CH₃ | Br | OCH₃ |

TABLE 2-continued

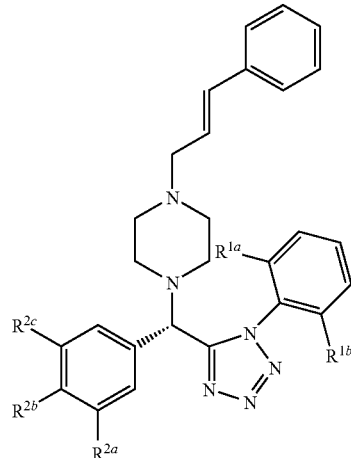

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1496 | CH₃ | Br | CH₃ | Br | Cl |
| 1497 | CH₃ | Br | CH₃ | Br | Br |
| 1498 | CH₃ | Br | CH₃ | Br | F |
| 1499 | CH₃ | Br | CH₃ | F | H |
| 1500 | CH₃ | Br | CH₃ | F | OCH₃ |
| 1501 | CH₃ | Br | CH₃ | F | Cl |
| 1502 | CH₃ | Br | CH₃ | F | Br |
| 1503 | CH₃ | Br | CH₃ | F | F |
| 1504 | CH₃ | Br | OCH₃ | H | H |
| 1505 | CH₃ | Br | OCH₃ | H | CH₃ |
| 1506 | CH₃ | Br | OCH₃ | H | OCH₃ |
| 1507 | CH₃ | Br | OCH₃ | H | Cl |
| 1508 | CH₃ | Br | OCH₃ | H | Br |
| 1509 | CH₃ | Br | OCH₃ | H | F |
| 1510 | CH₃ | Br | OCH₃ | CH₃ | H |
| 1511 | CH₃ | Br | OCH₃ | CH₃ | CH₃ |
| 1512 | CH₃ | Br | OCH₃ | CH₃ | Cl |
| 1513 | CH₃ | Br | OCH₃ | CH₃ | Br |
| 1514 | CH₃ | Br | OCH₃ | CH₃ | F |
| 1515 | CH₃ | Br | OCH₃ | OCH₃ | H |
| 1516 | CH₃ | Br | OCH₃ | OCH₃ | CH₃ |
| 1517 | CH₃ | Br | OCH₃ | OCH₃ | OCH₃ |
| 1518 | CH₃ | Br | OCH₃ | OCH₃ | Cl |
| 1519 | CH₃ | Br | OCH₃ | OCH₃ | Br |
| 1520 | CH₃ | Br | OCH₃ | OCH₃ | F |
| 1521 | CH₃ | Br | OCH₃ | Cl | H |
| 1522 | CH₃ | Br | OCH₃ | Cl | CH₃ |
| 1523 | CH₃ | Br | OCH₃ | Cl | Cl |
| 1524 | CH₃ | Br | OCH₃ | Cl | Br |
| 1525 | CH₃ | Br | OCH₃ | Cl | F |
| 1526 | CH₃ | Br | OCH₃ | Br | H |
| 1527 | CH₃ | Br | OCH₃ | Br | CH₃ |
| 1528 | CH₃ | Br | OCH₃ | Br | Cl |
| 1529 | CH₃ | Br | OCH₃ | Br | Br |
| 1530 | CH₃ | Br | OCH₃ | Br | F |
| 1531 | CH₃ | Br | OCH₃ | F | H |
| 1532 | CH₃ | Br | OCH₃ | F | CH₃ |
| 1533 | CH₃ | Br | OCH₃ | F | Cl |
| 1534 | CH₃ | Br | OCH₃ | F | Br |
| 1535 | CH₃ | Br | OCH₃ | F | F |
| 1536 | CH₃ | Br | Cl | H | H |
| 1537 | CH₃ | Br | Cl | H | CH₃ |
| 1538 | CH₃ | Br | Cl | H | OCH₃ |
| 1539 | CH₃ | Br | Cl | H | Cl |
| 1540 | CH₃ | Br | Cl | H | Br |
| 1541 | CH₃ | Br | Cl | H | F |
| 1542 | CH₃ | Br | Cl | CH₃ | H |
| 1543 | CH₃ | Br | Cl | CH₃ | CH₃ |
| 1544 | CH₃ | Br | Cl | CH₃ | OCH₃ |
| 1545 | CH₃ | Br | Cl | CH₃ | Br |
| 1546 | CH₃ | Br | Cl | CH₃ | F |
| 1547 | CH₃ | Br | Cl | OCH₃ | H |
| 1548 | CH₃ | Br | Cl | OCH₃ | CH₃ |
| 1549 | CH₃ | Br | Cl | OCH₃ | OCH₃ |
| 1550 | CH₃ | Br | Cl | OCH₃ | Br |
| 1551 | CH₃ | Br | Cl | OCH₃ | F |
| 1552 | CH₃ | Br | Cl | Cl | H |
| 1553 | CH₃ | Br | Cl | Cl | CH₃ |
| 1554 | CH₃ | Br | Cl | Cl | OCH₃ |
| 1555 | CH₃ | Br | Cl | Cl | Cl |
| 1556 | CH₃ | Br | Cl | Cl | Br |
| 1557 | CH₃ | Br | Cl | Cl | F |
| 1558 | CH₃ | Br | Cl | Br | H |
| 1559 | CH₃ | Br | Cl | Br | CH₃ |
| 1560 | CH₃ | Br | Cl | Br | OCH₃ |
| 1561 | CH₃ | Br | Cl | Br | Br |
| 1562 | CH₃ | Br | Cl | F | H |
| 1563 | CH₃ | Br | Cl | F | CH₃ |
| 1564 | CH₃ | Br | Cl | F | OCH₃ |
| 1565 | CH₃ | Br | Cl | F | Br |
| 1566 | CH₃ | Br | Cl | F | F |
| 1567 | CH₃ | Br | Br | H | H |
| 1568 | CH₃ | Br | Br | H | CH₃ |
| 1569 | CH₃ | Br | Br | H | OCH₃ |
| 1570 | CH₃ | Br | Br | H | Cl |
| 1571 | CH₃ | Br | Br | H | Br |
| 1572 | CH₃ | Br | Br | H | F |
| 1573 | CH₃ | Br | Br | CH₃ | H |
| 1574 | CH₃ | Br | Br | CH₃ | CH₃ |
| 1575 | CH₃ | Br | Br | CH₃ | OCH₃ |
| 1576 | CH₃ | Br | Br | CH₃ | Cl |
| 1577 | CH₃ | Br | Br | CH₃ | F |
| 1578 | CH₃ | Br | Br | OCH₃ | H |
| 1579 | CH₃ | Br | Br | OCH₃ | CH₃ |
| 1580 | CH₃ | Br | Br | OCH₃ | OCH₃ |
| 1581 | CH₃ | Br | Br | OCH₃ | Cl |
| 1582 | CH₃ | Br | Br | OCH₃ | F |
| 1583 | CH₃ | Br | Br | Cl | H |
| 1584 | CH₃ | Br | Br | Cl | CH₃ |
| 1585 | CH₃ | Br | Br | Cl | OCH₃ |
| 1586 | CH₃ | Br | Br | Cl | Cl |
| 1587 | CH₃ | Br | Br | Cl | F |
| 1588 | CH₃ | Br | Br | Br | H |
| 1589 | CH₃ | Br | Br | Br | CH₃ |
| 1590 | CH₃ | Br | Br | Br | OCH₃ |
| 1591 | CH₃ | Br | Br | Br | Cl |
| 1592 | CH₃ | Br | Br | Br | Br |
| 1593 | CH₃ | Br | Br | Br | F |
| 1594 | CH₃ | Br | Br | F | H |
| 1595 | CH₃ | Br | Br | F | CH₃ |

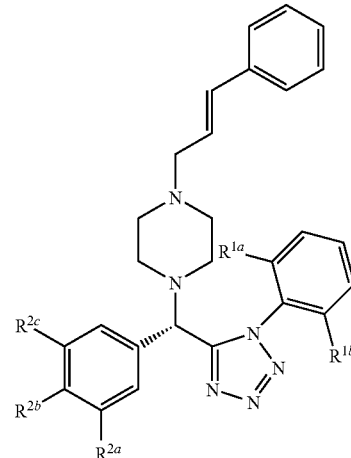

TABLE 2-continued

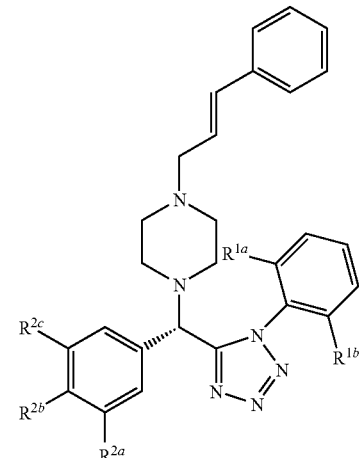

wherein $R^{1a}$, $R^{1b}$, $R^{2a}$, $R^{2b}$, and $R^{2c}$ are as defined in Table 2.

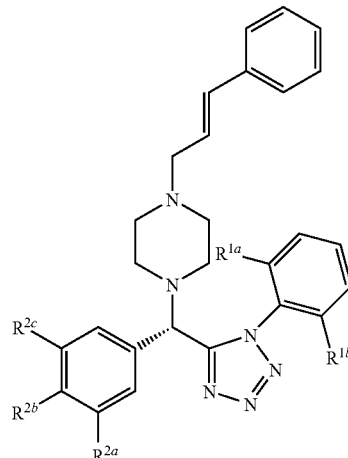

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ | Compound No. | $R^{1a}$ | $R^{1b}$ | $R^{2a}$ | $R^{2b}$ | $R^{2c}$ |
|---|---|---|---|---|---|---|---|---|---|---|---|
| 1596 | CH₃ | Br | Br | F | OCH₃ | 1646 | CH₃ | F | CH₃ | OCH₃ | Br |
| 1597 | CH₃ | Br | Br | F | Cl | 1647 | CH₃ | F | CH₃ | OCH₃ | F |
| 1598 | CH₃ | Br | Br | F | F | 1648 | CH₃ | F | CH₃ | Cl | H |
| 1599 | CH₃ | Br | F | H | H | 1649 | CH₃ | F | CH₃ | Cl | OCH₃ |
| 1600 | CH₃ | Br | F | H | CH₃ | 1650 | CH₃ | F | CH₃ | Cl | Cl |
| 1601 | CH₃ | Br | F | H | OCH₃ | 1651 | CH₃ | F | CH₃ | Cl | Br |
| 1602 | CH₃ | Br | F | H | Cl | 1652 | CH₃ | F | CH₃ | Cl | F |
| 1603 | CH₃ | Br | F | H | Br | 1653 | CH₃ | F | CH₃ | Br | H |
| 1604 | CH₃ | Br | F | H | F | 1654 | CH₃ | F | CH₃ | Br | OCH₃ |
| 1605 | CH₃ | Br | F | CH₃ | H | 1655 | CH₃ | F | CH₃ | Br | Cl |
| 1606 | CH₃ | Br | F | CH₃ | CH₃ | 1656 | CH₃ | F | CH₃ | Br | Br |
| 1607 | CH₃ | Br | F | CH₃ | OCH₃ | 1657 | CH₃ | F | CH₃ | Br | F |
| 1608 | CH₃ | Br | F | CH₃ | Cl | 1658 | CH₃ | F | CH₃ | F | H |
| 1609 | CH₃ | Br | F | CH₃ | Br | 1659 | CH₃ | F | CH₃ | F | OCH₃ |
| 1610 | CH₃ | Br | F | OCH₃ | H | 1660 | CH₃ | F | CH₃ | F | Cl |
| 1611 | CH₃ | Br | F | OCH₃ | CH₃ | 1661 | CH₃ | F | CH₃ | F | Br |
| 1612 | CH₃ | Br | F | OCH₃ | OCH₃ | 1662 | CH₃ | F | CH₃ | F | F |
| 1613 | CH₃ | Br | F | OCH₃ | Cl | 1663 | CH₃ | F | OCH₃ | H | H |
| 1614 | CH₃ | Br | F | OCH₃ | Br | 1664 | CH₃ | F | OCH₃ | H | CH₃ |
| 1615 | CH₃ | Br | F | Cl | H | 1665 | CH₃ | F | OCH₃ | H | OCH₃ |
| 1616 | CH₃ | Br | F | Cl | CH₃ | 1666 | CH₃ | F | OCH₃ | H | Cl |
| 1617 | CH₃ | Br | F | Cl | OCH₃ | 1667 | CH₃ | F | OCH₃ | H | Br |
| 1618 | CH₃ | Br | F | Cl | Cl | 1668 | CH₃ | F | OCH₃ | H | F |
| 1619 | CH₃ | Br | F | Cl | Br | 1669 | CH₃ | F | OCH₃ | CH₃ | H |
| 1620 | CH₃ | Br | F | Br | H | 1670 | CH₃ | F | OCH₃ | CH₃ | CH₃ |
| 1621 | CH₃ | Br | F | Br | CH₃ | 1671 | CH₃ | F | OCH₃ | CH₃ | Cl |
| 1622 | CH₃ | Br | F | Br | OCH₃ | 1672 | CH₃ | F | OCH₃ | CH₃ | Br |
| 1623 | CH₃ | Br | F | Br | Cl | 1673 | CH₃ | F | OCH₃ | CH₃ | F |
| 1624 | CH₃ | Br | F | Br | Br | 1674 | CH₃ | F | OCH₃ | OCH₃ | H |
| 1625 | CH₃ | Br | F | F | H | 1675 | CH₃ | F | OCH₃ | OCH₃ | CH₃ |
| 1626 | CH₃ | Br | F | F | CH₃ | 1676 | CH₃ | F | OCH₃ | OCH₃ | OCH₃ |
| 1627 | CH₃ | Br | F | F | OCH₃ | 1677 | CH₃ | F | OCH₃ | OCH₃ | Cl |
| 1628 | CH₃ | Br | F | F | Cl | 1678 | CH₃ | F | OCH₃ | OCH₃ | Br |
| 1629 | CH₃ | Br | F | F | Br | 1679 | CH₃ | F | OCH₃ | OCH₃ | F |
| 1630 | CH₃ | Br | F | F | F | 1680 | CH₃ | F | OCH₃ | Cl | H |
| 1631 | CH₃ | F | CH₃ | H | H | 1681 | CH₃ | F | OCH₃ | Cl | CH₃ |
| 1632 | CH₃ | F | CH₃ | H | CH₃ | 1682 | CH₃ | F | OCH₃ | Cl | Cl |
| 1633 | CH₃ | F | CH₃ | H | OCH₃ | 1683 | CH₃ | F | OCH₃ | Cl | Br |
| 1634 | CH₃ | F | CH₃ | H | Cl | 1684 | CH₃ | F | OCH₃ | Cl | F |
| 1635 | CH₃ | F | CH₃ | H | Br | 1685 | CH₃ | F | OCH₃ | Br | H |
| 1636 | CH₃ | F | CH₃ | H | F | 1686 | CH₃ | F | OCH₃ | Br | CH₃ |
| 1637 | CH₃ | F | CH₃ | CH₃ | H | 1687 | CH₃ | F | OCH₃ | Br | Cl |
| 1638 | CH₃ | F | CH₃ | CH₃ | CH₃ | 1688 | CH₃ | F | OCH₃ | Br | Br |
| 1639 | CH₃ | F | CH₃ | CH₃ | OCH₃ | 1689 | CH₃ | F | OCH₃ | Br | F |
| 1640 | CH₃ | F | CH₃ | CH₃ | Cl | 1690 | CH₃ | F | OCH₃ | F | H |
| 1641 | CH₃ | F | CH₃ | CH₃ | Br | 1691 | CH₃ | F | OCH₃ | F | CH₃ |
| 1642 | CH₃ | F | CH₃ | CH₃ | F | 1692 | CH₃ | F | OCH₃ | F | Cl |
| 1643 | CH₃ | F | CH₃ | OCH₃ | H | 1693 | CH₃ | F | OCH₃ | F | Br |
| 1644 | CH₃ | F | CH₃ | OCH₃ | OCH₃ | 1694 | CH₃ | F | OCH₃ | F | F |
| 1645 | CH₃ | F | CH₃ | OCH₃ | Cl | 1695 | CH₃ | F | Cl | H | H |

TABLE 2-continued

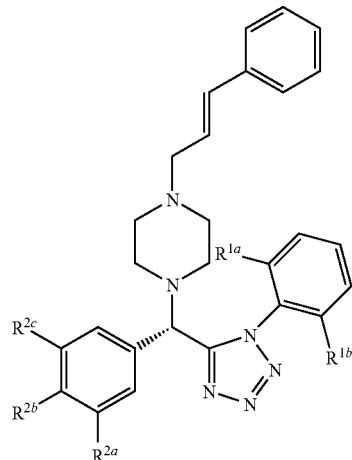

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1696 | CH₃ | F | Cl | H | CH₃ |
| 1697 | CH₃ | F | Cl | H | OCH₃ |
| 1698 | CH₃ | F | Cl | H | Cl |
| 1699 | CH₃ | F | Cl | H | Br |
| 1700 | CH₃ | F | Cl | H | F |
| 1701 | CH₃ | F | Cl | CH₃ | H |
| 1702 | CH₃ | F | Cl | CH₃ | CH₃ |
| 1703 | CH₃ | F | Cl | CH₃ | OCH₃ |
| 1704 | CH₃ | F | Cl | CH₃ | Br |
| 1705 | CH₃ | F | Cl | CH₃ | F |
| 1706 | CH₃ | F | Cl | OCH₃ | H |
| 1707 | CH₃ | F | Cl | OCH₃ | CH₃ |
| 1708 | CH₃ | F | Cl | OCH₃ | OCH₃ |
| 1709 | CH₃ | F | Cl | OCH₃ | Br |
| 1710 | CH₃ | F | Cl | OCH₃ | F |
| 1711 | CH₃ | F | Cl | Cl | H |
| 1712 | CH₃ | F | Cl | Cl | CH₃ |
| 1713 | CH₃ | F | Cl | Cl | OCH₃ |
| 1714 | CH₃ | F | Cl | Cl | Cl |
| 1715 | CH₃ | F | Cl | Cl | Br |
| 1716 | CH₃ | F | Cl | Cl | F |
| 1717 | CH₃ | F | Cl | Br | H |
| 1718 | CH₃ | F | Cl | Br | CH₃ |
| 1719 | CH₃ | F | Cl | Br | OCH₃ |
| 1720 | CH₃ | F | Cl | Br | Br |
| 1721 | CH₃ | F | Cl | F | H |
| 1722 | CH₃ | F | Cl | F | CH₃ |
| 1723 | CH₃ | F | Cl | F | OCH₃ |
| 1724 | CH₃ | F | Cl | F | Br |
| 1725 | CH₃ | F | Cl | F | F |
| 1726 | CH₃ | F | Br | H | H |
| 1727 | CH₃ | F | Br | H | CH₃ |
| 1728 | CH₃ | F | Br | H | OCH₃ |
| 1729 | CH₃ | F | Br | H | Cl |
| 1730 | CH₃ | F | Br | H | Br |
| 1731 | CH₃ | F | Br | H | F |
| 1732 | CH₃ | F | Br | CH₃ | H |
| 1733 | CH₃ | F | Br | CH₃ | CH₃ |
| 1734 | CH₃ | F | Br | CH₃ | OCH₃ |
| 1735 | CH₃ | F | Br | CH₃ | Cl |
| 1736 | CH₃ | F | Br | CH₃ | F |
| 1737 | CH₃ | F | Br | OCH₃ | H |
| 1738 | CH₃ | F | Br | OCH₃ | CH₃ |
| 1739 | CH₃ | F | Br | OCH₃ | OCH₃ |
| 1740 | CH₃ | F | Br | OCH₃ | Cl |
| 1741 | CH₃ | F | Br | OCH₃ | F |
| 1742 | CH₃ | F | Br | Cl | H |
| 1743 | CH₃ | F | Br | Cl | CH₃ |
| 1744 | CH₃ | F | Br | Cl | OCH₃ |
| 1745 | CH₃ | F | Br | Cl | Cl |

TABLE 2-continued

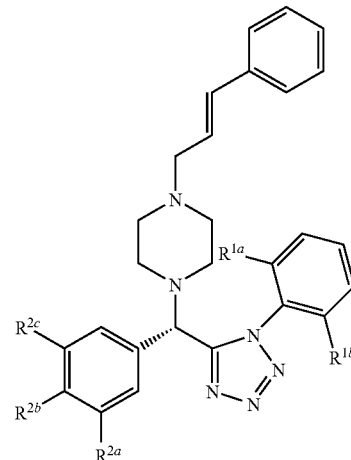

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1746 | CH₃ | F | Br | Cl | F |
| 1747 | CH₃ | F | Br | Br | H |
| 1748 | CH₃ | F | Br | Br | CH₃ |
| 1749 | CH₃ | F | Br | Br | OCH₃ |
| 1750 | CH₃ | F | Br | Br | Cl |
| 1751 | CH₃ | F | Br | Br | Br |
| 1752 | CH₃ | F | Br | Br | F |
| 1753 | CH₃ | F | Br | F | H |
| 1754 | CH₃ | F | Br | F | CH₃ |
| 1755 | CH₃ | F | Br | F | OCH₃ |
| 1756 | CH₃ | F | Br | F | Cl |
| 1757 | CH₃ | F | Br | F | F |
| 1758 | CH₃ | F | F | H | H |
| 1759 | CH₃ | F | F | H | CH₃ |
| 1760 | CH₃ | F | F | H | OCH₃ |
| 1761 | CH₃ | F | F | H | Cl |
| 1762 | CH₃ | F | F | H | Br |
| 1763 | CH₃ | F | F | H | F |
| 1764 | CH₃ | F | F | CH₃ | H |
| 1765 | CH₃ | F | F | CH₃ | CH₃ |
| 1766 | CH₃ | F | F | CH₃ | OCH₃ |
| 1767 | CH₃ | F | F | CH₃ | Cl |
| 1768 | CH₃ | F | F | CH₃ | Br |
| 1769 | CH₃ | F | F | OCH₃ | H |
| 1770 | CH₃ | F | F | OCH₃ | CH₃ |
| 1771 | CH₃ | F | F | OCH₃ | OCH₃ |
| 1772 | CH₃ | F | F | OCH₃ | Cl |
| 1773 | CH₃ | F | F | OCH₃ | Br |
| 1774 | CH₃ | F | F | Cl | H |
| 1775 | CH₃ | F | F | Cl | CH₃ |
| 1776 | CH₃ | F | F | Cl | OCH₃ |
| 1777 | CH₃ | F | F | Cl | Cl |
| 1778 | CH₃ | F | F | Cl | Br |
| 1779 | CH₃ | F | F | Br | H |
| 1780 | CH₃ | F | F | Br | CH₃ |
| 1781 | CH₃ | F | F | Br | OCH₃ |
| 1782 | CH₃ | F | F | Br | Cl |
| 1783 | CH₃ | F | F | Br | Br |
| 1784 | CH₃ | F | F | F | H |
| 1785 | CH₃ | F | F | F | CH₃ |
| 1786 | CH₃ | F | F | F | OCH₃ |
| 1787 | CH₃ | F | F | F | Cl |
| 1788 | CH₃ | F | F | F | Br |
| 1789 | CH₃ | F | F | F | F |
| 1790 | OCH₃ | CH₃ | CH₃ | H | H |
| 1791 | OCH₃ | CH₃ | CH₃ | CH₃ | H |
| 1792 | OCH₃ | CH₃ | CH₃ | OCH₃ | H |
| 1793 | OCH₃ | CH₃ | CH₃ | Cl | H |
| 1794 | OCH₃ | CH₃ | CH₃ | Br | H |
| 1795 | OCH₃ | CH₃ | CH₃ | F | H |

TABLE 2-continued

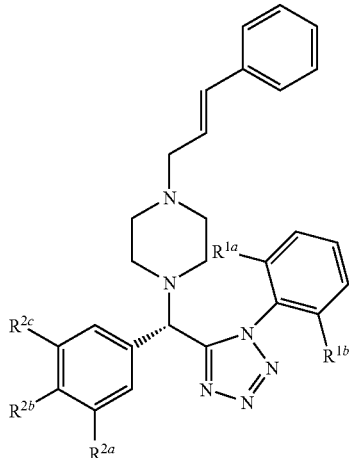

wherein $R^{1a}$, $R^{1b}$, $R^{2a}$, $R^{2b}$, and $R^{2c}$ are as defined in Table 2.

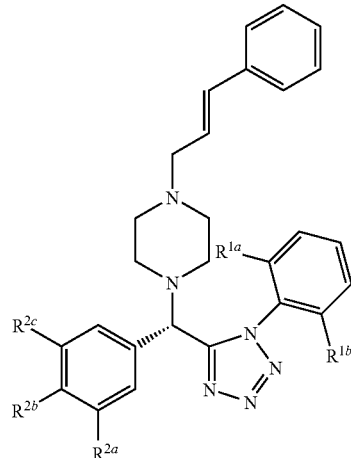

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1796 | OCH₃ | CH₃ | CH₃ | H | CH₃ |
| 1797 | OCH₃ | CH₃ | CH₃ | CH₃ | CH₃ |
| 1798 | OCH₃ | CH₃ | CH₃ | H | OCH₃ |
| 1799 | OCH₃ | CH₃ | CH₃ | CH₃ | OCH₃ |
| 1800 | OCH₃ | CH₃ | CH₃ | OCH₃ | OCH₃ |
| 1801 | OCH₃ | CH₃ | CH₃ | Cl | OCH₃ |
| 1802 | OCH₃ | CH₃ | CH₃ | Br | OCH₃ |
| 1803 | OCH₃ | CH₃ | CH₃ | F | OCH₃ |
| 1804 | OCH₃ | CH₃ | CH₃ | H | Cl |
| 1805 | OCH₃ | CH₃ | CH₃ | CH₃ | Cl |
| 1806 | OCH₃ | CH₃ | CH₃ | OCH₃ | Cl |
| 1807 | OCH₃ | CH₃ | CH₃ | Cl | Cl |
| 1808 | OCH₃ | CH₃ | CH₃ | Br | Cl |
| 1809 | OCH₃ | CH₃ | CH₃ | F | Cl |
| 1810 | OCH₃ | CH₃ | CH₃ | H | Br |
| 1811 | OCH₃ | CH₃ | CH₃ | CH₃ | Br |
| 1812 | OCH₃ | CH₃ | CH₃ | OCH₃ | Br |
| 1813 | OCH₃ | CH₃ | CH₃ | Cl | Br |
| 1814 | OCH₃ | CH₃ | CH₃ | Br | Br |
| 1815 | OCH₃ | CH₃ | CH₃ | F | Br |
| 1816 | OCH₃ | CH₃ | CH₃ | H | F |
| 1817 | OCH₃ | CH₃ | CH₃ | CH₃ | F |
| 1818 | OCH₃ | CH₃ | CH₃ | OCH₃ | F |
| 1819 | OCH₃ | CH₃ | CH₃ | Cl | F |
| 1820 | OCH₃ | CH₃ | CH₃ | Br | F |
| 1821 | OCH₃ | CH₃ | CH₃ | F | F |
| 1822 | OCH₃ | CH₃ | OCH₃ | H | H |
| 1823 | OCH₃ | CH₃ | OCH₃ | CH₃ | H |
| 1824 | OCH₃ | CH₃ | OCH₃ | OCH₃ | H |
| 1825 | OCH₃ | CH₃ | OCH₃ | Cl | H |
| 1826 | OCH₃ | CH₃ | OCH₃ | Br | H |
| 1827 | OCH₃ | CH₃ | OCH₃ | F | H |
| 1828 | OCH₃ | CH₃ | OCH₃ | H | CH₃ |
| 1829 | OCH₃ | CH₃ | OCH₃ | CH₃ | CH₃ |
| 1830 | OCH₃ | CH₃ | OCH₃ | OCH₃ | CH₃ |
| 1831 | OCH₃ | CH₃ | OCH₃ | Cl | CH₃ |
| 1832 | OCH₃ | CH₃ | OCH₃ | Br | CH₃ |
| 1833 | OCH₃ | CH₃ | OCH₃ | F | CH₃ |
| 1834 | OCH₃ | CH₃ | OCH₃ | H | OCH₃ |
| 1835 | OCH₃ | CH₃ | OCH₃ | OCH₃ | OCH₃ |
| 1836 | OCH₃ | CH₃ | OCH₃ | H | Cl |
| 1837 | OCH₃ | CH₃ | OCH₃ | CH₃ | Cl |
| 1838 | OCH₃ | CH₃ | OCH₃ | OCH₃ | Cl |
| 1839 | OCH₃ | CH₃ | OCH₃ | Cl | Cl |
| 1840 | OCH₃ | CH₃ | OCH₃ | Br | Cl |
| 1841 | OCH₃ | CH₃ | OCH₃ | F | Cl |
| 1842 | OCH₃ | CH₃ | OCH₃ | H | Br |
| 1843 | OCH₃ | CH₃ | OCH₃ | CH₃ | Br |
| 1844 | OCH₃ | CH₃ | OCH₃ | OCH₃ | Br |
| 1845 | OCH₃ | CH₃ | OCH₃ | Cl | Br |
| 1846 | OCH₃ | CH₃ | OCH₃ | Br | Br |
| 1847 | OCH₃ | CH₃ | OCH₃ | F | Br |
| 1848 | OCH₃ | CH₃ | OCH₃ | H | F |
| 1849 | OCH₃ | CH₃ | OCH₃ | CH₃ | F |
| 1850 | OCH₃ | CH₃ | OCH₃ | OCH₃ | F |
| 1851 | OCH₃ | CH₃ | OCH₃ | Cl | F |
| 1852 | OCH₃ | CH₃ | OCH₃ | Br | F |
| 1853 | OCH₃ | CH₃ | OCH₃ | F | F |
| 1854 | OCH₃ | CH₃ | Cl | H | H |
| 1855 | OCH₃ | CH₃ | Cl | CH₃ | H |
| 1856 | OCH₃ | CH₃ | Cl | OCH₃ | H |
| 1857 | OCH₃ | CH₃ | Cl | Cl | H |
| 1858 | OCH₃ | CH₃ | Cl | Br | H |
| 1859 | OCH₃ | CH₃ | Cl | F | H |
| 1860 | OCH₃ | CH₃ | Cl | H | CH₃ |
| 1861 | OCH₃ | CH₃ | Cl | CH₃ | CH₃ |
| 1862 | OCH₃ | CH₃ | Cl | OCH₃ | CH₃ |
| 1863 | OCH₃ | CH₃ | Cl | Cl | CH₃ |
| 1864 | OCH₃ | CH₃ | Cl | Br | CH₃ |
| 1865 | OCH₃ | CH₃ | Cl | F | CH₃ |
| 1866 | OCH₃ | CH₃ | Cl | H | OCH₃ |
| 1867 | OCH₃ | CH₃ | Cl | CH₃ | OCH₃ |
| 1868 | OCH₃ | CH₃ | Cl | OCH₃ | OCH₃ |
| 1869 | OCH₃ | CH₃ | Cl | Cl | OCH₃ |
| 1870 | OCH₃ | CH₃ | Cl | Br | OCH₃ |
| 1871 | OCH₃ | CH₃ | Cl | F | OCH₃ |
| 1872 | OCH₃ | CH₃ | Cl | H | Cl |
| 1873 | OCH₃ | CH₃ | Cl | Cl | Cl |
| 1874 | OCH₃ | CH₃ | Cl | H | Br |
| 1875 | OCH₃ | CH₃ | Cl | CH₃ | Br |
| 1876 | OCH₃ | CH₃ | Cl | OCH₃ | Br |
| 1877 | OCH₃ | CH₃ | Cl | Cl | Br |
| 1878 | OCH₃ | CH₃ | Cl | Br | Br |
| 1879 | OCH₃ | CH₃ | Cl | F | Br |
| 1880 | OCH₃ | CH₃ | Cl | H | F |
| 1881 | OCH₃ | CH₃ | Cl | CH₃ | F |
| 1882 | OCH₃ | CH₃ | Cl | OCH₃ | F |
| 1883 | OCH₃ | CH₃ | Cl | Cl | F |
| 1884 | OCH₃ | CH₃ | Cl | F | F |
| 1885 | OCH₃ | CH₃ | Br | H | H |
| 1886 | OCH₃ | CH₃ | Br | CH₃ | H |
| 1887 | OCH₃ | CH₃ | Br | OCH₃ | H |
| 1888 | OCH₃ | CH₃ | Br | Cl | H |
| 1889 | OCH₃ | CH₃ | Br | Br | H |
| 1890 | OCH₃ | CH₃ | Br | F | H |
| 1891 | OCH₃ | CH₃ | Br | H | CH₃ |
| 1892 | OCH₃ | CH₃ | Br | CH₃ | CH₃ |
| 1893 | OCH₃ | CH₃ | Br | OCH₃ | CH₃ |
| 1894 | OCH₃ | CH₃ | Br | Cl | CH₃ |
| 1895 | OCH₃ | CH₃ | Br | Br | CH₃ |

TABLE 2-continued

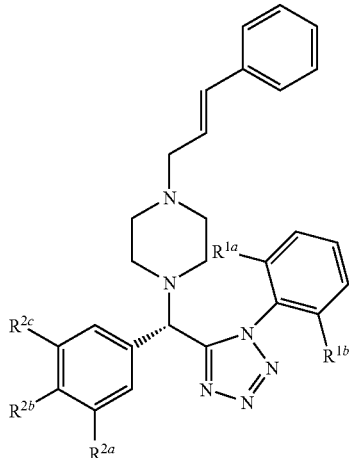

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1896 | OCH₃ | CH₃ | Br | F | CH₃ |
| 1897 | OCH₃ | CH₃ | Br | H | OCH₃ |
| 1898 | OCH₃ | CH₃ | Br | CH₃ | OCH₃ |
| 1899 | OCH₃ | CH₃ | Br | OCH₃ | OCH₃ |
| 1900 | OCH₃ | CH₃ | Br | Cl | OCH₃ |
| 1901 | OCH₃ | CH₃ | Br | Br | OCH₃ |
| 1902 | OCH₃ | CH₃ | Br | F | OCH₃ |
| 1903 | OCH₃ | CH₃ | Br | H | Cl |
| 1904 | OCH₃ | CH₃ | Br | CH₃ | Cl |
| 1905 | OCH₃ | CH₃ | Br | OCH₃ | Cl |
| 1906 | OCH₃ | CH₃ | Br | Cl | Cl |
| 1907 | OCH₃ | CH₃ | Br | Br | Cl |
| 1908 | OCH₃ | CH₃ | Br | F | Cl |
| 1909 | OCH₃ | CH₃ | Br | H | Br |
| 1910 | OCH₃ | CH₃ | Br | Br | Br |
| 1911 | OCH₃ | CH₃ | Br | H | F |
| 1912 | OCH₃ | CH₃ | Br | CH₃ | F |
| 1913 | OCH₃ | CH₃ | Br | OCH₃ | F |
| 1914 | OCH₃ | CH₃ | Br | Cl | F |
| 1915 | OCH₃ | CH₃ | Br | Br | F |
| 1916 | OCH₃ | CH₃ | Br | F | F |
| 1917 | OCH₃ | CH₃ | F | H | H |
| 1918 | OCH₃ | CH₃ | F | CH₃ | H |
| 1919 | OCH₃ | CH₃ | F | OCH₃ | H |
| 1920 | OCH₃ | CH₃ | F | Cl | H |
| 1921 | OCH₃ | CH₃ | F | Br | H |
| 1922 | OCH₃ | CH₃ | F | F | H |
| 1923 | OCH₃ | CH₃ | F | H | CH₃ |
| 1924 | OCH₃ | CH₃ | F | CH₃ | CH₃ |
| 1925 | OCH₃ | CH₃ | F | OCH₃ | CH₃ |
| 1926 | OCH₃ | CH₃ | F | Cl | CH₃ |
| 1927 | OCH₃ | CH₃ | F | Br | CH₃ |
| 1928 | OCH₃ | CH₃ | F | F | CH₃ |
| 1929 | OCH₃ | CH₃ | F | H | OCH₃ |
| 1930 | OCH₃ | CH₃ | F | CH₃ | OCH₃ |
| 1931 | OCH₃ | CH₃ | F | OCH₃ | OCH₃ |
| 1932 | OCH₃ | CH₃ | F | Cl | OCH₃ |
| 1933 | OCH₃ | CH₃ | F | Br | OCH₃ |
| 1934 | OCH₃ | CH₃ | F | F | OCH₃ |
| 1935 | OCH₃ | CH₃ | F | H | Cl |
| 1936 | OCH₃ | CH₃ | F | CH₃ | Cl |
| 1937 | OCH₃ | CH₃ | F | OCH₃ | Cl |
| 1938 | OCH₃ | CH₃ | F | Cl | Cl |
| 1939 | OCH₃ | CH₃ | F | Br | Cl |
| 1940 | OCH₃ | CH₃ | F | F | Cl |
| 1941 | OCH₃ | CH₃ | F | H | Br |
| 1942 | OCH₃ | CH₃ | F | CH₃ | Br |
| 1943 | OCH₃ | CH₃ | F | OCH₃ | Br |
| 1944 | OCH₃ | CH₃ | F | Cl | Br |
| 1945 | OCH₃ | CH₃ | F | Br | Br |

TABLE 2-continued

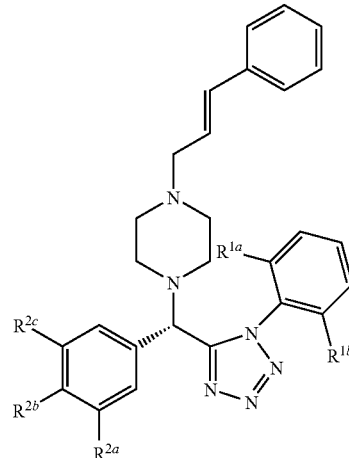

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1946 | OCH₃ | CH₃ | F | F | Br |
| 1947 | OCH₃ | CH₃ | F | H | F |
| 1948 | OCH₃ | CH₃ | F | F | F |
| 1949 | OCH₃ | OCH₃ | CH₃ | H | H |
| 1950 | OCH₃ | OCH₃ | CH₃ | H | CH₃ |
| 1951 | OCH₃ | OCH₃ | CH₃ | H | OCH₃ |
| 1952 | OCH₃ | OCH₃ | CH₃ | H | Cl |
| 1953 | OCH₃ | OCH₃ | CH₃ | H | Br |
| 1954 | OCH₃ | OCH₃ | CH₃ | H | F |
| 1955 | OCH₃ | OCH₃ | CH₃ | CH₃ | H |
| 1956 | OCH₃ | OCH₃ | CH₃ | CH₃ | CH₃ |
| 1957 | OCH₃ | OCH₃ | CH₃ | CH₃ | OCH₃ |
| 1958 | OCH₃ | OCH₃ | CH₃ | CH₃ | Cl |
| 1959 | OCH₃ | OCH₃ | CH₃ | CH₃ | Br |
| 1960 | OCH₃ | OCH₃ | CH₃ | CH₃ | F |
| 1961 | OCH₃ | OCH₃ | CH₃ | OCH₃ | H |
| 1962 | OCH₃ | OCH₃ | CH₃ | OCH₃ | OCH₃ |
| 1963 | OCH₃ | OCH₃ | CH₃ | OCH₃ | Cl |
| 1964 | OCH₃ | OCH₃ | CH₃ | OCH₃ | Br |
| 1965 | OCH₃ | OCH₃ | CH₃ | OCH₃ | F |
| 1966 | OCH₃ | OCH₃ | CH₃ | Cl | H |
| 1967 | OCH₃ | OCH₃ | CH₃ | Cl | OCH₃ |
| 1968 | OCH₃ | OCH₃ | CH₃ | Cl | Cl |
| 1969 | OCH₃ | OCH₃ | CH₃ | Cl | Br |
| 1970 | OCH₃ | OCH₃ | CH₃ | Cl | F |
| 1971 | OCH₃ | OCH₃ | CH₃ | Br | H |
| 1972 | OCH₃ | OCH₃ | CH₃ | Br | OCH₃ |
| 1973 | OCH₃ | OCH₃ | CH₃ | Br | Cl |
| 1974 | OCH₃ | OCH₃ | CH₃ | Br | Br |
| 1975 | OCH₃ | OCH₃ | CH₃ | Br | F |
| 1976 | OCH₃ | OCH₃ | CH₃ | F | H |
| 1977 | OCH₃ | OCH₃ | CH₃ | F | OCH₃ |
| 1978 | OCH₃ | OCH₃ | CH₃ | F | Cl |
| 1979 | OCH₃ | OCH₃ | CH₃ | F | Br |
| 1980 | OCH₃ | OCH₃ | CH₃ | F | F |
| 1981 | OCH₃ | OCH₃ | OCH₃ | H | H |
| 1982 | OCH₃ | OCH₃ | OCH₃ | H | CH₃ |
| 1983 | OCH₃ | OCH₃ | OCH₃ | H | OCH₃ |
| 1984 | OCH₃ | OCH₃ | OCH₃ | H | Cl |
| 1985 | OCH₃ | OCH₃ | OCH₃ | H | Br |
| 1986 | OCH₃ | OCH₃ | OCH₃ | H | F |
| 1987 | OCH₃ | OCH₃ | OCH₃ | CH₃ | H |
| 1988 | OCH₃ | OCH₃ | OCH₃ | CH₃ | CH₃ |
| 1989 | OCH₃ | OCH₃ | OCH₃ | CH₃ | Cl |
| 1990 | OCH₃ | OCH₃ | OCH₃ | CH₃ | Br |
| 1991 | OCH₃ | OCH₃ | OCH₃ | CH₃ | F |
| 1992 | OCH₃ | OCH₃ | OCH₃ | OCH₃ | H |
| 1993 | OCH₃ | OCH₃ | OCH₃ | OCH₃ | CH₃ |
| 1994 | OCH₃ | OCH₃ | OCH₃ | OCH₃ | OCH₃ |
| 1995 | OCH₃ | OCH₃ | OCH₃ | OCH₃ | Cl |

TABLE 2-continued

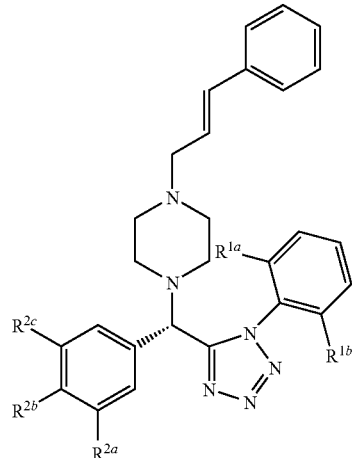

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 1996 | OCH₃ | OCH₃ | OCH₃ | OCH₃ | Br |
| 1997 | OCH₃ | OCH₃ | OCH₃ | OCH₃ | F |
| 1998 | OCH₃ | OCH₃ | OCH₃ | Cl | H |
| 1999 | OCH₃ | OCH₃ | OCH₃ | Cl | CH₃ |
| 2000 | OCH₃ | OCH₃ | OCH₃ | Cl | Cl |
| 2001 | OCH₃ | OCH₃ | OCH₃ | Cl | Br |
| 2002 | OCH₃ | OCH₃ | OCH₃ | Cl | F |
| 2003 | OCH₃ | OCH₃ | OCH₃ | Br | H |
| 2004 | OCH₃ | OCH₃ | OCH₃ | Br | CH₃ |
| 2005 | OCH₃ | OCH₃ | OCH₃ | Br | Cl |
| 2006 | OCH₃ | OCH₃ | OCH₃ | Br | Br |
| 2007 | OCH₃ | OCH₃ | OCH₃ | Br | F |
| 2008 | OCH₃ | OCH₃ | OCH₃ | F | H |
| 2009 | OCH₃ | OCH₃ | OCH₃ | F | CH₃ |
| 2010 | OCH₃ | OCH₃ | OCH₃ | F | Cl |
| 2011 | OCH₃ | OCH₃ | OCH₃ | F | Br |
| 2012 | OCH₃ | OCH₃ | OCH₃ | F | F |
| 2013 | OCH₃ | OCH₃ | Cl | H | H |
| 2014 | OCH₃ | OCH₃ | Cl | H | CH₃ |
| 2015 | OCH₃ | OCH₃ | Cl | H | OCH₃ |
| 2016 | OCH₃ | OCH₃ | Cl | H | Cl |
| 2017 | OCH₃ | OCH₃ | Cl | H | Br |
| 2018 | OCH₃ | OCH₃ | Cl | H | F |
| 2019 | OCH₃ | OCH₃ | Cl | CH₃ | H |
| 2020 | OCH₃ | OCH₃ | Cl | CH₃ | CH₃ |
| 2021 | OCH₃ | OCH₃ | Cl | CH₃ | OCH₃ |
| 2022 | OCH₃ | OCH₃ | Cl | CH₃ | Br |
| 2023 | OCH₃ | OCH₃ | Cl | CH₃ | F |
| 2024 | OCH₃ | OCH₃ | Cl | OCH₃ | H |
| 2025 | OCH₃ | OCH₃ | Cl | OCH₃ | CH₃ |
| 2026 | OCH₃ | OCH₃ | Cl | OCH₃ | OCH₃ |
| 2027 | OCH₃ | OCH₃ | Cl | OCH₃ | Br |
| 2028 | OCH₃ | OCH₃ | Cl | OCH₃ | F |
| 2029 | OCH₃ | OCH₃ | Cl | Cl | H |
| 2030 | OCH₃ | OCH₃ | Cl | Cl | CH₃ |
| 2031 | OCH₃ | OCH₃ | Cl | Cl | OCH₃ |
| 2032 | OCH₃ | OCH₃ | Cl | Cl | Cl |
| 2033 | OCH₃ | OCH₃ | Cl | Cl | Br |
| 2034 | OCH₃ | OCH₃ | Cl | Cl | F |
| 2035 | OCH₃ | OCH₃ | Cl | Br | H |
| 2036 | OCH₃ | OCH₃ | Cl | Br | CH₃ |
| 2037 | OCH₃ | OCH₃ | Cl | Br | OCH₃ |
| 2038 | OCH₃ | OCH₃ | Cl | Br | Br |
| 2039 | OCH₃ | OCH₃ | Cl | F | H |
| 2040 | OCH₃ | OCH₃ | Cl | F | CH₃ |
| 2041 | OCH₃ | OCH₃ | Cl | F | OCH₃ |
| 2042 | OCH₃ | OCH₃ | Cl | F | Br |
| 2043 | OCH₃ | OCH₃ | Cl | F | F |
| 2044 | OCH₃ | OCH₃ | Br | H | H |
| 2045 | OCH₃ | OCH₃ | Br | H | CH₃ |

TABLE 2-continued

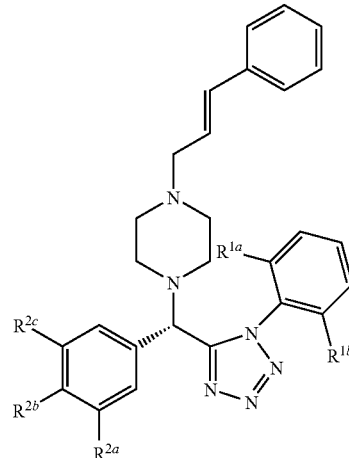

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2046 | OCH₃ | OCH₃ | Br | H | OCH₃ |
| 2047 | OCH₃ | OCH₃ | Br | H | Cl |
| 2048 | OCH₃ | OCH₃ | Br | H | Br |
| 2049 | OCH₃ | OCH₃ | Br | H | F |
| 2050 | OCH₃ | OCH₃ | Br | CH₃ | H |
| 2051 | OCH₃ | OCH₃ | Br | CH₃ | CH₃ |
| 2052 | OCH₃ | OCH₃ | Br | CH₃ | OCH₃ |
| 2053 | OCH₃ | OCH₃ | Br | CH₃ | Cl |
| 2054 | OCH₃ | OCH₃ | Br | CH₃ | F |
| 2055 | OCH₃ | OCH₃ | Br | OCH₃ | H |
| 2056 | OCH₃ | OCH₃ | Br | OCH₃ | CH₃ |
| 2057 | OCH₃ | OCH₃ | Br | OCH₃ | OCH₃ |
| 2058 | OCH₃ | OCH₃ | Br | OCH₃ | Cl |
| 2059 | OCH₃ | OCH₃ | Br | OCH₃ | F |
| 2060 | OCH₃ | OCH₃ | Br | Cl | H |
| 2061 | OCH₃ | OCH₃ | Br | Cl | CH₃ |
| 2062 | OCH₃ | OCH₃ | Br | Cl | OCH₃ |
| 2063 | OCH₃ | OCH₃ | Br | Cl | Cl |
| 2064 | OCH₃ | OCH₃ | Br | Cl | F |
| 2065 | OCH₃ | OCH₃ | Br | Br | H |
| 2066 | OCH₃ | OCH₃ | Br | Br | CH₃ |
| 2067 | OCH₃ | OCH₃ | Br | Br | OCH₃ |
| 2068 | OCH₃ | OCH₃ | Br | Br | Cl |
| 2069 | OCH₃ | OCH₃ | Br | Br | Br |
| 2070 | OCH₃ | OCH₃ | Br | Br | F |
| 2071 | OCH₃ | OCH₃ | Br | F | H |
| 2072 | OCH₃ | OCH₃ | Br | F | CH₃ |
| 2073 | OCH₃ | OCH₃ | Br | F | OCH₃ |
| 2074 | OCH₃ | OCH₃ | Br | F | Cl |
| 2075 | OCH₃ | OCH₃ | Br | F | F |
| 2076 | OCH₃ | OCH₃ | F | H | H |
| 2077 | OCH₃ | OCH₃ | F | H | CH₃ |
| 2078 | OCH₃ | OCH₃ | F | H | OCH₃ |
| 2079 | OCH₃ | OCH₃ | F | H | Cl |
| 2080 | OCH₃ | OCH₃ | F | H | Br |
| 2081 | OCH₃ | OCH₃ | F | H | F |
| 2082 | OCH₃ | OCH₃ | F | CH₃ | H |
| 2083 | OCH₃ | OCH₃ | F | CH₃ | CH₃ |
| 2084 | OCH₃ | OCH₃ | F | CH₃ | OCH₃ |
| 2085 | OCH₃ | OCH₃ | F | CH₃ | Cl |
| 2086 | OCH₃ | OCH₃ | F | CH₃ | Br |
| 2087 | OCH₃ | OCH₃ | F | OCH₃ | H |
| 2088 | OCH₃ | OCH₃ | F | OCH₃ | CH₃ |
| 2089 | OCH₃ | OCH₃ | F | OCH₃ | OCH₃ |
| 2090 | OCH₃ | OCH₃ | F | OCH₃ | Cl |
| 2091 | OCH₃ | OCH₃ | F | OCH₃ | Br |
| 2092 | OCH₃ | OCH₃ | F | Cl | H |
| 2093 | OCH₃ | OCH₃ | F | Cl | CH₃ |
| 2094 | OCH₃ | OCH₃ | F | Cl | OCH₃ |
| 2095 | OCH₃ | OCH₃ | F | Cl | Cl |

TABLE 2-continued

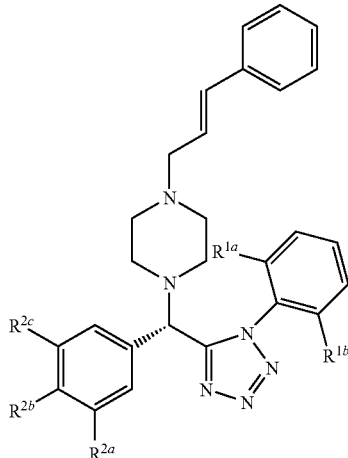

wherein $R^{1a}$, $R^{1b}$, $R^{2a}$, $R^{2b}$, and $R^{2c}$ are as defined in Table 2.

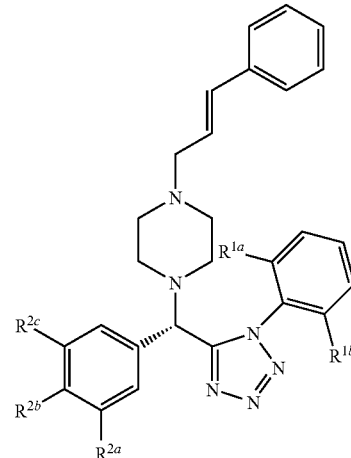

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2096 | OCH₃ | OCH₃ | F | Cl | Br |
| 2097 | OCH₃ | OCH₃ | F | Br | H |
| 2098 | OCH₃ | OCH₃ | F | Br | CH₃ |
| 2099 | OCH₃ | OCH₃ | F | Br | OCH₃ |
| 2100 | OCH₃ | OCH₃ | F | Br | Cl |
| 2101 | OCH₃ | OCH₃ | F | Br | Br |
| 2102 | OCH₃ | OCH₃ | F | F | H |
| 2103 | OCH₃ | OCH₃ | F | F | CH₃ |
| 2104 | OCH₃ | OCH₃ | F | F | OCH₃ |
| 2105 | OCH₃ | OCH₃ | F | F | Cl |
| 2106 | OCH₃ | OCH₃ | F | F | Br |
| 2107 | OCH₃ | OCH₃ | F | F | F |
| 2108 | OCH₃ | Cl | CH₃ | H | H |
| 2109 | OCH₃ | Cl | CH₃ | H | CH₃ |
| 2110 | OCH₃ | Cl | CH₃ | H | OCH₃ |
| 2111 | OCH₃ | Cl | CH₃ | H | Cl |
| 2112 | OCH₃ | Cl | CH₃ | H | Br |
| 2113 | OCH₃ | Cl | CH₃ | H | F |
| 2114 | OCH₃ | Cl | CH₃ | CH₃ | H |
| 2115 | OCH₃ | Cl | CH₃ | CH₃ | CH₃ |
| 2116 | OCH₃ | Cl | CH₃ | CH₃ | OCH₃ |
| 2117 | OCH₃ | Cl | CH₃ | CH₃ | Cl |
| 2118 | OCH₃ | Cl | CH₃ | CH₃ | Br |
| 2119 | OCH₃ | Cl | CH₃ | CH₃ | F |
| 2120 | OCH₃ | Cl | CH₃ | OCH₃ | H |
| 2121 | OCH₃ | Cl | CH₃ | OCH₃ | OCH₃ |
| 2122 | OCH₃ | Cl | CH₃ | OCH₃ | Cl |
| 2123 | OCH₃ | Cl | CH₃ | OCH₃ | Br |
| 2124 | OCH₃ | Cl | CH₃ | OCH₃ | F |
| 2125 | OCH₃ | Cl | CH₃ | Cl | H |
| 2126 | OCH₃ | Cl | CH₃ | Cl | OCH₃ |
| 2127 | OCH₃ | Cl | CH₃ | Cl | Cl |
| 2128 | OCH₃ | Cl | CH₃ | Cl | Br |
| 2129 | OCH₃ | Cl | CH₃ | Cl | F |
| 2130 | OCH₃ | Cl | CH₃ | Br | H |
| 2131 | OCH₃ | Cl | CH₃ | Br | OCH₃ |
| 2132 | OCH₃ | Cl | CH₃ | Br | Cl |
| 2133 | OCH₃ | Cl | CH₃ | Br | Br |
| 2134 | OCH₃ | Cl | CH₃ | Br | F |
| 2135 | OCH₃ | Cl | CH₃ | F | H |
| 2136 | OCH₃ | Cl | CH₃ | F | OCH₃ |
| 2137 | OCH₃ | Cl | CH₃ | F | Cl |
| 2138 | OCH₃ | Cl | CH₃ | F | Br |
| 2139 | OCH₃ | Cl | CH₃ | F | F |
| 2140 | OCH₃ | Cl | OCH₃ | H | H |
| 2141 | OCH₃ | Cl | OCH₃ | H | CH₃ |
| 2142 | OCH₃ | Cl | OCH₃ | H | OCH₃ |
| 2143 | OCH₃ | Cl | OCH₃ | H | Cl |
| 2144 | OCH₃ | Cl | OCH₃ | H | Br |
| 2145 | OCH₃ | Cl | OCH₃ | H | F |
| 2146 | OCH₃ | Cl | OCH₃ | CH₃ | H |
| 2147 | OCH₃ | Cl | OCH₃ | CH₃ | CH₃ |
| 2148 | OCH₃ | Cl | OCH₃ | CH₃ | Cl |
| 2149 | OCH₃ | Cl | OCH₃ | CH₃ | Br |
| 2150 | OCH₃ | Cl | OCH₃ | CH₃ | F |
| 2151 | OCH₃ | Cl | OCH₃ | OCH₃ | H |
| 2152 | OCH₃ | Cl | OCH₃ | OCH₃ | CH₃ |
| 2153 | OCH₃ | Cl | OCH₃ | OCH₃ | OCH₃ |
| 2154 | OCH₃ | Cl | OCH₃ | OCH₃ | Cl |
| 2155 | OCH₃ | Cl | OCH₃ | OCH₃ | Br |
| 2156 | OCH₃ | Cl | OCH₃ | OCH₃ | F |
| 2157 | OCH₃ | Cl | OCH₃ | Cl | H |
| 2158 | OCH₃ | Cl | OCH₃ | Cl | CH₃ |
| 2159 | OCH₃ | Cl | OCH₃ | Cl | Cl |
| 2160 | OCH₃ | Cl | OCH₃ | Cl | Br |
| 2161 | OCH₃ | Cl | OCH₃ | Cl | F |
| 2162 | OCH₃ | Cl | OCH₃ | Br | H |
| 2163 | OCH₃ | Cl | OCH₃ | Br | CH₃ |
| 2164 | OCH₃ | Cl | OCH₃ | Br | Cl |
| 2165 | OCH₃ | Cl | OCH₃ | Br | Br |
| 2166 | OCH₃ | Cl | OCH₃ | Br | F |
| 2167 | OCH₃ | Cl | OCH₃ | F | H |
| 2168 | OCH₃ | Cl | OCH₃ | F | CH₃ |
| 2169 | OCH₃ | Cl | OCH₃ | F | Cl |
| 2170 | OCH₃ | Cl | OCH₃ | F | Br |
| 2171 | OCH₃ | Cl | OCH₃ | F | F |
| 2172 | OCH₃ | Cl | Cl | H | H |
| 2173 | OCH₃ | Cl | Cl | H | CH₃ |
| 2174 | OCH₃ | Cl | Cl | H | OCH₃ |
| 2175 | OCH₃ | Cl | Cl | H | Cl |
| 2176 | OCH₃ | Cl | Cl | H | Br |
| 2177 | OCH₃ | Cl | Cl | H | F |
| 2178 | OCH₃ | Cl | Cl | CH₃ | H |
| 2179 | OCH₃ | Cl | Cl | CH₃ | CH₃ |
| 2180 | OCH₃ | Cl | Cl | CH₃ | OCH₃ |
| 2181 | OCH₃ | Cl | Cl | CH₃ | Br |
| 2182 | OCH₃ | Cl | Cl | CH₃ | F |
| 2183 | OCH₃ | Cl | Cl | OCH₃ | H |
| 2184 | OCH₃ | Cl | Cl | OCH₃ | CH₃ |
| 2185 | OCH₃ | Cl | Cl | OCH₃ | OCH₃ |
| 2186 | OCH₃ | Cl | Cl | OCH₃ | Br |
| 2187 | OCH₃ | Cl | Cl | OCH₃ | F |
| 2188 | OCH₃ | Cl | Cl | Cl | H |
| 2189 | OCH₃ | Cl | Cl | Cl | CH₃ |
| 2190 | OCH₃ | Cl | Cl | Cl | OCH₃ |
| 2191 | OCH₃ | Cl | Cl | Cl | Cl |
| 2192 | OCH₃ | Cl | Cl | Cl | Br |
| 2193 | OCH₃ | Cl | Cl | Cl | F |
| 2194 | OCH₃ | Cl | Cl | Br | H |
| 2195 | OCH₃ | Cl | Cl | Br | CH₃ |

TABLE 2-continued

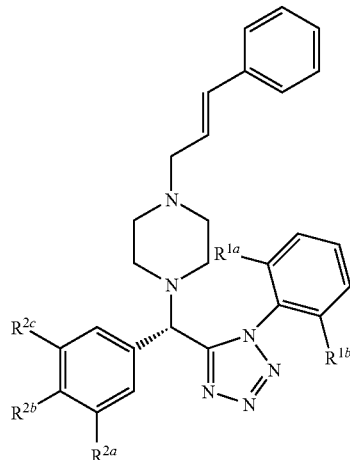

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2196 | OCH₃ | Cl | Cl | Br | OCH₃ |
| 2197 | OCH₃ | Cl | Cl | Br | Br |
| 2198 | OCH₃ | Cl | Cl | F | H |
| 2199 | OCH₃ | Cl | Cl | F | CH₃ |
| 2200 | OCH₃ | Cl | Cl | F | OCH₃ |
| 2201 | OCH₃ | Cl | Cl | F | Br |
| 2202 | OCH₃ | Cl | Cl | F | F |
| 2203 | OCH₃ | Cl | Br | H | H |
| 2204 | OCH₃ | Cl | Br | H | CH₃ |
| 2205 | OCH₃ | Cl | Br | H | OCH₃ |
| 2206 | OCH₃ | Cl | Br | H | Cl |
| 2207 | OCH₃ | Cl | Br | H | Br |
| 2208 | OCH₃ | Cl | Br | H | F |
| 2209 | OCH₃ | Cl | Br | CH₃ | H |
| 2210 | OCH₃ | Cl | Br | CH₃ | CH₃ |
| 2211 | OCH₃ | Cl | Br | CH₃ | OCH₃ |
| 2212 | OCH₃ | Cl | Br | CH₃ | Cl |
| 2213 | OCH₃ | Cl | Br | CH₃ | F |
| 2214 | OCH₃ | Cl | Br | OCH₃ | H |
| 2215 | OCH₃ | Cl | Br | OCH₃ | CH₃ |
| 2216 | OCH₃ | Cl | Br | OCH₃ | OCH₃ |
| 2217 | OCH₃ | Cl | Br | OCH₃ | Cl |
| 2218 | OCH₃ | Cl | Br | OCH₃ | F |
| 2219 | OCH₃ | Cl | Br | Cl | H |
| 2220 | OCH₃ | Cl | Br | Cl | CH₃ |
| 2221 | OCH₃ | Cl | Br | Cl | OCH₃ |
| 2222 | OCH₃ | Cl | Br | Cl | Cl |
| 2223 | OCH₃ | Cl | Br | Cl | F |
| 2224 | OCH₃ | Cl | Br | Br | H |
| 2225 | OCH₃ | Cl | Br | Br | CH₃ |
| 2226 | OCH₃ | Cl | Br | Br | OCH₃ |
| 2227 | OCH₃ | Cl | Br | Br | Cl |
| 2228 | OCH₃ | Cl | Br | Br | Br |
| 2229 | OCH₃ | Cl | Br | Br | F |
| 2230 | OCH₃ | Cl | Br | F | H |
| 2231 | OCH₃ | Cl | Br | F | CH₃ |
| 2232 | OCH₃ | Cl | Br | F | OCH₃ |
| 2233 | OCH₃ | Cl | Br | F | Cl |
| 2234 | OCH₃ | Cl | Br | F | F |
| 2235 | OCH₃ | Cl | F | H | H |
| 2236 | OCH₃ | Cl | F | H | CH₃ |
| 2237 | OCH₃ | Cl | F | H | OCH₃ |
| 2238 | OCH₃ | Cl | F | H | Cl |
| 2239 | OCH₃ | Cl | F | H | Br |
| 2240 | OCH₃ | Cl | F | H | F |
| 2241 | OCH₃ | Cl | F | CH₃ | H |
| 2242 | OCH₃ | Cl | F | CH₃ | CH₃ |
| 2243 | OCH₃ | Cl | F | CH₃ | OCH₃ |
| 2244 | OCH₃ | Cl | F | CH₃ | Cl |
| 2245 | OCH₃ | Cl | F | CH₃ | Br |

TABLE 2-continued

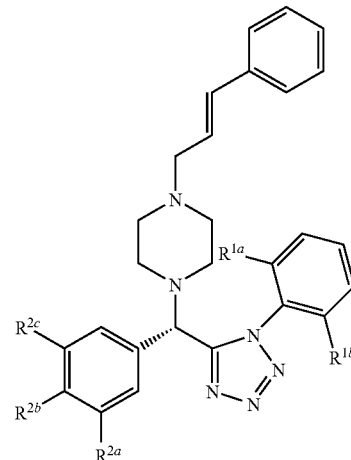

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2246 | OCH₃ | Cl | F | OCH₃ | H |
| 2247 | OCH₃ | Cl | F | OCH₃ | CH₃ |
| 2248 | OCH₃ | Cl | F | OCH₃ | OCH₃ |
| 2249 | OCH₃ | Cl | F | OCH₃ | Cl |
| 2250 | OCH₃ | Cl | F | OCH₃ | Br |
| 2251 | OCH₃ | Cl | F | Cl | H |
| 2252 | OCH₃ | Cl | F | Cl | CH₃ |
| 2253 | OCH₃ | Cl | F | Cl | OCH₃ |
| 2254 | OCH₃ | Cl | F | Cl | Cl |
| 2255 | OCH₃ | Cl | F | Cl | Br |
| 2256 | OCH₃ | Cl | F | Br | H |
| 2257 | OCH₃ | Cl | F | Br | CH₃ |
| 2258 | OCH₃ | Cl | F | Br | OCH₃ |
| 2259 | OCH₃ | Cl | F | Br | Cl |
| 2260 | OCH₃ | Cl | F | Br | Br |
| 2261 | OCH₃ | Cl | F | F | H |
| 2262 | OCH₃ | Cl | F | F | CH₃ |
| 2263 | OCH₃ | Cl | F | F | OCH₃ |
| 2264 | OCH₃ | Cl | F | F | Cl |
| 2265 | OCH₃ | Cl | F | F | Br |
| 2266 | OCH₃ | Cl | F | F | F |
| 2267 | OCH₃ | Br | CH₃ | H | H |
| 2268 | OCH₃ | Br | CH₃ | H | CH₃ |
| 2269 | OCH₃ | Br | CH₃ | H | OCH₃ |
| 2270 | OCH₃ | Br | CH₃ | H | Cl |
| 2271 | OCH₃ | Br | CH₃ | H | Br |
| 2272 | OCH₃ | Br | CH₃ | H | F |
| 2273 | OCH₃ | Br | CH₃ | CH₃ | H |
| 2274 | OCH₃ | Br | CH₃ | CH₃ | CH₃ |
| 2275 | OCH₃ | Br | CH₃ | CH₃ | OCH₃ |
| 2276 | OCH₃ | Br | CH₃ | CH₃ | Cl |
| 2277 | OCH₃ | Br | CH₃ | CH₃ | Br |
| 2278 | OCH₃ | Br | CH₃ | CH₃ | F |
| 2279 | OCH₃ | Br | CH₃ | OCH₃ | H |
| 2280 | OCH₃ | Br | CH₃ | OCH₃ | OCH₃ |
| 2281 | OCH₃ | Br | CH₃ | OCH₃ | Cl |
| 2282 | OCH₃ | Br | CH₃ | OCH₃ | Br |
| 2283 | OCH₃ | Br | CH₃ | OCH₃ | F |
| 2284 | OCH₃ | Br | CH₃ | Cl | H |
| 2285 | OCH₃ | Br | CH₃ | Cl | OCH₃ |
| 2286 | OCH₃ | Br | CH₃ | Cl | Cl |
| 2287 | OCH₃ | Br | CH₃ | Cl | Br |
| 2288 | OCH₃ | Br | CH₃ | Cl | F |
| 2289 | OCH₃ | Br | CH₃ | Br | H |
| 2290 | OCH₃ | Br | CH₃ | Br | OCH₃ |
| 2291 | OCH₃ | Br | CH₃ | Br | Cl |
| 2292 | OCH₃ | Br | CH₃ | Br | Br |
| 2293 | OCH₃ | Br | CH₃ | Br | F |
| 2294 | OCH₃ | Br | CH₃ | F | H |
| 2295 | OCH₃ | Br | CH₃ | F | OCH₃ |

TABLE 2-continued

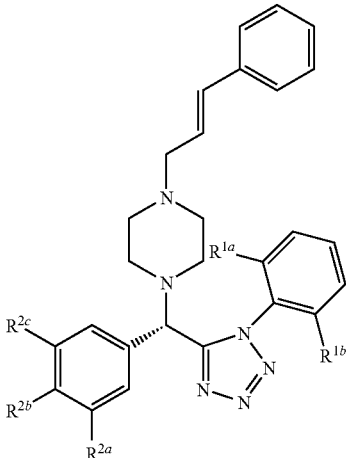

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2296 | OCH$_3$ | Br | CH$_3$ | F | Cl |
| 2297 | OCH$_3$ | Br | CH$_3$ | F | Br |
| 2298 | OCH$_3$ | Br | CH$_3$ | F | F |
| 2299 | OCH$_3$ | Br | OCH$_3$ | H | H |
| 2300 | OCH$_3$ | Br | OCH$_3$ | H | CH$_3$ |
| 2301 | OCH$_3$ | Br | OCH$_3$ | H | OCH$_3$ |
| 2302 | OCH$_3$ | Br | OCH$_3$ | H | Cl |
| 2303 | OCH$_3$ | Br | OCH$_3$ | H | Br |
| 2304 | OCH$_3$ | Br | OCH$_3$ | H | F |
| 2305 | OCH$_3$ | Br | OCH$_3$ | CH$_3$ | H |
| 2306 | OCH$_3$ | Br | OCH$_3$ | CH$_3$ | CH$_3$ |
| 2307 | OCH$_3$ | Br | OCH$_3$ | CH$_3$ | Cl |
| 2308 | OCH$_3$ | Br | OCH$_3$ | CH$_3$ | Br |
| 2309 | OCH$_3$ | Br | OCH$_3$ | CH$_3$ | F |
| 2310 | OCH$_3$ | Br | OCH$_3$ | OCH$_3$ | H |
| 2311 | OCH$_3$ | Br | OCH$_3$ | OCH$_3$ | CH$_3$ |
| 2312 | OCH$_3$ | Br | OCH$_3$ | OCH$_3$ | OCH$_3$ |
| 2313 | OCH$_3$ | Br | OCH$_3$ | OCH$_3$ | Cl |
| 2314 | OCH$_3$ | Br | OCH$_3$ | OCH$_3$ | Br |
| 2315 | OCH$_3$ | Br | OCH$_3$ | OCH$_3$ | F |
| 2316 | OCH$_3$ | Br | OCH$_3$ | Cl | H |
| 2317 | OCH$_3$ | Br | OCH$_3$ | Cl | CH$_3$ |
| 2318 | OCH$_3$ | Br | OCH$_3$ | Cl | Cl |
| 2319 | OCH$_3$ | Br | OCH$_3$ | Cl | Br |
| 2320 | OCH$_3$ | Br | OCH$_3$ | Cl | F |
| 2321 | OCH$_3$ | Br | OCH$_3$ | Br | H |
| 2322 | OCH$_3$ | Br | OCH$_3$ | Br | CH$_3$ |
| 2323 | OCH$_3$ | Br | OCH$_3$ | Br | Cl |
| 2324 | OCH$_3$ | Br | OCH$_3$ | Br | Br |
| 2325 | OCH$_3$ | Br | OCH$_3$ | Br | F |
| 2326 | OCH$_3$ | Br | OCH$_3$ | F | H |
| 2327 | OCH$_3$ | Br | OCH$_3$ | F | CH$_3$ |
| 2328 | OCH$_3$ | Br | OCH$_3$ | F | Cl |
| 2329 | OCH$_3$ | Br | OCH$_3$ | F | Br |
| 2330 | OCH$_3$ | Br | OCH$_3$ | F | F |
| 2331 | OCH$_3$ | Br | Cl | H | H |
| 2332 | OCH$_3$ | Br | Cl | H | CH$_3$ |
| 2333 | OCH$_3$ | Br | Cl | H | OCH$_3$ |
| 2334 | OCH$_3$ | Br | Cl | H | Cl |
| 2335 | OCH$_3$ | Br | Cl | H | Br |
| 2336 | OCH$_3$ | Br | Cl | H | F |
| 2337 | OCH$_3$ | Br | Cl | CH$_3$ | H |
| 2338 | OCH$_3$ | Br | Cl | CH$_3$ | CH$_3$ |
| 2339 | OCH$_3$ | Br | Cl | CH$_3$ | OCH$_3$ |
| 2340 | OCH$_3$ | Br | Cl | CH$_3$ | Br |
| 2341 | OCH$_3$ | Br | Cl | CH$_3$ | F |
| 2342 | OCH$_3$ | Br | Cl | OCH$_3$ | H |
| 2343 | OCH$_3$ | Br | Cl | OCH$_3$ | CH$_3$ |
| 2344 | OCH$_3$ | Br | Cl | OCH$_3$ | OCH$_3$ |
| 2345 | OCH$_3$ | Br | Cl | OCH$_3$ | Br |
| 2346 | OCH$_3$ | Br | Cl | OCH$_3$ | F |
| 2347 | OCH$_3$ | Br | Cl | Cl | H |
| 2348 | OCH$_3$ | Br | Cl | Cl | CH$_3$ |
| 2349 | OCH$_3$ | Br | Cl | Cl | OCH$_3$ |
| 2350 | OCH$_3$ | Br | Cl | Cl | Cl |
| 2351 | OCH$_3$ | Br | Cl | Cl | Br |
| 2352 | OCH$_3$ | Br | Cl | Cl | F |
| 2353 | OCH$_3$ | Br | Cl | Br | H |
| 2354 | OCH$_3$ | Br | Cl | Br | CH$_3$ |
| 2355 | OCH$_3$ | Br | Cl | Br | OCH$_3$ |
| 2356 | OCH$_3$ | Br | Cl | Br | Br |
| 2357 | OCH$_3$ | Br | Cl | F | H |
| 2358 | OCH$_3$ | Br | Cl | F | CH$_3$ |
| 2359 | OCH$_3$ | Br | Cl | F | OCH$_3$ |
| 2360 | OCH$_3$ | Br | Cl | F | Br |
| 2361 | OCH$_3$ | Br | Cl | F | F |
| 2362 | OCH$_3$ | Br | Br | H | H |
| 2363 | OCH$_3$ | Br | Br | H | CH$_3$ |
| 2364 | OCH$_3$ | Br | Br | H | OCH$_3$ |
| 2365 | OCH$_3$ | Br | Br | H | Cl |
| 2366 | OCH$_3$ | Br | Br | H | Br |
| 2367 | OCH$_3$ | Br | Br | H | F |
| 2368 | OCH$_3$ | Br | Br | CH$_3$ | H |
| 2369 | OCH$_3$ | Br | Br | CH$_3$ | CH$_3$ |
| 2370 | OCH$_3$ | Br | Br | CH$_3$ | OCH$_3$ |
| 2371 | OCH$_3$ | Br | Br | CH$_3$ | Cl |
| 2372 | OCH$_3$ | Br | Br | CH$_3$ | F |
| 2373 | OCH$_3$ | Br | Br | OCH$_3$ | H |
| 2374 | OCH$_3$ | Br | Br | OCH$_3$ | CH$_3$ |
| 2375 | OCH$_3$ | Br | Br | OCH$_3$ | OCH$_3$ |
| 2376 | OCH$_3$ | Br | Br | OCH$_3$ | Cl |
| 2377 | OCH$_3$ | Br | Br | OCH$_3$ | F |
| 2378 | OCH$_3$ | Br | Br | Cl | H |
| 2379 | OCH$_3$ | Br | Br | Cl | CH$_3$ |
| 2380 | OCH$_3$ | Br | Br | Cl | OCH$_3$ |
| 2381 | OCH$_3$ | Br | Br | Cl | Cl |
| 2382 | OCH$_3$ | Br | Br | Cl | F |
| 2383 | OCH$_3$ | Br | Br | Br | H |
| 2384 | OCH$_3$ | Br | Br | Br | CH$_3$ |
| 2385 | OCH$_3$ | Br | Br | Br | OCH$_3$ |
| 2386 | OCH$_3$ | Br | Br | Br | Cl |
| 2387 | OCH$_3$ | Br | Br | Br | Br |
| 2388 | OCH$_3$ | Br | Br | Br | F |
| 2389 | OCH$_3$ | Br | Br | F | H |
| 2390 | OCH$_3$ | Br | Br | F | CH$_3$ |
| 2391 | OCH$_3$ | Br | Br | F | OCH$_3$ |
| 2392 | OCH$_3$ | Br | Br | F | Cl |
| 2393 | OCH$_3$ | Br | Br | F | F |
| 2394 | OCH$_3$ | Br | F | H | H |
| 2395 | OCH$_3$ | Be | F | H | CH$_3$ |

TABLE 2-continued

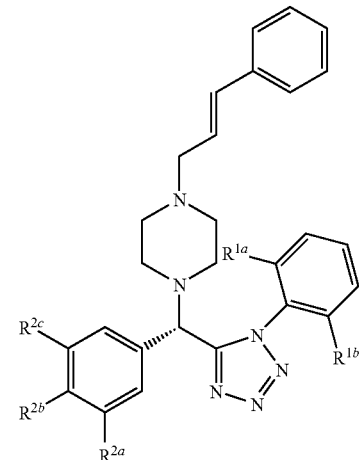

wherein $R^{1a}$, $R^{1b}$, $R^{2a}$, $R^{2b}$, and $R^{2c}$ are as defined in Table 2.

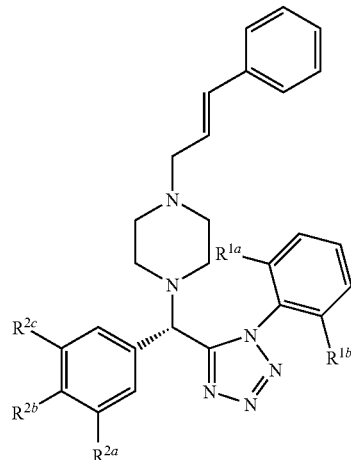

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ | Compound No. | $R^{1a}$ | $R^{1b}$ | $R^{2a}$ | $R^{2b}$ | $R^{2c}$ |
|---|---|---|---|---|---|---|---|---|---|---|---|
| 2396 | OCH₃ | Br | F | H | OCH₃ | 2446 | OCH₃ | F | CH₃ | Cl | Br |
| 2397 | OCH₃ | Br | F | H | Cl | 2447 | OCH₃ | F | CH₃ | Cl | F |
| 2398 | OCH₃ | Br | F | H | Br | 2448 | OCH₃ | F | CH₃ | Br | H |
| 2399 | OCH₃ | Br | F | H | F | 2449 | OCH₃ | F | CH₃ | Br | OCH₃ |
| 2400 | OCH₃ | Br | F | CH₃ | H | 2450 | OCH₃ | F | CH₃ | Br | Cl |
| 2401 | OCH₃ | Br | F | CH₃ | CH₃ | 2451 | OCH₃ | F | CH₃ | Br | Br |
| 2402 | OCH₃ | Br | F | CH₃ | OCH₃ | 2452 | OCH₃ | F | CH₃ | Br | F |
| 2403 | OCH₃ | Br | F | CH₃ | Cl | 2453 | OCH₃ | F | CH₃ | F | H |
| 2404 | OCH₃ | Br | F | CH₃ | Br | 2454 | OCH₃ | F | CH₃ | F | OCH₃ |
| 2405 | OCH₃ | Br | F | OCH₃ | H | 2455 | OCH₃ | F | CH₃ | F | Cl |
| 2406 | OCH₃ | Br | F | OCH₃ | CH₃ | 2456 | OCH₃ | F | CH₃ | F | Br |
| 2407 | OCH₃ | Br | F | OCH₃ | OCH₃ | 2457 | OCH₃ | F | CH₃ | F | F |
| 2408 | OCH₃ | Br | F | OCH₃ | Cl | 2458 | OCH₃ | F | OCH₃ | H | H |
| 2409 | OCH₃ | Br | F | OCH₃ | Br | 2459 | OCH₃ | F | OCH₃ | H | CH₃ |
| 2410 | OCH₃ | Br | F | Cl | H | 2460 | OCH₃ | F | OCH₃ | H | OCH₃ |
| 2411 | OCH₃ | Br | F | Cl | CH₃ | 2461 | OCH₃ | F | OCH₃ | H | Cl |
| 2412 | OCH₃ | Br | F | Cl | OCH₃ | 2462 | OCH₃ | F | OCH₃ | H | Br |
| 2413 | OCH₃ | Br | F | Cl | Cl | 2463 | OCH₃ | F | OCH₃ | H | F |
| 2414 | OCH₃ | Br | F | Cl | Br | 2464 | OCH₃ | F | OCH₃ | CH₃ | H |
| 2415 | OCH₃ | Br | F | Br | H | 2465 | OCH₃ | F | OCH₃ | CH₃ | CH₃ |
| 2416 | OCH₃ | Br | F | Br | CH₃ | 2466 | OCH₃ | F | OCH₃ | CH₃ | Cl |
| 2417 | OCH₃ | Br | F | Br | OCH₃ | 2467 | OCH₃ | F | OCH₃ | CH₃ | Br |
| 2418 | OCH₃ | Br | F | Br | Cl | 2468 | OCH₃ | F | OCH₃ | CH₃ | F |
| 2419 | OCH₃ | Br | F | Br | Br | 2469 | OCH₃ | F | OCH₃ | OCH₃ | H |
| 2420 | OCH₃ | Br | F | F | H | 2470 | OCH₃ | F | OCH₃ | OCH₃ | CH₃ |
| 2421 | OCH₃ | Br | F | F | CH₃ | 2471 | OCH₃ | F | OCH₃ | OCH₃ | OCH₃ |
| 2422 | OCH₃ | Br | F | F | OCH₃ | 2472 | OCH₃ | F | OCH₃ | OCH₃ | Cl |
| 2423 | OCH₃ | Br | F | F | Cl | 2473 | OCH₃ | F | OCH₃ | OCH₃ | Br |
| 2424 | OCH₃ | Br | F | F | Br | 2474 | OCH₃ | F | OCH₃ | OCH₃ | F |
| 2425 | OCH₃ | Br | F | F | F | 2475 | OCH₃ | F | OCH₃ | Cl | H |
| 2426 | OCH₃ | F | CH₃ | H | H | 2476 | OCH₃ | F | OCH₃ | Cl | CH₃ |
| 2427 | OCH₃ | F | CH₃ | H | CH₃ | 2477 | OCH₃ | F | OCH₃ | Cl | Cl |
| 2428 | OCH₃ | F | CH₃ | H | OCH₃ | 2478 | OCH₃ | F | OCH₃ | Cl | Br |
| 2429 | OCH₃ | F | CH₃ | H | Cl | 2479 | OCH₃ | F | OCH₃ | Cl | F |
| 2430 | OCH₃ | F | CH₃ | H | Br | 2480 | OCH₃ | F | OCH₃ | Br | H |
| 2431 | OCH₃ | F | CH₃ | H | F | 2481 | OCH₃ | F | OCH₃ | Br | CH₃ |
| 2432 | OCH₃ | F | CH₃ | CH₃ | H | 2482 | OCH₃ | F | OCH₃ | Br | Cl |
| 2433 | OCH₃ | F | CH₃ | CH₃ | CH₃ | 2483 | OCH₃ | F | OCH₃ | Br | Br |
| 2434 | OCH₃ | F | CH₃ | CH₃ | OCH₃ | 2484 | OCH₃ | F | OCH₃ | Br | F |
| 2435 | OCH₃ | F | CH₃ | CH₃ | Cl | 2485 | OCH₃ | F | OCH₃ | F | H |
| 2436 | OCH₃ | F | CH₃ | CH₃ | Br | 2486 | OCH₃ | F | OCH₃ | F | CH₃ |
| 2437 | OCH₃ | F | CH₃ | CH₃ | F | 2487 | OCH₃ | F | OCH₃ | F | Cl |
| 2438 | OCH₃ | F | CH₃ | OCH₃ | H | 2488 | OCH₃ | F | OCH₃ | F | Br |
| 2439 | OCH₃ | F | CH₃ | OCH₃ | OCH₃ | 2489 | OCH₃ | F | OCH₃ | F | F |
| 2440 | OCH₃ | F | CH₃ | OCH₃ | Cl | 2490 | OCH₃ | F | Cl | H | H |
| 2441 | OCH₃ | F | CH₃ | OCH₃ | Br | 2491 | OCH₃ | F | Cl | H | CH₃ |
| 2442 | OCH₃ | F | CH₃ | OCH₃ | F | 2492 | OCH₃ | F | Cl | H | OCH₃ |
| 2443 | OCH₃ | F | CH₃ | Cl | H | 2493 | OCH₃ | F | Cl | H | Cl |
| 2444 | OCH₃ | F | CH₃ | Cl | OCH₃ | 2494 | OCH₃ | F | Cl | H | Br |
| 2445 | OCH₃ | F | CH₃ | Cl | Cl | 2495 | OCH₃ | F | Cl | H | F |

TABLE 2-continued

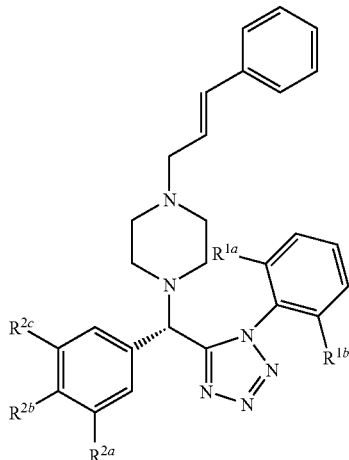

wherein $R^{1a}$, $R^{1b}$, $R^{2a}$, $R^{2b}$, and $R^{2c}$ are as defined in Table 2.

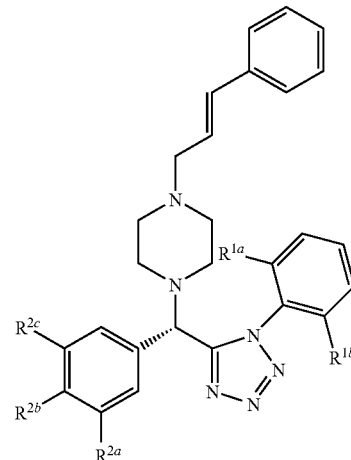

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2496 | OCH₃ | F | Cl | CH₃ | H |
| 2497 | OCH₃ | F | Cl | CH₃ | CH₃ |
| 2498 | OCH₃ | F | Cl | CH₃ | OCH₃ |
| 2499 | OCH₃ | F | Cl | CH₃ | Br |
| 2500 | OCH₃ | F | Cl | CH₃ | F |
| 2501 | OCH₃ | F | Cl | OCH₃ | H |
| 2502 | OCH₃ | F | Cl | OCH₃ | CH₃ |
| 2503 | OCH₃ | F | Cl | OCH₃ | OCH₃ |
| 2504 | OCH₃ | F | Cl | OCH₃ | Br |
| 2505 | OCH₃ | F | Cl | OCH₃ | F |
| 2506 | OCH₃ | F | Cl | Cl | H |
| 2507 | OCH₃ | F | Cl | Cl | CH₃ |
| 2508 | OCH₃ | F | Cl | Cl | OCH₃ |
| 2509 | OCH₃ | F | Cl | Cl | Cl |
| 2510 | OCH₃ | F | Cl | Cl | Br |
| 2511 | OCH₃ | F | Cl | Cl | F |
| 2512 | OCH₃ | F | Cl | Br | H |
| 2513 | OCH₃ | F | Cl | Br | CH₃ |
| 2514 | OCH₃ | F | Cl | Br | OCH₃ |
| 2515 | OCH₃ | F | Cl | Br | Br |
| 2516 | OCH₃ | F | Cl | F | H |
| 2517 | OCH₃ | F | Cl | F | CH₃ |
| 2518 | OCH₃ | F | Cl | F | OCH₃ |
| 2519 | OCH₃ | F | Cl | F | Br |
| 2520 | OCH₃ | F | Cl | F | F |
| 2521 | OCH₃ | F | Br | H | H |
| 2522 | OCH₃ | F | Br | H | CH₃ |
| 2523 | OCH₃ | F | Br | H | OCH₃ |
| 2524 | OCH₃ | F | Br | H | Cl |
| 2525 | OCH₃ | F | Br | H | Br |
| 2526 | OCH₃ | F | Br | H | F |
| 2527 | OCH₃ | F | Br | CH₃ | H |
| 2528 | OCH₃ | F | Br | CH₃ | CH₃ |
| 2529 | OCH₃ | F | Br | CH₃ | OCH₃ |
| 2530 | OCH₃ | F | Br | CH₃ | Cl |
| 2531 | OCH₃ | F | Br | CH₃ | F |
| 2532 | OCH₃ | F | Br | OCH₃ | H |
| 2533 | OCH₃ | F | Br | OCH₃ | CH₃ |
| 2534 | OCH₃ | F | Br | OCH₃ | OCH₃ |
| 2535 | OCH₃ | F | Br | OCH₃ | Cl |
| 2536 | OCH₃ | F | Br | OCH₃ | F |
| 2537 | OCH₃ | F | Br | Cl | H |
| 2538 | OCH₃ | F | Br | Cl | CH₃ |
| 2539 | OCH₃ | F | Br | Cl | OCH₃ |
| 2540 | OCH₃ | F | Br | Cl | Cl |
| 2541 | OCH₃ | F | Br | Cl | F |
| 2542 | OCH₃ | F | Br | Br | H |
| 2543 | OCH₃ | F | Br | Br | CH₃ |
| 2544 | OCH₃ | F | Br | Br | OCH₃ |
| 2545 | OCH₃ | F | Br | Br | Cl |
| 2546 | OCH₃ | F | Br | Br | Br |
| 2547 | OCH₃ | F | Br | Br | F |
| 2548 | OCH₃ | F | Br | F | H |
| 2549 | OCH₃ | F | Br | F | CH₃ |
| 2550 | OCH₃ | F | Br | F | OCH₃ |
| 2551 | OCH₃ | F | Br | F | Cl |
| 2552 | OCH₃ | F | Br | F | F |
| 2553 | OCH₃ | F | F | H | H |
| 2554 | OCH₃ | F | F | H | CH₃ |
| 2555 | OCH₃ | F | F | H | OCH₃ |
| 2556 | OCH₃ | F | F | H | Cl |
| 2557 | OCH₃ | F | F | H | Br |
| 2558 | OCH₃ | F | F | H | F |
| 2559 | OCH₃ | F | F | CH₃ | H |
| 2560 | OCH₃ | F | F | CH₃ | CH₃ |
| 2561 | OCH₃ | F | F | CH₃ | OCH₃ |
| 2562 | OCH₃ | F | F | CH₃ | Cl |
| 2563 | OCH₃ | F | F | CH₃ | Br |
| 2564 | OCH₃ | F | F | OCH₃ | H |
| 2565 | OCH₃ | F | F | OCH₃ | CH₃ |
| 2566 | OCH₃ | F | F | OCH₃ | OCH₃ |
| 2567 | OCH₃ | F | F | OCH₃ | Cl |
| 2568 | OCH₃ | F | F | OCH₃ | Br |
| 2569 | OCH₃ | F | F | Cl | H |
| 2570 | OCH₃ | F | F | Cl | CH₃ |
| 2571 | OCH₃ | F | F | Cl | OCH₃ |
| 2572 | OCH₃ | F | F | Cl | Cl |
| 2573 | OCH₃ | F | F | Cl | Br |
| 2574 | OCH₃ | F | F | Br | H |
| 2575 | OCH₃ | F | F | Br | CH₃ |
| 2576 | OCH₃ | F | F | Br | OCH₃ |
| 2577 | OCH₃ | F | F | Br | Cl |
| 2578 | OCH₃ | F | F | Br | Br |
| 2579 | OCH₃ | F | F | F | H |
| 2580 | OCH₃ | F | F | F | CH₃ |
| 2581 | OCH₃ | F | F | F | OCH₃ |
| 2582 | OCH₃ | F | F | F | Cl |
| 2583 | OCH₃ | F | F | F | Br |
| 2584 | OCH₃ | F | F | F | F |
| 2585 | Cl | CH₃ | CH₃ | H | H |
| 2586 | Cl | CH₃ | CH₃ | CH₃ | H |
| 2587 | Cl | CH₃ | CH₃ | OCH₃ | H |
| 2588 | Cl | CH₃ | CH₃ | Cl | H |
| 2589 | Cl | CH₃ | CH₃ | Br | H |
| 2590 | Cl | CH₃ | CH₃ | F | H |
| 2591 | Cl | CH₃ | CH₃ | H | CH₃ |
| 2592 | Cl | CH₃ | CH₃ | CH₃ | CH₃ |
| 2593 | Cl | CH₃ | CH₃ | H | OCH₃ |
| 2594 | Cl | CH₃ | CH₃ | CH₃ | OCH₃ |
| 2595 | Cl | CH₃ | CH₃ | OCH₃ | OCH₃ |

TABLE 2-continued

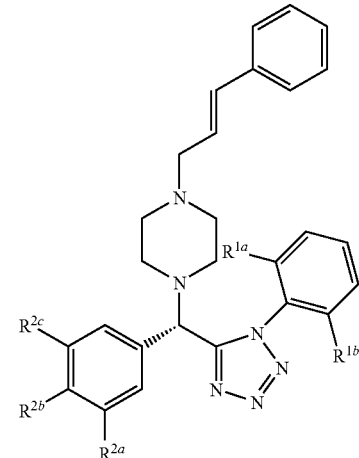

wherein $R^{1a}$, $R^{1b}$, $R^{2a}$, $R^{2b}$, and $R^{2c}$ are as defined in Table 2.

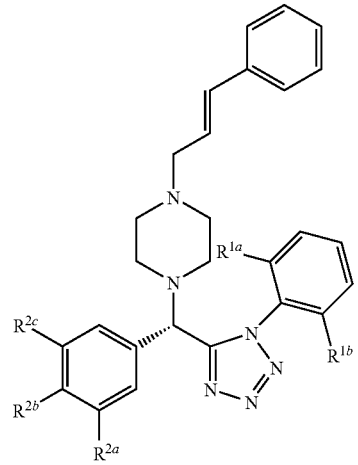

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2596 | Cl | CH₃ | CH₃ | Cl | OCH₃ |
| 2597 | Cl | CH₃ | CH₃ | Br | OCH₃ |
| 2598 | Cl | CH₃ | CH₃ | F | OCH₃ |
| 2599 | Cl | CH₃ | CH₃ | H | Cl |
| 2600 | Cl | CH₃ | CH₃ | CH₃ | Cl |
| 2601 | Cl | CH₃ | CH₃ | OCH₃ | Cl |
| 2602 | Cl | CH₃ | CH₃ | Cl | Cl |
| 2603 | Cl | CH₃ | CH₃ | Br | Cl |
| 2604 | Cl | CH₃ | CH₃ | F | Cl |
| 2605 | Cl | CH₃ | CH₃ | H | Br |
| 2606 | Cl | CH₃ | CH₃ | CH₃ | Br |
| 2607 | Cl | CH₃ | CH₃ | OCH₃ | Br |
| 2608 | Cl | CH₃ | CH₃ | Cl | Br |
| 2609 | Cl | CH₃ | CH₃ | Br | Br |
| 2610 | Cl | CH₃ | CH₃ | F | Br |
| 2611 | Cl | CH₃ | CH₃ | H | F |
| 2612 | Cl | CH₃ | CH₃ | CH₃ | F |
| 2613 | Cl | CH₃ | CH₃ | OCH₃ | F |
| 2614 | Cl | CH₃ | CH₃ | Cl | F |
| 2615 | Cl | CH₃ | CH₃ | Br | F |
| 2616 | Cl | CH₃ | CH₃ | F | F |
| 2617 | Cl | CH₃ | OCH₃ | H | H |
| 2618 | Cl | CH₃ | OCH₃ | CH₃ | H |
| 2619 | Cl | CH₃ | OCH₃ | OCH₃ | H |
| 2620 | Cl | CH₃ | OCH₃ | Cl | H |
| 2621 | Cl | CH₃ | OCH₃ | Br | H |
| 2622 | Cl | CH₃ | OCH₃ | F | H |
| 2623 | Cl | CH₃ | OCH₃ | H | CH₃ |
| 2624 | Cl | CH₃ | OCH₃ | CH₃ | CH₃ |
| 2625 | Cl | CH₃ | OCH₃ | OCH₃ | CH₃ |
| 2626 | Cl | CH₃ | OCH₃ | Cl | CH₃ |
| 2627 | Cl | CH₃ | OCH₃ | Br | CH₃ |
| 2628 | Cl | CH₃ | OCH₃ | F | CH₃ |
| 2629 | Cl | CH₃ | OCH₃ | H | OCH₃ |
| 2630 | Cl | CH₃ | OCH₃ | OCH₃ | OCH₃ |
| 2631 | Cl | CH₃ | OCH₃ | H | Cl |
| 2632 | Cl | CH₃ | OCH₃ | CH₃ | Cl |
| 2633 | Cl | CH₃ | OCH₃ | OCH₃ | Cl |
| 2634 | Cl | CH₃ | OCH₃ | Cl | Cl |
| 2635 | Cl | CH₃ | OCH₃ | Br | Cl |
| 2636 | Cl | CH₃ | OCH₃ | F | Cl |
| 2637 | Cl | CH₃ | OCH₃ | H | Br |
| 2638 | Cl | CH₃ | OCH₃ | CH₃ | Br |
| 2639 | Cl | CH₃ | OCH₃ | OCH₃ | Br |
| 2640 | Cl | CH₃ | OCH₃ | Cl | Br |
| 2641 | Cl | CH₃ | OCH₃ | Br | Br |
| 2642 | Cl | CH₃ | OCH₃ | F | Br |
| 2643 | Cl | CH₃ | OCH₃ | H | F |
| 2644 | Cl | CH₃ | OCH₃ | CH₃ | F |
| 2645 | Cl | CH₃ | OCH₃ | OCH₃ | F |
| 2646 | Cl | CH₃ | OCH₃ | Cl | F |
| 2647 | Cl | CH₃ | OCH₃ | Br | F |
| 2648 | Cl | CH₃ | OCH₃ | F | F |
| 2649 | Cl | CH₃ | Cl | H | H |
| 2650 | Cl | CH₃ | Cl | CH₃ | H |
| 2651 | Cl | CH₃ | Cl | OCH₃ | H |
| 2652 | Cl | CH₃ | Cl | Cl | H |
| 2653 | Cl | CH₃ | Cl | Br | H |
| 2654 | Cl | CH₃ | Cl | F | H |
| 2655 | Cl | CH₃ | Cl | H | CH₃ |
| 2656 | Cl | CH₃ | Cl | CH₃ | CH₃ |
| 2657 | Cl | CH₃ | Cl | OCH₃ | CH₃ |
| 2658 | Cl | CH₃ | Cl | Cl | CH₃ |
| 2659 | Cl | CH₃ | Cl | Br | CH₃ |
| 2660 | Cl | CH₃ | Cl | F | CH₃ |
| 2661 | Cl | CH₃ | Cl | H | OCH₃ |
| 2662 | Cl | CH₃ | Cl | CH₃ | OCH₃ |
| 2663 | Cl | CH₃ | Cl | OCH₃ | OCH₃ |
| 2664 | Cl | CH₃ | Cl | Cl | OCH₃ |
| 2665 | Cl | CH₃ | Cl | Br | OCH₃ |
| 2666 | Cl | CH₃ | Cl | F | OCH₃ |
| 2667 | Cl | CH₃ | Cl | H | Cl |
| 2668 | Cl | CH₃ | Cl | Cl | Cl |
| 2669 | Cl | CH₃ | Cl | H | Br |
| 2670 | Cl | CH₃ | Cl | CH₃ | Br |
| 2671 | Cl | CH₃ | Cl | OCH₃ | Br |
| 2672 | Cl | CH₃ | Cl | Cl | Br |
| 2673 | Cl | CH₃ | Cl | Br | Br |
| 2674 | Cl | CH₃ | Cl | F | Br |
| 2675 | Cl | CH₃ | Cl | H | F |
| 2676 | Cl | CH₃ | Cl | CH₃ | F |
| 2677 | Cl | CH₃ | Cl | OCH₃ | F |
| 2678 | Cl | CH₃ | Cl | Cl | F |
| 2679 | Cl | CH₃ | Cl | F | F |
| 2680 | Cl | CH₃ | Br | H | H |
| 2681 | Cl | CH₃ | Br | CH₃ | H |
| 2682 | Cl | CH₃ | Br | OCH₃ | H |
| 2683 | Cl | CH₃ | Br | Cl | H |
| 2684 | Cl | CH₃ | Br | Br | H |
| 2685 | Cl | CH₃ | Br | F | H |
| 2686 | Cl | CH₃ | Br | H | CH₃ |
| 2687 | Cl | CH₃ | Br | CH₃ | CH₃ |
| 2688 | Cl | CH₃ | Br | OCH₃ | CH₃ |
| 2689 | Cl | CH₃ | Br | Cl | CH₃ |
| 2690 | Cl | CH₃ | Br | Br | CH₃ |
| 2691 | Cl | CH₃ | Br | F | CH₃ |
| 2692 | Cl | CH₃ | Br | H | OCH₃ |
| 2693 | Cl | CH₃ | Br | CH₃ | OCH₃ |
| 2694 | Cl | CH₃ | Br | OCH₃ | OCH₃ |
| 2695 | Cl | CH₃ | Br | Cl | OCH₃ |

TABLE 2-continued

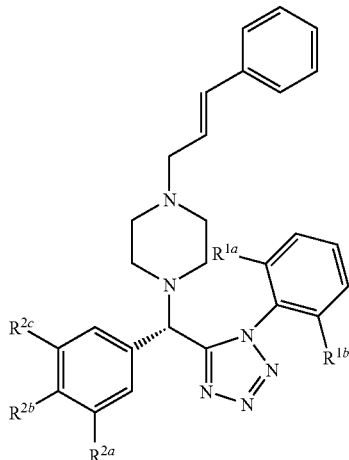

wherein $R^{1a}$, $R^{1b}$, $R^{2a}$, $R^{2b}$, and $R^{2c}$ are as defined in Table 2.

TABLE 2-continued

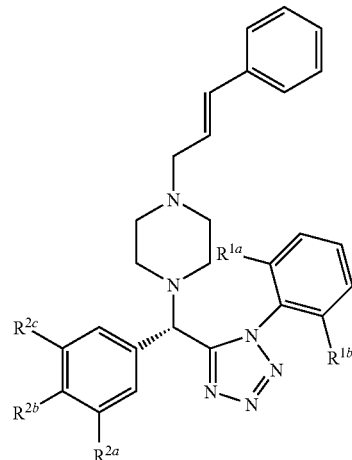

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ | Compound No. | $R^{1a}$ | $R^{1b}$ | $R^{2a}$ | $R^{2b}$ | $R^{2c}$ |
|---|---|---|---|---|---|---|---|---|---|---|---|
| 2696 | Cl | CH₃ | Br | Br | OCH₃ | 2746 | Cl | OCH₃ | CH₃ | H | OCH₃ |
| 2697 | Cl | CH₃ | Br | F | OCH₃ | 2747 | Cl | OCH₃ | CH₃ | H | Cl |
| 2698 | Cl | CH₃ | Br | H | Cl | 2748 | Cl | OCH₃ | CH₃ | H | Br |
| 2699 | Cl | CH₃ | Br | CH₃ | Cl | 2749 | Cl | OCH₃ | CH₃ | H | F |
| 2700 | Cl | CH₃ | Br | OCH₃ | Cl | 2750 | Cl | OCH₃ | CH₃ | CH₃ | H |
| 2701 | Cl | CH₃ | Br | Cl | Cl | 2751 | Cl | OCH₃ | CH₃ | CH₃ | CH₃ |
| 2702 | Cl | CH₃ | Br | Br | Cl | 2752 | Cl | OCH₃ | CH₃ | CH₃ | OCH₃ |
| 2703 | Cl | CH₃ | Br | F | Cl | 2753 | Cl | OCH₃ | CH₃ | CH₃ | Cl |
| 2704 | Cl | CH₃ | Br | H | Br | 2754 | Cl | OCH₃ | CH₃ | CH₃ | Br |
| 2705 | Cl | CH₃ | Br | Br | Br | 2755 | Cl | OCH₃ | CH₃ | CH₃ | F |
| 2706 | Cl | CH₃ | Br | H | F | 2756 | Cl | OCH₃ | CH₃ | OCH₃ | H |
| 2707 | Cl | CH₃ | Br | CH₃ | F | 2757 | Cl | OCH₃ | CH₃ | OCH₃ | OCH₃ |
| 2708 | Cl | CH₃ | Br | OCH₃ | F | 2758 | Cl | OCH₃ | CH₃ | OCH₃ | Cl |
| 2709 | Cl | CH₃ | Br | Cl | F | 2759 | Cl | OCH₃ | CH₃ | OCH₃ | Br |
| 2710 | Cl | CH₃ | Br | Br | F | 2760 | Cl | OCH₃ | CH₃ | OCH₃ | F |
| 2711 | Cl | CH₃ | Br | F | F | 2761 | Cl | OCH₃ | CH₃ | Cl | H |
| 2712 | Cl | CH₃ | F | H | H | 2762 | Cl | OCH₃ | CH₃ | Cl | OCH₃ |
| 2713 | Cl | CH₃ | F | CH₃ | H | 2763 | Cl | OCH₃ | CH₃ | Cl | Cl |
| 2714 | Cl | CH₃ | F | OCH₃ | H | 2764 | Cl | OCH₃ | CH₃ | Cl | Br |
| 2715 | Cl | CH₃ | F | Cl | H | 2765 | Cl | OCH₃ | CH₃ | Cl | F |
| 2716 | Cl | CH₃ | F | Br | H | 2766 | Cl | OCH₃ | CH₃ | Br | H |
| 2717 | Cl | CH₃ | F | F | H | 2767 | Cl | OCH₃ | CH₃ | Br | OCH₃ |
| 2718 | Cl | CH₃ | F | H | CH₃ | 2768 | Cl | OCH₃ | CH₃ | Br | Cl |
| 2719 | Cl | CH₃ | F | CH₃ | CH₃ | 2769 | Cl | OCH₃ | CH₃ | Br | Br |
| 2720 | Cl | CH₃ | F | OCH₃ | CH₃ | 2770 | Cl | OCH₃ | CH₃ | Br | F |
| 2721 | Cl | CH₃ | F | Cl | CH₃ | 2771 | Cl | OCH₃ | CH₃ | F | H |
| 2722 | Cl | CH₃ | F | Br | CH₃ | 2772 | Cl | OCH₃ | CH₃ | F | OCH₃ |
| 2723 | Cl | CH₃ | F | F | CH₃ | 2773 | Cl | OCH₃ | CH₃ | F | Cl |
| 2724 | Cl | CH₃ | F | H | OCH₃ | 2774 | Cl | OCH₃ | CH₃ | F | Br |
| 2725 | Cl | CH₃ | F | CH₃ | OCH₃ | 2775 | Cl | OCH₃ | CH₃ | F | F |
| 2726 | Cl | CH₃ | F | OCH₃ | OCH₃ | 2776 | Cl | OCH₃ | OCH₃ | H | H |
| 2727 | Cl | CH₃ | F | Cl | OCH₃ | 2777 | Cl | OCH₃ | OCH₃ | H | CH₃ |
| 2728 | Cl | CH₃ | F | Br | OCH₃ | 2778 | Cl | OCH₃ | OCH₃ | H | OCH₃ |
| 2729 | Cl | CH₃ | F | F | OCH₃ | 2779 | Cl | OCH₃ | OCH₃ | H | Cl |
| 2730 | Cl | CH₃ | F | H | Cl | 2780 | Cl | OCH₃ | OCH₃ | H | Br |
| 2731 | Cl | CH₃ | F | CH₃ | Cl | 2781 | Cl | OCH₃ | OCH₃ | H | F |
| 2732 | Cl | CH₃ | F | OCH₃ | Cl | 2782 | Cl | OCH₃ | OCH₃ | CH₃ | H |
| 2733 | Cl | CH₃ | F | Cl | Cl | 2783 | Cl | OCH₃ | OCH₃ | CH₃ | CH₃ |
| 2734 | Cl | CH₃ | F | Br | Cl | 2784 | Cl | OCH₃ | OCH₃ | CH₃ | Cl |
| 2735 | Cl | CH₃ | F | F | Cl | 2785 | Cl | OCH₃ | OCH₃ | CH₃ | Br |
| 2736 | Cl | CH₃ | F | H | Br | 2786 | Cl | OCH₃ | OCH₃ | CH₃ | F |
| 2737 | Cl | CH₃ | F | CH₃ | Br | 2787 | Cl | OCH₃ | OCH₃ | OCH₃ | H |
| 2738 | Cl | CH₃ | F | OCH₃ | Br | 2788 | Cl | OCH₃ | OCH₃ | OCH₃ | CH₃ |
| 2739 | Cl | CH₃ | F | Cl | Br | 2789 | Cl | OCH₃ | OCH₃ | OCH₃ | OCH₃ |
| 2740 | Cl | CH₃ | F | Br | Br | 2790 | Cl | OCH₃ | OCH₃ | OCH₃ | Cl |
| 2741 | Cl | CH₃ | F | F | Br | 2791 | Cl | OCH₃ | OCH₃ | OCH₃ | Br |
| 2742 | Cl | CH₃ | F | H | F | 2792 | Cl | OCH₃ | OCH₃ | OCH₃ | F |
| 2743 | Cl | CH₃ | F | F | F | 2793 | Cl | OCH₃ | OCH₃ | Cl | H |
| 2744 | Cl | OCH₃ | CH₃ | H | H | 2794 | Cl | OCH₃ | OCH₃ | Cl | CH₃ |
| 2745 | Cl | OCH₃ | CH₃ | H | CH₃ | 2795 | Cl | OCH₃ | OCH₃ | Cl | Cl |

TABLE 2-continued

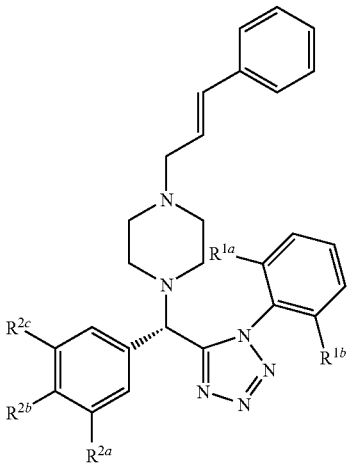

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2796 | Cl | OCH₃ | OCH₃ | Cl | Br |
| 2797 | Cl | OCH₃ | OCH₃ | Cl | F |
| 2798 | Cl | OCH₃ | OCH₃ | Br | H |
| 2799 | Cl | OCH₃ | OCH₃ | Br | CH₃ |
| 2800 | Cl | OCH₃ | OCH₃ | Br | Cl |
| 2801 | Cl | OCH₃ | OCH₃ | Br | Br |
| 2802 | Cl | OCH₃ | OCH₃ | Br | F |
| 2803 | Cl | OCH₃ | OCH₃ | F | H |
| 2804 | Cl | OCH₃ | OCH₃ | F | CH₃ |
| 2805 | Cl | OCH₃ | OCH₃ | F | Cl |
| 2806 | Cl | OCH₃ | OCH₃ | F | Br |
| 2807 | Cl | OCH₃ | OCH₃ | F | F |
| 2808 | Cl | OCH₃ | Cl | H | H |
| 2809 | Cl | OCH₃ | Cl | H | CH₃ |
| 2810 | Cl | OCH₃ | Cl | H | OCH₃ |
| 2811 | Cl | OCH₃ | Cl | H | Cl |
| 2812 | Cl | OCH₃ | Cl | H | Br |
| 2813 | Cl | OCH₃ | Cl | H | F |
| 2814 | Cl | OCH₃ | Cl | CH₃ | H |
| 2815 | Cl | OCH₃ | Cl | CH₃ | CH₃ |
| 2816 | Cl | OCH₃ | Cl | CH₃ | OCH₃ |
| 2817 | Cl | OCH₃ | Cl | CH₃ | Br |
| 2818 | Cl | OCH₃ | Cl | CH₃ | F |
| 2819 | Cl | OCH₃ | Cl | OCH₃ | H |
| 2820 | Cl | OCH₃ | Cl | OCH₃ | CH₃ |
| 2821 | Cl | OCH₃ | Cl | OCH₃ | OCH₃ |
| 2822 | Cl | OCH₃ | Cl | OCH₃ | Br |
| 2823 | Cl | OCH₃ | Cl | OCH₃ | F |
| 2824 | Cl | OCH₃ | Cl | Cl | H |
| 2825 | Cl | OCH₃ | Cl | Cl | CH₃ |
| 2826 | Cl | OCH₃ | Cl | Cl | OCH₃ |
| 2827 | Cl | OCH₃ | Cl | Cl | Cl |
| 2828 | Cl | OCH₃ | Cl | Cl | Br |
| 2829 | Cl | OCH₃ | Cl | Cl | F |
| 2830 | Cl | OCH₃ | Cl | Br | H |
| 2831 | Cl | OCH₃ | Cl | Br | CH₃ |
| 2832 | Cl | OCH₃ | Cl | Br | OCH₃ |
| 2833 | Cl | OCH₃ | Cl | Br | Br |
| 2834 | Cl | OCH₃ | Cl | F | H |
| 2835 | Cl | OCH₃ | Cl | F | CH₃ |
| 2836 | Cl | OCH₃ | Cl | F | OCH₃ |
| 2837 | Cl | OCH₃ | Cl | F | Br |
| 2838 | Cl | OCH₃ | Cl | F | F |
| 2839 | Cl | OCH₃ | Br | H | H |
| 2840 | Cl | OCH₃ | Br | H | CH₃ |
| 2841 | Cl | OCH₃ | Br | H | OCH₃ |
| 2842 | Cl | OCH₃ | Br | H | Cl |
| 2843 | Cl | OCH₃ | Br | H | Br |
| 2844 | Cl | OCH₃ | Br | H | F |
| 2845 | Cl | OCH₃ | Br | CH₃ | H |

TABLE 2-continued

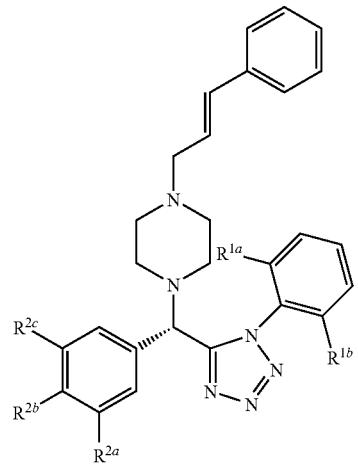

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2846 | Cl | OCH₃ | Br | CH₃ | CH₃ |
| 2847 | Cl | OCH₃ | Br | CH₃ | OCH₃ |
| 2848 | Cl | OCH₃ | Br | CH₃ | Cl |
| 2849 | Cl | OCH₃ | Br | CH₃ | F |
| 2850 | Cl | OCH₃ | Br | OCH₃ | H |
| 2851 | Cl | OCH₃ | Br | OCH₃ | CH₃ |
| 2852 | Cl | OCH₃ | Br | OCH₃ | OCH₃ |
| 2853 | Cl | OCH₃ | Br | OCH₃ | Cl |
| 2854 | Cl | OCH₃ | Br | OCH₃ | F |
| 2855 | Cl | OCH₃ | Br | Cl | H |
| 2856 | Cl | OCH₃ | Br | Cl | CH₃ |
| 2857 | Cl | OCH₃ | Br | Cl | OCH₃ |
| 2858 | Cl | OCH₃ | Br | Cl | Cl |
| 2859 | Cl | OCH₃ | Br | Cl | F |
| 2860 | Cl | OCH₃ | Br | Br | H |
| 2861 | Cl | OCH₃ | Br | Br | CH₃ |
| 2862 | Cl | OCH₃ | Br | Br | OCH₃ |
| 2863 | Cl | OCH₃ | Br | Br | Cl |
| 2864 | Cl | OCH₃ | Br | Br | Br |
| 2865 | Cl | OCH₃ | Br | Br | F |
| 2866 | Cl | OCH₃ | Br | F | H |
| 2867 | Cl | OCH₃ | Br | F | CH₃ |
| 2868 | Cl | OCH₃ | Br | F | OCH₃ |
| 2869 | Cl | OCH₃ | Br | F | Cl |
| 2870 | Cl | OCH₃ | Br | F | F |
| 2871 | Cl | OCH₃ | F | H | H |
| 2872 | Cl | OCH₃ | F | H | CH₃ |
| 2873 | Cl | OCH₃ | F | H | OCH₃ |
| 2874 | Cl | OCH₃ | F | H | Cl |
| 2875 | Cl | OCH₃ | F | H | Br |
| 2876 | Cl | OCH₃ | F | H | F |
| 2877 | Cl | OCH₃ | F | CH₃ | H |
| 2878 | Cl | OCH₃ | F | CH₃ | CH₃ |
| 2879 | Cl | OCH₃ | F | CH₃ | OCH₃ |
| 2880 | Cl | OCH₃ | F | CH₃ | Cl |
| 2881 | Cl | OCH₃ | F | CH₃ | Br |
| 2882 | Cl | OCH₃ | F | OCH₃ | H |
| 2883 | Cl | OCH₃ | F | OCH₃ | CH₃ |
| 2884 | Cl | OCH₃ | F | OCH₃ | OCH₃ |
| 2885 | Cl | OCH₃ | F | OCH₃ | Cl |
| 2886 | Cl | OCH₃ | F | OCH₃ | Br |
| 2887 | Cl | OCH₃ | F | Cl | H |
| 2888 | Cl | OCH₃ | F | Cl | CH₃ |
| 2889 | Cl | OCH₃ | F | Cl | OCH₃ |
| 2890 | Cl | OCH₃ | F | Cl | Cl |
| 2891 | Cl | OCH₃ | F | Cl | Br |
| 2892 | Cl | OCH₃ | F | Br | H |
| 2893 | Cl | OCH₃ | F | Br | CH₃ |
| 2894 | Cl | OCH₃ | F | Br | OCH₃ |
| 2895 | Cl | OCH₃ | F | Br | Cl |

TABLE 2-continued

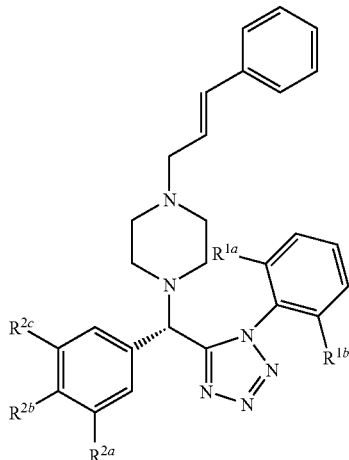

wherein $R^{1a}$, $R^{1b}$, $R^{2a}$, $R^{2b}$, and $R^{2c}$ are as defined in Table 2.

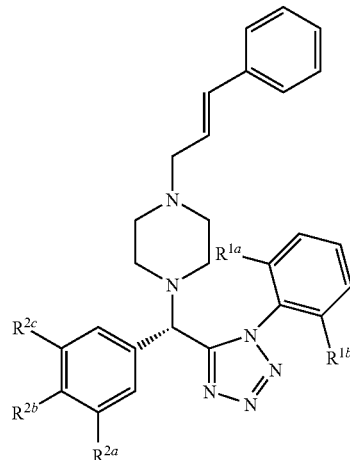

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2896 | Cl | OCH3 | F | Br | Br |
| 2897 | Cl | OCH3 | F | F | H |
| 2898 | Cl | OCH3 | F | F | CH3 |
| 2899 | Cl | OCH3 | F | F | OCH3 |
| 2900 | Cl | OCH3 | F | F | Cl |
| 2901 | Cl | OCH3 | F | F | Br |
| 2902 | Cl | OCH3 | F | F | F |
| 2903 | Cl | Cl | CH3 | H | H |
| 2904 | Cl | Cl | CH3 | H | CH3 |
| 2905 | Cl | Cl | CH3 | H | OCH3 |
| 2906 | Cl | Cl | CH3 | H | Cl |
| 2907 | Cl | Cl | CH3 | H | Br |
| 2908 | Cl | Cl | CH3 | H | F |
| 2909 | Cl | Cl | CH3 | CH3 | H |
| 2910 | Cl | Cl | CH3 | CH3 | CH3 |
| 2911 | Cl | Cl | CH3 | CH3 | OCH3 |
| 2912 | Cl | Cl | CH3 | CH3 | Cl |
| 2913 | Cl | Cl | CH3 | CH3 | Br |
| 2914 | Cl | Cl | CH3 | CH3 | F |
| 2915 | Cl | Cl | CH3 | OCH3 | H |
| 2916 | Cl | Cl | CH3 | OCH3 | OCH3 |
| 2917 | Cl | Cl | CH3 | OCH3 | Cl |
| 2918 | Cl | Cl | CH3 | OCH3 | Br |
| 2919 | Cl | Cl | CH3 | OCH3 | F |
| 2920 | Cl | Cl | CH3 | Cl | H |
| 2921 | Cl | Cl | CH3 | Cl | OCH3 |
| 2922 | Cl | Cl | CH3 | Cl | Cl |
| 2923 | Cl | Cl | CH3 | Cl | Br |
| 2924 | Cl | Cl | CH3 | Cl | F |
| 2925 | Cl | Cl | CH3 | Br | H |
| 2926 | Cl | Cl | CH3 | Br | OCH3 |
| 2927 | Cl | Cl | CH3 | Br | Cl |
| 2928 | Cl | Cl | CH3 | Br | Br |
| 2929 | Cl | Cl | CH3 | Br | F |
| 2930 | Cl | Cl | CH3 | F | H |
| 2931 | Cl | Cl | CH3 | F | OCH3 |
| 2932 | Cl | Cl | CH3 | F | Cl |
| 2933 | Cl | Cl | CH3 | F | Br |
| 2934 | Cl | Cl | CH3 | F | F |
| 2935 | Cl | Cl | OCH3 | H | H |
| 2936 | Cl | Cl | OCH3 | H | CH3 |
| 2937 | Cl | Cl | OCH3 | H | OCH3 |
| 2938 | Cl | Cl | OCH3 | H | Cl |
| 2939 | Cl | Cl | OCH3 | H | Br |
| 2940 | Cl | Cl | OCH3 | H | F |
| 2941 | Cl | Cl | OCH3 | CH3 | H |
| 2942 | Cl | Cl | OCH3 | CH3 | CH3 |
| 2943 | Cl | Cl | OCH3 | CH3 | Cl |
| 2944 | Cl | Cl | OCH3 | CH3 | Br |
| 2945 | Cl | Cl | OCH3 | CH3 | F |
| 2946 | Cl | Cl | OCH3 | OCH3 | H |
| 2947 | Cl | Cl | OCH3 | OCH3 | CH3 |
| 2948 | Cl | Cl | OCH3 | OCH3 | OCH3 |
| 2949 | Cl | Cl | OCH3 | OCH3 | Cl |
| 2950 | Cl | Cl | OCH3 | OCH3 | Br |
| 2951 | Cl | Cl | OCH3 | OCH3 | F |
| 2952 | Cl | Cl | OCH3 | Cl | H |
| 2953 | Cl | Cl | OCH3 | Cl | CH3 |
| 2954 | Cl | Cl | OCH3 | Cl | Cl |
| 2955 | Cl | Cl | OCH3 | Cl | Br |
| 2956 | Cl | Cl | OCH3 | Cl | F |
| 2957 | Cl | Cl | OCH3 | Br | H |
| 2958 | Cl | Cl | OCH3 | Br | CH3 |
| 2959 | Cl | Cl | OCH3 | Br | Cl |
| 2960 | Cl | Cl | OCH3 | Br | Br |
| 2961 | Cl | Cl | OCH3 | Br | F |
| 2962 | Cl | Cl | OCH3 | F | H |
| 2963 | Cl | Cl | OCH3 | F | CH3 |
| 2964 | Cl | Cl | OCH3 | F | Cl |
| 2965 | Cl | Cl | OCH3 | F | Br |
| 2966 | Cl | Cl | OCH3 | F | F |
| 2967 | Cl | Cl | Cl | H | H |
| 2968 | Cl | Cl | Cl | H | CH3 |
| 2969 | Cl | Cl | Cl | H | OCH3 |
| 2970 | Cl | Cl | Cl | H | Cl |
| 2971 | Cl | Cl | Cl | H | Br |
| 2972 | Cl | Cl | Cl | H | F |
| 2973 | Cl | Cl | Cl | CH3 | H |
| 2974 | Cl | Cl | Cl | CH3 | CH3 |
| 2975 | Cl | Cl | Cl | CH3 | OCH3 |
| 2976 | Cl | Cl | Cl | CH3 | Br |
| 2977 | Cl | Cl | Cl | CH3 | F |
| 2978 | Cl | Cl | Cl | OCH3 | H |
| 2979 | Cl | Cl | Cl | OCH3 | CH3 |
| 2980 | Cl | Cl | Cl | OCH3 | OCH3 |
| 2981 | Cl | Cl | Cl | OCH3 | Br |
| 2982 | Cl | Cl | Cl | OCH3 | F |
| 2983 | Cl | Cl | Cl | Cl | H |
| 2984 | Cl | Cl | Cl | Cl | CH3 |
| 2985 | Cl | Cl | Cl | Cl | OCH3 |
| 2986 | Cl | Cl | Cl | Cl | Cl |
| 2987 | Cl | Cl | Cl | Cl | Br |
| 2988 | Cl | Cl | Cl | Cl | F |
| 2989 | Cl | Cl | Cl | Br | H |
| 2990 | Cl | Cl | Cl | Br | CH3 |
| 2991 | Cl | Cl | Cl | Br | OCH3 |
| 2992 | Cl | Cl | Cl | Br | Br |
| 2993 | Cl | Cl | Cl | F | H |
| 2994 | Cl | Cl | Cl | F | CH3 |
| 2995 | Cl | Cl | Cl | F | OCH3 |

TABLE 2-continued

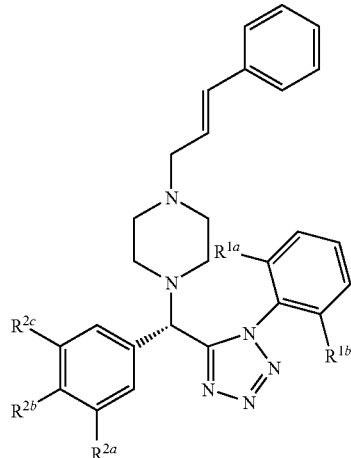

wherein $R^{1a}$, $R^{1b}$, $R^{2a}$, $R^{2b}$, and $R^{2c}$ are as defined in Table 2.

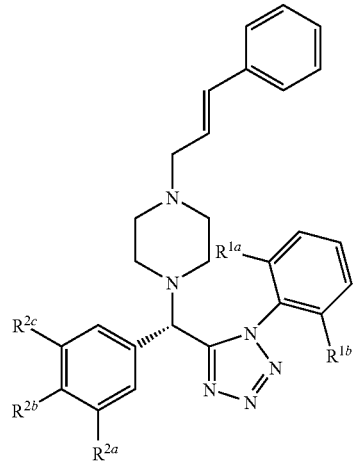

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 2996 | Cl | Cl | Cl | F | Br |
| 2997 | Cl | Cl | Cl | F | F |
| 2998 | Cl | Cl | Br | H | H |
| 2999 | Cl | Cl | Br | H | CH$_3$ |
| 3000 | Cl | Cl | Br | H | OCH$_3$ |
| 3001 | Cl | Cl | Br | H | Cl |
| 3002 | Cl | Cl | Br | H | Br |
| 3003 | Cl | Cl | Br | H | F |
| 3004 | Cl | Cl | Br | CH$_3$ | H |
| 3005 | Cl | Cl | Br | CH$_3$ | CH$_3$ |
| 3006 | Cl | Cl | Br | CH$_3$ | OCH$_3$ |
| 3007 | Cl | Cl | Br | CH$_3$ | Cl |
| 3008 | Cl | Cl | Br | CH$_3$ | F |
| 3009 | Cl | Cl | Br | OCH$_3$ | H |
| 3010 | Cl | Cl | Br | OCH$_3$ | CH$_3$ |
| 3011 | Cl | Cl | Br | OCH$_3$ | OCH$_3$ |
| 3012 | Cl | Cl | Br | OCH$_3$ | Cl |
| 3013 | Cl | Cl | Br | OCH$_3$ | F |
| 3014 | Cl | Cl | Br | Cl | H |
| 3015 | Cl | Cl | Br | Cl | CH$_3$ |
| 3016 | Cl | Cl | Br | Cl | OCH$_3$ |
| 3017 | Cl | Cl | Br | Cl | Cl |
| 3018 | Cl | Cl | Br | Cl | F |
| 3019 | Cl | Cl | Br | Br | H |
| 3020 | Cl | Cl | Br | Br | CH$_3$ |
| 3021 | Cl | Cl | Br | Br | OCH$_3$ |
| 3022 | Cl | Cl | Br | Br | Cl |
| 3023 | Cl | Cl | Br | Br | Br |
| 3024 | Cl | Cl | Br | Br | F |
| 3025 | Cl | Cl | Br | F | H |
| 3026 | Cl | Cl | Br | F | CH$_3$ |
| 3027 | Cl | Cl | Br | F | OCH$_3$ |
| 3028 | Cl | Cl | Br | F | Cl |
| 3029 | Cl | Cl | Br | F | F |
| 3030 | Cl | Cl | F | H | H |
| 3031 | Cl | Cl | F | H | CH$_3$ |
| 3032 | Cl | Cl | F | H | OCH$_3$ |
| 3033 | Cl | Cl | F | H | Cl |
| 3034 | Cl | Cl | F | H | Br |
| 3035 | Cl | Cl | F | H | F |
| 3036 | Cl | Cl | F | CH$_3$ | H |
| 3037 | Cl | Cl | F | CH$_3$ | CH$_3$ |
| 3038 | Cl | Cl | F | CH$_3$ | OCH$_3$ |
| 3039 | Cl | Cl | F | CH$_3$ | Cl |
| 3040 | Cl | Cl | F | CH$_3$ | Br |
| 3041 | Cl | Cl | F | OCH$_3$ | H |
| 3042 | Cl | Cl | F | OCH$_3$ | CH$_3$ |
| 3043 | Cl | Cl | F | OCH$_3$ | OCH$_3$ |
| 3044 | Cl | Cl | F | OCH$_3$ | Cl |
| 3045 | Cl | Cl | F | OCH$_3$ | Br |
| 3046 | Cl | Cl | F | Cl | H |
| 3047 | Cl | Cl | F | Cl | CH$_3$ |
| 3048 | Cl | Cl | F | Cl | OCH$_3$ |
| 3049 | Cl | Cl | F | Cl | Cl |
| 3050 | Cl | Cl | F | Cl | Br |
| 3051 | Cl | Cl | F | Br | H |
| 3052 | Cl | Cl | F | Br | CH$_3$ |
| 3053 | Cl | Cl | F | Br | OCH$_3$ |
| 3054 | Cl | Cl | F | Br | Cl |
| 3055 | Cl | Cl | F | Br | Br |
| 3056 | Cl | Cl | F | F | H |
| 3057 | Cl | Cl | F | F | CH$_3$ |
| 3058 | Cl | Cl | F | F | OCH$_3$ |
| 3059 | Cl | Cl | F | F | Cl |
| 3060 | Cl | Cl | F | F | Br |
| 3061 | Cl | Cl | F | F | F |
| 3062 | Cl | Br | CH$_3$ | H | H |
| 3063 | Cl | Br | CH$_3$ | H | CH$_3$ |
| 3064 | Cl | Br | CH$_3$ | H | OCH$_3$ |
| 3065 | Cl | Br | CH$_3$ | H | Cl |
| 3066 | Cl | Br | CH$_3$ | H | Br |
| 3067 | Cl | Br | CH$_3$ | H | F |
| 3068 | Cl | Br | CH$_3$ | CH$_3$ | H |
| 3069 | Cl | Br | CH$_3$ | CH$_3$ | CH$_3$ |
| 3070 | Cl | Br | CH$_3$ | CH$_3$ | OCH$_3$ |
| 3071 | Cl | Br | CH$_3$ | CH$_3$ | Cl |
| 3072 | Cl | Br | CH$_3$ | CH$_3$ | Br |
| 3073 | Cl | Br | CH$_3$ | CH$_3$ | F |
| 3074 | Cl | Br | CH$_3$ | OCH$_3$ | H |
| 3075 | Cl | Br | CH$_3$ | OCH$_3$ | OCH$_3$ |
| 3076 | Cl | Br | CH$_3$ | OCH$_3$ | Cl |
| 3077 | Cl | Br | CH$_3$ | OCH$_3$ | Br |
| 3078 | Cl | Br | CH$_3$ | OCH$_3$ | F |
| 3079 | Cl | Br | CH$_3$ | Cl | H |
| 3080 | Cl | Br | CH$_3$ | Cl | OCH$_3$ |
| 3081 | Cl | Br | CH$_3$ | Cl | Cl |
| 3082 | Cl | Br | CH$_3$ | Cl | Br |
| 3083 | Cl | Br | CH$_3$ | Cl | F |
| 3084 | Cl | Br | CH$_3$ | Br | H |
| 3085 | Cl | Br | CH$_3$ | Br | OCH$_3$ |
| 3086 | Cl | Br | CH$_3$ | Br | Cl |
| 3087 | Cl | Br | CH$_3$ | Br | Br |
| 3088 | Cl | Br | CH$_3$ | Br | F |
| 3089 | Cl | Br | CH$_3$ | F | H |
| 3090 | Cl | Br | CH$_3$ | F | OCH$_3$ |
| 3091 | Cl | Br | CH$_3$ | F | Cl |
| 3092 | Cl | Br | CH$_3$ | F | Br |
| 3093 | Cl | Br | CH$_3$ | F | F |
| 3094 | Cl | Br | OCH$_3$ | H | H |
| 3095 | Cl | Br | OCH$_3$ | H | CH$_3$ |

TABLE 2-continued

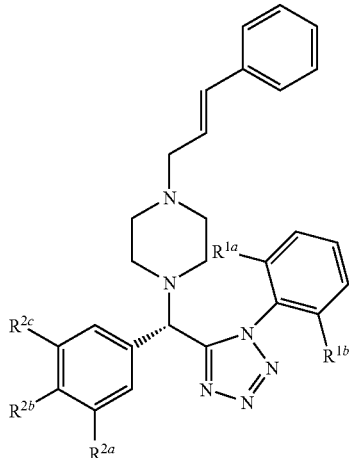

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 3096 | Cl | Br | OCH₃ | H | OCH₃ |
| 3097 | Cl | Br | OCH₃ | H | Cl |
| 3098 | Cl | Br | OCH₃ | H | Br |
| 3099 | Cl | Br | OCH₃ | H | F |
| 3100 | Cl | Br | OCH₃ | CH₃ | H |
| 3101 | Cl | Br | OCH₃ | CH₃ | CH₃ |
| 3102 | Cl | Br | OCH₃ | CH₃ | Cl |
| 3103 | Cl | Br | OCH₃ | CH₃ | Br |
| 3104 | Cl | Br | OCH₃ | CH₃ | F |
| 3105 | Cl | Br | OCH₃ | OCH₃ | H |
| 3106 | Cl | Br | OCH₃ | OCH₃ | CH₃ |
| 3107 | Cl | Br | OCH₃ | OCH₃ | OCH₃ |
| 3108 | Cl | Br | OCH₃ | OCH₃ | Cl |
| 3109 | Cl | Br | OCH₃ | OCH₃ | Br |
| 3110 | Cl | Br | OCH₃ | OCH₃ | F |
| 3111 | Cl | Br | OCH₃ | Cl | H |
| 3112 | Cl | Br | OCH₃ | Cl | CH₃ |
| 3113 | Cl | Br | OCH₃ | Cl | Cl |
| 3114 | Cl | Br | OCH₃ | Cl | Br |
| 3115 | Cl | Br | OCH₃ | Cl | F |
| 3116 | Cl | Br | OCH₃ | Br | H |
| 3117 | Cl | Br | OCH₃ | Br | CH₃ |
| 3118 | Cl | Br | OCH₃ | Br | Cl |
| 3119 | Cl | Br | OCH₃ | Br | Br |
| 3120 | Cl | Br | OCH₃ | Br | F |
| 3121 | Cl | Br | OCH₃ | F | H |
| 3122 | Cl | Br | OCH₃ | F | CH₃ |
| 3123 | Cl | Br | OCH₃ | F | Cl |
| 3124 | Cl | Br | OCH₃ | F | Br |
| 3125 | Cl | Br | OCH₃ | F | F |
| 3126 | Cl | Br | Cl | H | H |
| 3127 | Cl | Br | Cl | H | CH₃ |
| 3128 | Cl | Br | Cl | H | OCH₃ |
| 3129 | Cl | Br | Cl | H | Cl |
| 3130 | Cl | Br | Cl | H | Br |
| 3131 | Cl | Br | Cl | H | F |
| 3132 | Cl | Br | Cl | CH₃ | H |
| 3133 | Cl | Br | Cl | CH₃ | CH₃ |
| 3134 | Cl | Br | Cl | CH₃ | OCH₃ |
| 3135 | Cl | Br | Cl | CH₃ | Br |
| 3136 | Cl | Br | Cl | CH₃ | F |
| 3137 | Cl | Br | Cl | OCH₃ | H |
| 3138 | Cl | Br | Cl | OCH₃ | CH₃ |
| 3139 | Cl | Br | Cl | OCH₃ | OCH₃ |
| 3140 | Cl | Br | Cl | OCH₃ | Br |
| 3141 | Cl | Br | Cl | OCH₃ | F |
| 3142 | Cl | Br | Cl | Cl | H |
| 3143 | Cl | Br | Cl | Cl | CH₃ |
| 3144 | Cl | Br | Cl | Cl | OCH₃ |
| 3145 | Cl | Br | Cl | Cl | Cl |

TABLE 2-continued

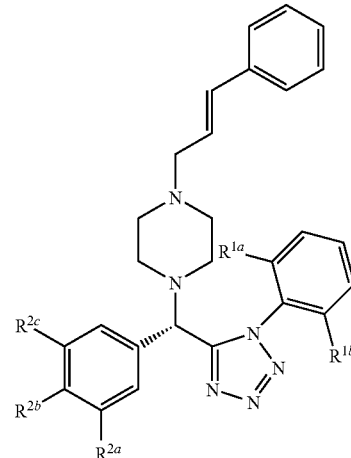

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 3146 | Cl | Br | Cl | Cl | Br |
| 3147 | Cl | Br | Cl | Cl | F |
| 3148 | Cl | Br | Cl | Br | H |
| 3149 | Cl | Br | Cl | Br | CH₃ |
| 3150 | Cl | Br | Cl | Br | OCH₃ |
| 3151 | Cl | Br | Cl | Br | Br |
| 3152 | Cl | Br | Cl | F | H |
| 3153 | Cl | Br | Cl | F | CH₃ |
| 3154 | Cl | Br | Cl | F | OCH₃ |
| 3155 | Cl | Br | Cl | F | Br |
| 3156 | Cl | Br | Cl | F | F |
| 3157 | Cl | Br | Br | H | H |
| 3158 | Cl | Br | Br | H | CH₃ |
| 3159 | Cl | Br | Br | H | OCH₃ |
| 3160 | Cl | Br | Br | H | Cl |
| 3161 | Cl | Br | Br | H | Br |
| 3162 | Cl | Br | Br | H | F |
| 3163 | Cl | Br | Br | CH₃ | H |
| 3164 | Cl | Br | Br | CH₃ | CH₃ |
| 3165 | Cl | Br | Br | CH₃ | OCH₃ |
| 3166 | Cl | Br | Br | CH₃ | Cl |
| 3167 | Cl | Br | Br | CH₃ | F |
| 3168 | Cl | Br | Br | OCH₃ | H |
| 3169 | Cl | Br | Br | OCH₃ | CH₃ |
| 3170 | Cl | Br | Br | OCH₃ | OCH₃ |
| 3171 | Cl | Br | Br | OCH₃ | Cl |
| 3172 | Cl | Br | Br | OCH₃ | F |
| 3173 | Cl | Br | Br | Cl | H |
| 3174 | Cl | Br | Br | Cl | CH₃ |
| 3175 | Cl | Br | Br | Cl | OCH₃ |
| 3176 | Cl | Br | Br | Cl | Cl |
| 3177 | Cl | Br | Br | Cl | F |
| 3178 | Cl | Br | Br | Br | H |
| 3179 | Cl | Br | Br | Br | CH₃ |
| 3180 | Cl | Br | Br | Br | OCH₃ |
| 3181 | Cl | Br | Br | Br | Cl |
| 3182 | Cl | Br | Br | Br | Br |
| 3183 | Cl | Br | Br | Br | F |
| 3184 | Cl | Br | Br | F | H |
| 3185 | Cl | Br | Br | F | CH₃ |
| 3186 | Cl | Br | Br | F | OCH₃ |
| 3187 | Cl | Br | Br | F | Cl |
| 3188 | Cl | Br | Br | F | F |
| 3189 | Cl | Br | F | H | H |
| 3190 | Cl | Br | F | H | CH₃ |
| 3191 | Cl | Br | F | H | OCH₃ |
| 3192 | Cl | Br | F | H | Cl |
| 3193 | Cl | Br | F | H | Br |
| 3194 | Cl | Br | F | H | F |
| 3195 | Cl | Br | F | CH₃ | H |

TABLE 2-continued

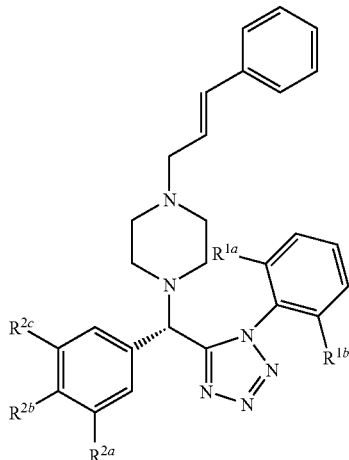

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 3196 | Cl | Br | F | CH$_3$ | CH$_3$ |
| 3197 | Cl | Br | F | CH$_3$ | OCH$_3$ |
| 3198 | Cl | Br | F | CH$_3$ | Cl |
| 3199 | Cl | Br | F | CH$_3$ | Br |
| 3200 | Cl | Br | F | OCH$_3$ | H |
| 3201 | Cl | Br | F | OCH$_3$ | CH$_3$ |
| 3202 | Cl | Br | F | OCH$_3$ | OCH$_3$ |
| 3203 | Cl | Br | F | OCH$_3$ | Cl |
| 3204 | Cl | Br | F | OCH$_3$ | Br |
| 3205 | Cl | Br | F | Cl | H |
| 3206 | Cl | Br | F | Cl | CH$_3$ |
| 3207 | Cl | Br | F | Cl | OCH$_3$ |
| 3208 | Cl | Br | F | Cl | Cl |
| 3209 | Cl | Br | F | Cl | Br |
| 3210 | Cl | Br | F | Br | H |
| 3211 | Cl | Br | F | Br | CH$_3$ |
| 3212 | Cl | Br | F | Br | OCH$_3$ |
| 3213 | Cl | Br | F | Br | Cl |
| 3214 | Cl | Br | F | Br | Br |
| 3215 | Cl | Br | F | F | H |
| 3216 | Cl | Br | F | F | CH$_3$ |
| 3217 | Cl | Br | F | F | OCH$_3$ |
| 3218 | Cl | Br | F | F | Cl |
| 3219 | Cl | Br | F | F | Br |
| 3220 | Cl | Br | F | F | F |
| 3221 | Cl | F | CH$_3$ | H | H |
| 3222 | Cl | F | CH$_3$ | H | CH$_3$ |
| 3223 | Cl | F | CH$_3$ | H | OCH$_3$ |
| 3224 | Cl | F | CH$_3$ | H | Cl |
| 3225 | Cl | F | CH$_3$ | H | Br |
| 3226 | Cl | F | CH$_3$ | H | F |
| 3227 | Cl | F | CH$_3$ | CH$_3$ | H |
| 3228 | Cl | F | CH$_3$ | CH$_3$ | CH$_3$ |
| 3229 | Cl | F | CH$_3$ | CH$_3$ | OCH$_3$ |
| 3230 | Cl | F | CH$_3$ | CH$_3$ | Cl |
| 3231 | Cl | F | CH$_3$ | CH$_3$ | Br |
| 3232 | Cl | F | CH$_3$ | CH$_3$ | F |
| 3233 | Cl | F | CH$_3$ | OCH$_3$ | H |
| 3234 | Cl | F | CH$_3$ | OCH$_3$ | OCH$_3$ |
| 3235 | Cl | F | CH$_3$ | OCH$_3$ | Cl |
| 3236 | Cl | F | CH$_3$ | OCH$_3$ | Br |
| 3237 | Cl | F | CH$_3$ | OCH$_3$ | F |
| 3238 | Cl | F | CH$_3$ | Cl | H |
| 3239 | Cl | F | CH$_3$ | Cl | OCH$_3$ |
| 3240 | Cl | F | CH$_3$ | Cl | Cl |
| 3241 | Cl | F | CH$_3$ | Cl | Br |
| 3242 | Cl | F | CH$_3$ | Cl | F |
| 3243 | Cl | F | CH$_3$ | Br | H |
| 3244 | Cl | F | CH$_3$ | Br | OCH$_3$ |
| 3245 | Cl | F | CH$_3$ | Br | Cl |

TABLE 2-continued

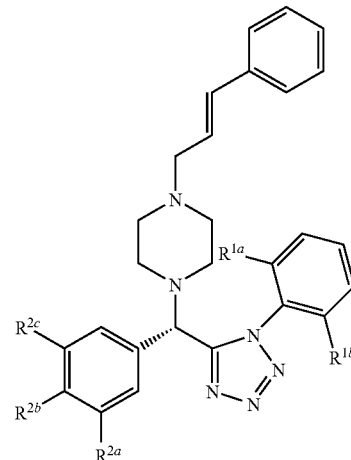

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 3246 | Cl | F | CH$_3$ | Br | Br |
| 3247 | Cl | F | CH$_3$ | Br | F |
| 3248 | Cl | F | CH$_3$ | F | H |
| 3249 | Cl | F | CH$_3$ | F | OCH$_3$ |
| 3250 | Cl | F | CH$_3$ | F | Cl |
| 3251 | Cl | F | CH$_3$ | F | Br |
| 3252 | Cl | F | CH$_3$ | F | F |
| 3253 | Cl | F | OCH$_3$ | H | H |
| 3254 | Cl | F | OCH$_3$ | H | CH$_3$ |
| 3255 | Cl | F | OCH$_3$ | H | OCH$_3$ |
| 3256 | Cl | F | OCH$_3$ | H | Cl |
| 3257 | Cl | F | OCH$_3$ | H | Br |
| 3258 | Cl | F | OCH$_3$ | H | F |
| 3259 | Cl | F | OCH$_3$ | CH$_3$ | H |
| 3260 | Cl | F | OCH$_3$ | CH$_3$ | CH$_3$ |
| 3261 | Cl | F | OCH$_3$ | CH$_3$ | Cl |
| 3262 | Cl | F | OCH$_3$ | CH$_3$ | Br |
| 3263 | Cl | F | OCH$_3$ | CH$_3$ | F |
| 3264 | Cl | F | OCH$_3$ | OCH$_3$ | H |
| 3265 | Cl | F | OCH$_3$ | OCH$_3$ | CH$_3$ |
| 3266 | Cl | F | OCH$_3$ | OCH$_3$ | OCH$_3$ |
| 3267 | Cl | F | OCH$_3$ | OCH$_3$ | Cl |
| 3268 | Cl | F | OCH$_3$ | OCH$_3$ | Br |
| 3269 | Cl | F | OCH$_3$ | OCH$_3$ | F |
| 3270 | Cl | F | OCH$_3$ | Cl | H |
| 3271 | Cl | F | OCH$_3$ | Cl | CH$_3$ |
| 3272 | Cl | F | OCH$_3$ | Cl | Cl |
| 3273 | Cl | F | oCH$_3$ | Cl | Br |
| 3274 | Cl | F | OCH$_3$ | Cl | F |
| 3275 | Cl | F | OCH$_3$ | Br | H |
| 3276 | Cl | F | OCH$_3$ | Br | CH$_3$ |
| 3277 | Cl | F | OCH$_3$ | Br | Cl |
| 3278 | Cl | F | OCH$_3$ | Br | Br |
| 3279 | Cl | F | OCH$_3$ | Br | F |
| 3280 | Cl | F | OCH$_3$ | F | H |
| 3281 | Cl | F | OCH$_3$ | F | CH$_3$ |
| 3282 | Cl | F | OCH$_3$ | F | Cl |
| 3283 | Cl | F | OCH$_3$ | F | Br |
| 3284 | Cl | F | OCH$_3$ | F | F |
| 3285 | Cl | F | Cl | H | H |
| 3286 | Cl | F | Cl | H | CH$_3$ |
| 3287 | Cl | F | Cl | H | OCH$_3$ |
| 3288 | Cl | F | Cl | H | Cl |
| 3289 | Cl | F | Cl | H | Br |
| 3290 | Cl | F | Cl | H | F |
| 3291 | Cl | F | Cl | CH$_3$ | H |
| 3292 | Cl | F | Cl | CH$_3$ | CH$_3$ |
| 3293 | Cl | F | Cl | CH$_3$ | OCH$_3$ |
| 3294 | Cl | F | Cl | CH$_3$ | Br |
| 3295 | Cl | F | Cl | CH$_3$ | F |

TABLE 2-continued

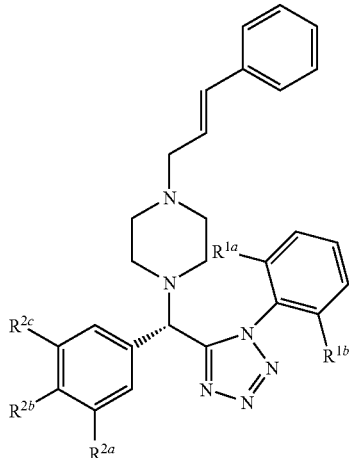

wherein $R^{1a}$, $R^{1b}$, $R^{2a}$, $R^{2b}$, and $R^{2c}$ are as defined in Table 2.

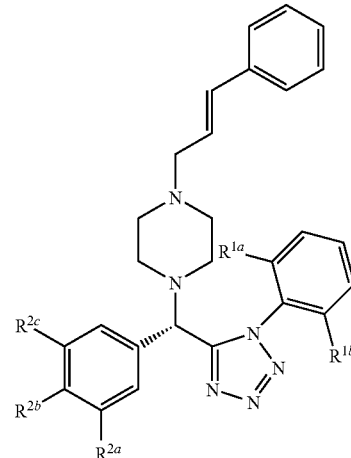

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ | Compound No. | $R^{1a}$ | $R^{1b}$ | $R^{2a}$ | $R^{2b}$ | $R^{2c}$ |
|---|---|---|---|---|---|---|---|---|---|---|---|
| 3296 | Cl | F | Cl | OCH₃ | H | 3346 | Cl | F | Br | F | Cl |
| 3297 | Cl | F | Cl | OCH₃ | CH₃ | 3347 | Cl | F | Br | F | F |
| 3298 | Cl | F | Cl | OCH₃ | OCH₃ | 3348 | Cl | F | F | H | H |
| 3299 | Cl | F | Cl | OCH₃ | Br | 3349 | Cl | F | F | H | CH₃ |
| 3300 | Cl | F | Cl | OCH₃ | F | 3350 | Cl | F | F | H | OCH₃ |
| 3301 | Cl | F | Cl | Cl | H | 3351 | Cl | F | F | H | Cl |
| 3302 | Cl | F | Cl | Cl | CH₃ | 3352 | Cl | F | F | H | Br |
| 3303 | Cl | F | Cl | Cl | OCH₃ | 3353 | Cl | F | F | H | F |
| 3304 | Cl | F | Cl | Cl | Cl | 3354 | Cl | F | F | CH₃ | H |
| 3305 | Cl | F | Cl | Cl | Br | 3355 | Cl | F | F | CH₃ | CH₃ |
| 3306 | Cl | F | Cl | Cl | F | 3356 | Cl | F | F | CH₃ | OCH₃ |
| 3307 | Cl | F | Cl | Br | H | 3357 | Cl | F | F | CH₃ | Cl |
| 3308 | Cl | F | Cl | Br | CH₃ | 3358 | Cl | F | F | CH₃ | Br |
| 3309 | Cl | F | Cl | Br | OCH₃ | 3359 | Cl | F | F | OCH₃ | H |
| 3310 | Cl | F | Cl | Br | Br | 3360 | Cl | F | F | OCH₃ | CH₃ |
| 3311 | Cl | F | Cl | F | H | 3361 | Cl | F | F | OCH₃ | OCH₃ |
| 3312 | Cl | F | Cl | F | CH₃ | 3362 | Cl | F | F | OCH₃ | Cl |
| 3313 | Cl | F | Cl | F | OCH₃ | 3363 | Cl | F | F | OCH₃ | Br |
| 3314 | Cl | F | Cl | F | Br | 3364 | Cl | F | F | Cl | H |
| 3315 | Cl | F | Cl | F | F | 3365 | Cl | F | F | Cl | CH₃ |
| 3316 | Cl | F | Br | H | H | 3366 | Cl | F | F | Cl | OCH₃ |
| 3317 | Cl | F | Br | H | CH₃ | 3367 | Cl | F | F | Cl | Cl |
| 3318 | Cl | F | Br | H | OCH₃ | 3368 | Cl | F | F | Cl | Br |
| 3319 | Cl | F | Br | H | Cl | 3369 | Cl | F | F | Br | H |
| 3320 | Cl | F | Br | H | Br | 3370 | Cl | F | F | Br | CH₃ |
| 3321 | Cl | F | Br | H | F | 3371 | Cl | F | F | Br | OCH₃ |
| 3322 | Cl | F | Br | CH₃ | H | 3372 | Cl | F | F | Br | Cl |
| 3323 | Cl | F | Br | CH₃ | CH₃ | 3373 | Cl | F | F | Br | Br |
| 3324 | Cl | F | Br | CH₃ | OCH₃ | 3374 | Cl | F | F | F | H |
| 3325 | Cl | F | Br | CH₃ | Cl | 3375 | Cl | F | F | F | CH₃ |
| 3326 | Cl | F | Br | CH₃ | F | 3376 | Cl | F | F | F | OCH₃ |
| 3327 | Cl | F | Br | OCH₃ | H | 3377 | Cl | F | F | F | Cl |
| 3328 | Cl | F | Br | OCH₃ | CH₃ | 3378 | Cl | F | F | F | Br |
| 3329 | Cl | F | Br | OCH₃ | OCH₃ | 3379 | Cl | F | F | F | F |
| 3330 | Cl | F | Br | OCH₃ | Cl | 3380 | Br | CH₃ | CH₃ | H | H |
| 3331 | Cl | F | Br | OCH₃ | F | 3381 | Br | CH₃ | CH₃ | CH₃ | H |
| 3332 | Cl | F | Br | Cl | H | 3382 | Br | CH₃ | CH₃ | OCH₃ | H |
| 3333 | Cl | F | Br | Cl | CH₃ | 3383 | Br | CH₃ | CH₃ | Cl | H |
| 3334 | Cl | F | Br | Cl | OCH₃ | 3384 | Br | CH₃ | CH₃ | Br | H |
| 3335 | Cl | F | Br | Cl | Cl | 3385 | Br | CH₃ | CH₃ | F | H |
| 3336 | Cl | F | Br | Cl | F | 3386 | Br | CH₃ | CH₃ | H | CH₃ |
| 3337 | Cl | F | Br | Br | H | 3387 | Br | CH₃ | CH₃ | CH₃ | CH₃ |
| 3338 | Cl | F | Br | Br | CH₃ | 3388 | Br | CH₃ | CH₃ | H | OCH₃ |
| 3339 | Cl | F | Br | Br | OCH₃ | 3389 | Br | CH₃ | CH₃ | CH₃ | OCH₃ |
| 3340 | Cl | F | Br | Br | Cl | 3390 | Br | CH₃ | CH₃ | OCH₃ | OCH₃ |
| 3341 | Cl | F | Br | Br | Br | 3391 | Br | CH₃ | CH₃ | Cl | OCH₃ |
| 3342 | Cl | F | Br | Br | F | 3392 | Br | CH₃ | CH₃ | Br | OCH₃ |
| 3343 | Cl | F | Br | F | H | 3393 | Br | CH₃ | CH₃ | F | OCH₃ |
| 3344 | Cl | F | Br | F | CH₃ | 3394 | Br | CH₃ | CH₃ | H | Cl |
| 3345 | Cl | F | Br | F | OCH₃ | 3395 | Br | CH₃ | CH₃ | CH₃ | Cl |

TABLE 2-continued

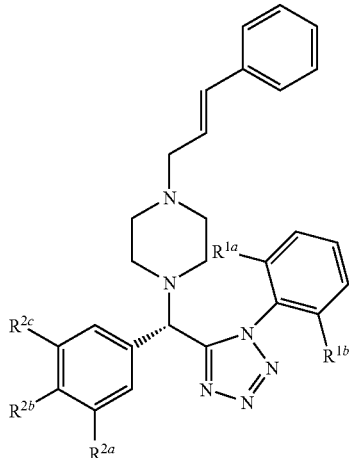

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 3396 | Br | CH$_3$ | CH$_3$ | OCH$_3$ | Cl |
| 3397 | Br | CH$_3$ | CH$_3$ | Cl | Cl |
| 3398 | Br | CH$_3$ | CH$_3$ | Br | Cl |
| 3399 | Br | CH$_3$ | CH$_3$ | F | Cl |
| 3400 | Br | CH$_3$ | CH$_3$ | H | Br |
| 3401 | Br | CH$_3$ | CH$_3$ | CH$_3$ | Br |
| 3402 | Br | CH$_3$ | CH$_3$ | OCH$_3$ | Br |
| 3403 | Br | CH$_3$ | CH$_3$ | Cl | Br |
| 3404 | Br | CH$_3$ | CH$_3$ | Br | Br |
| 3405 | Br | CH$_3$ | CH$_3$ | F | Br |
| 3406 | Br | CH$_3$ | CH$_3$ | H | F |
| 3407 | Br | CH$_3$ | CH$_3$ | CH$_3$ | F |
| 3408 | Br | CH$_3$ | CH$_3$ | OCH$_3$ | F |
| 3409 | Br | CH$_3$ | CH$_3$ | Cl | F |
| 3410 | Br | CH$_3$ | CH$_3$ | Br | F |
| 3411 | Br | CH$_3$ | CH$_3$ | F | F |
| 3412 | Br | CH$_3$ | OCH$_3$ | H | H |
| 3413 | Br | CH$_3$ | OCH$_3$ | CH$_3$ | H |
| 3414 | Br | CH$_3$ | OCH$_3$ | OCH$_3$ | H |
| 3415 | Br | CH$_3$ | OCH$_3$ | Cl | H |
| 3416 | Br | CH$_3$ | OCH$_3$ | Br | H |
| 3417 | Br | CH$_3$ | OCH$_3$ | F | H |
| 3418 | Br | CH$_3$ | OCH$_3$ | H | CH$_3$ |
| 3419 | Br | CH$_3$ | OCH$_3$ | CH$_3$ | CH$_3$ |
| 3420 | Br | CH$_3$ | OCH$_3$ | OCH$_3$ | CH$_3$ |
| 3421 | Br | CH$_3$ | OCH$_3$ | Cl | CH$_3$ |
| 3422 | Br | CH$_3$ | OCH$_3$ | Br | CH$_3$ |
| 3423 | Br | CH$_3$ | OCH$_3$ | F | CH$_3$ |
| 3424 | Br | CH$_3$ | OCH$_3$ | H | OCH$_3$ |
| 3425 | Br | CH$_3$ | OCH$_3$ | OCH$_3$ | OCH$_3$ |
| 3426 | Br | CH$_3$ | OCH$_3$ | H | Cl |
| 3427 | Br | CH$_3$ | OCH$_3$ | CH$_3$ | Cl |
| 3428 | Br | CH$_3$ | OCH$_3$ | OCH$_3$ | Cl |
| 3429 | Br | CH$_3$ | OCH$_3$ | Cl | Cl |
| 3430 | Br | CH$_3$ | OCH$_3$ | Br | Cl |
| 3431 | Br | CH$_3$ | OCH$_3$ | F | Cl |
| 3432 | Br | CH$_3$ | OCH$_3$ | H | Br |
| 3433 | Br | CH$_3$ | OCH$_3$ | CH$_3$ | Br |
| 3434 | Br | CH$_3$ | OCH$_3$ | OCH$_3$ | Br |
| 3435 | Br | CH$_3$ | OCH$_3$ | Cl | Br |
| 3436 | Br | CH$_3$ | OCH$_3$ | Br | Br |
| 3437 | Br | CH$_3$ | OCH$_3$ | F | Br |
| 3438 | Br | CH$_3$ | OCH$_3$ | H | F |
| 3439 | Br | CH$_3$ | OCH$_3$ | CH$_3$ | F |
| 3440 | Br | CH$_3$ | OCH$_3$ | OCH$_3$ | F |
| 3441 | Br | CH$_3$ | OCH$_3$ | Cl | F |
| 3442 | Br | CH$_3$ | OCH$_3$ | Br | F |
| 3443 | Br | CH$_3$ | OCH$_3$ | F | F |
| 3444 | Br | CH$_3$ | Cl | H | H |
| 3445 | Br | CH$_3$ | Cl | CH$_3$ | H |

TABLE 2-continued

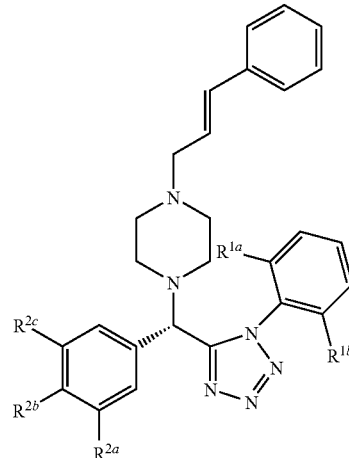

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 3446 | Br | CH$_3$ | Cl | OCH$_3$ | H |
| 3447 | Br | CH$_3$ | Cl | Cl | H |
| 3448 | Br | CH$_3$ | Cl | Br | H |
| 3449 | Br | CH$_3$ | Cl | F | H |
| 3450 | Br | CH$_3$ | Cl | H | CH$_3$ |
| 3451 | Br | CH$_3$ | Cl | CH$_3$ | CH$_3$ |
| 3452 | Br | CH$_3$ | Cl | OCH$_3$ | CH$_3$ |
| 3453 | Br | CH$_3$ | Cl | Cl | CH$_3$ |
| 3454 | Br | CH$_3$ | Cl | Br | CH$_3$ |
| 3455 | Br | CH$_3$ | Cl | F | CH$_3$ |
| 3456 | Br | CH$_3$ | Cl | H | OCH$_3$ |
| 3457 | Br | CH$_3$ | Cl | CH$_3$ | OCH$_3$ |
| 3458 | Br | CH$_3$ | Cl | OCH$_3$ | OCH$_3$ |
| 3459 | Br | CH$_3$ | Cl | Cl | OCH$_3$ |
| 3460 | Br | CH$_3$ | Cl | Br | OCH$_3$ |
| 3461 | Br | CH$_3$ | Cl | F | OCH$_3$ |
| 3462 | Br | CH$_3$ | Cl | H | Cl |
| 3463 | Br | CH$_3$ | Cl | Cl | Cl |
| 3464 | Br | CH$_3$ | Cl | H | Br |
| 3465 | Br | CH$_3$ | Cl | CH$_3$ | Br |
| 3466 | Br | CH$_3$ | Cl | OCH$_3$ | Br |
| 3467 | Br | CH$_3$ | Cl | Cl | Br |
| 3468 | Br | CH$_3$ | Cl | Br | Br |
| 3469 | Br | CH$_3$ | Cl | F | Br |
| 3470 | Br | CH$_3$ | Cl | H | F |
| 3471 | Br | CH$_3$ | Cl | CH$_3$ | F |
| 3472 | Br | CH$_3$ | Cl | OCH$_3$ | F |
| 3473 | Br | CH$_3$ | Cl | Cl | F |
| 3474 | Br | CH$_3$ | Cl | F | F |
| 3475 | Br | CH$_3$ | Br | H | H |
| 3476 | Br | CH$_3$ | Br | CH$_3$ | H |
| 3477 | Br | CH$_3$ | Br | OCH$_3$ | H |
| 3478 | Br | CH$_3$ | Br | Cl | H |
| 3479 | Br | CH$_3$ | Br | Br | H |
| 3480 | Br | CH$_3$ | Br | F | H |
| 3481 | Br | CH$_3$ | Br | H | CH$_3$ |
| 3482 | Br | CH$_3$ | Br | CH$_3$ | CH$_3$ |
| 3483 | Br | CH$_3$ | Br | OCH$_3$ | CH$_3$ |
| 3484 | Br | CH$_3$ | Br | Cl | CH$_3$ |
| 3485 | Br | CH$_3$ | Br | Br | CH$_3$ |
| 3486 | Br | CH$_3$ | Br | F | CH$_3$ |
| 3487 | Br | CH$_3$ | Br | H | OCH$_3$ |
| 3488 | Br | CH$_3$ | Br | CH$_3$ | OCH$_3$ |
| 3489 | Br | CH$_3$ | Br | OCH$_3$ | OCH$_3$ |
| 3490 | Br | CH$_3$ | Br | Cl | OCH$_3$ |
| 3491 | Br | CH$_3$ | Br | Br | OCH$_3$ |
| 3492 | Br | CH$_3$ | Br | F | OCH$_3$ |
| 3493 | Br | CH$_3$ | Br | H | Cl |
| 3494 | Br | CH$_3$ | Br | CH$_3$ | Cl |
| 3495 | Br | CH$_3$ | Br | OCH$_3$ | Cl |

TABLE 2-continued

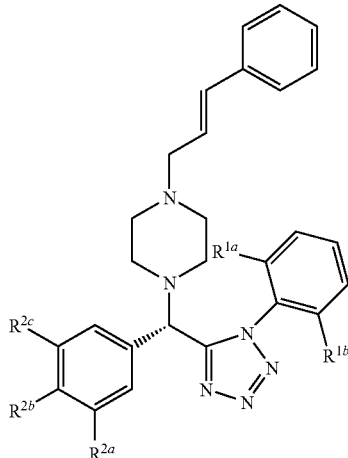

wherein $R^{1a}$, $R^{1b}$, $R^{2a}$, $R^{2b}$, and $R^{2c}$ are as defined in Table 2.

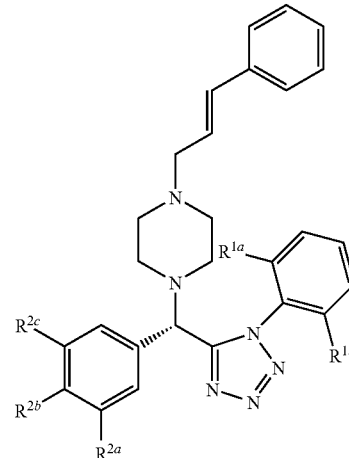

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 3496 | Br | CH₃ | Br | Cl | Cl |
| 3497 | Br | CH₃ | Br | Br | Cl |
| 3498 | Br | CH₃ | Br | F | Cl |
| 3499 | Br | CH₃ | Br | H | Br |
| 3500 | Br | CH₃ | Br | Br | Br |
| 3501 | Br | CH₃ | Br | H | F |
| 3502 | Br | CH₃ | Br | CH₃ | F |
| 3503 | Br | CH₃ | Br | OCH₃ | F |
| 3504 | Br | CH₃ | Br | Cl | F |
| 3505 | Br | CH₃ | Br | Br | F |
| 3506 | Br | CH₃ | Br | F | F |
| 3507 | Br | CH₃ | F | H | H |
| 3508 | Br | CH₃ | F | CH₃ | H |
| 3509 | Br | CH₃ | F | OCH₃ | H |
| 3510 | Br | CH₃ | F | Cl | H |
| 3511 | Br | CH₃ | F | Br | H |
| 3512 | Br | CH₃ | F | F | H |
| 3513 | Br | CH₃ | F | H | CH₃ |
| 3514 | Br | CH₃ | F | CH₃ | CH₃ |
| 3515 | Br | CH₃ | F | OCH₃ | CH₃ |
| 3516 | Br | CH₃ | F | Cl | CH₃ |
| 3517 | Br | CH₃ | F | Br | CH₃ |
| 3518 | Br | CH₃ | F | F | CH₃ |
| 3519 | Br | CH₃ | F | H | OCH₃ |
| 3520 | Br | CH₃ | F | CH₃ | OCH₃ |
| 3521 | Br | CH₃ | F | OCH₃ | OCH₃ |
| 3522 | Br | CH₃ | F | Cl | OCH₃ |
| 3523 | Br | CH₃ | F | Br | OCH₃ |
| 3524 | Br | CH₃ | F | F | OCH₃ |
| 3525 | Br | CH₃ | F | H | Cl |
| 3526 | Br | CH₃ | F | CH₃ | Cl |
| 3527 | Br | CH₃ | F | OCH₃ | Cl |
| 3528 | Br | CH₃ | F | Cl | Cl |
| 3529 | Br | CH₃ | F | Br | Cl |
| 3530 | Br | CH₃ | F | F | Cl |
| 3531 | Br | CH₃ | F | H | Br |
| 3532 | Br | CH₃ | F | CH₃ | Br |
| 3533 | Br | CH₃ | F | OCH₃ | Br |
| 3534 | Br | CH₃ | F | Cl | Br |
| 3535 | Br | CH₃ | F | Br | Br |
| 3536 | Br | CH₃ | F | F | Br |
| 3537 | Br | CH₃ | F | H | F |
| 3538 | Br | CH₃ | F | F | F |
| 3539 | Br | OCH₃ | CH₃ | H | H |
| 3540 | Br | OCH₃ | CH₃ | H | CH₃ |
| 3541 | Br | OCH₃ | CH₃ | H | OCH₃ |
| 3542 | Br | OCH₃ | CH₃ | H | Cl |
| 3543 | Br | OCH₃ | CH₃ | H | Br |
| 3544 | Br | OCH₃ | CH₃ | H | F |
| 3545 | Br | OCH₃ | CH₃ | CH₃ | H |
| 3546 | Br | OCH₃ | CH₃ | CH₃ | CH₃ |
| 3547 | Br | OCH₃ | CH₃ | CH₃ | OCH₃ |
| 3548 | Br | OCH₃ | CH₃ | CH₃ | Cl |
| 3549 | Br | OCH₃ | CH₃ | CH₃ | Br |
| 3550 | Br | OCH₃ | CH₃ | CH₃ | F |
| 3551 | Br | OCH₃ | CH₃ | OCH₃ | H |
| 3552 | Br | OCH₃ | CH₃ | OCH₃ | OCH₃ |
| 3553 | Br | OCH₃ | CH₃ | OCH₃ | Cl |
| 3554 | Br | OCH₃ | CH₃ | OCH₃ | Br |
| 3555 | Br | OCH₃ | CH₃ | OCH₃ | F |
| 3556 | Br | OCH₃ | CH₃ | Cl | H |
| 3557 | Br | OCH₃ | CH₃ | Cl | OCH₃ |
| 3558 | Br | OCH₃ | CH₃ | Cl | Cl |
| 3559 | Br | OCH₃ | CH₃ | Cl | Br |
| 3560 | Br | OCH₃ | CH₃ | Cl | F |
| 3561 | Br | OCH₃ | CH₃ | Br | H |
| 3562 | Br | OCH₃ | CH₃ | Br | OCH₃ |
| 3563 | Br | OCH₃ | CH₃ | Br | Cl |
| 3564 | Br | OCH₃ | CH₃ | Br | Br |
| 3565 | Br | OCH₃ | CH₃ | Br | F |
| 3566 | Br | OCH₃ | CH₃ | F | H |
| 3567 | Br | OCH₃ | CH₃ | F | OCH₃ |
| 3568 | Br | OCH₃ | CH₃ | F | Cl |
| 3569 | Br | OCH₃ | CH₃ | F | Br |
| 3570 | Br | OCH₃ | CH₃ | F | F |
| 3571 | Br | OCH₃ | OCH₃ | H | H |
| 3572 | Br | OCH₃ | OCH₃ | H | CH₃ |
| 3573 | Br | OCH₃ | OCH₃ | H | OCH₃ |
| 3574 | Br | OCH₃ | OCH₃ | H | Cl |
| 3575 | Br | OCH₃ | OCH₃ | H | Br |
| 3576 | Br | OCH₃ | OCH₃ | H | F |
| 3577 | Br | OCH₃ | OCH₃ | CH₃ | H |
| 3578 | Br | OCH₃ | OCH₃ | CH₃ | CH₃ |
| 3579 | Br | OCH₃ | OCH₃ | CH₃ | Cl |
| 3580 | Br | OCH₃ | OCH₃ | CH₃ | Br |
| 3581 | Br | OCH₃ | OCH₃ | CH₃ | F |
| 3582 | Br | OCH₃ | OCH₃ | OCH₃ | H |
| 3583 | Br | OCH₃ | OCH₃ | OCH₃ | CH₃ |
| 3584 | Br | OCH₃ | OCH₃ | OCH₃ | OCH₃ |
| 3585 | Br | OCH₃ | OCH₃ | OCH₃ | Cl |
| 3586 | Br | OCH₃ | OCH₃ | OCH₃ | Br |
| 3587 | Br | OCH₃ | OCH₃ | OCH₃ | F |
| 3588 | Br | OCH₃ | OCH₃ | Cl | H |
| 3589 | Br | OCH₃ | OCH₃ | Cl | CH₃ |
| 3590 | Br | OCH₃ | OCH₃ | Cl | Cl |
| 3591 | Br | OCH₃ | OCH₃ | Cl | Br |
| 3592 | Br | OCH₃ | OCH₃ | Cl | F |
| 3593 | Br | OCH₃ | OCH₃ | Br | H |
| 3594 | Br | OCH₃ | OCH₃ | Br | CH₃ |
| 3595 | Br | OCH₃ | OCH₃ | Br | Cl |

TABLE 2-continued

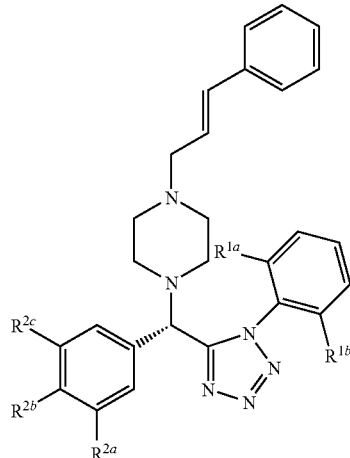

wherein $R^{1a}$, $R^{1b}$, $R^{2a}$, $R^{2b}$, and $R^{2c}$ are as defined in Table 2.

TABLE 2-continued

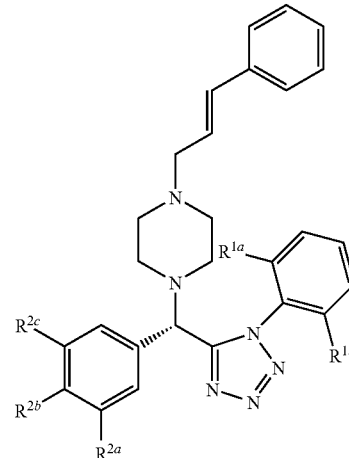

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ | Compound No. | $R^{1a}$ | $R^{1b}$ | $R^{2a}$ | $R^{2b}$ | $R^{2c}$ |
|---|---|---|---|---|---|---|---|---|---|---|---|
| 3596 | Br | OCH₃ | OCH₃ | Br | Br | 3646 | Br | OCH₃ | Br | OCH₃ | CH₃ |
| 3597 | Br | OCH₃ | OCH₃ | Br | F | 3647 | Br | OCH₃ | Br | OCH₃ | OCH₃ |
| 3598 | Br | OCH₃ | OCH₃ | F | H | 3648 | Br | OCH₃ | Br | OCH₃ | Cl |
| 3599 | Br | OCH₃ | OCH₃ | F | CH₃ | 3649 | Br | OCH₃ | Br | OCH₃ | F |
| 3600 | Br | OCH₃ | OCH₃ | F | Cl | 3650 | Br | OCH₃ | Br | Cl | H |
| 3601 | Br | OCH₃ | OCH₃ | F | Br | 3651 | Br | OCH₃ | Br | Cl | CH₃ |
| 3602 | Br | OCH₃ | OCH₃ | F | F | 3652 | Br | OCH₃ | Br | Cl | OCH₃ |
| 3603 | Br | OCH₃ | Cl | H | H | 3653 | Br | OCH₃ | Br | Cl | Cl |
| 3604 | Br | OCH₃ | Cl | H | CH₃ | 3654 | Br | OCH₃ | Br | Cl | F |
| 3605 | Br | OCH₃ | Cl | H | OCH₃ | 3655 | Br | OCH₃ | Br | Br | H |
| 3606 | Br | OCH₃ | Cl | H | Cl | 3656 | Br | OCH₃ | Br | Br | CH₃ |
| 3607 | Br | OCH₃ | Cl | H | Br | 3657 | Br | OCH₃ | Br | Br | OCH₃ |
| 3608 | Br | OCH₃ | Cl | H | F | 3658 | Br | OCH₃ | Br | Br | Cl |
| 3609 | Br | OCH₃ | Cl | CH₃ | H | 3659 | Br | OCH₃ | Br | Br | Br |
| 3610 | Br | OCH₃ | Cl | CH₃ | CH₃ | 3660 | Br | OCH₃ | Br | Br | F |
| 3611 | Br | OCH₃ | Cl | CH₃ | OCH₃ | 3661 | Br | OCH₃ | Br | F | H |
| 3612 | Br | OCH₃ | Cl | CH₃ | Br | 3662 | Br | OCH₃ | Br | F | CH₃ |
| 3613 | Br | OCH₃ | Cl | CH₃ | F | 3663 | Br | OCH₃ | Br | F | OCH₃ |
| 3614 | Br | OCH₃ | Cl | OCH₃ | H | 3664 | Br | OCH₃ | Br | F | Cl |
| 3615 | Br | OCH₃ | Cl | OCH₃ | CH₃ | 3665 | Br | OCH₃ | Br | F | F |
| 3616 | Br | OCH₃ | Cl | OCH₃ | OCH₃ | 3666 | Br | OCH₃ | F | H | H |
| 3617 | Br | OCH₃ | Cl | OCH₃ | Br | 3667 | Br | OCH₃ | F | H | CH₃ |
| 3618 | Br | OCH₃ | Cl | OCH₃ | F | 3668 | Br | OCH₃ | F | H | OCH₃ |
| 3619 | Br | OCH₃ | Cl | Cl | H | 3669 | Br | OCH₃ | F | H | Cl |
| 3620 | Br | OCH₃ | Cl | Cl | CH₃ | 3670 | Br | OCH₃ | F | H | Br |
| 3621 | Br | OCH₃ | Cl | Cl | OCH₃ | 3671 | Br | OCH₃ | F | H | F |
| 3622 | Br | OCH₃ | Cl | Cl | Cl | 3672 | Br | OCH₃ | F | CH₃ | H |
| 3623 | Br | OCH₃ | Cl | Cl | Br | 3673 | Br | OCH₃ | F | CH₃ | CH₃ |
| 3624 | Br | OCH₃ | Cl | Cl | F | 3674 | Br | OCH₃ | F | CH₃ | OCH₃ |
| 3625 | Br | OCH₃ | Cl | Br | H | 3675 | Br | OCH₃ | F | CH₃ | Cl |
| 3626 | Br | OCH₃ | Cl | Br | CH₃ | 3676 | Br | OCH₃ | F | CH₃ | Br |
| 3627 | Br | OCH₃ | Cl | Br | OCH₃ | 3677 | Br | OCH₃ | F | OCH₃ | H |
| 3628 | Br | OCH₃ | Cl | Br | Br | 3678 | Br | OCH₃ | F | OCH₃ | CH₃ |
| 3629 | Br | OCH₃ | Cl | F | H | 3679 | Br | OCH₃ | F | OCH₃ | OCH₃ |
| 3630 | Br | OCH₃ | Cl | F | CH₃ | 3680 | Br | OCH₃ | F | OCH₃ | Cl |
| 3631 | Br | OCH₃ | Cl | F | OCH₃ | 3681 | Br | OCH₃ | F | OCH₃ | Br |
| 3632 | Br | OCH₃ | Cl | F | Br | 3682 | Br | OCH₃ | F | Cl | H |
| 3633 | Br | OCH₃ | Cl | F | F | 3683 | Br | OCH₃ | F | Cl | CH₃ |
| 3634 | Br | OCH₃ | Br | H | H | 3684 | Br | OCH₃ | F | Cl | OCH₃ |
| 3635 | Br | OCH₃ | Br | H | CH₃ | 3685 | Br | OCH₃ | F | Cl | Cl |
| 3636 | Br | OCH₃ | Br | H | OCH₃ | 3686 | Br | OCH₃ | F | Cl | Br |
| 3637 | Br | OCH₃ | Br | H | Cl | 3687 | Br | OCH₃ | F | Br | H |
| 3638 | Br | OCH₃ | Br | H | Br | 3688 | Br | OCH₃ | F | Br | CH₃ |
| 3639 | Br | OCH₃ | Br | H | F | 3689 | Br | OCH₃ | F | Br | OCH₃ |
| 3640 | Br | OCH₃ | Br | CH₃ | H | 3690 | Br | OCH₃ | F | Br | Cl |
| 3641 | Br | OCH₃ | Br | CH₃ | CH₃ | 3691 | Br | OCH₃ | F | Br | Br |
| 3642 | Br | OCH₃ | Br | CH₃ | OCH₃ | 3692 | Br | OCH₃ | F | F | H |
| 3643 | Br | OCH₃ | Br | CH₃ | Cl | 3693 | Br | OCH₃ | F | F | CH₃ |
| 3644 | Br | OCH₃ | Br | CH₃ | F | 3694 | Br | OCH₃ | F | F | OCH₃ |
| 3645 | Br | OCH₃ | Br | OCH₃ | H | 3695 | Br | OCH₃ | F | F | Cl |

TABLE 2-continued

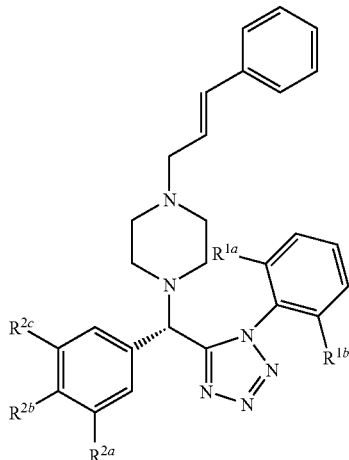

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 3696 | Br | OCH$_3$ | F | F | Br |
| 3697 | Br | OCH$_3$ | F | F | F |
| 3698 | Br | Cl | CH$_3$ | H | H |
| 3699 | Br | Cl | CH$_3$ | H | CH$_3$ |
| 3700 | Br | Cl | CH$_3$ | H | OCH$_3$ |
| 3701 | Br | Cl | CH$_3$ | H | Cl |
| 3702 | Br | Cl | CH$_3$ | H | Br |
| 3703 | Br | Cl | CH$_3$ | H | F |
| 3704 | Br | Cl | CH$_3$ | CH$_3$ | H |
| 3705 | Br | Cl | CH$_3$ | CH$_3$ | CH$_3$ |
| 3706 | Br | Cl | CH$_3$ | CH$_3$ | OCH$_3$ |
| 3707 | Br | Cl | CH$_3$ | CH$_3$ | Cl |
| 3708 | Br | Cl | CH$_3$ | CH$_3$ | Br |
| 3709 | Br | Cl | CH$_3$ | CH$_3$ | F |
| 3710 | Br | Cl | CH$_3$ | OCH$_3$ | H |
| 3711 | Br | Cl | CH$_3$ | OCH$_3$ | OCH$_3$ |
| 3712 | Br | Cl | CH$_3$ | OCH$_3$ | Cl |
| 3713 | Br | Cl | CH$_3$ | OCH$_3$ | Br |
| 3714 | Br | Cl | CH$_3$ | OCH$_3$ | F |
| 3715 | Br | Cl | CH$_3$ | Cl | H |
| 3716 | Br | Cl | CH$_3$ | Cl | OCH$_3$ |
| 3717 | Br | Cl | CH$_3$ | Cl | Cl |
| 3718 | Br | Cl | CH$_3$ | Cl | Br |
| 3719 | Br | Cl | CH$_3$ | Cl | F |
| 3720 | Br | Cl | CH$_3$ | Br | H |
| 3721 | Br | Cl | CH$_3$ | Br | OCH$_3$ |
| 3722 | Br | Cl | CH$_3$ | Br | Cl |
| 3723 | Br | Cl | CH$_3$ | Br | Br |
| 3724 | Br | Cl | CH$_3$ | Br | F |
| 3725 | Br | Cl | CH$_3$ | F | H |
| 3726 | Br | Cl | CH$_3$ | F | OCH$_3$ |
| 3727 | Br | Cl | CH$_3$ | F | Cl |
| 3728 | Br | Cl | CH$_3$ | F | Br |
| 3729 | Br | Cl | CH$_3$ | F | F |
| 3730 | Br | Cl | OCH$_3$ | H | H |
| 3731 | Br | Cl | OCH$_3$ | H | CH$_3$ |
| 3732 | Br | Cl | OCH$_3$ | H | OCH$_3$ |
| 3733 | Br | Cl | OCH$_3$ | H | Cl |
| 3734 | Br | Cl | OCH$_3$ | H | Br |
| 3735 | Br | Cl | OCH$_3$ | H | F |
| 3736 | Br | Cl | OCH$_3$ | CH$_3$ | H |
| 3737 | Br | Cl | OCH$_3$ | CH$_3$ | CH$_3$ |
| 3738 | Br | Cl | OCH$_3$ | CH$_3$ | Cl |
| 3739 | Br | Cl | OCH$_3$ | CH$_3$ | Br |
| 3740 | Br | Cl | OCH$_3$ | CH$_3$ | F |
| 3741 | Br | Cl | OCH$_3$ | OCH$_3$ | H |
| 3742 | Br | Cl | OCH$_3$ | OCH$_3$ | CH$_3$ |
| 3743 | Br | Cl | OCH$_3$ | OCH$_3$ | OCH$_3$ |
| 3744 | Br | Cl | OCH$_3$ | OCH$_3$ | Cl |
| 3745 | Br | Cl | OCH$_3$ | OCH$_3$ | Br |

TABLE 2-continued

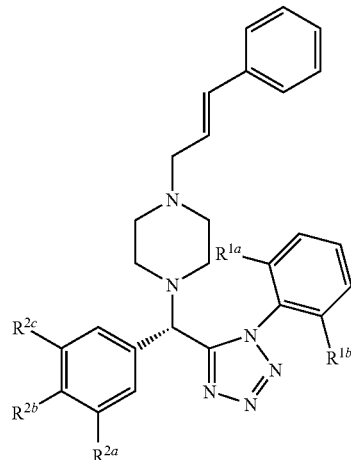

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 3746 | Br | Cl | OCH$_3$ | OCH$_3$ | F |
| 3747 | Br | Cl | OCH$_3$ | Cl | H |
| 3748 | Br | Cl | OCH$_3$ | Cl | CH$_3$ |
| 3749 | Br | Cl | OCH$_3$ | Cl | Cl |
| 3750 | Br | Cl | OCH$_3$ | Cl | Br |
| 3751 | Br | Cl | OCH$_3$ | Cl | F |
| 3752 | Br | Cl | OCH$_3$ | Br | H |
| 3753 | Br | Cl | OCH$_3$ | Br | CH$_3$ |
| 3754 | Br | Cl | OCH$_3$ | Br | Cl |
| 3755 | Br | Cl | OCH$_3$ | Br | Br |
| 3756 | Br | Cl | OCH$_3$ | Br | F |
| 3757 | Br | Cl | OCH$_3$ | F | H |
| 3758 | Br | Cl | OCH$_3$ | F | CH$_3$ |
| 3759 | Br | Cl | OCH$_3$ | F | Cl |
| 3760 | Br | Cl | OCH$_3$ | F | Br |
| 3761 | Br | Cl | OCH$_3$ | F | F |
| 3762 | Br | Cl | Cl | H | H |
| 3763 | Br | Cl | Cl | H | CH$_3$ |
| 3764 | Br | Cl | Cl | H | OCH$_3$ |
| 3765 | Br | Cl | Cl | H | Cl |
| 3766 | Br | Cl | Cl | H | Br |
| 3767 | Br | Cl | Cl | H | F |
| 3768 | Br | Cl | Cl | CH$_3$ | H |
| 3769 | Br | Cl | Cl | CH$_3$ | CH$_3$ |
| 3770 | Br | Cl | Cl | CH$_3$ | OCH$_3$ |
| 3771 | Br | Cl | Cl | CH$_3$ | Br |
| 3772 | Br | Cl | Cl | CH$_3$ | F |
| 3773 | Br | Cl | Cl | OCH$_3$ | H |
| 3774 | Br | Cl | Cl | OCH$_3$ | CH$_3$ |
| 3775 | Br | Cl | Cl | OCH$_3$ | OCH$_3$ |
| 3776 | Br | Cl | Cl | OCH$_3$ | Br |
| 3777 | Br | Cl | Cl | OCH$_3$ | F |
| 3778 | Br | Cl | Cl | Cl | H |
| 3779 | Br | Cl | Cl | Cl | CH$_3$ |
| 3780 | Br | Cl | Cl | Cl | OCH$_3$ |
| 3781 | Br | Cl | Cl | Cl | Cl |
| 3782 | Br | Cl | Cl | Cl | Br |
| 3783 | Br | Cl | Cl | Cl | F |
| 3784 | Br | Cl | Cl | Br | H |
| 3785 | Br | Cl | Cl | Br | CH$_3$ |
| 3786 | Br | Cl | Cl | Br | OCH$_3$ |
| 3787 | Br | Cl | Cl | Br | Br |
| 3788 | Br | Cl | Cl | F | H |
| 3789 | Br | Cl | Cl | F | CH$_3$ |
| 3790 | Br | Cl | Cl | F | OCH$_3$ |
| 3791 | Br | Cl | Cl | F | Br |
| 3792 | Br | Cl | Cl | F | F |
| 3793 | Br | Cl | Br | H | H |
| 3794 | Br | Cl | Br | H | CH$_3$ |
| 3795 | Br | Cl | Br | H | OCH$_3$ |

TABLE 2-continued

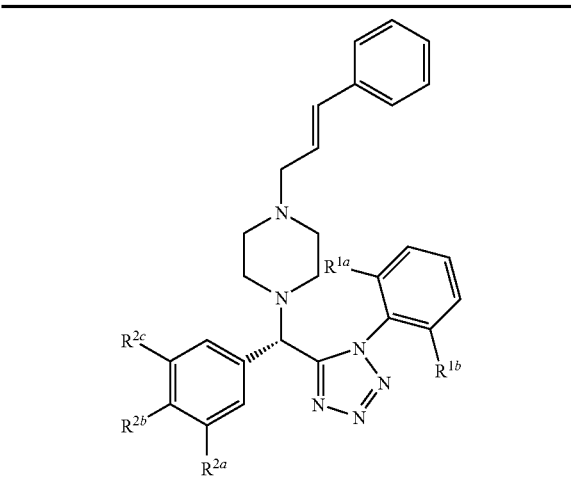

wherein $R^{1a}$, $R^{1b}$, $R^{2a}$, $R^{2b}$, and $R^{2c}$ are as defined in Table 2.

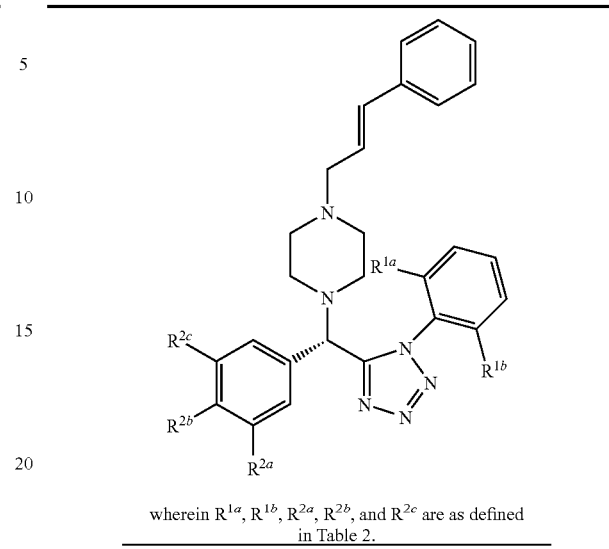

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ | Compound No. | $R^{1a}$ | $R^{1b}$ | $R^{2a}$ | $R^{2b}$ | $R^{2c}$ |
|---|---|---|---|---|---|---|---|---|---|---|---|
| 3796 | Br | Cl | Br | H | Cl | 3846 | Br | Cl | F | Br | H |
| 3797 | Br | Cl | Br | H | Br | 3847 | Br | Cl | F | Br | CH₃ |
| 3798 | Br | Cl | Br | H | F | 3848 | Br | Cl | F | Br | OCH₃ |
| 3799 | Br | Cl | Br | CH₃ | H | 3849 | Br | Cl | F | Br | Cl |
| 3800 | Br | Cl | Br | CH₃ | CH₃ | 3850 | Br | Cl | F | Br | Br |
| 3801 | Br | Cl | Br | CH₃ | OCH₃ | 3851 | Br | Cl | F | F | H |
| 3802 | Br | Cl | Br | CH₃ | Cl | 3852 | Br | Cl | F | F | CH₃ |
| 3803 | Br | Cl | Br | CH₃ | F | 3853 | Br | Cl | F | F | OCH₃ |
| 3804 | Br | Cl | Br | OCH₃ | H | 3854 | Br | Cl | F | F | Cl |
| 3805 | Br | Cl | Br | OCH₃ | CH₃ | 3855 | Br | Cl | F | F | Br |
| 3806 | Br | Cl | Br | OCH₃ | OCH₃ | 3856 | Br | Cl | F | F | F |
| 3807 | Br | Cl | Br | OCH₃ | Cl | 3857 | Br | Br | CH₃ | H | H |
| 3808 | Br | Cl | Br | OCH₃ | F | 3858 | Br | Br | CH₃ | H | CH₃ |
| 3809 | Br | Cl | Br | Cl | H | 3859 | Br | Br | CH₃ | H | OCH₃ |
| 3810 | Br | Cl | Br | Cl | CH₃ | 3860 | Br | Br | CH₃ | H | Cl |
| 3811 | Br | Cl | Br | Cl | OCH₃ | 3861 | Br | Br | CH₃ | H | Br |
| 3812 | Br | Cl | Br | Cl | Cl | 3862 | Br | Br | CH₃ | H | F |
| 3813 | Br | Cl | Br | Cl | F | 3863 | Br | Br | CH₃ | CH₃ | H |
| 3814 | Br | Cl | Br | Br | H | 3864 | Br | Br | CH₃ | CH₃ | CH₃ |
| 3815 | Br | Cl | Br | Br | CH₃ | 3865 | Br | Br | CH₃ | CH₃ | OCH₃ |
| 3816 | Br | Cl | Br | Br | OCH₃ | 3866 | Br | Br | CH₃ | CH₃ | Cl |
| 3817 | Br | Cl | Br | Br | Cl | 3867 | Br | Br | CH₃ | CH₃ | Br |
| 3818 | Br | Cl | Br | Br | Br | 3868 | Br | Br | CH₃ | CH₃ | F |
| 3819 | Br | Cl | Br | Br | F | 3869 | Br | Br | CH₃ | OCH₃ | H |
| 3820 | Br | Cl | Br | F | H | 3870 | Br | Br | CH₃ | OCH₃ | OCH₃ |
| 3821 | Br | Cl | Br | F | CH₃ | 3871 | Br | Br | CH₃ | OCH₃ | Cl |
| 3822 | Br | Cl | Br | F | OCH₃ | 3872 | Br | Br | CH₃ | OCH₃ | Br |
| 3823 | Br | Cl | Br | F | Cl | 3873 | Br | Br | CH₃ | OCH₃ | F |
| 3824 | Br | Cl | Br | F | F | 3874 | Br | Br | CH₃ | Cl | H |
| 3825 | Br | Cl | F | H | H | 3875 | Br | Br | CH₃ | Cl | OCH₃ |
| 3826 | Br | Cl | F | H | CH₃ | 3876 | Br | Br | CH₃ | Cl | Cl |
| 3827 | Br | Cl | F | H | OCH₃ | 3877 | Br | Br | CH₃ | Cl | Br |
| 3828 | Br | Cl | F | H | Cl | 3878 | Br | Br | CH₃ | Cl | F |
| 3829 | Br | Cl | F | H | Br | 3879 | Br | Br | CH₃ | Br | H |
| 3830 | Br | Cl | F | H | F | 3880 | Br | Br | CH₃ | Br | OCH₃ |
| 3831 | Br | Cl | F | CH₃ | H | 3881 | Br | Br | CH₃ | Br | Cl |
| 3832 | Br | Cl | F | CH₃ | CH₃ | 3882 | Br | Br | CH₃ | Br | Br |
| 3833 | Br | Cl | F | CH₃ | OCH₃ | 3883 | Br | Br | CH₃ | Br | F |
| 3834 | Br | Cl | F | CH₃ | Cl | 3884 | Br | Br | CH₃ | F | H |
| 3835 | Br | Cl | F | CH₃ | Br | 3885 | Br | Br | CH₃ | F | OCH₃ |
| 3836 | Br | Cl | F | OCH₃ | H | 3886 | Br | Br | CH₃ | F | Cl |
| 3837 | Br | Cl | F | OCH₃ | CH₃ | 3887 | Br | Br | CH₃ | F | Br |
| 3838 | Br | Cl | F | OCH₃ | OCH₃ | 3888 | Br | Br | CH₃ | F | F |
| 3839 | Br | Cl | F | OCH₃ | Cl | 3889 | Br | Br | OCH₃ | H | H |
| 3840 | Br | Cl | F | OCH₃ | Br | 3890 | Br | Br | OCH₃ | H | CH₃ |
| 3841 | Br | Cl | F | Cl | H | 3891 | Br | Br | OCH₃ | H | OCH₃ |
| 3842 | Br | Cl | F | Cl | CH₃ | 3892 | Br | Br | OCH₃ | H | Cl |
| 3843 | Br | Cl | F | Cl | OCH₃ | 3893 | Br | Br | OCH₃ | H | Br |
| 3844 | Br | Cl | F | Cl | Cl | 3894 | Br | Br | OCH₃ | H | F |
| 3845 | Br | Cl | F | Cl | Br | 3895 | Br | Br | OCH₃ | CH₃ | H |

TABLE 2-continued

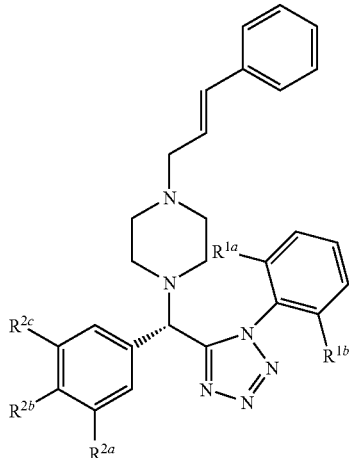

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
| --- | --- | --- | --- | --- | --- |
| 3896 | Br | Br | OCH$_3$ | CH$_3$ | CH$_3$ |
| 3897 | Br | Br | OCH$_3$ | CH$_3$ | Cl |
| 3898 | Br | Br | OCH$_3$ | CH$_3$ | Br |
| 3899 | Br | Br | OCH$_3$ | CH$_3$ | F |
| 3900 | Br | Br | OCH$_3$ | OCH$_3$ | H |
| 3901 | Br | Br | OCH$_3$ | OCH$_3$ | CH$_3$ |
| 3902 | Br | Br | OCH$_3$ | OCH$_3$ | OCH$_3$ |
| 3903 | Br | Br | OCH$_3$ | OCH$_3$ | Cl |
| 3904 | Br | Br | OCH$_3$ | OCH$_3$ | Br |
| 3905 | Br | Br | OCH$_3$ | OCH$_3$ | F |
| 3906 | Br | Br | OCH$_3$ | Cl | H |
| 3907 | Br | Br | OCH$_3$ | Cl | CH$_3$ |
| 3908 | Br | Br | OCH$_3$ | Cl | Cl |
| 3909 | Br | Br | OCH$_3$ | Cl | Br |
| 3910 | Br | Br | OCH$_3$ | Cl | F |
| 3911 | Br | Br | OCH$_3$ | Br | H |
| 3912 | Br | Br | OCH$_3$ | Br | CH$_3$ |
| 3913 | Br | Br | OCH$_3$ | Br | Cl |
| 3914 | Br | Br | OCH$_3$ | Br | Br |
| 3915 | Br | Br | OCH$_3$ | Br | F |
| 3916 | Br | Br | OCH$_3$ | F | H |
| 3917 | Br | Br | OCH$_3$ | F | CH$_3$ |
| 3918 | Br | Br | OCH$_3$ | F | Cl |
| 3919 | Br | Br | OCH$_3$ | F | Br |
| 3920 | Br | Br | OCH$_3$ | F | F |
| 3921 | Br | Br | Cl | H | H |
| 3922 | Br | Br | Cl | H | CH$_3$ |
| 3923 | Br | Br | Cl | H | OCH$_3$ |
| 3924 | Br | Br | Cl | H | Cl |
| 3925 | Br | Br | Cl | H | Br |
| 3926 | Br | Br | Cl | H | F |
| 3927 | Br | Br | Cl | CH$_3$ | H |
| 3928 | Br | Br | Cl | CH$_3$ | CH$_3$ |
| 3929 | Br | Br | Cl | CH$_3$ | OCH$_3$ |
| 3930 | Br | Br | Cl | CH$_3$ | Br |
| 3931 | Br | Br | Cl | CH$_3$ | F |
| 3932 | Br | Br | Cl | OCH$_3$ | H |
| 3933 | Br | Br | Cl | OCH$_3$ | CH$_3$ |
| 3934 | Br | Br | Cl | OCH$_3$ | OCH$_3$ |
| 3935 | Br | Br | Cl | OCH$_3$ | Br |
| 3936 | Br | Br | Cl | OCH$_3$ | F |
| 3937 | Br | Br | Cl | Cl | H |
| 3938 | Br | Br | Cl | Cl | CH$_3$ |
| 3939 | Br | Br | Cl | Cl | OCH$_3$ |
| 3940 | Br | Br | Cl | Cl | Cl |
| 3941 | Br | Br | Cl | Cl | Br |
| 3942 | Br | Br | Cl | Cl | F |
| 3943 | Br | Br | Cl | Br | H |
| 3944 | Br | Br | Cl | Br | CH$_3$ |
| 3945 | Br | Br | Cl | Br | OCH$_3$ |

TABLE 2-continued

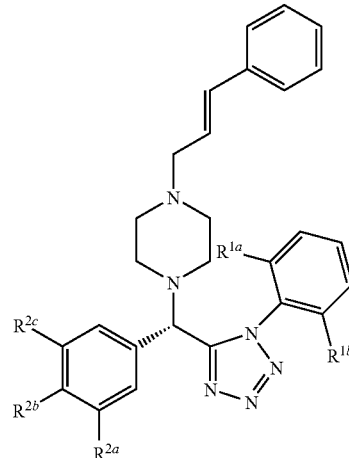

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
| --- | --- | --- | --- | --- | --- |
| 3946 | Br | Br | Cl | Br | Br |
| 3947 | Br | Br | Cl | F | H |
| 3948 | Br | Br | Cl | F | CH$_3$ |
| 3949 | Br | Br | Cl | F | OCH$_3$ |
| 3950 | Br | Br | Cl | F | Br |
| 3951 | Br | Br | Cl | F | F |
| 3952 | Br | Br | Br | H | H |
| 3953 | Br | Br | Br | H | CH$_3$ |
| 3954 | Br | Br | Br | H | OCH$_3$ |
| 3955 | Br | Br | Br | H | Cl |
| 3956 | Br | Br | Br | H | Br |
| 3957 | Br | Br | Br | H | F |
| 3958 | Br | Br | Br | CH$_3$ | H |
| 3959 | Br | Br | Br | CH$_3$ | CH$_3$ |
| 3960 | Br | Br | Br | CH$_3$ | OCH$_3$ |
| 3961 | Br | Br | Br | CH$_3$ | Cl |
| 3962 | Br | Br | Br | CH$_3$ | F |
| 3963 | Br | Br | Br | OCH$_3$ | H |
| 3964 | Br | Br | Br | OCH$_3$ | CH$_3$ |
| 3965 | Br | Br | Br | OCH$_3$ | OCH$_3$ |
| 3966 | Br | Br | Br | OCH$_3$ | Cl |
| 3967 | Br | Br | Br | OCH$_3$ | F |
| 3968 | Br | Br | Br | Cl | H |
| 3969 | Br | Br | Br | Cl | CH$_3$ |
| 3970 | Br | Br | Br | Cl | OCH$_3$ |
| 3971 | Br | Br | Br | Cl | Cl |
| 3972 | Br | Br | Br | Cl | F |
| 3973 | Br | Br | Br | Br | H |
| 3974 | Br | Br | Br | Br | CH$_3$ |
| 3975 | Br | Br | Br | Br | OCH$_3$ |
| 3976 | Br | Br | Br | Br | Cl |
| 3977 | Br | Br | Br | Br | Br |
| 3978 | Br | Br | Br | Br | F |
| 3979 | Br | Br | Br | F | H |
| 3980 | Br | Br | Br | F | CH$_3$ |
| 3981 | Br | Br | Br | F | OCH$_3$ |
| 3982 | Br | Br | Br | F | Cl |
| 3983 | Br | Br | Br | F | F |
| 3984 | Br | Br | F | H | H |
| 3985 | Br | Br | F | H | CH$_3$ |
| 3986 | Br | Br | F | H | OCH$_3$ |
| 3987 | Br | Br | F | H | Cl |
| 3988 | Br | Br | F | H | Br |
| 3989 | Br | Br | F | H | F |
| 3990 | Br | Br | F | CH$_3$ | H |
| 3991 | Br | Br | F | CH$_3$ | CH$_3$ |
| 3992 | Br | Br | F | CH$_3$ | OCH$_3$ |
| 3993 | Br | Br | F | CH$_3$ | Cl |
| 3994 | Br | Br | F | CH$_3$ | Br |
| 3995 | Br | Br | F | OCH$_3$ | H |

TABLE 2-continued

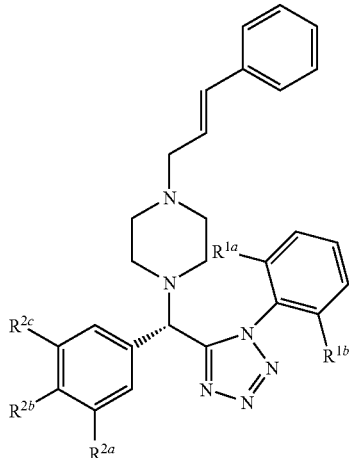

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 3996 | Br | Br | F | OCH₃ | CH₃ |
| 3997 | Br | Br | F | OCH₃ | OCH₃ |
| 3998 | Br | Br | F | OCH₃ | Cl |
| 3999 | Br | Br | F | OCH₃ | Br |
| 4000 | Br | Br | F | Cl | H |
| 4001 | Br | Br | F | Cl | CH₃ |
| 4002 | Br | Br | F | Cl | OCH₃ |
| 4003 | Br | Br | F | Cl | Cl |
| 4004 | Br | Br | F | Cl | Br |
| 4005 | Br | Br | F | Br | H |
| 4006 | Br | Br | F | Br | CH₃ |
| 4007 | Br | Br | F | Br | OCH₃ |
| 4008 | Br | Br | F | Br | Cl |
| 4009 | Br | Br | F | Br | Br |
| 4010 | Br | Br | F | F | H |
| 4011 | Br | Br | F | F | CH₃ |
| 4012 | Br | Br | F | F | OCH₃ |
| 4013 | Br | Br | F | F | Cl |
| 4014 | Br | Br | F | F | Br |
| 4015 | Br | Br | F | F | F |
| 4016 | Br | F | CH₃ | H | H |
| 4017 | Br | F | CH₃ | H | CH₃ |
| 4018 | Br | F | CH₃ | H | OCH₃ |
| 4019 | Br | F | CH₃ | H | Cl |
| 4020 | Br | F | CH₃ | H | Br |
| 4021 | Br | F | CH₃ | H | F |
| 4022 | Br | F | CH₃ | CH₃ | H |
| 4023 | Br | F | CH₃ | CH₃ | CH₃ |
| 4024 | Br | F | CH₃ | CH₃ | OCH₃ |
| 4025 | Br | F | CH₃ | CH₃ | Cl |
| 4026 | Br | F | CH₃ | CH₃ | Br |
| 4027 | Br | F | CH₃ | CH₃ | F |
| 4028 | Br | F | CH₃ | OCH₃ | H |
| 4029 | Br | F | CH₃ | OCH₃ | OCH₃ |
| 4030 | Br | F | CH₃ | OCH₃ | Cl |
| 4031 | Br | F | CH₃ | OCH₃ | Br |
| 4032 | Br | F | CH₃ | OCH₃ | F |
| 4033 | Br | F | CH₃ | Cl | H |
| 4034 | Br | F | CH₃ | Cl | OCH₃ |
| 4035 | Br | F | CH₃ | Cl | Cl |
| 4036 | Br | F | CH₃ | Cl | Br |
| 4037 | Br | F | CH₃ | Cl | F |
| 4038 | Br | F | CH₃ | Br | H |
| 4039 | Br | F | CH₃ | Br | OCH₃ |
| 4040 | Br | F | CH₃ | Br | Cl |
| 4041 | Br | F | CH₃ | Br | Br |
| 4042 | Br | F | CH₃ | Br | F |
| 4043 | Br | F | CH₃ | F | H |
| 4044 | Br | F | CH₃ | F | OCH₃ |
| 4045 | Br | F | CH₃ | F | Cl |

TABLE 2-continued

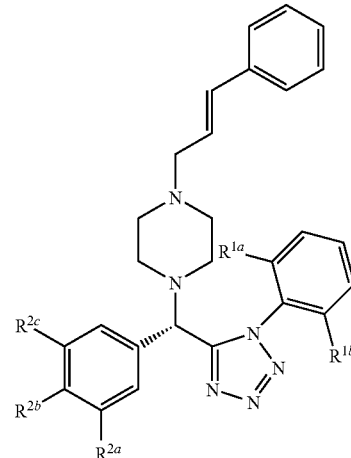

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4046 | Br | F | CH₃ | F | Br |
| 4047 | Br | F | CH₃ | F | F |
| 4048 | Br | F | OCH₃ | H | H |
| 4049 | Br | F | OCH₃ | H | CH₃ |
| 4050 | Br | F | OCH₃ | H | OCH₃ |
| 4051 | Br | F | OCH₃ | H | Cl |
| 4052 | Br | F | OCH₃ | H | Br |
| 4053 | Br | F | OCH₃ | H | F |
| 4054 | Br | F | OCH₃ | CH₃ | H |
| 4055 | Br | F | OCH₃ | CH₃ | CH₃ |
| 4056 | Br | F | OCH₃ | CH₃ | Cl |
| 4057 | Br | F | OCH₃ | CH₃ | Br |
| 4058 | Br | F | OCH₃ | CH₃ | F |
| 4059 | Br | F | OCH₃ | OCH₃ | H |
| 4060 | Br | F | OCH₃ | OCH₃ | CH₃ |
| 4061 | Br | F | OCH₃ | OCH₃ | OCH₃ |
| 4062 | Br | F | OCH₃ | OCH₃ | Cl |
| 4063 | Br | F | OCH₃ | OCH₃ | Br |
| 4064 | Br | F | OCH₃ | OCH₃ | F |
| 4065 | Br | F | OCH₃ | Cl | H |
| 4066 | Br | F | OCH₃ | Cl | CH₃ |
| 4067 | Br | F | OCH₃ | Cl | Cl |
| 4068 | Br | F | OCH₃ | Cl | Br |
| 4069 | Br | F | OCH₃ | Cl | F |
| 4070 | Br | F | OCH₃ | Br | H |
| 4071 | Br | F | OCH₃ | Br | CH₃ |
| 4072 | Br | F | OCH₃ | Br | Cl |
| 4073 | Br | F | OCH₃ | Br | Br |
| 4074 | Br | F | OCH₃ | Br | F |
| 4075 | Br | F | OCH₃ | F | H |
| 4076 | Br | F | OCH₃ | F | CH₃ |
| 4077 | Br | F | OCH₃ | F | Cl |
| 4078 | Br | F | OCH₃ | F | Br |
| 4079 | Br | F | OCH₃ | F | F |
| 4080 | Br | F | Cl | H | H |
| 4081 | Br | F | Cl | H | CH₃ |
| 4082 | Br | F | Cl | H | OCH₃ |
| 4083 | Br | F | Cl | H | Cl |
| 4084 | Br | F | Cl | H | Br |
| 4085 | Br | F | Cl | H | F |
| 4086 | Br | F | Cl | CH₃ | H |
| 4087 | Br | F | Cl | CH₃ | CH₃ |
| 4088 | Br | F | Cl | CH₃ | OCH₃ |
| 4089 | Br | F | Cl | CH₃ | Br |
| 4090 | Br | F | Cl | CH₃ | F |
| 4091 | Br | F | Cl | OCH₃ | H |
| 4092 | Br | F | Cl | OCH₃ | CH₃ |
| 4093 | Br | F | Cl | OCH₃ | OCH₃ |
| 4094 | Br | F | Cl | OCH₃ | Br |
| 4095 | Br | F | Cl | OCH₃ | F |

TABLE 2-continued

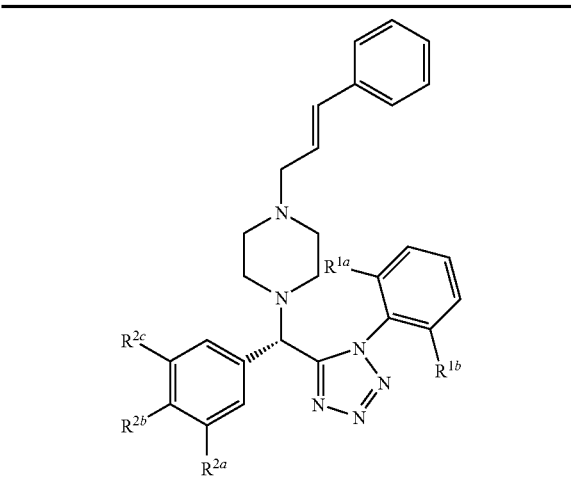

wherein $R^{1a}$, $R^{1b}$, $R^{2a}$, $R^{2b}$, and $R^{2c}$ are as defined in Table 2.

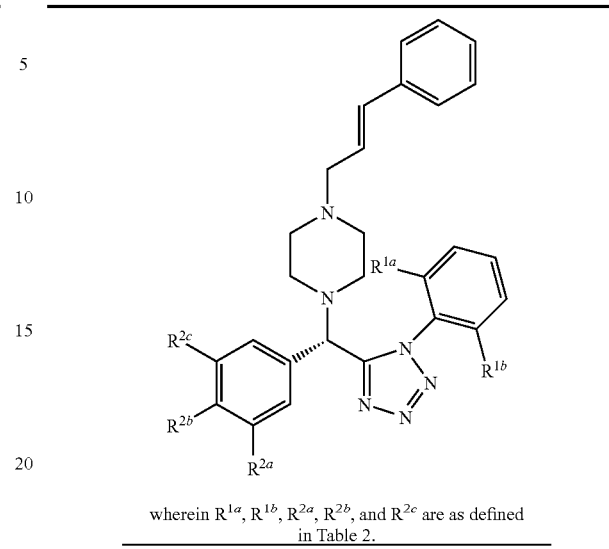

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ | Compound No. | $R^{1a}$ | $R^{1b}$ | $R^{2a}$ | $R^{2b}$ | $R^{2c}$ |
|---|---|---|---|---|---|---|---|---|---|---|---|
| 4096 | Br | F | Cl | Cl | H | 4146 | Br | F | F | H | Cl |
| 4097 | Br | F | Cl | Cl | CH₃ | 4147 | Br | F | F | H | Br |
| 4098 | Br | F | Cl | Cl | OCH₃ | 4148 | Br | F | F | H | F |
| 4099 | Br | F | Cl | Cl | Cl | 4149 | Br | F | F | CH₃ | H |
| 4100 | Br | F | Cl | Cl | Br | 4150 | Br | F | F | CH₃ | CH₃ |
| 4101 | Br | F | Cl | Cl | F | 4151 | Br | F | F | CH₃ | OCH₃ |
| 4102 | Br | F | Cl | Br | H | 4152 | Br | F | F | CH₃ | Cl |
| 4103 | Br | F | Cl | Br | CH₃ | 4153 | Br | F | F | CH₃ | Br |
| 4104 | Br | F | Cl | Br | OCH₃ | 4154 | Br | F | F | OCH₃ | H |
| 4105 | Br | F | Cl | Br | Br | 4155 | Br | F | F | OCH₃ | CH₃ |
| 4106 | Br | F | Cl | F | H | 4156 | Br | F | F | OCH₃ | OCH₃ |
| 4107 | Br | F | Cl | F | CH₃ | 4157 | Br | F | F | OCH₃ | Cl |
| 4108 | Br | F | Cl | F | OCH₃ | 4158 | Br | F | F | OCH₃ | Br |
| 4109 | Br | F | Cl | F | Br | 4159 | Br | F | F | Cl | H |
| 4110 | Br | F | Cl | F | F | 4160 | Br | F | F | Cl | CH₃ |
| 4111 | Br | F | Br | H | H | 4161 | Br | F | F | Cl | OCH₃ |
| 4112 | Br | F | Br | H | CH₃ | 4162 | Br | F | F | Cl | Cl |
| 4113 | Br | F | Br | H | OCH₃ | 4163 | Br | F | F | Cl | Br |
| 4114 | Br | F | Br | H | Cl | 4164 | Br | F | F | Br | H |
| 4115 | Br | F | Br | H | Br | 4165 | Br | F | F | Br | CH₃ |
| 4116 | Br | F | Br | H | F | 4166 | Br | F | F | Br | OCH₃ |
| 4117 | Br | F | Br | CH₃ | H | 4167 | Br | F | F | Br | Cl |
| 4118 | Br | F | Br | CH₃ | CH₃ | 4168 | Br | F | F | Br | Br |
| 4119 | Br | F | Br | CH₃ | OCH₃ | 4169 | Br | F | F | F | H |
| 4120 | Br | F | Br | CH₃ | Cl | 4170 | Br | F | F | F | CH₃ |
| 4121 | Br | F | Br | CH₃ | F | 4171 | Br | F | F | F | OCH₃ |
| 4122 | Br | F | Br | OCH₃ | H | 4172 | Br | F | F | F | Cl |
| 4123 | Br | F | Br | OCH₃ | CH₃ | 4173 | Br | F | F | F | Br |
| 4124 | Br | F | Br | OCH₃ | OCH₃ | 4174 | Br | F | F | F | F |
| 4125 | Br | F | Br | OCH₃ | Cl | 4175 | F | CH₃ | CH₃ | H | H |
| 4126 | Br | F | Br | OCH₃ | F | 4176 | F | CH₃ | CH₃ | CH₃ | H |
| 4127 | Br | F | Br | Cl | H | 4177 | F | CH₃ | CH₃ | OCH₃ | H |
| 4128 | Br | F | Br | Cl | CH₃ | 4178 | F | CH₃ | CH₃ | Cl | H |
| 4129 | Br | F | Br | Cl | OCH₃ | 4179 | F | CH₃ | CH₃ | Br | H |
| 4130 | Br | F | Br | Cl | Cl | 4180 | F | CH₃ | CH₃ | F | H |
| 4131 | Br | F | Br | Cl | F | 4181 | F | CH₃ | CH₃ | H | CH₃ |
| 4132 | Br | F | Br | Br | H | 4182 | F | CH₃ | CH₃ | CH₃ | CH₃ |
| 4133 | Br | F | Br | Br | CH₃ | 4183 | F | CH₃ | CH₃ | H | OCH₃ |
| 4134 | Br | F | Br | Br | OCH₃ | 4184 | F | CH₃ | CH₃ | CH₃ | OCH₃ |
| 4135 | Br | F | Br | Br | Cl | 4185 | F | CH₃ | CH₃ | OCH₃ | OCH₃ |
| 4136 | Br | F | Br | Br | Br | 4186 | F | CH₃ | CH₃ | Cl | OCH₃ |
| 4137 | Br | F | Br | Br | F | 4187 | F | CH₃ | CH₃ | Br | OCH₃ |
| 4138 | Br | F | Br | F | H | 4188 | F | CH₃ | CH₃ | F | OCH₃ |
| 4139 | Br | F | Br | F | CH₃ | 4189 | F | CH₃ | CH₃ | H | Cl |
| 4140 | Br | F | Br | F | OCH₃ | 4190 | F | CH₃ | CH₃ | CH₃ | Cl |
| 4141 | Br | F | Br | F | Cl | 4191 | F | CH₃ | CH₃ | OCH₃ | Cl |
| 4142 | Br | F | Br | F | F | 4192 | F | CH₃ | CH₃ | Cl | Cl |
| 4143 | Br | F | F | H | H | 4193 | F | CH₃ | CH₃ | Br | Cl |
| 4144 | Br | F | F | H | CH₃ | 4194 | F | CH₃ | CH₃ | F | Cl |
| 4145 | Br | F | F | H | OCH₃ | 4195 | F | CH₃ | CH₃ | H | Br |

TABLE 2-continued

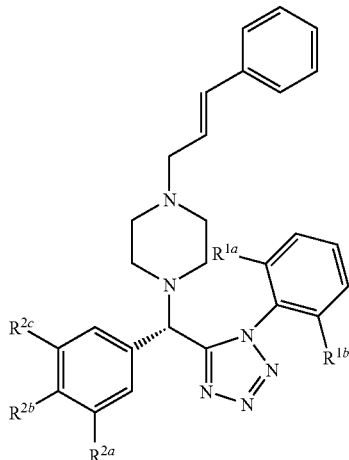

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4196 | F | CH₃ | CH₃ | CH₃ | Br |
| 4197 | F | CH₃ | CH₃ | OCH₃ | Br |
| 4198 | F | CH₃ | CH₃ | Cl | Br |
| 4199 | F | CH₃ | CH₃ | Br | Br |
| 4200 | F | CH₃ | CH₃ | F | Br |
| 4201 | F | CH₃ | CH₃ | H | F |
| 4202 | F | CH₃ | CH₃ | CH₃ | F |
| 4203 | F | CH₃ | CH₃ | OCH₃ | F |
| 4204 | F | CH₃ | CH₃ | Cl | F |
| 4205 | F | CH₃ | CH₃ | Br | F |
| 4206 | F | CH₃ | CH₃ | F | F |
| 4207 | F | CH₃ | OCH₃ | H | H |
| 4208 | F | CH₃ | OCH₃ | CH₃ | H |
| 4209 | F | CH₃ | OCH₃ | OCH₃ | H |
| 4210 | F | CH₃ | OCH₃ | Cl | H |
| 4211 | F | CH₃ | OCH₃ | Br | H |
| 4212 | F | CH₃ | OCH₃ | F | H |
| 4213 | F | CH₃ | OCH₃ | H | CH₃ |
| 4214 | F | CH₃ | OCH₃ | CH₃ | CH₃ |
| 4215 | F | CH₃ | OCH₃ | OCH₃ | CH₃ |
| 4216 | F | CH₃ | OCH₃ | Cl | CH₃ |
| 4217 | F | CH₃ | OCH₃ | Br | CH₃ |
| 4218 | F | CH₃ | OCH₃ | F | CH₃ |
| 4219 | F | CH₃ | OCH₃ | H | OCH₃ |
| 4220 | F | CH₃ | OCH₃ | OCH₃ | OCH₃ |
| 4221 | F | CH₃ | OCH₃ | H | Cl |
| 4222 | F | CH₃ | OCH₃ | CH₃ | Cl |
| 4223 | F | CH₃ | OCH₃ | OCH₃ | Cl |
| 4224 | F | CH₃ | OCH₃ | Cl | Cl |
| 4225 | F | CH₃ | OCH₃ | Br | Cl |
| 4226 | F | CH₃ | OCH₃ | F | Cl |
| 4227 | F | CH₃ | OCH₃ | H | Br |
| 4228 | F | CH₃ | OCH₃ | CH₃ | Br |
| 4229 | F | CH₃ | OCH₃ | OCH₃ | Br |
| 4230 | F | CH₃ | OCH₃ | Cl | Br |
| 4231 | F | CH₃ | OCH₃ | Br | Br |
| 4232 | F | CH₃ | OCH₃ | F | Br |
| 4233 | F | CH₃ | OCH₃ | H | F |
| 4234 | F | CH₃ | OCH₃ | CH₃ | F |
| 4235 | F | CH₃ | OCH₃ | OCH₃ | F |
| 4236 | F | CH₃ | OCH₃ | Cl | F |
| 4237 | F | CH₃ | OCH₃ | Br | F |
| 4238 | F | CH₃ | OCH₃ | F | F |
| 4239 | F | CH₃ | Cl | H | H |
| 4240 | F | CH₃ | Cl | CH₃ | H |
| 4241 | F | CH₃ | Cl | OCH₃ | H |
| 4242 | F | CH₃ | Cl | Cl | H |
| 4243 | F | CH₃ | Cl | Br | H |
| 4244 | F | CH₃ | Cl | F | H |
| 4245 | F | CH₃ | Cl | H | CH₃ |

TABLE 2-continued

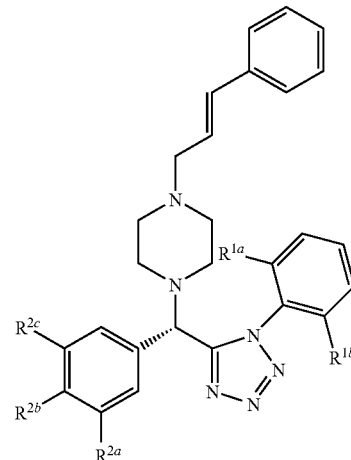

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4246 | F | CH₃ | Cl | CH₃ | CH₃ |
| 4247 | F | CH₃ | Cl | OCH₃ | CH₃ |
| 4248 | F | CH₃ | Cl | Cl | CH₃ |
| 4249 | F | CH₃ | Cl | Br | CH₃ |
| 4250 | F | CH₃ | Cl | F | CH₃ |
| 4251 | F | CH₃ | Cl | H | OCH₃ |
| 4252 | F | CH₃ | Cl | CH₃ | OCH₃ |
| 4253 | F | CH₃ | Cl | OCH₃ | OCH₃ |
| 4254 | F | CH₃ | Cl | Cl | OCH₃ |
| 4255 | F | CH₃ | Cl | Br | OCH₃ |
| 4256 | F | CH₃ | Cl | F | OCH₃ |
| 4257 | F | CH₃ | Cl | H | Cl |
| 4258 | F | CH₃ | Cl | Cl | Cl |
| 4259 | F | CH₃ | Cl | H | Br |
| 4260 | F | CH₃ | Cl | CH₃ | Br |
| 4261 | F | CH₃ | Cl | OCH₃ | Br |
| 4262 | F | CH₃ | Cl | Cl | Br |
| 4263 | F | CH₃ | Cl | Br | Br |
| 4264 | F | CH₃ | Cl | F | Br |
| 4265 | F | CH₃ | Cl | H | F |
| 4266 | F | CH₃ | Cl | CH₃ | F |
| 4267 | F | CH₃ | Cl | OCH₃ | F |
| 4268 | F | CH₃ | Cl | Cl | F |
| 4269 | F | CH₃ | Cl | F | F |
| 4270 | F | CH₃ | Br | H | H |
| 4271 | F | CH₃ | Br | CH₃ | H |
| 4272 | F | CH₃ | Br | OCH₃ | H |
| 4273 | F | CH₃ | Br | Cl | H |
| 4274 | F | CH₃ | Br | Br | H |
| 4275 | F | CH₃ | Br | F | H |
| 4276 | F | CH₃ | Br | H | CH₃ |
| 4277 | F | CH₃ | Br | CH₃ | CH₃ |
| 4278 | F | CH₃ | Br | OCH₃ | CH₃ |
| 4279 | F | CH₃ | Br | Cl | CH₃ |
| 4280 | F | CH₃ | Br | Br | CH₃ |
| 4281 | F | CH₃ | Br | F | CH₃ |
| 4282 | F | CH₃ | Br | H | OCH₃ |
| 4283 | F | CH₃ | Br | CH₃ | OCH₃ |
| 4284 | F | CH₃ | Br | OCH₃ | OCH₃ |
| 4285 | F | CH₃ | Br | Cl | OCH₃ |
| 4286 | F | CH₃ | Br | Br | OCH₃ |
| 4287 | F | CH₃ | Br | F | OCH₃ |
| 4288 | F | CH₃ | Br | H | Cl |
| 4289 | F | CH₃ | Br | CH₃ | Cl |
| 4290 | F | CH₃ | Br | OCH₃ | Cl |
| 4291 | F | CH₃ | Br | Cl | Cl |
| 4292 | F | CH₃ | Br | Br | Cl |
| 4293 | F | CH₃ | Br | F | Cl |
| 4294 | F | CH₃ | Br | H | Br |
| 4295 | F | CH₃ | Br | Br | Br |

TABLE 2-continued

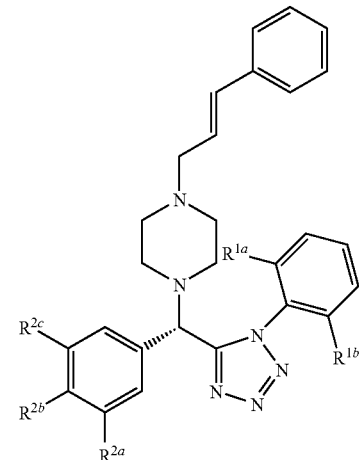

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4296 | F | CH₃ | Br | H | F |
| 4297 | F | CH₃ | Br | CH₃ | F |
| 4298 | F | CH₃ | Br | OCH₃ | F |
| 4299 | F | CH₃ | Br | Cl | F |
| 4300 | F | CH₃ | Br | Br | F |
| 4301 | F | CH₃ | Br | F | F |
| 4302 | F | CH₃ | F | H | H |
| 4303 | F | CH₃ | F | CH₃ | H |
| 4304 | F | CH₃ | F | OCH₃ | H |
| 4305 | F | CH₃ | F | Cl | H |
| 4306 | F | CH₃ | F | Br | H |
| 4307 | F | CH₃ | F | F | H |
| 4308 | F | CH₃ | F | H | CH₃ |
| 4309 | F | CH₃ | F | CH₃ | CH₃ |
| 4310 | F | CH₃ | F | OCH₃ | CH₃ |
| 4311 | F | CH₃ | F | Cl | CH₃ |
| 4312 | F | CH₃ | F | Br | CH₃ |
| 4313 | F | CH₃ | F | F | CH₃ |
| 4314 | F | CH₃ | F | H | OCH₃ |
| 4315 | F | CH₃ | F | CH₃ | OCH₃ |
| 4316 | F | CH₃ | F | OCH₃ | OCH₃ |
| 4317 | F | CH₃ | F | Cl | OCH₃ |
| 4318 | F | CH₃ | F | Br | OCH₃ |
| 4319 | F | CH₃ | F | F | OCH₃ |
| 4320 | F | CH₃ | F | H | Cl |
| 4321 | F | CH₃ | F | CH₃ | Cl |
| 4322 | F | CH₃ | F | OCH₃ | Cl |
| 4323 | F | CH₃ | F | Cl | Cl |
| 4324 | F | CH₃ | F | Br | Cl |
| 4325 | F | CH₃ | F | F | Cl |
| 4326 | F | CH₃ | F | H | Br |
| 4327 | F | CH₃ | F | CH₃ | Br |
| 4328 | F | CH₃ | F | OCH₃ | Br |
| 4329 | F | CH₃ | F | Cl | Br |
| 4330 | F | CH₃ | F | Br | Br |
| 4331 | F | CH₃ | F | F | Br |
| 4332 | F | CH₃ | F | H | F |
| 4333 | F | CH₃ | F | F | F |
| 4334 | F | OCH₃ | CH₃ | H | H |
| 4335 | F | OCH₃ | CH₃ | H | CH₃ |
| 4336 | F | OCH₃ | CH₃ | H | OCH₃ |
| 4337 | F | OCH₃ | CH₃ | H | Cl |
| 4338 | F | OCH₃ | CH₃ | H | Br |
| 4339 | F | OCH₃ | CH₃ | H | F |
| 4340 | F | OCH₃ | CH₃ | CH₃ | H |
| 4341 | F | OCH₃ | CH₃ | CH₃ | CH₃ |
| 4342 | F | OCH₃ | CH₃ | CH₃ | OCH₃ |
| 4343 | F | OCH₃ | CH₃ | CH₃ | Cl |
| 4344 | F | OCH₃ | CH₃ | CH₃ | Br |
| 4345 | F | OCH₃ | CH₃ | CH₃ | F |

TABLE 2-continued

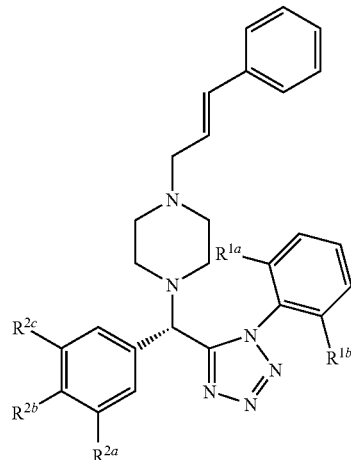

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4346 | F | OCH₃ | CH₃ | OCH₃ | H |
| 4347 | F | OCH₃ | CH₃ | OCH₃ | OCH₃ |
| 4348 | F | OCH₃ | CH₃ | OCH₃ | Cl |
| 4349 | F | OCH₃ | CH₃ | OCH₃ | Br |
| 4350 | F | OCH₃ | CH₃ | OCH₃ | F |
| 4351 | F | OCH₃ | CH₃ | Cl | H |
| 4352 | F | OCH₃ | CH₃ | Cl | OCH₃ |
| 4353 | F | OCH₃ | CH₃ | Cl | Cl |
| 4354 | F | OCH₃ | CH₃ | Cl | Br |
| 4355 | F | OCH₃ | CH₃ | Cl | F |
| 4356 | F | OCH₃ | CH₃ | Br | H |
| 4357 | F | OCH₃ | CH₃ | Br | OCH₃ |
| 4358 | F | OCH₃ | CH₃ | Br | Cl |
| 4359 | F | OCH₃ | CH₃ | Br | Br |
| 4360 | F | OCH₃ | CH₃ | Br | F |
| 4361 | F | OCH₃ | CH₃ | F | H |
| 4362 | F | OCH₃ | CH₃ | F | OCH₃ |
| 4363 | F | OCH₃ | CH₃ | F | Cl |
| 4364 | F | OCH₃ | CH₃ | F | Br |
| 4365 | F | OCH₃ | CH₃ | F | F |
| 4366 | F | OCH₃ | OCH₃ | H | H |
| 4367 | F | OCH₃ | OCH₃ | H | CH₃ |
| 4368 | F | OCH₃ | OCH₃ | H | OCH₃ |
| 4369 | F | OCH₃ | OCH₃ | H | Cl |
| 4370 | F | OCH₃ | OCH₃ | H | Br |
| 4371 | F | OCH₃ | OCH₃ | H | F |
| 4372 | F | OCH₃ | OCH₃ | CH₃ | H |
| 4373 | F | OCH₃ | OCH₃ | CH₃ | CH₃ |
| 4374 | F | OCH₃ | OCH₃ | CH₃ | Cl |
| 4375 | F | OCH₃ | OCH₃ | CH₃ | Br |
| 4376 | F | OCH₃ | OCH₃ | CH₃ | F |
| 4377 | F | OCH₃ | OCH₃ | OCH₃ | H |
| 4378 | F | OCH₃ | OCH₃ | OCH₃ | CH₃ |
| 4379 | F | OCH₃ | OCH₃ | OCH₃ | OCH₃ |
| 4380 | F | OCH₃ | OCH₃ | OCH₃ | Cl |
| 4381 | F | OCH₃ | OCH₃ | OCH₃ | Br |
| 4382 | F | OCH₃ | OCH₃ | OCH₃ | F |
| 4383 | F | OCH₃ | OCH₃ | Cl | H |
| 4384 | F | OCH₃ | OCH₃ | Cl | CH₃ |
| 4385 | F | OCH₃ | OCH₃ | Cl | Cl |
| 4386 | F | OCH₃ | OCH₃ | Cl | Br |
| 4387 | F | OCH₃ | OCH₃ | Cl | F |
| 4388 | F | OCH₃ | OCH₃ | Br | H |
| 4389 | F | OCH₃ | OCH₃ | Br | CH₃ |
| 4390 | F | OCH₃ | OCH₃ | Br | Cl |
| 4391 | F | OCH₃ | OCH₃ | Br | Br |
| 4392 | F | OCH₃ | OCH₃ | Br | F |
| 4393 | F | OCH₃ | OCH₃ | F | H |
| 4394 | F | OCH₃ | OCH₃ | F | CH₃ |
| 4395 | F | OCH₃ | OCH₃ | F | Cl |

TABLE 2-continued

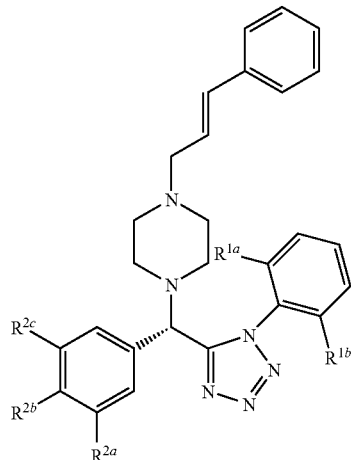

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4396 | F | OCH₃ | OCH₃ | F | Br |
| 4397 | F | OCH₃ | OCH₃ | F | F |
| 4398 | F | OCH₃ | Cl | H | H |
| 4399 | F | OCH₃ | Cl | H | CH₃ |
| 4400 | F | OCH₃ | Cl | H | OCH₃ |
| 4401 | F | OCH₃ | Cl | H | Cl |
| 4402 | F | OCH₃ | Cl | H | Br |
| 4403 | F | OCH₃ | Cl | H | F |
| 4404 | F | OCH₃ | Cl | CH₃ | H |
| 4405 | F | OCH₃ | Cl | CH₃ | CH₃ |
| 4406 | F | OCH₃ | Cl | CH₃ | OCH₃ |
| 4407 | F | OCH₃ | Cl | CH₃ | Br |
| 4408 | F | OCH₃ | Cl | CH₃ | F |
| 4409 | F | OCH₃ | Cl | OCH₃ | H |
| 4410 | F | OCH₃ | Cl | OCH₃ | CH₃ |
| 4411 | F | OCH₃ | Cl | OCH₃ | OCH₃ |
| 4412 | F | OCH₃ | Cl | OCH₃ | Br |
| 4413 | F | OCH₃ | Cl | OCH₃ | F |
| 4414 | F | OCH₃ | Cl | Cl | H |
| 4415 | F | OCH₃ | Cl | Cl | CH₃ |
| 4416 | F | OCH₃ | Cl | Cl | OCH₃ |
| 4417 | F | OCH₃ | Cl | Cl | Cl |
| 4418 | F | OCH₃ | Cl | Cl | Br |
| 4419 | F | OCH₃ | Cl | Cl | F |
| 4420 | F | OCH₃ | Cl | Br | H |
| 4421 | F | OCH₃ | Cl | Br | CH₃ |
| 4422 | F | OCH₃ | Cl | Br | OCH₃ |
| 4423 | F | OCH₃ | Cl | Br | Br |
| 4424 | F | OCH₃ | Cl | F | H |
| 4425 | F | OCH₃ | Cl | F | CH₃ |
| 4426 | F | OCH₃ | Cl | F | OCH₃ |
| 4427 | F | OCH₃ | Cl | F | Br |
| 4428 | F | OCH₃ | Cl | F | F |
| 4429 | F | OCH₃ | Br | H | H |
| 4430 | F | OCH₃ | Br | H | CH₃ |
| 4431 | F | OCH₃ | Br | H | OCH₃ |
| 4432 | F | OCH₃ | Br | H | Cl |
| 4433 | F | OCH₃ | Br | H | Br |
| 4434 | F | OCH₃ | Br | H | F |
| 4435 | F | OCH₃ | Br | CH₃ | H |
| 4436 | F | OCH₃ | Br | CH₃ | CH₃ |
| 4437 | F | OCH₃ | Br | CH₃ | OCH₃ |
| 4438 | F | OCH₃ | Br | CH₃ | Cl |
| 4439 | F | OCH₃ | Br | CH₃ | F |
| 4440 | F | OCH₃ | Br | OCH₃ | H |
| 4441 | F | OCH₃ | Br | OCH₃ | CH₃ |
| 4442 | F | OCH₃ | Br | OCH₃ | OCH₃ |
| 4443 | F | OCH₃ | Br | OCH₃ | Cl |
| 4444 | F | OCH₃ | Br | OCH₃ | F |
| 4445 | F | OCH₃ | Br | Cl | H |

TABLE 2-continued

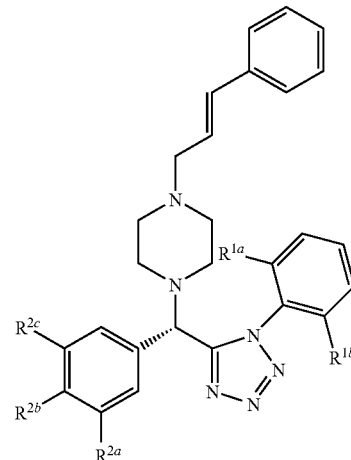

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4446 | F | OCH₃ | Br | Cl | CH₃ |
| 4447 | F | OCH₃ | Br | Cl | OCH₃ |
| 4448 | F | OCH₃ | Br | Cl | Cl |
| 4449 | F | OCH₃ | Br | Cl | F |
| 4450 | F | OCH₃ | Br | Br | H |
| 4451 | F | OCH₃ | Br | Br | CH₃ |
| 4452 | F | OCH₃ | Br | Br | OCH₃ |
| 4453 | F | OCH₃ | Br | Br | Cl |
| 4454 | F | OCH₃ | Br | Br | Br |
| 4455 | F | OCH₃ | Br | Br | F |
| 4456 | F | OCH₃ | Br | F | H |
| 4457 | F | OCH₃ | Br | F | CH₃ |
| 4458 | F | OCH₃ | Br | F | OCH₃ |
| 4459 | F | OCH₃ | Br | F | Cl |
| 4460 | F | OCH₃ | Br | F | F |
| 4461 | F | OCH₃ | F | H | H |
| 4462 | F | OCH₃ | F | H | CH₃ |
| 4463 | F | OCH₃ | F | H | OCH₃ |
| 4464 | F | OCH₃ | F | H | Cl |
| 4465 | F | OCH₃ | F | H | Br |
| 4466 | F | OCH₃ | F | H | F |
| 4467 | F | OCH₃ | F | CH₃ | H |
| 4468 | F | OCH₃ | F | CH₃ | CH₃ |
| 4469 | F | OCH₃ | F | CH₃ | OCH₃ |
| 4470 | F | OCH₃ | F | CH₃ | Cl |
| 4471 | F | OCH₃ | F | CH₃ | Br |
| 4472 | F | OCH₃ | F | OCH₃ | H |
| 4473 | F | OCH₃ | F | OCH₃ | CH₃ |
| 4474 | F | OCH₃ | F | OCH₃ | OCH₃ |
| 4475 | F | OCH₃ | F | OCH₃ | Cl |
| 4476 | F | OCH₃ | F | OCH₃ | Br |
| 4477 | F | OCH₃ | F | Cl | H |
| 4478 | F | OCH₃ | F | Cl | CH₃ |
| 4479 | F | OCH₃ | F | Cl | OCH₃ |
| 4480 | F | OCH₃ | F | Cl | Cl |
| 4481 | F | OCH₃ | F | Cl | Br |
| 4482 | F | OCH₃ | F | Br | H |
| 4483 | F | OCH₃ | F | Br | CH₃ |
| 4484 | F | OCH₃ | F | Br | OCH₃ |
| 4485 | F | OCH₃ | F | Br | Cl |
| 4486 | F | OCH₃ | F | Br | Br |
| 4487 | F | OCH₃ | F | F | H |
| 4488 | F | OCH₃ | F | F | CH₃ |
| 4489 | F | OCH₃ | F | F | OCH₃ |
| 4490 | F | OCH₃ | F | F | Cl |
| 4491 | F | OCH₃ | F | F | Br |
| 4492 | F | OCH₃ | F | F | F |
| 4493 | F | Cl | CH₃ | H | H |
| 4494 | F | Cl | CH₃ | H | CH₃ |
| 4495 | F | Cl | CH₃ | H | OCH₃ |

TABLE 2-continued

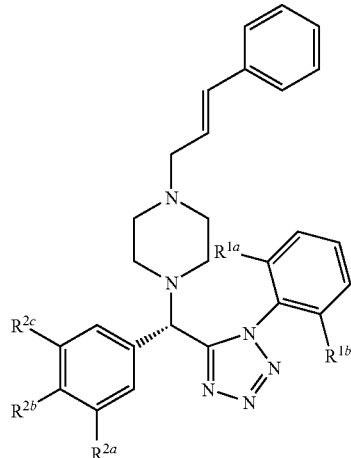

wherein $R^{1a}$, $R^{1b}$, $R^{2a}$, $R^{2b}$, and $R^{2c}$ are as defined in Table 2.

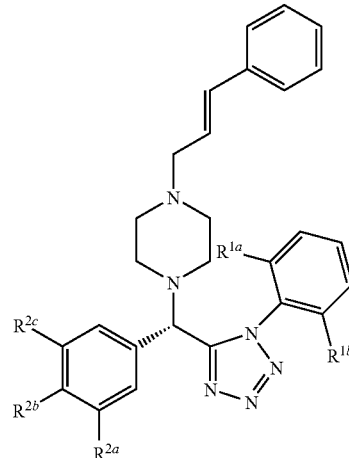

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4496 | F | Cl | CH₃ | H | Cl |
| 4497 | F | Cl | CH₃ | H | Br |
| 4498 | F | Cl | CH₃ | H | F |
| 4499 | F | Cl | CH₃ | CH₃ | H |
| 4500 | F | Cl | CH₃ | CH₃ | CH₃ |
| 4501 | F | Cl | CH₃ | CH₃ | OCH₃ |
| 4502 | F | Cl | CH₃ | CH₃ | Cl |
| 4503 | F | Cl | CH₃ | CH₃ | Br |
| 4504 | F | Cl | CH₃ | CH₃ | F |
| 4505 | F | Cl | CH₃ | OCH₃ | H |
| 4506 | F | Cl | CH₃ | OCH₃ | OCH₃ |
| 4507 | F | Cl | CH₃ | OCH₃ | Cl |
| 4508 | F | Cl | CH₃ | OCH₃ | Br |
| 4509 | F | Cl | CH₃ | OCH₃ | F |
| 4510 | F | Cl | CH₃ | Cl | H |
| 4511 | F | Cl | CH₃ | Cl | OCH₃ |
| 4512 | F | Cl | CH₃ | Cl | Cl |
| 4513 | F | Cl | CH₃ | Cl | Br |
| 4514 | F | Cl | CH₃ | Cl | F |
| 4515 | F | Cl | CH₃ | Br | H |
| 4516 | F | Cl | CH₃ | Br | OCH₃ |
| 4517 | F | Cl | CH₃ | Br | Cl |
| 4518 | F | Cl | CH₃ | Br | Br |
| 4519 | F | Cl | CH₃ | Br | F |
| 4520 | F | Cl | CH₃ | F | H |
| 4521 | F | Cl | CH₃ | F | OCH₃ |
| 4522 | F | Cl | CH₃ | F | Cl |
| 4523 | F | Cl | CH₃ | F | Br |
| 4524 | F | Cl | CH₃ | F | F |
| 4525 | F | Cl | OCH₃ | H | H |
| 4526 | F | Cl | OCH₃ | H | CH₃ |
| 4527 | F | Cl | OCH₃ | H | OCH₃ |
| 4528 | F | Cl | OCH₃ | H | Cl |
| 4529 | F | Cl | OCH₃ | H | Br |
| 4530 | F | Cl | OCH₃ | H | F |
| 4531 | F | Cl | OCH₃ | CH₃ | H |
| 4532 | F | Cl | OCH₃ | CH₃ | CH₃ |
| 4533 | F | Cl | OCH₃ | CH₃ | Cl |
| 4534 | F | Cl | OCH₃ | CH₃ | Br |
| 4535 | F | Cl | OCH₃ | CH₃ | F |
| 4536 | F | Cl | OCH₃ | OCH₃ | H |
| 4537 | F | Cl | OCH₃ | OCH₃ | CH₃ |
| 4538 | F | Cl | OCH₃ | OCH₃ | OCH₃ |
| 4539 | F | Cl | OCH₃ | OCH₃ | Cl |
| 4540 | F | Cl | OCH₃ | OCH₃ | Br |
| 4541 | F | Cl | OCH₃ | OCH₃ | F |
| 4542 | F | Cl | OCH₃ | Cl | H |
| 4543 | F | Cl | OCH₃ | Cl | CH₃ |
| 4544 | F | Cl | OCH₃ | Cl | Cl |
| 4545 | F | Cl | OCH₃ | Cl | Br |
| 4546 | F | Cl | OCH₃ | Cl | F |
| 4547 | F | Cl | OCH₃ | Br | H |
| 4548 | F | Cl | OCH₃ | Br | CH₃ |
| 4549 | F | Cl | OCH₃ | Br | Cl |
| 4550 | F | Cl | OCH₃ | Br | Br |
| 4551 | F | Cl | OCH₃ | Br | F |
| 4552 | F | Cl | OCH₃ | F | H |
| 4553 | F | Cl | OCH₃ | F | CH₃ |
| 4554 | F | Cl | OCH₃ | F | Cl |
| 4555 | F | Cl | OCH₃ | F | Br |
| 4556 | F | Cl | OCH₃ | F | F |
| 4557 | F | Cl | Cl | H | H |
| 4558 | F | Cl | Cl | H | CH₃ |
| 4559 | F | Cl | Cl | H | OCH₃ |
| 4560 | F | Cl | Cl | H | Cl |
| 4561 | F | Cl | Cl | H | Br |
| 4562 | F | Cl | Cl | H | F |
| 4563 | F | Cl | Cl | CH₃ | H |
| 4564 | F | Cl | Cl | CH₃ | CH₃ |
| 4565 | F | Cl | Cl | CH₃ | OCH₃ |
| 4566 | F | Cl | Cl | CH₃ | Br |
| 4567 | F | Cl | Cl | CH₃ | F |
| 4568 | F | Cl | Cl | OCH₃ | H |
| 4569 | F | Cl | Cl | OCH₃ | CH₃ |
| 4570 | F | Cl | Cl | OCH₃ | OCH₃ |
| 4571 | F | Cl | Cl | OCH₃ | Br |
| 4572 | F | Cl | Cl | OCH₃ | F |
| 4573 | F | Cl | Cl | Cl | H |
| 4574 | F | Cl | Cl | Cl | CH₃ |
| 4575 | F | Cl | Cl | CL | OCH₃ |
| 4576 | F | Cl | Cl | Cl | Cl |
| 4577 | F | Cl | Cl | Cl | Br |
| 4578 | F | Cl | Cl | Cl | F |
| 4579 | F | Cl | Cl | Br | H |
| 4580 | F | Cl | Cl | Br | CH₃ |
| 4581 | F | Cl | Cl | Br | OCH₃ |
| 4582 | F | Cl | Cl | Br | Br |
| 4583 | F | Cl | Cl | F | H |
| 4584 | F | Cl | Cl | F | CH₃ |
| 4585 | F | Cl | Cl | F | OCH₃ |
| 4586 | F | Cl | Cl | F | Br |
| 4587 | F | Cl | Cl | F | F |
| 4588 | F | Cl | Br | H | H |
| 4589 | F | Cl | Br | H | CH₃ |
| 4590 | F | Cl | Br | H | OCH₃ |
| 4591 | F | Cl | Br | H | Cl |
| 4592 | F | Cl | Br | H | Br |
| 4593 | F | Cl | Br | H | F |
| 4594 | F | Cl | Br | CH₃ | H |
| 4595 | F | Cl | Br | CH₃ | CH₃ |

TABLE 2-continued

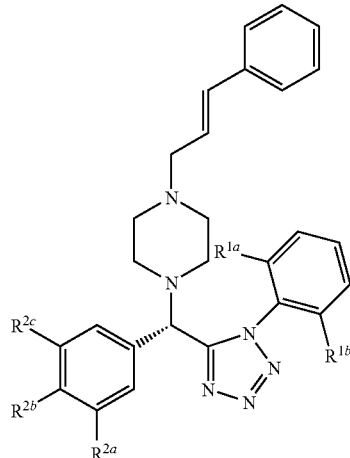

wherein $R^{1a}$, $R^{1b}$, $R^{2a}$, $R^{2b}$, and $R^{2c}$ are as defined in Table 2.

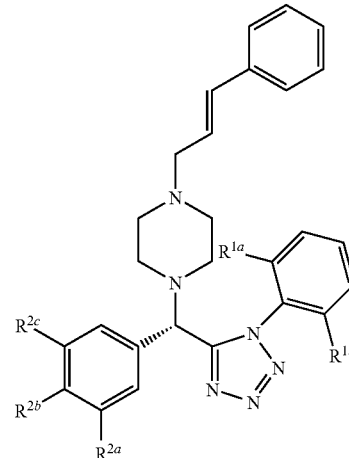

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ | Compound No. | $R^{1a}$ | $R^{1b}$ | $R^{2a}$ | $R^{2b}$ | $R^{2c}$ |
|---|---|---|---|---|---|---|---|---|---|---|---|
| 4596 | F | Cl | Br | CH₃ | OCH₃ | 4646 | F | Cl | F | F | H |
| 4597 | F | Cl | Br | CH₃ | Cl | 4647 | F | Cl | F | F | CH₃ |
| 4598 | F | Cl | Br | CH₃ | F | 4648 | F | Cl | F | F | OCH₃ |
| 4599 | F | Cl | Br | OCH₃ | H | 4649 | F | Cl | F | F | Cl |
| 4600 | F | Cl | Br | OCH₃ | CH₃ | 4650 | F | Cl | F | F | Br |
| 4601 | F | Cl | Br | OCH₃ | OCH₃ | 4651 | F | Cl | F | F | F |
| 4602 | F | Cl | Br | OCH₃ | Cl | 4652 | F | Br | CH₃ | H | H |
| 4603 | F | Cl | Br | OCH₃ | F | 4653 | F | Br | CH₃ | H | CH₃ |
| 4604 | F | Cl | Br | Cl | H | 4654 | F | Br | CH₃ | H | OCH₃ |
| 4605 | F | Cl | Br | Cl | CH₃ | 4655 | F | Br | CH₃ | H | Cl |
| 4606 | F | Cl | Br | Cl | OCH₃ | 4656 | F | Br | CH₃ | H | Br |
| 4607 | F | Cl | Br | Cl | Cl | 4657 | F | Br | CH₃ | H | F |
| 4608 | F | Cl | Br | Cl | F | 4658 | F | Br | CH₃ | CH₃ | H |
| 4609 | F | Cl | Br | Br | H | 4659 | F | Br | CH₃ | CH₃ | CH₃ |
| 4610 | F | Cl | Br | Br | CH₃ | 4660 | F | Br | CH₃ | CH₃ | OCH₃ |
| 4611 | F | Cl | Br | Br | OCH₃ | 4661 | F | Br | CH₃ | CH₃ | Cl |
| 4612 | F | Cl | Br | Br | Cl | 4662 | F | Br | CH₃ | CH₃ | Br |
| 4613 | F | Cl | Br | Br | Br | 4663 | F | Br | CH₃ | CH₃ | F |
| 4614 | F | Cl | Br | Br | F | 4664 | F | Br | CH₃ | OCH₃ | H |
| 4615 | F | Cl | Br | F | H | 4665 | F | Br | CH₃ | OCH₃ | OCH₃ |
| 4616 | F | Cl | Br | F | CH₃ | 4666 | F | Br | CH₃ | OCH₃ | Cl |
| 4617 | F | Cl | Br | F | OCH₃ | 4667 | F | Br | CH₃ | OCH₃ | Br |
| 4618 | F | Cl | Br | F | Cl | 4668 | F | Br | CH₃ | OCH₃ | F |
| 4619 | F | Cl | Br | F | F | 4669 | F | Br | CH₃ | Cl | H |
| 4620 | F | Cl | F | H | H | 4670 | F | Br | CH₃ | Cl | OCH₃ |
| 4621 | F | Cl | F | H | CH₃ | 4671 | F | Br | CH₃ | Cl | Cl |
| 4622 | F | Cl | F | H | OCH₃ | 4672 | F | Br | CH₃ | Cl | Br |
| 4623 | F | Cl | F | H | Cl | 4673 | F | Br | CH₃ | Cl | F |
| 4624 | F | Cl | F | H | Br | 4674 | F | Br | CH₃ | Br | H |
| 4625 | F | Cl | F | H | F | 4675 | F | Br | CH₃ | Br | OCH₃ |
| 4626 | F | Cl | F | CH₃ | H | 4676 | F | Br | CH₃ | Br | Cl |
| 4627 | F | Cl | F | CH₃ | CH₃ | 4677 | F | Br | CH₃ | Br | Br |
| 4628 | F | Cl | F | CH₃ | OCH₃ | 4678 | F | Br | CH₃ | Br | F |
| 4629 | F | Cl | F | CH₃ | Cl | 4679 | F | Br | CH₃ | F | H |
| 4630 | F | Cl | F | CH₃ | Br | 4680 | F | Br | CH₃ | F | OCH₃ |
| 4631 | F | Cl | F | OCH₃ | H | 4681 | F | Br | CH₃ | F | Cl |
| 4632 | F | Cl | F | OCH₃ | CH₃ | 4682 | F | Br | CH₃ | F | Br |
| 4633 | F | Cl | F | OCH₃ | OCH₃ | 4683 | F | Br | CH₃ | F | F |
| 4634 | F | Cl | F | OCH₃ | Cl | 4684 | F | Br | OCH₃ | H | H |
| 4635 | F | Cl | F | OCH₃ | Br | 4685 | F | Br | OCH₃ | H | CH₃ |
| 4636 | F | Cl | F | Cl | H | 4686 | F | Br | OCH₃ | H | OCH₃ |
| 4637 | F | Cl | F | Cl | CH₃ | 4687 | F | Br | OCH₃ | H | Cl |
| 4638 | F | Cl | F | Cl | OCH₃ | 4688 | F | Br | OCH₃ | H | Br |
| 4639 | F | Cl | F | Cl | Cl | 4689 | F | Br | OCH₃ | H | F |
| 4640 | F | Cl | F | Cl | Br | 4690 | F | Br | OCH₃ | CH₃ | H |
| 4641 | F | Cl | F | Br | H | 4691 | F | Br | OCH₃ | CH₃ | CH₃ |
| 4642 | F | Cl | F | Br | CH₃ | 4692 | F | Br | OCH₃ | CH₃ | Cl |
| 4643 | F | Cl | F | Br | OCH₃ | 4693 | F | Br | OCH₃ | CH₃ | Br |
| 4644 | F | Cl | F | Br | Cl | 4694 | F | Br | OCH₃ | CH₃ | F |
| 4645 | F | Cl | F | Br | Br | 4695 | F | Br | OCH₃ | OCH₃ | H |

TABLE 2-continued

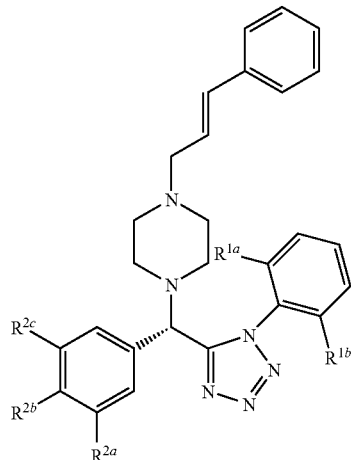

wherein $R^{1a}$, $R^{1b}$, $R^{2a}$, $R^{2b}$, and $R^{2c}$ are as defined in Table 2.

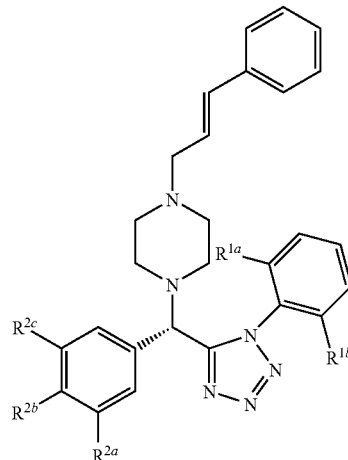

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4696 | F | Br | OCH$_3$ | OCH$_3$ | CH$_3$ |
| 4697 | F | Br | OCH$_3$ | OCH$_3$ | OCH$_3$ |
| 4698 | F | Br | OCH$_3$ | OCH$_3$ | Cl |
| 4699 | F | Br | OCH$_3$ | OCH$_3$ | Br |
| 4700 | F | Br | OCH$_3$ | OCH$_3$ | F |
| 4701 | F | Br | OCH$_3$ | Cl | H |
| 4702 | F | Br | OCH$_3$ | Cl | CH$_3$ |
| 4703 | F | Br | OCH$_3$ | Cl | Cl |
| 4704 | F | Br | OCH$_3$ | Cl | Br |
| 4705 | F | Br | OCH$_3$ | Cl | F |
| 4706 | F | Br | OCH$_3$ | Br | H |
| 4707 | F | Br | OCH$_3$ | Br | CH$_3$ |
| 4708 | F | Br | OCH$_3$ | Br | Cl |
| 4709 | F | Br | OCH$_3$ | Br | Br |
| 4710 | F | Br | OCH$_3$ | Br | F |
| 4711 | F | Br | OCH$_3$ | F | H |
| 4712 | F | Br | OCH$_3$ | F | CH$_3$ |
| 4713 | F | Br | OCH$_3$ | F | Cl |
| 4714 | F | Br | OCH$_3$ | F | Br |
| 4715 | F | Br | OCH$_3$ | F | F |
| 4716 | F | Br | Cl | H | H |
| 4717 | F | Br | Cl | H | CH$_3$ |
| 4718 | F | Br | Cl | H | OCH$_3$ |
| 4719 | F | Br | Cl | H | Cl |
| 4720 | F | Br | Cl | H | Br |
| 4721 | F | Br | Cl | H | F |
| 4722 | F | Br | Cl | CH$_3$ | H |
| 4723 | F | Br | Cl | CH$_3$ | CH$_3$ |
| 4724 | F | Br | Cl | CH$_3$ | OCH$_3$ |
| 4725 | F | Br | Cl | CH$_3$ | Br |
| 4726 | F | Br | Cl | CH$_3$ | F |
| 4727 | F | Br | Cl | OCH$_3$ | H |
| 4728 | F | Br | Cl | OCH$_3$ | CH$_3$ |
| 4729 | F | Br | Cl | OCH$_3$ | OCH$_3$ |
| 4730 | F | Br | Cl | OCH$_3$ | Br |
| 4731 | F | Br | Cl | OCH$_3$ | F |
| 4732 | F | Br | Cl | Cl | H |
| 4733 | F | Br | Cl | Cl | CH$_3$ |
| 4734 | F | Br | Cl | Cl | OCH$_3$ |
| 4735 | F | Br | Cl | Cl | Cl |
| 4736 | F | Br | Cl | Cl | Br |
| 4737 | F | Br | Cl | Cl | F |
| 4738 | F | Br | Cl | Br | H |
| 4739 | F | Br | Cl | Br | CH$_3$ |
| 4740 | F | Br | Cl | Br | OCH$_3$ |
| 4741 | F | Br | Cl | Br | Br |
| 4742 | F | Br | Cl | F | H |
| 4743 | F | Br | Cl | F | CH$_3$ |
| 4744 | F | Br | Cl | F | OCH$_3$ |
| 4745 | F | Br | Cl | F | Br |
| 4746 | F | Br | Cl | F | F |
| 4747 | F | Br | Br | H | H |
| 4748 | F | Br | Br | H | CH$_3$ |
| 4749 | F | Br | Br | H | OCH$_3$ |
| 4750 | F | Br | Br | H | Cl |
| 4751 | F | Br | Br | H | Br |
| 4752 | F | Br | Br | H | F |
| 4753 | F | Br | Br | CH$_3$ | H |
| 4754 | F | Br | Br | CH$_3$ | CH$_3$ |
| 4755 | F | Br | Br | CH$_3$ | OCH$_3$ |
| 4756 | F | Br | Br | CH$_3$ | Cl |
| 4757 | F | Br | Br | CH$_3$ | F |
| 4758 | F | Br | Br | OCH$_3$ | H |
| 4759 | F | Br | Br | OCH$_3$ | CH$_3$ |
| 4760 | F | Br | Br | OCH$_3$ | OCH$_3$ |
| 4761 | F | Br | Br | OCH$_3$ | Cl |
| 4762 | F | Br | Br | OCH$_3$ | F |
| 4763 | F | Br | Br | Cl | H |
| 4764 | F | Br | Br | Cl | CH$_3$ |
| 4765 | F | Br | Br | Cl | OCH$_3$ |
| 4766 | F | Br | Br | Cl | Cl |
| 4767 | F | Br | Br | Cl | F |
| 4768 | F | Br | Br | Br | H |
| 4769 | F | Br | Br | Br | CH$_3$ |
| 4770 | F | Br | Br | Br | OCH$_3$ |
| 4771 | F | Br | Br | Br | Cl |
| 4772 | F | Br | Br | Br | Br |
| 4773 | F | Br | Br | Br | F |
| 4774 | F | Br | Br | F | H |
| 4775 | F | Br | Br | F | CH$_3$ |
| 4776 | F | Br | Br | F | OCH$_3$ |
| 4777 | F | Br | Br | F | Cl |
| 4778 | F | Br | Br | F | F |
| 4779 | F | Br | F | H | H |
| 4780 | F | Br | F | H | CH$_3$ |
| 4781 | F | Br | F | H | OCH$_3$ |
| 4782 | F | Br | F | H | Cl |
| 4783 | F | Br | F | H | Br |
| 4784 | F | Br | F | H | F |
| 4785 | F | Br | F | CH$_3$ | H |
| 4786 | F | Br | F | CH$_3$ | CH$_3$ |
| 4787 | F | Br | F | CH$_3$ | OCH$_3$ |
| 4788 | F | Br | F | CH$_3$ | Cl |
| 4789 | F | Br | F | CH$_3$ | Br |
| 4790 | F | Br | F | OCH$_3$ | H |
| 4791 | F | Br | F | OCH$_3$ | CH$_3$ |
| 4792 | F | Br | F | OCH$_3$ | OCH$_3$ |
| 4793 | F | Br | F | OCH$_3$ | Cl |
| 4794 | F | Br | F | OCH$_3$ | Br |
| 4795 | F | Br | F | Cl | H |

TABLE 2-continued

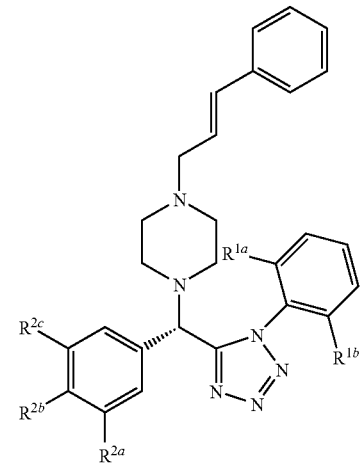

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4796 | F | Br | F | Cl | $CH_3$ |
| 4797 | F | Br | F | Cl | $OCH_3$ |
| 4798 | F | Br | F | Cl | Cl |
| 4799 | F | Br | F | Cl | Br |
| 4800 | F | Br | F | Br | H |
| 4801 | F | Br | F | Br | $CH_3$ |
| 4802 | F | Br | F | Br | $OCH_3$ |
| 4803 | F | Br | F | Br | Cl |
| 4804 | F | Br | F | Br | Br |
| 4805 | F | Br | F | F | H |
| 4806 | F | Br | F | F | $CH_3$ |
| 4807 | F | Br | F | F | $OCH_3$ |
| 4808 | F | Br | F | F | Cl |
| 4809 | F | Br | F | F | Br |
| 4810 | F | Br | F | F | F |
| 4811 | F | F | $CH_3$ | H | H |
| 4812 | F | F | $CH_3$ | H | $CH_3$ |
| 4813 | F | F | $CH_3$ | H | $OCH_3$ |
| 4814 | F | F | $CH_3$ | H | Cl |
| 4815 | F | F | $CH_3$ | H | Br |
| 4816 | F | F | $CH_3$ | H | F |
| 4817 | F | F | $CH_3$ | $CH_3$ | H |
| 4818 | F | F | $CH_3$ | $CH_3$ | $CH_3$ |
| 4819 | F | F | $CH_3$ | $CH_3$ | $OCH_3$ |
| 4820 | F | F | $CH_3$ | $CH_3$ | Cl |
| 4821 | F | F | $CH_3$ | $CH_3$ | Br |
| 4822 | F | F | $CH_3$ | $CH_3$ | F |
| 4823 | F | F | $CH_3$ | $OCH_3$ | H |
| 4824 | F | F | $CH_3$ | $OCH_3$ | $OCH_3$ |
| 4825 | F | F | $CH_3$ | $OCH_3$ | Cl |
| 4826 | F | F | $CH_3$ | $OCH_3$ | Br |
| 4827 | F | F | $CH_3$ | $OCH_3$ | F |
| 4828 | F | F | $CH_3$ | Cl | H |
| 4829 | F | F | $CH_3$ | Cl | $OCH_3$ |
| 4830 | F | F | $CH_3$ | Cl | Cl |
| 4831 | F | F | $CH_3$ | Cl | Br |
| 4832 | F | F | $CH_3$ | Cl | F |
| 4833 | F | F | $CH_3$ | Br | H |
| 4834 | F | F | $CH_3$ | Br | $OCH_3$ |
| 4835 | F | F | $CH_3$ | Br | Cl |
| 4836 | F | F | $CH_3$ | Br | Br |
| 4837 | F | F | $CH_3$ | Br | F |
| 4838 | F | F | $CH_3$ | F | H |
| 4839 | F | F | $CH_3$ | F | $OCH_3$ |
| 4840 | F | F | $CH_3$ | F | Cl |
| 4841 | F | F | $CH_3$ | F | Br |
| 4842 | F | F | $CH_3$ | F | F |
| 4843 | F | F | $OCH_3$ | H | H |
| 4844 | F | F | $OCH_3$ | H | $CH_3$ |
| 4845 | F | F | $OCH_3$ | H | $OCH_3$ |

TABLE 2-continued

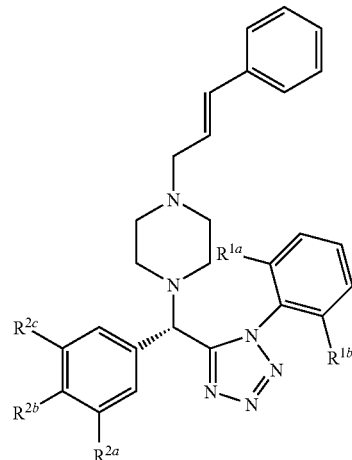

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4846 | F | F | $OCH_3$ | H | Cl |
| 4847 | F | F | $OCH_3$ | H | Br |
| 4848 | F | F | $OCH_3$ | H | F |
| 4849 | F | F | $OCH_3$ | $CH_3$ | H |
| 4850 | F | F | $OCH_3$ | $CH_3$ | $CH_3$ |
| 4851 | F | F | $OCH_3$ | $CH_3$ | Cl |
| 4852 | F | F | $OCH_3$ | $CH_3$ | Br |
| 4853 | F | F | $OCH_3$ | $CH_3$ | F |
| 4854 | F | F | $OCH_3$ | $OCH_3$ | H |
| 4855 | F | F | $OCH_3$ | $OCH_3$ | $CH_3$ |
| 4856 | F | F | $OCH_3$ | $OCH_3$ | $OCH_3$ |
| 4857 | F | F | $OCH_3$ | $OCH_3$ | Cl |
| 4858 | F | F | $OCH_3$ | $OCH_3$ | Br |
| 4859 | F | F | $OCH_3$ | $OCH_3$ | F |
| 4860 | F | F | $OCH_3$ | Cl | H |
| 4861 | F | F | $OCH_3$ | Cl | $CH_3$ |
| 4862 | F | F | $OCH_3$ | Cl | Cl |
| 4863 | F | F | $OCH_3$ | Cl | Br |
| 4864 | F | F | $OCH_3$ | Cl | F |
| 4865 | F | F | $OCH_3$ | Br | H |
| 4866 | F | F | $OCH_3$ | Br | $CH_3$ |
| 4867 | F | F | $OCH_3$ | Br | Cl |
| 4868 | F | F | $OCH_3$ | Br | Br |
| 4869 | F | F | $OCH_3$ | Br | F |
| 4870 | F | F | $OCH_3$ | F | H |
| 4871 | F | F | $OCH_3$ | F | $CH_3$ |
| 4872 | F | F | $OCH_3$ | F | Cl |
| 4873 | F | F | $OCH_3$ | F | Br |
| 4874 | F | F | $OCH_3$ | F | F |
| 4875 | F | F | Cl | H | H |
| 4876 | F | F | Cl | H | $CH_3$ |
| 4877 | F | F | Cl | H | $OCH_3$ |
| 4878 | F | F | Cl | H | Cl |
| 4879 | F | F | Cl | H | Br |
| 4880 | F | F | Cl | H | F |
| 4881 | F | F | Cl | $CH_3$ | H |
| 4882 | F | F | Cl | $CH_3$ | $CH_3$ |
| 4883 | F | F | Cl | $CH_3$ | $OCH_3$ |
| 4884 | F | F | Cl | $CH_3$ | Br |
| 4885 | F | F | Cl | $CH_3$ | F |
| 4886 | F | F | Cl | $OCH_3$ | H |
| 4887 | F | F | Cl | $OCH_3$ | $CH_3$ |
| 4888 | F | F | Cl | $OCH_3$ | $OCH_3$ |
| 4889 | F | F | Cl | $OCH_3$ | Br |
| 4890 | F | F | Cl | $OCH_3$ | F |
| 4891 | F | F | Cl | Cl | H |
| 4892 | F | F | Cl | Cl | $CH_3$ |
| 4893 | F | F | Cl | Cl | $OCH_3$ |
| 4894 | F | F | Cl | Cl | Cl |
| 4895 | F | F | Cl | Cl | Br |

TABLE 2-continued

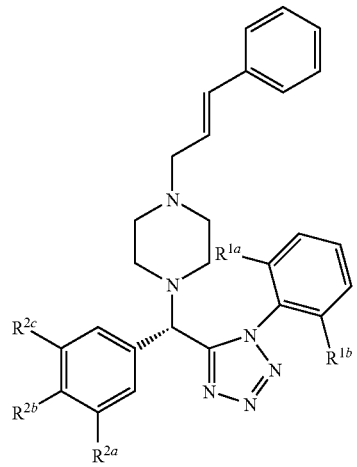

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4896 | F | F | Cl | Cl | F |
| 4897 | F | F | Cl | Br | H |
| 4898 | F | F | Cl | Br | $CH_3$ |
| 4899 | F | F | Cl | Br | $OCH_3$ |
| 4900 | F | F | Cl | Br | Br |
| 4901 | F | F | Cl | F | H |
| 4902 | F | F | Cl | F | $CH_3$ |
| 4903 | F | F | Cl | F | $OCH_3$ |
| 4904 | F | F | Cl | F | Br |
| 4905 | F | F | Cl | F | F |
| 4906 | F | F | Br | H | H |
| 4907 | F | F | Br | H | $CH_3$ |
| 4908 | F | F | Br | H | $OCH_3$ |
| 4909 | F | F | Br | H | Cl |
| 4910 | F | F | Br | H | Br |
| 4911 | F | F | Br | H | F |
| 4912 | F | F | Br | $CH_3$ | H |
| 4913 | F | F | Br | $CH_3$ | $CH_3$ |
| 4914 | F | F | Br | $CH_3$ | $OCH_3$ |
| 4915 | F | F | Br | $CH_3$ | Cl |
| 4916 | F | F | Br | $CH_3$ | F |
| 4917 | F | F | Br | $OCH_3$ | H |
| 4918 | F | F | Br | $OCH_3$ | $CH_3$ |
| 4919 | F | F | Br | $OCH_3$ | $OCH_3$ |
| 4920 | F | F | Br | $OCH_3$ | Cl |
| 4921 | F | F | Br | $OCH_3$ | F |
| 4922 | F | F | Br | Cl | H |
| 4923 | F | F | Br | Cl | $CH_3$ |
| 4924 | F | F | Br | Cl | $OCH_3$ |
| 4925 | F | F | Br | Cl | Cl |
| 4926 | F | F | Br | Cl | F |
| 4927 | F | F | Br | Br | H |
| 4928 | F | F | Br | Br | $CH_3$ |
| 4929 | F | F | Br | Br | $OCH_3$ |
| 4930 | F | F | Br | Br | Cl |
| 4931 | F | F | Br | Br | Br |
| 4932 | F | F | Br | Br | F |
| 4933 | F | F | Br | F | H |
| 4934 | F | F | Br | F | $CH_3$ |
| 4935 | F | F | Br | F | $OCH_3$ |
| 4936 | F | F | Br | F | Cl |
| 4937 | F | F | Br | F | F |
| 4938 | F | F | F | H | H |
| 4939 | F | F | F | H | $CH_3$ |
| 4940 | F | F | F | H | $OCH_3$ |
| 4941 | F | F | F | H | Cl |
| 4942 | F | F | F | H | Br |
| 4943 | F | F | F | H | F |
| 4944 | F | F | F | $CH_3$ | H |
| 4945 | F | F | F | $CH_3$ | $CH_3$ |

TABLE 2-continued

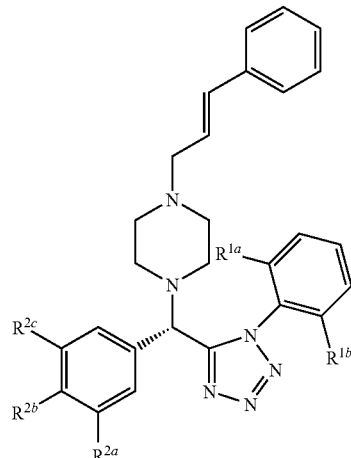

wherein $R^{1a}$, $R^{1b}$, $R^{2a}$, $R^{2b}$, and $R^{2c}$ are as defined in Table 2.

| Compound No. | $R^{1a}$ | $R^{1b}$ | $R^{2a}$ | $R^{2b}$ | $R^{2c}$ |
|---|---|---|---|---|---|
| 4946 | F | F | F | $CH_3$ | $OCH_3$ |
| 4947 | F | F | F | $CH_3$ | Cl |
| 4948 | F | F | F | $CH_3$ | Br |
| 4949 | F | F | F | $OCH_3$ | H |
| 4950 | F | F | F | $OCH_3$ | $CH_3$ |
| 4951 | F | F | F | $OCH_3$ | $OCH_3$ |
| 4952 | F | F | F | $OCH_3$ | Cl |
| 4953 | F | F | F | $OCH_3$ | Br |
| 4954 | F | F | F | Cl | H |
| 4955 | F | F | F | Cl | $CH_3$ |
| 4956 | F | F | F | Cl | $OCH_3$ |
| 4957 | F | F | F | Cl | Cl |
| 4958 | F | F | F | Cl | Br |
| 4959 | F | F | F | Br | H |
| 4960 | F | F | F | Br | $CH_3$ |
| 4961 | F | F | F | Br | $OCH_3$ |
| 4962 | F | F | F | Br | Cl |
| 4963 | F | F | F | Br | Br |
| 4964 | F | F | F | F | H |
| 4965 | F | F | F | F | $CH_3$ |
| 4966 | F | F | F | F | $OCH_3$ |
| 4967 | F | F | F | F | Cl |
| 4968 | F | F | F | F | Br |
| 4969 | F | F | F | F | F |

The compounds of Formulas I, II, III, IV, and V are MCH receptor antagonists, as demonstrated by the ligand binding assays described hereinbelow. MCH receptor antagonist activity has been correlated with pharmaceutical activity for the treatment of eating disorders such as obesity and hyperphagia, and diabetes. Compounds of Formula I exhibit good activity in standard in vitro MCH calcium mobilization assays and/or receptor binding assays, specifically in the assays described hereinbelow, see Examples 6 and 7. Generally, compounds of Formula I have a $K_i$ of about 10 μM or less, preferably about 1 μM or less, more preferably about 100 nM or less, or even more preferably about 10 nM or less, as determined by a standard in vitro MCH receptor mediated calcium mobilization assay as exemplified by Example 6, hereinbelow. Generally compounds of Formula I are MCH receptor antagonists and exhibit $IC_{50}$ values of about 10 μM or less, preferably about 1 μM or less, more preferably about 100 nM or less, or even more preferably about 10 nM or less, as determined by a standard in vitro MCH receptor binding assay such as is described hereinbelow in Example 7.

Preferably, the MCH receptor antagonists of Formula I bind specifically, and still more preferably with high affinity, to MCH receptors.

General Synthetic Procedures

The compounds described herein may be synthesized according to the following procedures of Schemes 1-3, wherein A, W, X, Z, and $R^1$-$R^8$ are as defined for Formulas I-V, above.

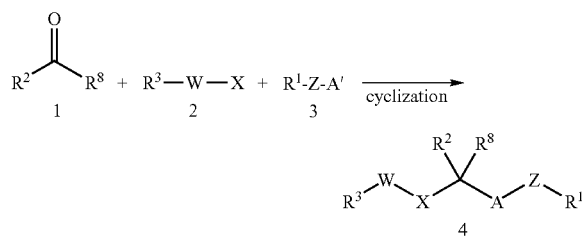

Compounds of Formula I can be prepared by the methods of generic scheme 1. Coupling of carbonyl compounds such as aldehydes or ketones 1 with amines 2 and compounds 3 (where A' is a ring precursor) forms an intermediate precursor that is then cyclized to form the compounds 4 of Formula I.

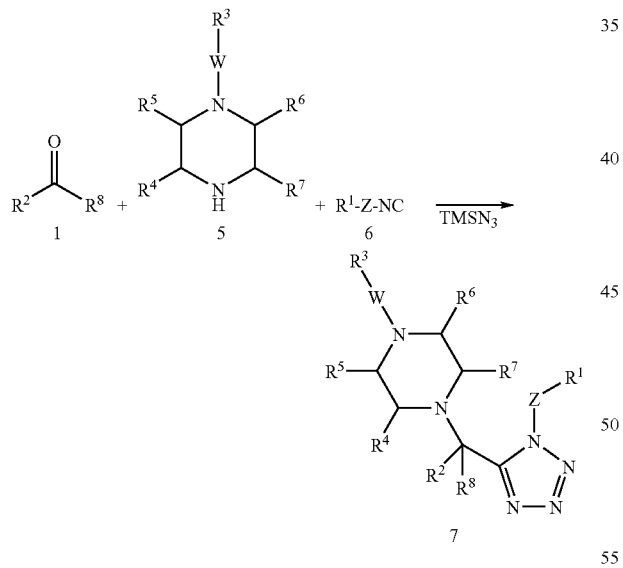

Compounds of Formula II-V can be prepared by general scheme 2. Using a modified Ugi synthesis, [(a) Ugi, I., *Angew. Chem. Int. Ed. Engl.* 1962, 1, 8; (b) Ugi, I. and Steinbruckner, C., *Chem. Ber.* 1961, 94, 734; (c) Ugi, I. et al., *Endeavor* 1994, 18, 115; (d) Domling, A., *Combinatorial Chemistry & High Throughput Screening* 1998, 1, 1]carbonyl compounds such as aldehydes or ketones 1 with piperazines 5 and isocyanides 6 forms an intermediate precursor that is cyclized, such as with TMSN$_3$, to form tetrazoles 7.

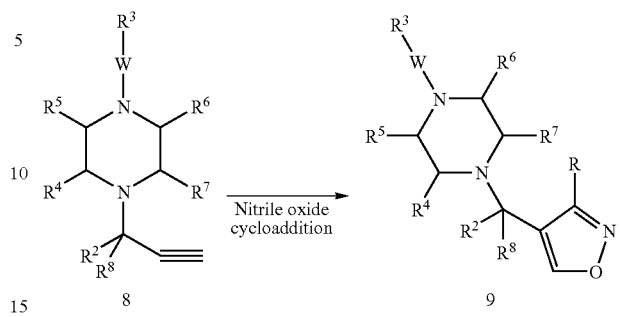

Isoxazoles compounds can be prepared by general scheme 3. Cycloaddition reactions of substituted propynyl piperazines 8, such as with nitrile oxide, form isoxazoles 9.

The following examples illustrate the invention.

EXAMPLE 1

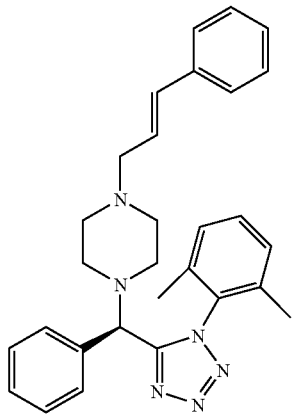

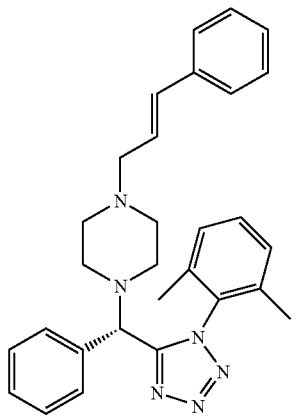

Benzaldehyde (102 mL, 1 mmol), trans-cinnamylpiperazine (202 mg, 1 mmol), 2,6-dimethylphenylisocyanide (131 mg, 1 mmol), and TMSN$_3$ (132 mL, 1 mmol) were added to 40 mL methanol in order of their participation in the Ugi reaction. After 18 hours the solution was concentrated to yield a colorless oil. The product was purified by FCC (2% MeOH/CHCl₃) to yield a colorless oil.

EXAMPLE 2

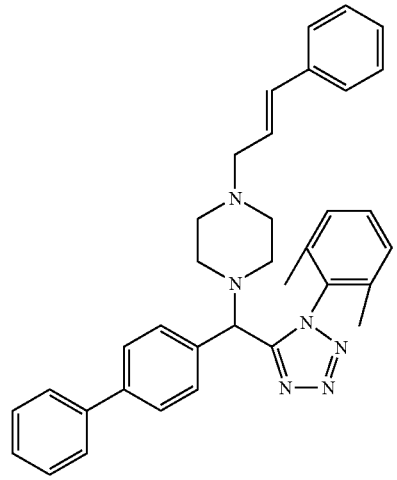

Biphenylcarboxaldehyde (182 mg, 1 mmol), TMSN₃ (132 mL, 1 mmol), 2,6-dimethylphenylisocyanide (131 mg, 1 mmol) and trans-cinnamylpiperazine (202 mg, 1 mmol) were added to 40 mL methanol in order of their participation in the Ugi reaction. After 18 hours, the solution was concentrated to yield a colorless oil, which was purified by FCC (1% MeOH/CHCl₃). Because of rapid elution of product in 1% MeOH/CHCl₃, only one fraction was pure. Other fractions were combined and evaporated. The product was a light yellow oil, which was briefly a white solid during evaporation.

EXAMPLE 3

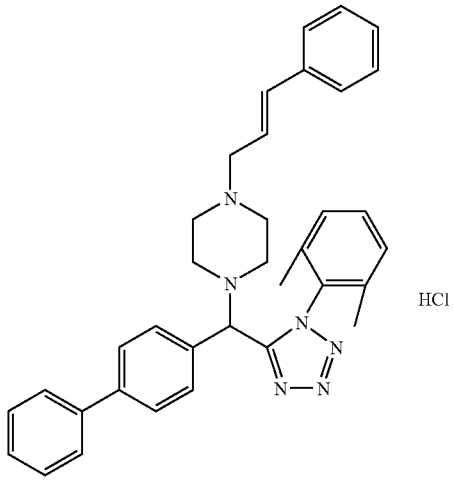

The compound of Example 2 (168 mg, 0.359 mmol) was dissolved in 5 mL DCM and 1.0 M HCl/ether (0.72 mL) was added. After 1 hour, the resulting white precipitate was filtered.

EXAMPLE 4

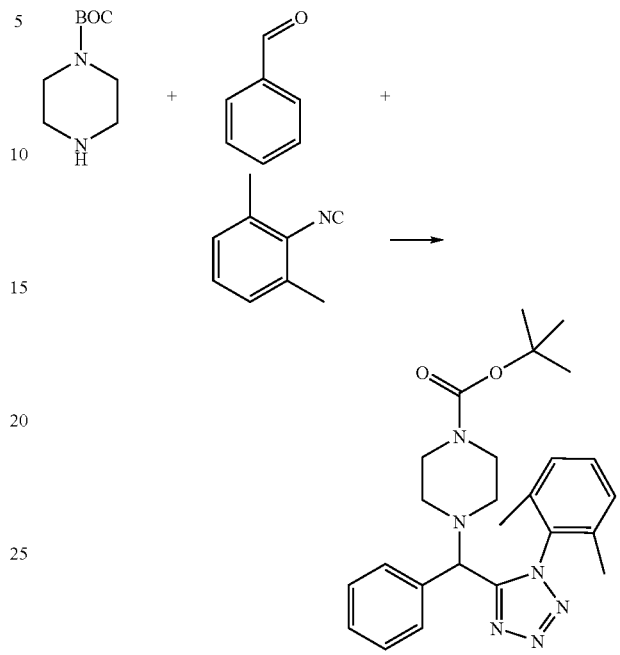

Amine (0.93 g, 5 mmol), aldehyde (0.51 mL, mmol), TMSN₃ (0.66 mL, 5 mmol) and isocyanide (0.66 g, mmol) were dissolved in 200 mL MeOH in order of participation in the Ugi reaction. After 4 days, the reaction solution was about 75% evaporated, and the white precipitate was filtered, washed with cold MeOH, and air dried.

EXAMPLE 5

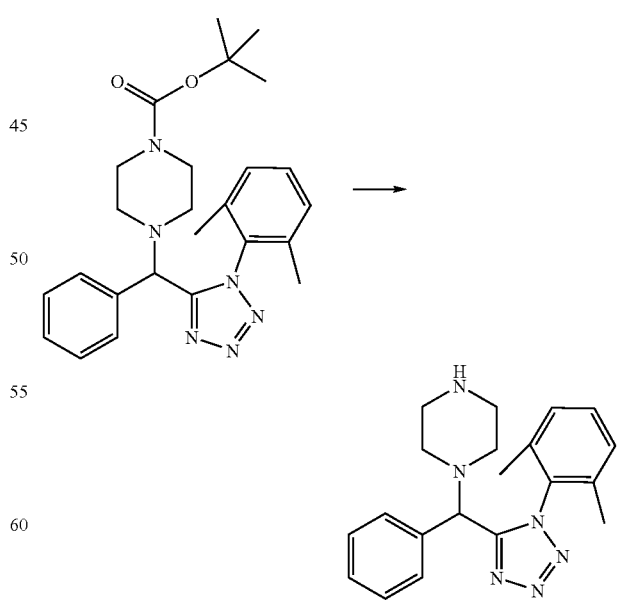

The compound of Example 4 (37 mg) and 2 mL 10% TFA/DCE were shaken for 18 hours and concentrated to give a colorless oil. The product was purified by LC.

EXAMPLE 6

Functional Assays

Human embryonic kidney cells (293 total) expressing either human, rat, or mouse MCH receptor were harvested from 150 mm culture dishes using PBS. Spinning at 1500 rpm for 2 minutes initially pelleted cells. The resulting pellet was then homogenized in 15 mL ice cold sucrose buffer (25 mM HEPES, 0.3 M sucrose, pH 7.4) with a motorized, glass fitted, Teflon® homogenizer. The homogenate was centrifuged at 48,000×g at 4° C. for 10 minutes, resuspended in 15 mL assay buffer (25 mM HEPES, 10 mM mgCl$_2$, 0.2% BSA, 0.1 mg/mL STI, 0.1 mg/mL Pefabloc®, 1 µM Phosphoramidon, pH 7.4) with a Tissue-Tearor® (Biospec Products) and centrifuged again at 48,000×g for 10 minutes. The pellet was homogenized for a third time in 15 mL assay buffer using the Tissue-Tearor® and again centrifuged at 48,000×g for 10 minutes. The resulting pellet was resuspended in assay buffer at a wet weight concentration of 10-20 mg/mL.

Pharmacological analyses were conducted using either a HT-PS100 device (Axiom Biotechnologies, San Diego, Calif.), which provides high-resolution dose-response fluorometric measurements of $[Ca^{++}]_i$ mobilization, or using a FLIPR® device (Molecular Devices, Sunnyvale, Calif.).

HT-PS100 Protocol:

Materials: HEK 293 cells were stably transfected with the rat MCH1 receptor and maintained under G418 antibiotic pressure. HT-PS100 assay buffer consisted of Physiological Saline Solution (145 mM NaCl, 5.4 mM KCL, 1.0 mM NaH$_2$PO$_4$, 1.8 mM CaCl$_2$, 0.8 mM mgSO$_4$, 15.0 mM HEPES, pH 7.4, 11.2 mM glucose)+50 µM Pluronic-F127. MCH peptide (Amgen, Inc.) was reconstituted in assay buffer and served as the positive agonist control for all experiments. Test compounds were prepared as 10 mM stocks in 100% DMSO and diluted to a top end working concentration of 100 µM in 96 well plates.

Methods: HEK 293 stably expressing MCH1R were maintained in Dulbeco's modified Eagle's medium (GIBCO/Life Technologies, Rockville, Md.) supplemented with 2 mM glutamine and 10% dialyzed fetal bovine serum (HyClone, Logan, Utah) at 37° C., 5% CO$_2$. Cells were harvested by 10' treatment with Versene (GIBCO/Life Technologies) followed by trituration, washing twice with cold (4° C.) hybridoma medium (Serum/Protein free, with L-glutamine, sodium bicarbonate, MOPS buffer) (Sigma-Aldrich Corp, St. Louis, Mo.) and resuspended at 2×10$^6$ cells/mL in the same medium. The resuspended cells were loaded with the fluorescent calcium indicator Fura-2 by incubating with Fura-2AM (Molecular Probes, Eugene, Oreg.) at 1.6 µM for 60' at room temperature. The loaded cells were then washed twice with hybridoma medium, adjusted to 2×10$^5$ cells/mL and kept at ambient temperature in a spinner flask under gentle stirring for up to 6 hours during the experiment.

Receptor-stimulated intracellular calcium responses were detected in the flow-through detector cuvette of the HT-PS100 by monitoring increases in the ratio of Fura-2 fluorescence intensities $R_{340/380}$ measured at alternating 340/380 nm excitation and 510 nm emission.

Preliminary static experiments, conducted to determine the kinetics of MCH1R's dose response to MCH peptide, indicated the optimum time point to capture the maximum Ca$^{++}$ transients was 30 s. No interference with DMSO was seen up to 1%. Based on these observations, subsequent experiments were conducted on the HT-PS100 to generate high resolution dose response curves, characterize agonist/antagonist properties, and evaluate antagonist potencies via Schild experiments. During HT-PS100 validation, reproducible EC$_{50}$s for MCH of 10 nM were generated within a broad range of cell passage and harvest density. HT-PS100 gradient generation was calibrated with a standardized stock of fluorescein.

Test compounds were screened for MCH1R activity in the HT-PS100 for both agonist and antagonist action. Agonist mode challenges were conducted at a maximum gradient concentration of 100 µM. Antagonist activity was tested by 30 s pre-incubation of cells at a compound concentration of 100 µM, with subsequent introduction of MCH at a concentration 5-fold of EC$_{50}$ as determined in preliminary experiments. Compounds that showed inhibition of the MCH-induced Ca$^{++}$ response were automatically tagged for re-interrogation, IC$_{50}$ generation, and Schild analysis.

Schild experiments were conducted on the HT-PS100 for selected compounds by 30 s pre-incubation of cells with antagonist compounds prior to administering MCH peptide. Several fixed concentrations of antagonist compounds were prepared in 10-fold increments, and presented to the cells 30 s before introducing a gradient of increasing MCH concentration. Values for compound pA$_2$ were calculated by linear regression of Log(DR−1) MCH EC$_{50}$ as a function of Log (antagonist concentration), where DR is the dose ratio of MCH EC$_{50}$ values determined in the presence and absence of antagonist.

The following compounds had K$_i$ values of 100 nM or less in the HT-PS100 assay: Compound Nos. 1, 4, 48, 53, 55, 56, 57, 60, 61, 62, 64, 70, 76, 77, 78, 79, 82, 83, and 84.

FLIPR® Protocol:

Materials: Pharmacological analysis was conducted using a FLIPR® device (Molecular Devices, Sunnyvale, Calif.). CHOK1-Gqi cells were stably transfected with the rat MCH1 receptor and maintained under G418 antibiotic pressure. FLIPR® assay buffer consisted of phenol red-free DMEM+ 2.5 mM probenecid. MCH peptide (Amgen, Inc.) was reconstituted in assay buffer and served as the positive agonist control for all experiments. Test compounds were prepared as 10 mM stocks in 100% DMSO and diluted to a top end working concentration of 10 µM in 96 well black, flat bottom, collagen-I coated plates (Becton Dickinson, Bedford, Mass.).

Methods: CHOK1-Gqi cells stably expressing MCH1R were maintained in Dulbeco's modified Eagle's medium (GIBCO/Life Technologies, Rockville, Md.) supplemented with 2 mM glutamine and 10% dialyzed fetal bovine serum (HyClone, Logan, Utah) at 37° C., 5% CO$_2$. Cells were harvested by 10' treatment with Versene (GIBCO/Life Technologies) followed by trituration, washing twice with cold (4° C.) hybridoma medium (Serum/Protein free, with L-glutamine, sodium bicarbonate, MOPS buffer) (Sigma-Aldrich Corp, St. Louis, Mo.) and replated onto 96 well black, flat bottom, collagen-I coated plates to a density of 10,000 cells/well. The cells were then loaded with the fluorescent calcium indicator Fura-2 (Molecular Probes, Eugene, Oreg.) at 1.6 µM for 60' at room temperature. The loaded cells were then washed twice with 90 µl/well of wash buffer (1×HBSS, 20 mM HEPES, 2.5 mM probenecid).

Receptor-stimulated intracellular calcium responses were detected using FLIPR® by monitoring increases in the Fura-2 fluorescence response.

Test compounds were screened for MCH1R activity in the FLIPR® for both agonist and antagonist action. Agonist mode challenges were conducted at a maximum gradient concentration of 1 µM. Antagonist activity was tested by 10 min pre-incubation of cells at a compound concentration of defined to be 300× the $EC_{50}$ of MCH (typically 1 µM), with subsequent introduction of MCH at a concentration 5-fold of $EC_{50}$ as determined in preliminary experiments. Compounds that showed inhibition of MCH induced MCH1R dependant $Ca^{++}$ responses were automatically tagged for re-interrogation, $IC_{50}$ generation, and Schild analysis.

Schild experiments were conducted on the FLIPR® for selected compounds by co-administering antagonist compounds together with MCH peptide. Several fixed concentrations of antagonist compounds were prepared in 10-fold increments, and presented to the cells in a gradient of increasing MCH concentration. Values for compound $pA_2$ were calculated by linear regression of MCH $EC_{50}$s as a function of antagonist concentration.

The following compounds had $K_i$ values of 100 µM or less in the rMCH FLIPR® assay: Compound Nos. 1, 4, 11, 12, 20, 48, 53, 55, 56, 57, 60, 61, 62, 64, 70, 76, 77, 78, 79, 82, 83, 84, 86, 87, 92, 133, 134, 135, 143, 144, 145, 145, 147, 148, 150, and 151. Of these, Compound Nos. 11 and 56 had $K_i$ values of 100 nM or less in this assay.

The following compounds had $K_i$ values of 100 µM or less in the hMCH FLIPR® assay: Compound Nos. 1, 4, 20, 48, 53, 55, 56, 57, 60, 61, 62, 70, 77, 78, 79, 82, 83, 84, 86, 87, 133, 134, 135, 143, 144, 145, 147, 148, 150, and 151. Of these, Compound Nos. 4, 48, 53, 55, 56, 70, 79, and 82 had $K_i$ values of 100 nM or less in this assay.

EXAMPLE 7

Ligand Binding Assay

Binding assays were determined as described below using mouse, rat or human MCH 1 receptors (mMCH1R, rMCH1R, and hMCH1R, respectively) expressed in HEK 293; $IC_{50}$ values were calculated.

Binding assays were performed in 96-well U-bottom plates. Membranes (100 µg tissue) were incubated at 30° C. for 90 minutes in assay buffer with various peptides in the presence of 0.2 nM $^{125}$I native-MCH (Perkin-Elmer Life Sciences, Boston, Mass.) in 100 µL total volume. Non-specific binding was assessed in the presence of 1 µM cold native-MCH. The reaction was terminated by rapid filtration through Unfilter-96 GF/C glass fiber filter plates (FilterMate® 196 Harvester, Packard Instrument Co., Meriden, Conn.) pre-soaked in PBS/0.5% BSA, followed by three washes with 300 µL ice-cold water. Bound radioactivity was determined using a TopCount® microplate scintillation and luminescence counter (Packard Instrument Co., Meriden, Conn.). Nonlinear regression analyses of drug concentration curves were performed using GraphPad Prism® (GraphPad Software, Inc., San Diego, Calif.).

The following compounds had $IC_{50}$ values of 100 µM or less in the rMCH assay: Compound Nos. 1, 4, 11, 12, 14, 15, 19, 20, 21, 22, 24, 26, 27, 28, 29, 29, 30, 31, 33, 35, 36, 37, 38, 39, 46, 48, 52, 53, 55, 56, 57, 58, 60, 61, 62, 63, 64, 68, 69, 70, 71, 72, 73, 74, 75, 76, 77, 78, 79, 80, 81, 82, 83, 84, 92, 99, 118, 122, 123, 124, 125, 126, 127, 128, 129, 130, 131, 133, 134, 135, 136, 137, 138, 139, 140, 142, 143, 144, 145, 147, 148, 150, 151, 154, 156, 162, 163, and 164. Of these, Compound Nos. 1, 11, 56, 70, 79, 84, 129, 134, 136, 137, 138, 139, 140, 142, 144, and 163 had $IC_{50}$ values of 100 nM or less in the rMCH assay.

The following compounds had $IC_{50}$ values of 100 µM or less in the hMCH assay: Compound Nos. 1, 4, 11, 12, 14, 15, 16, 17, 19, 20, 21, 22, 26, 29, 30, 31, 33, 35, 36, 37, 38, 39, 42, 46, 48, 52, 53, 55, 56, 57, 58, 60, 61, 62, 63, 64, 66, 67, 68, 69, 70, 71, 72, 73, 74, 76, 77, 78, 79, 80, 81, 82, 83, 84, 85, 86, 87, 91, 92, 133, 134, 135, 142, 143, 144, 145, 147, 148, 150, 151, and 164. Of these, Compound Nos. 1, 4, 20, 55, 56, 62, 64, 70, 76, 77, 78, 84, 134, 142, and 144 had $IC_{50}$ values of 100 nM or less in the hMCH assay.

In view of the above, it will be seen that the several objects of the invention are achieved.

The above description of the embodiments and examples are intended only to acquaint others skilled in the art with the invention, its principles, and its practical application, so that others skilled in the art may adapt and apply the invention in its numerous forms, as may be best suited to the requirements of a particular use. The present invention, therefore, is not limited to the above embodiments, and may be variously modified.

With reference to the use of the word(s) "comprise" or "comprises" or "comprising" or "including" or "having" in the above description and/or in the following claims, it should be noted that unless the context requires otherwise, those words are used on the basis and clear understanding that they are to be interpreted inclusively, rather than exclusively, and that each of those words is to be so interpreted in construing the above description and/or the following claims. When introducing elements of the present invention or the preferred embodiment(s) thereof, the articles "a," "an," "the," and "said" are intended to mean that there are one or more of the elements.

In view of the above, it will be seen that the several objects of the invention are achieved and other advantageous results attained.

As various changes could be made in the above compounds and methods without departing from the scope of the invention, it is intended that all matter contained in the above description shall be interpreted as illustrative and not in a limiting sense.

The entire texts of all U.S. patents and other references cited herein are hereby incorporated by reference into this patent.

What is claimed is:

1. A method of treating obesity in a subject, the method comprising administering to a subject in need of such treatment a compound, pharmaceutically-acceptable salt or tautomer of a compound of Formula IV

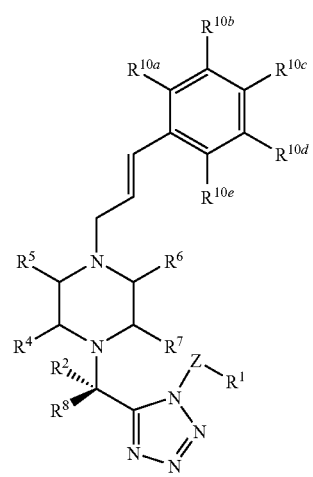

IV wherein Z is selected from the group consisting of a bond, methyl, ethyl, propyl, t-butyl, phenyl, tetrahydronaphthyl, biphenyl, naphthyl, phenylpropyl, indolylethyl, and piperidyl;

$R^1$ is selected from the group consisting of methoxycarbonyl, ethoxycarbonyl, t-butoxycarbonyl, isopropyl, n-butyl, t-butyl, cyclopropyl, cyclobutyl, cyclopentyl, cyclohexyl, benzyl, phenyl, tetrahydronaphthyl, indolyl, tetrahydrofuryl, pyrrolidinyl, and morpholinyl, wherein $R^1$ is optionally substituted by one or more substituents selected from the group consisting of methyl, ethyl, propyl, bromo, fluoro, chloro, and keto;

$R^2$ is selected from the group consisting of methyl, phenyl, biphenyl, naphthyl, tetrahydrofuryl, pyrrolidinyl, morpholinyl, piperidyl, thienyl, pyrrolyl, and pyridyl, or $R^2$ and $R^8$ together with the atom to which they are both attached form a piperidyl or cyclohexyl group, wherein $R^2$ of the piperidyl or cyclohexyl group formed with $R^8$ is optionally substituted by one or more substituents selected from the group consisting of methoxy, ethoxy, methyl, ethyl, isopropyl, isobutyl, methylphenoxy, methylthio, phenylethenyl, benzyloxy, phenylethoxy, benzyl, phenoxy, cyano, fluoro, chloro, bromo, trifluoromethyl, trifluoromethylphenyl, dichlorophenoxy, imidazole, benzodioxole, hydroxy, hydroxyethoxy, N-(methylcarbonyl)amino, and nitro;

$R^4$, $R^5$, $R^6$, and $R^7$ are independently selected from the group consisting of hydrogen, methyl, ethyl, n-propyl, isopropyl, fluoro, chloro, and bromo;

$R^8$ is hydrogen or alkyl; and $R^{10a}$, $R^{10b}$, $R^{10c}$, $R^{10d}$, and $R^{10e}$ are independently selected from the group consisting of hydrogen, methyl, hydroxy, and methoxy.

2. The method of claim 1 wherein the compound is selected from the group consisting of:

1-{[1-(2,6-dimethylphenyl)-1H-tetrazol-5-yl]phenylmethyl}-4-(3-phenylallyl)piperazine,
1-{biphenyl-4-yl-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(3-phenoxyphenyl)methyl]-4-(3-phenylallyl)piperazine,
1-[(1-tert-butyl-1H-tetrazol-5-yl)phenylmethyl]-4-(3-phenylallyl)piperazine,
1-[(1-benzyl-1H-tetrazol-5-yl)phenylmethyl]-4-(3-phenylallyl)piperazine,
(5-{phenyl-[4-(3-phenylallyl)piperazin-1-yl]methyl}tetrazol-1-yl)acetic acid methyl ester,
1-[(1-butyl-1H-tetrazol-5-yl)phenylmethyl]-4-(3-phenylallyl)piperazine,
1-[(1-isopropyl-1H-tetrazol-5-yl)phenylmethyl]-4-(3-phenylallyl)piperazine,
5-(5-{phenyl-[4-(3-phenylallyl)piperazin-1-yl]methyl}tetrazol-1-yl)-1H-indole,
(5-{phenyl-[4-(3-phenylallyl)piperazin-1-yl]methyl}tetrazol-1-yl)acetic acid ethyl ester,
1-(3-phenylallyl)-4-{phenyl-[1-(1,1,3,3-tetramethylbutyl)-1H-tetrazol-5-yl]methyl}piperazine,
(5-{phenyl-[4-(3-phenylallyl)piperazin-1-yl]methyl}tetrazol-1-yl)acetic acid tert-butyl ester,
1-{[1-(3,3-diphenylpropyl)-1H-tetrazol-5-yl]phenylmethyl}-4-(3-phenylallyl)piperazine,
1-{[1-(1-benzylpiperidin-4-yl)-1H-tetrazol-5-yl]phenylmethyl}-4-(3-phenylallyl)piperazine,
3-[2-(5-{phenyl-[4-(3-phenylallyl)piperazin-1-yl]methyl}tetrazol-1-yl)ethyl]-1H-indole,
1-{[1-(3,4-dichlorobenzyl)-1H-tetrazol-5-yl]phenylmethyl}-4-(3-phenylallyl)piperazine,
3-(1H-indol-3-yl)-2-(5-{phenyl-[4-(3-phenylallyl)piperazin-1-yl]methyl}tetrazol-1-yl)propionic acid methyl ester,
1-(3-phenylallyl)-4-{phenyl-[1-(tetrahydrofuran-2-ylmethyl)-1H-tetrazol-5-yl]methyl}piperazine,
1-[(1-phenethyl-1H-tetrazol-5-yl)phenylmethyl]-4-(3-phenylallyl)piperazine,
1-[3-(5-{phenyl-[4-(3-phenylallyl)piperazin-1-yl]methyl}tetrazol-1-yl)propyl]pyrrolidin-2-one,
1-({1-[2-(1-methyl-pyrrolidin-2-yl)ethyl]-1H-tetrazol-5-yl}phenylmethyl)-4-(3-phenylallyl)piperazine,
1-(3-phenylallyl)-4-{phenyl-[1-(5,6,7,8-tetrahydronaphthalen-1-yl)-1H-tetrazol-5-yl]methyl}piperazine,
1-({1-[2-(4-chlorophenyl)ethyl]-1H-tetrazol-5-yl}phenylmethyl)-4-(3-phenylallyl)piperazine,
4-[3-(5-{phenyl-[4-(3-phenylallyl)piperazin-1-yl]methyl}tetrazol-1-yl)propyl]morpholine,
1-{[1-(2,6-dimethylphenyl)-1H-tetrazol-5-yl]naphthalen-1-ylmethyl}-4-(3-phenylallyl)piperazine,
1-[[1-(2,6-dimethylphenyl)-1H-tetrazol-5-yl]-(3-fluorophenyl)methyl]-4-(3-phenylallyl)piperazine,
1-[[1-(2,6-dimethylphenyl)-1H-tetrazol-5-yl]-(4-styrylphenyl)methyl]-4-(3-phenylallyl)piperazine,
1-{[1-(2,6-dimethylphenyl)-1H-tetrazol-5-yl]thiophen-2-ylmethyl}-4-(3-phenylallyl)piperazine,
1-{[1-(2,6-dimethylphenyl)-1H-tetrazol-5-yl]-p-tolylmethyl}-4-(3-phenylallyl)piperazine,
1-[[1-(2,6-dimethylphenyl)-1H-tetrazol-5-yl]-(3-trifluoromethylphenyl)methyl]-4-(3-phenylallyl)piperazine,
1-{(4-chlorophenyl)-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(4-fluorophenyl)methyl]-4-(3-phenylallyl)piperazine,
1-{(3,4-dichlorophenyl)-[1-(2,6-dimethylphenyl)-1H-tetrazol-5-yl]methyl}-4-(3-phenylallyl)piperazine,
1-{[1-(2,6-dimethylphenyl)-1H-tetrazol-5-yl]-m-tolylmethyl}-4-(3-phenylallyl)piperazine,
1-{[1-(2,6-dimethylphenyl)-1H-tetrazol-5-yl]naphthalen-2-ylmethyl}-4-(3-phenylallyl)piperazine,
1-[[1-(2,6-dimethylphenyl)-1H-tetrazol-5-yl]-(4-trifluoromethylphenyl)methyl]-4-(3-phenylallyl)piperazine,
1-{biphenyl-4-yl-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(1-methyl-1H-pyrrol-2-yl)methyl]-4-(3-phenylallyl)piperazine,
1-{(2-benzyloxyphenyl)-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(2-methoxyphenyl)methyl]-4-(3-phenylallyl)piperazine,
1-{2-benzyloxy-1-[1-(2,6-dimethylphenyl)-1H-tetrazol-5-yl]ethyl}-4-(3-phenylallyl)piperazine,
1-{(4-benzyloxyphenyl)-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(6-methylpyridin-2-yl)methyl]-4-(3-phenylallyl)piperazine,
1-{[3-(3,4-dichlorophenoxy)phenyl]-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(3-p-tolyloxyphenyl)methyl]-4-(3-phenylallyl)piperazine,
1-{[1-(2,6-dimethylphenyl)-1H-tetrazol-5-yl]pyridin-3-ylmethyl}-4-(3-phenylallyl)piperazine,
1-{[1-(2,6-dimethylphenyl)-1H-tetrazol-5-yl]pyridin-2-ylmethyl}-4-(3-phenylallyl)piperazine,
1-[[1-(2,6-dimethylphenyl)-1H-tetrazol-5-yl]-(4-phenoxyphenyl)methyl]-4-(3-phenylallyl)piperazine, 1-[[1-(2,6-dimethylphenyl)-1H-tetrazol-5-yl]-(3-methoxyphenyl)methyl]-4-(3-phenylallyl)piperazine,
1-[[1-(2,6-dimethylphenyl)-1H-tetrazol-5-yl]-(4-imidazol-1-ylphenyl)methyl]-4-(3-phenylallyl)piperazine,
3-{[1-(2,6-dimethylphenyl)-1H-tetrazol-5-yl]-[4-(3-phenylallyl)piperazin-1-yl]methyl}benzonitrile,
2-{[1-(2,6-dimethylphenyl)-1H-tetrazol-5-yl]-[4-(3-phenylallyl)piperazin-1-yl]methyl}benzonitrile,
3-{[1-(2,6-dimethylphenyl)-1H-tetrazol-5-yl]-[4-(3-phenylallyl)piperazin-1-yl]methyl}phenol,
2-(3-{[1-(2,6-dimethylphenyl)-1H-tetrazol-5-yl]-[4-(3-phenylallyl)piperazin-1-yl]methyl}phenoxy)ethanol,
1-{1-[1-(2,6-dimethylphenyl)-1H-tetrazol-5-yl]-2-phenethyloxyethyl}-4-(3-phenylallyl)piperazine,
1-{[1-(2,6-dimethylphenyl)-1H-tetrazol-5-yl]pyridin-4-ylmethyl}-4-(3-phenylallyl)piperazine,
1-{[3-(3,5-dichloro-phenoxy)-phenyl]-[1-(2,6-dimethylphenyl)-1H-tetrazol-5-yl]methyl}-4-(3-phenylallyl)piperazine,
1-{1-benzyl-4-[1-(2,6-dimethylphenyl)-1H-tetrazol-5-yl]piperidin-4-yl}-4-(3-phenylallyl)piperazine,
1-{1-[1-(2,6-dimethylphenyl)-1H-tetrazol-5-yl]-cyclohexyl}-4-(3-phenylallyl)piperazine,
1-{4-[1-(2,6-dimethylphenyl)-1H-tetrazol-5-yl]-1-methylpiperidin-4-yl}-4-(3-phenylallyl)piperazine,
1-{(4-bromophenyl)-[1-(2,6-dimethylphenyl)-1H-tetrazol-5-yl]methyl}-4-(3-phenylallyl)piperazine,
1-{(4-bromophenyl)-[1-(2,6-dimethylphenyl)-1H-tetrazol-5-yl]methyl}-4-(3-phenylallyl)piperazine,
1-{(4-chlorophenyl)-[1-(2,6-dimethylphenyl)-1H-tetrazol-5-yl]methyl}-4-(3-phenylallyl)piperazine,
1-(3-phenylallyl)-4-[phenyl-(1-phenyl-1H-tetrazol-5-yl)methyl]piperazine,
1-[(4-imidazol-1-ylphenyl)-(1-phenyl-1H-tetrazol-5-yl)methyl]-4-(3-phenylallyl)piperazine,
1-[[1-(2,6-dimethylphenyl)-1H-tetrazol-5-yl]-(4-methoxyphenyl)methyl]-4-(3-phenylallyl)piperazine,
1-{(3,4-dimethylphenyl)-[1-(2,6-dimethylphenyl)-1H-tetrazol-5-yl]methyl}-4-(3-phenylallyl)piperazine,
1-{(3,4-difluorophenyl)-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(4-isopropylphenyl)methyl]-4-(3-phenylallyl)piperazine,
1-[[1-(2,6-dimethylphenyl)-1H-tetrazol-5-yl]-(4-methylsulfanylphenyl)methyl]-4-(3-phenylallyl)piperazine,
1-[[1-(2,6-dimethylphenyl)-1H-tetrazol-5-yl]-(4-ethylphenyl)methyl]-4-(3-phenylallyl)piperazine,
1-{(3,4-dimethoxyphenyl)-[1-(2,6-dimethylphenyl)-1H-tetrazol-5-yl]methyl}-4-(3-phenylallyl)piperazine,
1-{(4-benzyloxy-3-methoxyphenyl)-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(4-isobutylphenyl)methyl]-4-(3-phenylallyl)piperazine,
n-(4-{[1-(2,6-dimethylphenyl)-1H-tetrazol-5-yl]-[4-(3-phenylallyl)piperazin-1-yl]methyl}phenyl)acetamide,
3-{[1-(2,6-dimethylphenyl)-1H-tetrazol-5-yl]-[4-(3-phenylallyl)piperazin-1-yl]methyl}benzonitrile,
1-[[1-(2,6-dimethylphenyl)-1H-tetrazol-5-yl]-(4-imidazol-1-ylphenyl)methyl]-4-(3-phenylallyl)piperazine,
1-[[1-(2,6-dimethylphenyl)-1H-tetrazol-5-yl]-(4-ethoxyphenyl)methyl]-4-(3-phenylallyl)piperazine,
1-{(3,5-dichlorophenyl)-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(3-nitrophenyl)methyl]-4-(3-phenylallyl)piperazine,
1-{(3-bromophenyl)-[1-(2,6-dimethylphenyl)-1H-tetrazol-5-yl]methyl}-4-(3-phenylallyl)piperazine,
1-{(3-chlorophenyl)-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(3-trifluoromethylphenyl)methyl]-4-(3-phenylallyl)piperazine,
1-{biphenyl-3-yl-[1-(2,6-dimethylphenyl)-1H-tetrazol-5-yl]methyl}-4-(3-phenylallyl)piperazine,
1-[[1-(2,6-dimethylphenyl)-1H-tetrazol-5-yl]-(3-trifluoromethylphenyl)methyl]-4-[3-(4-methoxyphenyl)allyl]piperazine,
2-(3-{4-[[1-(2,6-dimethylphenyl)-1H-tetrazol-5-yl]-(3-trifluoromethylphenyl)methyl]piperazin-1-yl}propenyl)phenol,
4-(3-{4-[[1-(2,6-dimethylphenyl)-1H-tetrazol-5-yl]-(3-trifluoromethylphenyl)methyl]piperazin-1-yl}propenyl)-2-methoxyphenol, and
1-[[1-(2,6-dichlorophenyl)-1H-tetrazol-5-yl]-(3-trifluoromethylphenyl)methyl]-4-(3-phenylallyl)piperazine;
or a pharmaceutically-acceptable salt or tautomer thereof.

3. The method of claim 2 wherein the compound is 1-{[1-(2,6-dimethylphenyl)-1H-tetrazol-5-yl]phenylmethyl}-4-(3-phenylallyl)piperazine or a pharmaceutically-acceptable salt or tautomer thereof.

4. A method of treating obesity comprising administering to a subject in need of such treatment a compound, pharmaceutically-acceptable salt or tautomer of the Formula

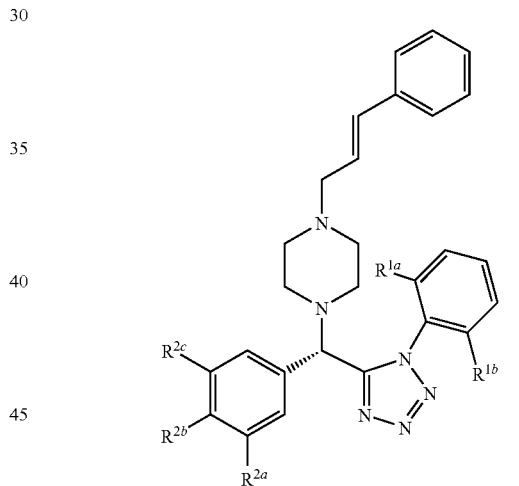

wherein
$R^{1a}$ is independently selected from the group consisting of hydrogen, methyl, methoxy, chloro, bromo, and fluoro;
$R^{1b}$ is independently selected from the group consisting of methyl, methoxy, chloro, bromo, and fluoro;
$R^{2a}$ is independently selected from the group consisting of methyl, methoxy, chloro, bromo, and fluoro;
$R^{2b}$ is independently selected from the group consisting of hydrogen, methyl, methoxy, chloro, bromo, and fluoro; and
$R^{2c}$ is independently selected from the group consisting of hydrogen, methyl, methoxy, chloro, bromo, and fluoro.

5. The method of claim 4, wherein $R^{1a}$ is methyl; and $R^{1b}$ is methyl.

6. The method of claim 4 wherein $R^{2b}$ is selected from the group consisting of chloro, bromo, and fluoro.

7. The method of claim 5 wherein $R^{2b}$ is selected from the group consisting of chloro, bromo, and fluoro.

8. The method of claim 1 wherein the compound, pharmaceutically-acceptable salt or tautomer is a compound of Formula V

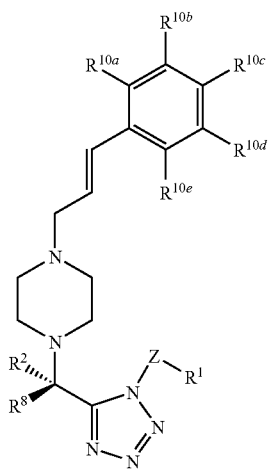

wherein Z is selected from the group consisting of a bond, methyl, ethyl, propyl, t-butyl, phenylpropyl, indolylethyl, and piperidyl;

$R^1$ is selected from the group consisting of methoxycarbonyl, ethoxycarbonyl, t-butoxycarbonyl, isopropyl, n-butyl, t-butyl, benzyl, phenyl, tetrahydronaphthyl, indolyl, tetrahydrofuryl, pyrrolidinyl, and morpholinyl, wherein $R^1$ is optionally substituted by one or more substituents selected from the group consisting of methyl, chloro, and keto;

$R^2$ is selected from the group consisting of methyl, phenyl, biphenyl, naphthyl, thienyl, pyrrolyl, and pyridyl, or $R^2$ and $R^8$ together with the atom to which they are both attached form a piperidyl or cyclohexyl group, wherein $R^2$ of the piperidyl or cyclohexyl group formed with $R^8$ is optionally substituted by one or more substituents selected from the group consisting of methoxy, ethoxy, methyl, ethyl, isopropyl, isobutyl, methylphenoxy, methylthio, phenylethenyl, benzyloxy, phenylethoxy, benzyl, phenoxy, cyano, fluoro, chloro, bromo, trifluoromethyl, trifluoromethylphenyl, dichlorophenoxy, imidazole, benzodioxole, hydroxy, hydroxyethoxy, N-(methylcarbonyl)amino, and nitro;

$R^8$ is hydrogen or alkyl; and $R^{10a}$, $R^{10b}$, $R^{10c}$, $R^{10d}$, and $R^{10e}$ are independently selected from the group consisting of hydrogen, methyl, hydroxy, and methoxy.

\* \* \* \* \*